(12) United States Patent
Kulkarni et al.

(10) Patent No.: US 9,006,442 B2
(45) Date of Patent: Apr. 14, 2015

(54) CANNABINOID RECEPTOR MODULATORS

(75) Inventors: Sanjeev Anant Kulkarni, Pune (IN); Sachin Madan, Pune (IN); Nirmal Kumar Jana, Pune (IN); Prashant Vitthalrao Tale, Pune (IN); Narasimha Murthy Cheemala, Pune (IN); Sachin Jaysing Mahangare, Pune (IN); Prashant Popatrao Vidhate, Pune (IN); Chaitanya Prabhakar Kulkarni, Pune (IN); Sapana Suresh Patel, Pune (IN); Amolsing Dattu Patil, Pune (IN); Seema Prabhakar Zade, Pune (IN); Rohan Mahadev Shinde, Pune (IN); Venkata P. Palle, Pune (IN); Rajender Kumar Kamboj, Pune (IN)

(73) Assignee: Lupin Limited (IN)

( * ) Notice: Subject to any disclaimer, the term of this patent is extended or adjusted under 35 U.S.C. 154(b) by 0 days.

(21) Appl. No.: 13/542,234

(22) Filed: Jul. 5, 2012

(65) Prior Publication Data

US 2013/0178457 A1 Jul. 11, 2013

Related U.S. Application Data

(63) Continuation-in-part of application No. PCT/IB2011/056007, filed on Dec. 29, 2011.

(30) Foreign Application Priority Data

| Jul. 5, 2011 | (IN) | 905/KOL/2011 |
| Jul. 5, 2011 | (IN) | 907/KOL/2011 |
| Jul. 5, 2011 | (IN) | 908/KOL/2011 |

(51) Int. Cl.

| C07D 491/107 | (2006.01) |
| C07D 498/08 | (2006.01) |
| C07D 295/16 | (2006.01) |
| C07D 217/26 | (2006.01) |
| C07D 401/06 | (2006.01) |
| C07D 309/04 | (2006.01) |
| C07D 491/08 | (2006.01) |
| C07D 213/40 | (2006.01) |
| A61K 31/541 | (2006.01) |
| A61K 31/5377 | (2006.01) |
| A61K 31/4725 | (2006.01) |
| C07C 237/48 | (2006.01) |
| C07D 209/52 | (2006.01) |
| C07D 213/53 | (2006.01) |
| C07D 217/14 | (2006.01) |
| C07D 217/22 | (2006.01) |
| C07D 217/24 | (2006.01) |
| C07D 265/30 | (2006.01) |
| C07D 295/192 | (2006.01) |
| C07D 401/12 | (2006.01) |
| C07D 405/12 | (2006.01) |
| C07D 413/06 | (2006.01) |
| C07D 417/06 | (2006.01) |
| C07D 471/08 | (2006.01) |
| C07D 487/10 | (2006.01) |

(52) U.S. Cl.
CPC .......... *C07D 217/26* (2013.01); *A61K 31/4725* (2013.01); *A61K 31/5377* (2013.01);

(Continued)

(58) Field of Classification Search
USPC .......................................... 546/139; 514/310
See application file for complete search history.

(56) References Cited

U.S. PATENT DOCUMENTS

| 4,426,385 A * | 1/1984 | Cain ............................. 514/594 |
| 6,544,992 B1 * | 4/2003 | Dhanak et al. ............. 514/235.5 |

(Continued)

FOREIGN PATENT DOCUMENTS

| GB | 1545767 | * | 5/1979 |
| JP | 32003568 | * | 7/1957 |

(Continued)

OTHER PUBLICATIONS

Saari; Bioorganic & Medicinal Chemistry 19 (2011) 939-950.*

(Continued)

*Primary Examiner* — John Mabry
*Assistant Examiner* — Daniel Carcanague
(74) *Attorney, Agent, or Firm* — Cantor Colburn LLP

(57) ABSTRACT

Compounds of Formula (I) along with processes for their preparation that are useful for treating, managing and/or lessening the diseases, disorders, syndromes or conditions associated with the modulation of cannabinoid (CB) receptors. Methods of treating, managing and/or lessening the diseases, disorders, syndromes or conditions associated with the modulation of cannabinoid (CB) receptors of Formula (I).

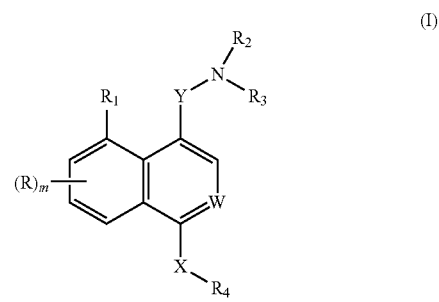

22 Claims, No Drawings

(52) U.S. Cl.
CPC ............ *A61K31/541* (2013.01); *C07C 237/48* (2013.01); *C07D 209/52* (2013.01); *C07D 213/40* (2013.01); *C07D 213/53* (2013.01); *C07D 217/14* (2013.01); *C07D 217/22* (2013.01); *C07D 217/24* (2013.01); *C07D 265/30* (2013.01); *C07D 295/192* (2013.01); *C07D 309/04* (2013.01); *C07D 401/06* (2013.01); *C07D 401/12* (2013.01); *C07D 405/12* (2013.01); *C07D 413/06* (2013.01); *C07D 417/06* (2013.01); *C07D 471/08* (2013.01); *C07D 487/10* (2013.01); *C07D 491/08* (2013.01); *C07D 491/107* (2013.01); *C07D 498/08* (2013.01); *C07D 295/16* (2013.01)

(56) References Cited

U.S. PATENT DOCUMENTS

| | | | |
|---|---|---|---|
| 7,119,122 B2* | 10/2006 | Connolly et al. | 514/655 |
| 7,812,040 B2* | 10/2010 | Wager | 514/364 |
| 8,124,610 B2* | 2/2012 | Fulp et al. | 514/275 |
| 2010/0004438 A1* | 1/2010 | Matsuyama et al. | 540/575 |

FOREIGN PATENT DOCUMENTS

| | | | |
|---|---|---|---|
| JP | 06059512 | * | 3/1994 |
| WO | 02/42248 A2 | | 5/2002 |
| WO | WO 2006/038594 | * | 4/2006 |
| WO | 2006/129178 A1 | | 12/2006 |
| WO | 2007/091950 A1 | | 8/2007 |
| WO | 2007/102059 A1 | | 9/2007 |
| WO | 2008/027812 A2 | | 3/2008 |
| WO | WO2008/121570 | * | 3/2008 |
| WO | WO2008039023 | * | 4/2008 |
| WO | 2008/115672 A1 | | 9/2008 |
| WO | 2009/053799 A1 | | 4/2009 |
| WO | WO2008142454 | * | 11/2009 |
| WO | 2010/084767 A1 | | 7/2010 |
| WO | 2010/096371 A1 | | 8/2010 |
| WO | 2010/133973 A1 | | 11/2010 |

OTHER PUBLICATIONS

Wermuth; Practice of Medicinal Chemistry, 2008, Third Edition, Elsevier; chapter 6, pp. 125-143; chapter 14, pp. 275-289; chapter 15, pp. 290-342 and chapter 20, pp. 431-463.*
Dorwald; Side Reactions in Organic Synthesis, 2005, Wiley; chapter 1, pp. 1-16.*
Silverman; The Organic Chemistry of Drug Design and Drug Action, 2nd Ed, 2004, Elsevier, pp. 29 to 34.*
Perrot; Chim. and Ind., 1959, 81, 690-694.*
Ji Zhang et al., "Induction of CB2 receptor expression in the rat spinal cord of neuropathic but not inflammatory chronic pain models", European Journal of Neuroscience, 2003, vol. 17, pp. 2750-2754.
Uma Anand et al. "Cannabinoid receptors CB2 localisation and agonist-mediated inhibition of capsaicin responses in human sensory neurons", Pain, 2008, vol. 138, pp. 667-680.
M. Beltramo et al. "CB2 receptor-mediated antihyperalgesia: possible direct involvement of neural mechanisms", European Journal of Neuroscience, 2006, vol. 23, pp. 1530-1538.
Cristina Benito et al. "Cannabinoid CB2 Receptors and Fatty Acid Amide Hydrolase Are Selectively Overexpressed in Neuritic Plaque-Associated Glia in Alzheimer's Disease Brains", The Journal of Neuroscience, 2003, vol. 23, No. 35, pp. 11136-11141.
GA Cabral et al. "CB2 receptors in the brain: role in central immune function", British Journal of Pharmacology (2008), vol. 153, pp. 240-251.
G.A. Cabral et al. "Effects on the Immune System", Handbook of Experimental Pharmacology, 2005, vol. 168, pp. 385-423.
S.J. Carlisle et al. "Differential expression of the CB2 cannabinoid receptor by rodent macrophages and macrophage-like cells in relation to cell activation", International Immunopharmacology 2, 2002, pp. 69-82.
BN Dittel, "Direct suppression of autoreactive lymphocytes in the central nervous system via the CB2 receptor", British Journal of Pharmacology, 2008, vol. 153, pp. 271-276.
Marnie Duncan et al. "Cannabinoid CB2 receptors in the enteric nervous system modulate gastrointestinal contractility in lipoploysaccharide-treated rats", American Journal of Physiology: Gastrointestinal and Liver Physiology, 2008, vol. 295, pp. G78-G87.
Andis Klegeris et al. "Reduction of human monocytic cell neurotoxicity and cytokine secretion by ligands of the cannabinoid-type CB2 receptor", British Journal of Pharmacology, 2003, vol. 139, pp. 775-786.
Katarzyna Maresz et al. "Direct Suppression of CNS autoimmune inflammation via the cannibinoid receptor of CB1 on neurons and CB2 on autoreactive T cells", Nature Medicine, 2007, vol. 13, No. 4, pp. 492-497.
Francisco Molina-Holgado et al., "CB2 cannabinoid receptors promote mouse neural stem cell proliferation", European Journal of Neuroscience, 2007, vol. 25, pp. 629-634.
Sean Munro et al. "Molecular Characterization of a peripheral receptor for cannabinoids", Nature, Sep. 2, 1993, vol. 365, pp. 61-62.
Orr Ofek et al. "Peripheral cannabinoid receptor, CB2, regulates bone mass", PNAS, 2006, vol. 103, No. 3, pp. 696-701.
Javier Palazuelos et al. Non-psychoactive CB2 cannabinoid agonists stimulate neural progenitor proliferation, The FASEB Journal, 2006, vol. 20, pp. 2405-2407.
R.G. Pertwee, "Pharmacological Actions of Cannibinoids", Handbook of Experimental Pharmacology, 2005, vol. 168, pp. 1-51.
Maciej Pietr et al. "Differential changes in GPR55 during microglial cell activation", FEBS Letters, 2009, vol. 583, pp. 2071-2076.
Raimo Saari et al. "Microwave-assisted synthesis of quinoline, isoquinoline, quinoxaline and quinazolin derivatives as CB2 receptor agonists", Bioorganic & Medicinal Chemistry, 2011, vol. 19, pp. 939-950.
Nephi Stella "Cannabinoid Signaling in Glial Cells", Glia, 2004, vol. 48, pp. 267-277.
Ivana Svizenska et al., "Cannabinoid receptors 1 and 2 (CB1 and CB2), their distribution, ligands and functional involvement in nervous system structures—a short review", Pharmacology, Biochemistry and Behavior, vol. 90 (2008), pp. 501-511.
Lisa Walter et al. "Nonpsychotropic Cannabinoid Receptors Regulate Microglial Cell Migration", The Journal of Neuroscience, 2003, Vo. 23(4), pp. 1398-1405.
Yiangos Yiangou et al. "COX-2, CB2 and P2X7-immunoreactivities are increased in activated microglial cells/macrophages of multiple sclerosis and amyotrophic lateral sclerosis spinal cord", BMC Neurology, 2006, vol. 6:12, pp. 1-14.

* cited by examiner

CANNABINOID RECEPTOR MODULATORS

RELATED APPLICATIONS

This application claims the benefit of PCT patent application no. PCT/IB2011/056007 filed on Dec. 29, 2011 which is hereby incorporated by reference in their entirety.

FIELD OF THE INVENTION

The present invention relates to compounds, pharmaceutically acceptable salts thereof and pharmaceutical compositions for the treatment, management, and/or lessening the severity of diseases, disorders, syndromes or conditions associated with the modulation of cannabinoid (CB) receptors. The invention also relates to methods of treating, managing and/or lessening the severity of the diseases disorders, syndromes or conditions associated with the modulation of cannabinoid (CB) receptors. The invention also relates to processes for the preparation of the compounds of the invention.

BACKGROUND OF THE INVENTION

A G-protein coupled receptor (CX5) expressed in human promyelocytic leukemic cell line (HL60) was discovered in 1993. This was later identified as type II Cannabinoid receptor (Munro et al. *Nature* (1993), 365, 61-65). $CB_2$ receptors are found to be expressed predominantly in immune cells. When activated they modulate immune cell migration and cytokine release outside and within the brain (Pertwee et al. *Handb. Exp. Pharmacol.* (2005), 168, 1-51). $CB_2$ activation affects a host of immune responses from inflammation to neuroprotection (Cabral at al. *Handb. Exp. Pharmacol.* (2005), 168, 385-423). The activation of $CB_2$ receptors is reported to have analgesic effect in many animal models of pain from acute pain to neuropathic pain (Anand et al. *Pain.* (2009), 138, 667-680).

Since $CB_2$ is an attractive therapeutic target for pain management and immune system modulation without overt psycho activity and substance abuse possibility, its presumed absence in the CNS was reviewed by many researchers. The findings of these recent investigations support the presence of $CB_2$ receptors in CNS. The $CB_2$ mRNA and protein have been found in microglia (Beltramo et al. *Eur. J. Neurosci.* (2006), 23, 1530-1538; Carlisle et al. *Int. Immunopharmacol.* (2002), 2, 69-82; Klegeris at al. *Br. J. Pharmacol.* (2003), 139, 775-786; Maresz et al., *Nat. Med.* (2007), 13, 492-497; Walter et al. *J. Neurosci.* (2003), 23, 1398-1405). The expression levels of $CB_2$ are proportional to the activation extent of microglia (Cabral et al., *Br. J. Pharmacol.* (2008), 153, 240-251; Pietr et al. *FEBS Lett.* (2009), 583, 2071-2076; Stella et al. *Glia.* (2004), 48, 267-277). Microglial migration and their infiltration into brain areas with active neuroinflammation and degeneration is modulated by $CB_2$. In healthy brain microglia does not express $CB_2$ but they do in Alzheimer's brain tissue in the neuritic-plaque associated microglia (Benito et al. *J Neurosci.* (2003), 23, 11136-11141). In the neuropathic pain models $CB_2$ mRNA is found to increase in association with activated microglia in the spinal cord (Zhang at al. *Eur. J. Neurosci.* (2003), 17, 2750-2754). Similarly in amyotrophic lateral sclerosis and multiple sclerosis, $CB_2$ microglial expression increases in spinal cord (Yiangou et al. *BMC. Neurol.* (2006), 6, 12).

As reported earlier highest $CB_2$ receptor distribution is also known in macrophages, CD4 T cells, CD8 T cells, B cells, natural killer cells, monocytes, and polymorphonuclear neutrophils (Dittel B N. et al. *BJP.* (2008), 153, (2), 271-276; Maresz K. et al. *Nature Medicine.* (2007), 13, 492-497). Similarly $CB_2$ receptor presence is also known in other brain areas like thalamus, straitum, hippocampus. Peripheral neurons, nociceptive neurons and sensory neurons also are known to express $CB_2$ receptors.

Apart from the relevance of $CB_2$ in the area of pain management, this receptor is also known to be involved in other functions. For example $CB_2$ receptor is expressed in the bone cells and is reported to have anabolic effect on bones (Ofek et al. *PNAS.* (2006), 103, 696-701). Presence of $CB_2$ is also reported in the enteric nervous system, (Duncan M Mouihate et al, *Am. J. Physiol. Gastrointest. Liver Physiol.* 295, G78-G87). Similar anabolic effect is also reported through CB2 receptor mediation in neurogenesis (Molina-Holgado et al. *Eur. J. Neurosci.* (2007), 25, 629-634 & Palazuelos J. et al. *FASEB J.* (2006), 20, 2405-2407).

Role of CB1 in pain management is also well known. This receptor is known to exist majorly in the central nervous system. To a minor extent, CB1 is also reported to exist in the periphery (Pharmacology, Biochemistry and Behavior 90 (2008) 501-511). Therefore, along with compounds that are CB2 selective modulators, dual modulators working through CB1 and CB2 are also targeted.

WO 2002/042248, WO 2010/096371, WO 2010/133973, WO 2006/129178, WO 2010/084767, WO 2009/053799, WO 2008/115672, WO 2008/027812, WO 2007/102059, WO 2007/091950 and WO 2002/42248 applications disclose compounds related to cannabinoid receptors for the treatment of various diseases mediated by cannabinoid receptors. Also, *Bioorganic Medicinal Chemistry*, (2011), 19, 939-950, discloses the compounds related to cannabinoid receptors.

SUMMARY OF THE INVENTION

In accordance with one aspect, the invention provides compounds having the structure of Formula (I):

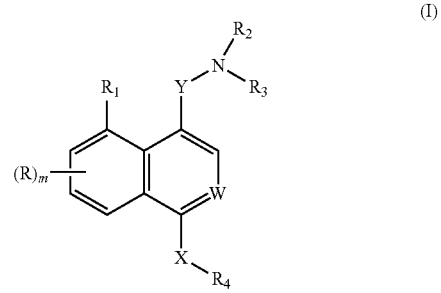

wherein,

W is —N— or —CH—;

X is selected from —$NR_a$, —O— and —$S(O)_n$—;

Y is selected from —C(O)—, —$S(O)_2$—, and —$CR_5R_6$—;

R, which may be same or different at each occurrence, is independently selected from halogen, cyano, nitro, hydroxy, alkyl, haloalkyl, hydroxyalkyl, cycloalkyl, alkoxy, cycloalkoxy, —C(O)OH, —$NR_aR_b$ and —$C(O)NR_aR_b$;

$R_1$ is selected from hydrogen, alkyl, halogen, cycloalkyl, hydroxy, cyano, amino, nitro, alkoxy, haloalkyl, haloalkoxy and cycloalkoxy;

with the proviso that when W is —N— then $R_1$ is not hydrogen;

$R_2$ is selected from hydrogen, alkyl, cycloalkyl, cycloalkylalkyl, aryl, arylalkyl, heteroaryl, heteroarylalkyl, heterocyclyl, and heterocyclylalkyl;

R₃ is selected from alkyl, cycloalkyl, cycloalkylalkyl, aryl, arylalkyl, heteroaryl, heteroarylalkyl, heterocyclyl, and heterocyclylalkyl; or R₂ and R₃, together with the nitrogen atom to which they are attached, may form a substituted or an unsubstituted 3 to 14 membered heterocyclic ring;

R₂ and R₃, together with the nitrogen atom to which they are attached, may form a substituted or an unsubstituted 5 to 14 membered heteroaryl ring;

R₄ is selected from aryl, cycloalkyl, heteroaryl and heterocyclyl;

R₅ and R₆, which may be same or different, are independently selected from hydrogen, alkyl and haloalkyl;

R$_a$ and R$_b$, which may be same or different at each occurrence, are independently selected from hydrogen, alkyl, haloalkyl, acyl, cycloalkyl, aryl, heteroaryl and heterocyclyl; or R$_a$ and R$_b$, together with the nitrogen atom to which they are attached, may form a substituted or unsubstituted 3 to 14 membered heteroaryl or heterocyclic ring;

'm' is an integer ranging from 0 to 3, both inclusive;

'n' is an integer ranging from 0 to 2, both inclusive; and wherein alkyl, alkoxy, acyl, cycloalkyl, cycloalkoxy, aryl, heteroaryl, heterocyclyl, heterocyclic ring, cycloalkylalkyl, arylalkyl, heteroarylalkyl, heterocyclylalkyl, haloalkyl, hydroxyalkyl, haloalkoxy, wherever they occur may optionally be substituted with one or more, same or different substituents, and wherein the substituents are independently selected from hydroxy, halo, cyano, nitro, oxo (=O), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, alkyl-C(O)OR$^x$, —C(O)OR$^x$, —C(O)R$^x$, —C(S)R$^x$, —C(O)NR$_a$R$_b$, —NR$^x$C(O) NR$_a$R$_b$, —N(R$^x$)S(O)R$^y$, —N(R$^x$)S(O)$_2$R$^y$, —NR$_a$R$_b$, —NR$^y$C(O)R$^y$, —NR$^x$C(S)R$^y$, —NR$^x$C(S)NR$_a$R$_b$, —S(O)$_2$ NR$_a$R$_b$, —OR$^x$, —OC(O)R$^x$, —OC(O)NR$_a$R$_b$, —R$^x$C(O) OR$^y$, —R$^x$C(O)NR$_a$R$_b$, —R$^x$C(O)R$^y$, —SR$^x$, and —S(O)$_2$ R$^x$; wherein at each occurrence, R$^x$, R$^y$ and R$^z$ are independently selected from hydrogen, alkyl, haloalkyl, alkenyl, alkynyl, aryl, arylalkyl, cycloalkyl, cycloalkenyl, heteroaryl, heterocyclyl, heterocyclylalkyl and heteroarylalkyl;

or its pharmaceutically acceptable salt thereof.

According to one embodiment, there is provided a compound of the formula (II):

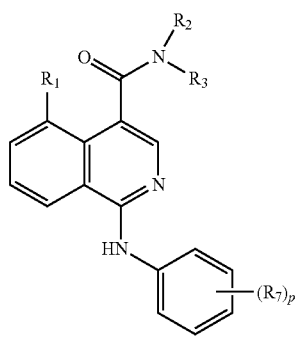

(II)

wherein,

R₁ is halogen, alkyl or cycloalkyl;

R₇, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;

R₂ is selected from hydrogen, alkyl, cycloalkyl, cycloalkylalkyl, aryl, arylalkyl, heteroaryl, heteroarylalkyl, heterocyclyl, and heterocyclylalkyl;

R₃ is selected from alkyl, cycloalkyl, cycloalkylalkyl, aryl, arylalkyl, heteroaryl, heteroarylalkyl, heterocyclyl, and heterocyclylalkyl;

R$_a$ and R$_b$ are as defined herein above;

R$_c$ is alkyl; and

'p' is an integer ranging from 0 to 4, both inclusive;

or its pharmaceutically acceptable salt thereof.

According to one embodiment, there is provided a compound of the formula (III):

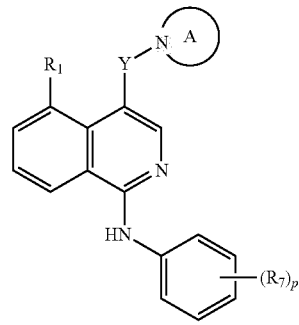

(III)

wherein, ring A is a substituted or unsubstituted 3 to 14 membered heterocyclic ring wherein substituents on ring A may be on same or different ring atom;

Y is —C(O)— or —CH₂—;

R₁ is halogen, alkyl or cycloalkyl;

R₇, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;

R$_a$ and R$_b$ are as defined herein above;

R$_c$ is alkyl; and

'p' is an integer ranging from 0 to 4, both inclusive;

or its pharmaceutically acceptable salt thereof.

According to another embodiment, there is provided a compound of the formula (IV):

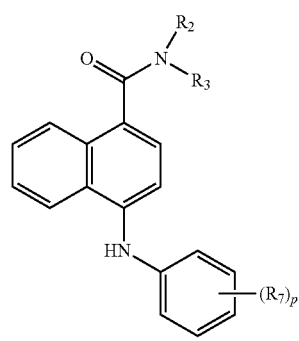

(IV)

wherein,

R₇, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;

R₂ is selected from hydrogen, alkyl, cycloalkyl, cycloalkylalkyl, aryl, arylalkyl, heteroaryl, heteroarylalkyl, heterocyclyl, and heterocyclylalkyl;

$R_3$ is selected from alkyl, cycloalkyl, cycloalkylalkyl, aryl, arylalkyl, heteroaryl, heteroarylalkyl, heterocyclyl, and heterocyclylalkyl; or $R_2$ and $R_3$, together with the nitrogen atom to which they are attached, may form a substituted or unsubstituted 3 to 14 membered heterocyclic ring;

$R_a$ and $R_b$ are as defined herein above;

$R_c$ is alkyl; and

'p' is an integer ranging from 0 to 4, both inclusive;

or its pharmaceutically acceptable salt thereof.

According to another embodiment, there is provided a compound of the formula (V):

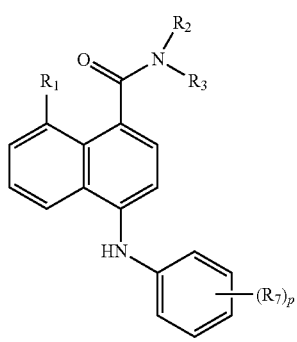

(V)

wherein, $R_1$ is halogen, alkyl or cycloalkyl;

$R_7$, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;

$R_2$ is selected from hydrogen, alkyl, cycloalkyl, cycloalkylalkyl, aryl, arylalkyl, heteroaryl, heteroarylalkyl, heterocyclyl, and heterocyclylalkyl;

$R_3$ is selected from alkyl, cycloalkyl, cycloalkylalkyl, aryl, arylalkyl, heteroaryl, heteroarylalkyl, heterocyclyl, and heterocyclylalkyl; or $R_2$ and $R_3$, together with the nitrogen atom to which they are attached, may form a substituted or unsubstituted 3 to 14 membered heterocyclic ring;

$R_a$ and $R_b$ are as defined herein above;

$R_c$ is alkyl; and

'p' is an integer ranging from 0 to 4, both inclusive;

or its pharmaceutically acceptable salt thereof.

According to another embodiment, there is provided a compound of the formula (VI):

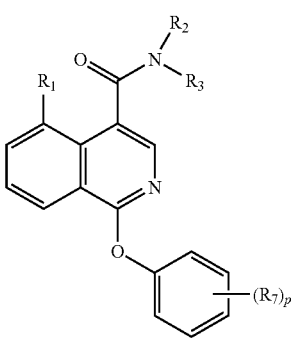

(VI)

wherein, $R_1$ is halogen, alkyl or cycloalkyl;

$R_7$, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;

$R_2$ is selected from hydrogen, alkyl, cycloalkyl, cycloalkylalkyl, aryl, arylalkyl, heteroaryl, heteroarylalkyl, heterocyclyl, and heterocyclylalkyl;

$R_3$ is selected from alkyl, cycloalkyl, cycloalkylalkyl, aryl, arylalkyl, heteroaryl, heteroarylalkyl, heterocyclyl, and heterocyclylalkyl; or $R_2$ and $R_3$, together with the nitrogen atom to which they are attached, may form a substituted or unsubstituted 3 to 14 membered heterocyclic ring;

$R_a$ and $R_b$ are as defined herein above;

$R_c$ is alkyl; and

'p' is an integer ranging from 0 to 4, both inclusive;

or its pharmaceutically acceptable salt thereof.

According to another embodiment, there is provided a compound of the formula (VII):

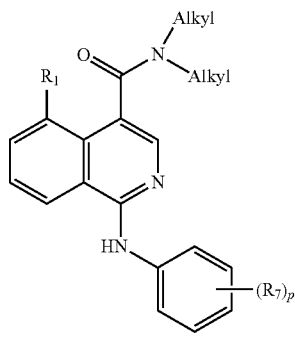

(VII)

wherein, $R_1$ is halogen or alkyl;

$R_7$, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;

$R_a$ and $R_b$ are as defined herein above;

$R_c$ is alkyl; and

'p' is an integer ranging from 0 to 4, both inclusive;

or its pharmaceutically acceptable salt thereof.

It should be understood that formulae (I), (II), (III) (IV), (V), (VI) or (VII) structurally encompasses all N-oxides, tautomers, stereoisomers including isotopes wherever applicable and pharmaceutically acceptable salts that may be contemplated from the chemical structure of the genera described herein.

According to one sub embodiment, there are provided compounds of formulae (II), (III), (V), (VI) and/or (VII) in which $R_1$ is halogen, substituted or unsubstituted alkyl (for example methyl or ethyl) or cycloalkyl for example cyclopropyl.

According to another sub embodiment, there are provided compounds of formulae (II), (III), (IV), (V), (VI) and/or (VII) in which $R_7$ is selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$; and 'p' is 0, 1, 2 or 3; R$_a$ and R$_b$ are as defined herein above; R$_c$ is alkyl.

According to another sub embodiment, there are provided compounds of formulae (II), (IV), (V) and/or (VI) in which one of R$_2$ and R$_3$ is hydrogen and the other is selected from alkyl, arylalkyl, heteroarylalkyl, heterocyclyl and heterocyclylalkyl.

According to another sub embodiment, there are provided compounds of formulae (IV), (V) and/or (VI) in which R$_2$ and R$_3$ together with nitrogen atom to which they are attached, may form a substituted or unsubstituted 3 to 12 membered heterocyclic ring wherein the heterocyclic ring is monocyclic (for example azetidine, pyrrolidine, piperidine, piperazine, morpholine, dioxidothiomorpholine or tetrahydropyran) fused or bridged bicyclic (for example 6-oxa-3-azabicyclo (3.1.1)heptane, 2-oxa-5-azabicyclo[2.2.1]heptane, 3-azabicyclo[3.1.0]hexane or 3-oxa-9-azabicyclo[3.3.1]nonane or spirocyclic for example 2-oxa-6-azaspiro[3.3]heptane, 2-oxa-6-azaspiro[3.5]nonane, 2-oxa-7-azaspiro[3.5]nonane.

According to another sub embodiment, there are provided compounds of formulae (III) in which ring A is substituted or unsubstituted 3 to 12 membered heterocyclic ring wherein the heterocyclic ring is monocyclic (for example azetidine, pyrrolidine, piperidine, piperazine or morpholine, tetrahydropyran) fused or bridged bicyclic (for example 6-oxa-3-azabicyclo[3.1.1]heptane, 2-oxa-5-azabicyclo[2.2.1]heptane, 3-azabicyclo[3.1.0]hexane or 3-oxa-9-azabicyclo[3.3.1] nonane or spirocyclic for example 2-oxa-6-azaspiro[3.3.1] heptane, 2-oxa-6-azaspiro[3.5]nonane, 2-oxa-7-azaspiro [3.5]nonane.

According to another sub embodiment provided are compounds of formulae (II), (V) and/or (VI) in which R$_1$ is halogen, substituted or unsubstituted alkyl (for example methyl or ethyl) or cycloalkyl for example cyclopropyl; R$_7$ is halogen, hydroxy, alkyl or alkoxy; 'p' is 0, 1, 2 or 3; and one of R$_2$ and R$_3$ is hydrogen and the other is selected from alkyl, arylalkyl, heteroarylalkyl, heterocyclyl and heterocyclylalkyl.

According to another sub embodiment provided are compounds of formulae (V) and/or (VI) in which R$_1$ is alkyl, substituted or unsubstituted alkyl (for example methyl or ethyl) or cycloalkyl for example cyclopropyl; R$_7$ is halogen, hydroxy, alkyl or alkoxy; 'p' is 0, 1, 2 or 3; and R$_2$ and R$_3$ together with nitrogen atom to which they are attached, may form a substituted or unsubstituted 3 to 12 membered heterocyclic ring wherein the heterocyclic ring may be mono or bicyclic, fused, bridged or spirocyclic ring.

According to another sub embodiment provided are compounds of formula (III) in which Y is —C(O)— or —CH$_2$—; R$_1$ is halogen, substituted or unsubstituted alkyl (for example methyl or ethyl) or cycloalkyl for example cyclopropyl; R$_7$ is halogen, hydroxy, alkyl or alkoxy; 'p' is 0, 1, 2 or 3; ring A is monocyclic (for example azetidine, pyrrolidine, piperidine, piperazine or morpholine, tetrahydropyran) fused or bridged bicyclic (for example 6-oxa-3-azabicyclo[3.1.1]heptane, 2-oxa-5-azabicyclo[2.2.1]heptane, 3-azabicyclo[3.1.0]hexane or 3-oxa-9-azabicyclo[3.3.1]nonane or spirocyclic for example 2-oxa-6-azaspiro[3.3]heptane, 2-oxa-6-azaspiro [3.5]nonane, 2-oxa-7-azaspiro[3.5]nonane.

According to another sub embodiment provided are compounds of formula (IV) in which R$_7$ is halogen, hydroxy, alkyl or alkoxy; is 0, 1, 2 or 3; and one of R$_2$ and R$_3$ is hydrogen and the other is selected from alkyl, arylalkyl, heteroarylalkyl, heterocyclyl and heterocyclylalkyl; or R$_2$ and R$_3$ together with nitrogen atom to which they are attached, may form a substituted or unsubstituted 3 to 12 membered heterocyclic ring wherein the heterocyclic ring may be monocyclic (for example azetidine, pyrrolidine, piperidine, piperazine or morpholine, dioxidothiomorpholine, tetrahydropyran) fused or bridged bicyclic (for example 6-oxa-3-azabicyclo[3.1.1] heptane, 2-oxa-5-azabicyclo[2.2.1]heptane, 3-azabicyclo [3.1.0]hexane or 3-oxa-9-azabicyclo[3.3.1]nonane or spirocyclic for example 2-oxa-6-azaspiro[3.3]heptane, 2-oxa-6-azaspiro[3.5]nonane, 2-oxa-7-azaspiro[3.5]nonane.

In another aspect of the invention, there is provided a compound of formula (I) useful in treating, preventing, managing and/or lessening the severity of diseases, disorders, syndromes or conditions associated with cannabinoid (CB) modulators.

In another aspect, the invention provides a pharmaceutical composition that includes at least one compound of formula (I) and at least one pharmaceutically acceptable excipient.

In another aspect, the invention provides a pharmaceutical composition of compound of formula (I) useful in treating, preventing, managing and/or lessening the severity of the diseases, disorders, syndromes or conditions associated with cannabinoid (CB) modulators in a subject, in need thereof by administering to the subject, one or more compounds described herein in a therapeutically effective amount to cause modulation of such receptor.

In another aspect of the invention are processes for the preparation of the compounds described herein.

In another aspect, there are provided a process for the preparation compounds of Formula (12):

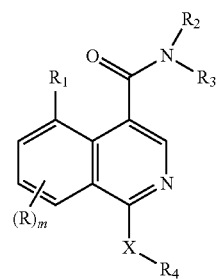

(12)

comprising:
a) reacting a compound of formula (18) with amine compound of formula R$_2$—NH—R$_3$ in presence of EDCI and HOBt to give compound of formula (19)

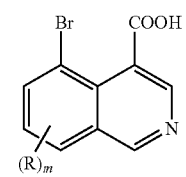

(18)

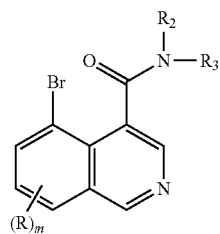

(19)

b) alkylating a compound of formula (19) in presence of palladium using R$_1$B(OH)$_2$ where R$_1$ is alkyl or cycloalkyl, to give compound of formula (20)

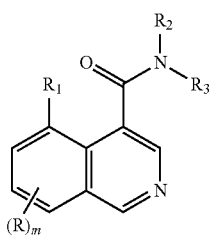

(20)

c) oxidizing a compound of formula (20) using mCPBA to obtain a N-oxide compound of formula (21)

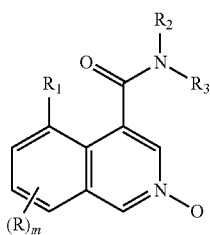

(21)

d) halogenating a compound of formula (21) in presence of POCl$_3$ to give halo compound of formula (22)

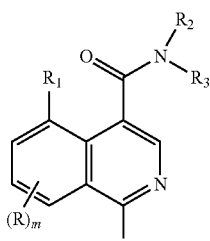

(22)

e) coupling of a compound of formula (22) with R$_4$—XH in presence of palladium and ligand to give compound of formula (12).

The details of one or more embodiments of the invention set forth in the below are illustrative in nature only and not intended to limit to the scope of the invention. Other features, objects and advantages of the inventions will be apparent from the description and claims.

DETAILED DESCRIPTION OF THE INVENTION

Definitions and Abbreviations

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the present invention.

The term "acyl" refers to a group or radical derived from carboxylic acid for example alkylcarbonyl (for example CH$_3$C(O)—) or arylcarbonyl. Unless set forth or recited to the contrary, all acyl groups described or claimed herein may be substituted or unsubstituted.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl(t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl(allyl), iso-propenyl, 2-methyl-I-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting examples of such groups are methoxy, ethoxy and propoxy and the like. Unless set forth or recited to the contrary, all alkoxy groups described or claimed herein may be straight chain or branched, substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapththyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkoxy" refers to an cycloalkyl, defined herein, group attached via an oxygen linkage. Non-limiting examples of such groups are cyclopropoxy, cyclobutoxy, cyclopentoxy, cyclohexyloxy and the like. Unless set forth or recited to the contrary, all alkoxy groups described or claimed herein may be straight chain or branched, substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms.

The term "haloalkoxy" refers to a haloalkyl, defined herein, group attached via an oxygen linkage. Non-limiting examples of such groups are monohaloalkoxy, dihaloalkoxy or polyhaloalkoxy including perhaloalkoxy. Unless set forth or recited to the contrary, all haloalkoxy groups described or claimed herein may be straight chain or branched, substituted or unsubstituted.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting examples of a hydroxyalkyl include 2-hydroxyethyl, 3-hydroxypropyl, 2-hydroxypropyl, and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —CH$_2$C$_6$H$_5$ and —C$_2$H$_4$C$_6$H$_5$. Unless set forth or recited to the contrary, all arylalkyl groups described or claimed herein may be substituted or unsubstituted.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —CF$_2$—, —C(O)—, —S(O)—, S(O)$_2$, —C(=N-alkyl)-, or —C(=N-cycloalkyl), etc. In addition heterocyclic ring may also be fused with aromatic ring. Non-limiting examples of heterocyclic rings include azepinyl, azetidinyl, benzodioxolyl, benzodioxanyl, benzopyranyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinyl sulfoxide, thiamorpholinyl sulfone indoline, tetrahydroquinoline, tetrahydrobenzopyran and the like. The heterocyclic ring may be attached to the main structure at any heteroatom or carbon atom that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached to the main structure at any heteroatom or carbon atom that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halo, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, amino, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$C(O) R$^y$, —NR$^x$C(S)R$^y$, —NR$^x$C(S)NR$^y$R$^z$, —S(O)$_2$NR$^x$R$^y$, —OR$^x$, —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, and —S(O)$_2$R$^x$; wherein each occurrence of R$^x$, R$^y$ and R$^z$ are independently selected from hydrogen, alkyl, haloalkyl, alkenyl, alkynyl, aryl, arylalkyl, cycloalkyl, cycloalkenyl, heteroaryl, heterocyclic ring, heterocyclylalkyl ring and heteroarylalkyl.

The phrase "may optionally be substituted" refers to a moiety or group that may or may not be substituted. For example, "optionally substituted aryl" means that the aryl radical may or may not be substituted and that the description includes both substituted and unsubstituted aryl radicals.

A "stereoisomer" refers to a compound having the same atoms bonded through the same bonds but having different three-dimensional orientations, which are not interchangeable. The invention contemplates various stereoisomers and mixtures thereof and includes enantiomers and diastereomers. The invention also includes geometric isomers "E" or "Z" or cis or trans configuration in a compound having either a double bond or having substituted cycloalkyl ring system.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of formula (I).

The term "treating" or "treatment" of a state, disease, disorder, condition or syndrome includes: (a) preventing or delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof; c) lessening the severity of a disease, disorder, syndrome or condition or at least one of its clinical or subclinical symptoms thereof; and/ or (d) relieving the disease, i.e., causing regression of the state, disorder or condition or at least one of its clinical or subclinical symptoms.

The term "modulate" or "modulating" or "modulation" or "modulator" refers to an increase or decrease in the amount, quality, or effect of a particular activity, function or molecule. By way of illustration and not limitation, it includes agonists, partial agonists, inverse agonists and antagonists of a cannabinoid (CB) receptor of the present invention.

The term "subject" includes mammals, preferably humans and other animals, such as domestic animals; e.g., household pets including cats and dogs.

A "therapeutically effective amount" refers to the amount of a compound that, when administered to a subject in need thereof, is sufficient to cause a desired effect. The "therapeutically effective amount" will vary depending on the compound, the disease and its severity, age, weight, physical condition and responsiveness of the subject to be treated.

Pharmaceutically Acceptable Salts:

The compounds of the invention may form salts. In cases where compounds are sufficiently basic or acidic to form stable nontoxic acid or base salts, administration of the compound as a pharmaceutically acceptable salt may be appropriate. Non-limiting examples of pharmaceutically acceptable salts are organic acid addition salts formed by addition of acids, which form a physiological acceptable anion, for example, tosylate, methanesulfonate, acetate, citrate, malonate, tartarate, succinate, benzoate, ascorbate, α-ketoglutarate, α-glycerophosphate, formate, fumarate, propionate, glycolate, lactate, pyruvate, oxalate, maleate, and salicylate. Suitable inorganic salts may also be formed, including, sulfate, nitrate, bicarbonate, carbonate salts, hydrobromate and phosphoric acid.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

With respect to the overall compounds described by the Formula (I) the invention extends to stereoisomeric forms and to mixtures thereof. The different stereoisomeric forms of the invention may be separated from one another by the method known in the art, or a given isomer may be obtained by stereospecific or asymmetric synthesis. Tautomeric forms and mixtures of compounds described herein are also contemplated.

Screening of compounds of invention for cannabinoid receptor modulation activity can be achieved by using various in vitro and in vivo protocols mentioned herein below or methods known in the art.

Pharmaceutical Compositions

The invention relates to pharmaceutical composition containing the compounds of the Formula (I) disclosed herein. In particular, pharmaceutical compositions containing a therapeutically effective amount of at least one compound of formula (I) described herein and at least one pharmaceutically acceptable excipient (such as a carrier or diluent). Preferably, the contemplated pharmaceutical compositions include the compound(s) described herein in an amount sufficient to modulate cannabinoid receptor mediated diseases described herein when administered to a subject.

The subjects contemplated include, for example, a living cell and a mammal, including human mammal. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes a pharmaceutical agent that does not itself induce the production of antibodies harmful to the individual receiving the composition, and which may be administered without undue toxicity.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions formulation.

Liquid formulations include, but are not limited to, syrups, emulsions, suspensions, solutions, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg according to the potency of the active component or mode of administration.

Suitable doses of the compounds for use in treating the diseases and disorders described herein can be determined by those skilled in the relevant art. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the CB modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Methods of Treatment

In an embodiment, the invention provides compounds and pharmaceutical compositions thereof that are useful in treating, preventing, managing and/or lessening the severity of diseases, disorders, syndromes or conditions modulated by cannabinoid receptor. The invention further provides method of treating diseases, disorders or conditions modulated by cannabinoid receptor in a subject in need thereof by administering to the subject a therapeutically effective amount of a compound or a pharmaceutical composition of the invention.

In another aspect of the invention, the methods provided are also useful for diagnosis of conditions that can be treated by acting on cannabinoid receptor for determining if a patient will be responsible to therapeutic agents.

In still another aspect, the invention provides a method for the treatment of diseases, disorders or conditions through modulating cannabinoid receptor. In this method, a subject in need of such treatment is administered a therapeutically effective amount of a compound of formula (I) described herein.

The compound of formula (I), being modulators of cannabinoid receptor, is potentially useful in treating, preventing, managing and/or lessening the severity of diseases, disorders, syndromes or conditions include but are not limited to pain, inflammation, analgesic conditions, healing of wounds and burns, movement disorders, immune disorders (such as autoimmune disorders), respiratory disorders, lung diseases associated with inflammation, pruritis associated with inflammation, allergic diseases associated with inflammation, organ contraction, preanesthetic medication, pre operative medication, muscle spasm, locomotor activity disorders, bone disorders, multiple sclerosis, glaucoma and related intra ocular pressure, cell growth disorders, gastrointestinal disorders, diseases of central nervous system (CNS) erythromyalgia, neurological disorders, neurodegenerative disorders, neuromuscular conditions, neuroinflammatory pathologies and the like.

Pain includes, but is not limited to, acute pain, chronic pain, musculoskeletal pain, post-operative pain, visceral pain, peripherally mediated pain, centrally mediated pain, inflammatory pain, neuropathic pain, nociceptive pain, and idiopathic pain.

The compounds, compositions and methods of the invention are of particular use in treating, preventing or lessening of pain includes but is not limited to acute pain, chronic pain, visceral pain, neuropathic pain, inflammatory pain or nociceptive pain or pain associated with, such as but are not limited to dental pain, eye pain, ear pain, preoperative, traumatic pain, muscle pain, pain in burned skin, sun burn, trigeminal neuralgia, spasm of the gastrointestinal tract or uterus, colics, back pain, chronic fatigue syndrome, clinical depression, complex regional pain syndrome, myofascial pain syndrome, post-vasectomy pain syndrome, restless leg syndrome, spinal stenosis, chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia, non-herpetic neuralgia, post herpetic neuralgia, diabetic neuropathy, nerve injury, acquired immune deficiency syndrome (AIDS) related pain, herpes virus infection, head trauma, causalgia, plexus avulsion, neuroma, limb amputation, vasculitis, painful traumatic mononeuropathy, phantom limb pain, painful polyneuropathy, thalamic pain syndrome, post-stroke pain, central nervous system injury, stump pain, repetitive motion pain, pain induced by post mastectomy syndrome, multiple sclerosis, root avulsions, postthoracotomy syndrome, hyperalgesia, allodynia, nerve damage from chronic alcoholism, arthritis pain, osteoarthritis, rheumatoid arthritis, rheumatic disease, teno-synovitis, gout, vulvodynia, myofascial pain (muscular injury, fibromyalgia), tendonitis, juvenile arthritis, spondylitis, gouty arthritis, psoriatic arthritis, muscoskeletal pain, fibromyalgia, sprains and strains, sympathetically maintained pain, myositis, pain associated with migraine, dental pain, systemic lupus erythematosus, central and peripheral pathway mediated pain, bone and joint pain, pain associated with cancer including chemotherapy pain, orofacial pain, somatic pain, sciatica pain, intestinal obstruction pain, colicky pain, myofacial pain, trauma pain, labour pain, brachial plexus avulsion, reflex sympathetic dystrophy, fibromyalgia, phantom limb pain, pain following stroke, thalamic lesions, radiculopathy, migraine pain, menstrual cramps, dermatitis, immunodeficiency, HIV-related neuropathy; familial hemiplegic migraine, conditions associated with cephalic pain, headache (e.g., chronic headache, sinus headache, headache associated with stress, headache with different origins), cardiac pain arising from an ischemic myocardium, pain following stroke, neuropathy secondary to metastatic inflammation, pain due to connective tissue damage, and other forms of neuralgic, neuropathic, and idiopathic pain syndromes.

The compounds of the invention may be useful for treating various types of inflammatory disease such as inflammations due to immune system, inflammations due to cancer, atherosclerosis, ischaemic heart diseases, pancreatitis, which includes but is not limited to acute pancreatitis and chronic pancreatitis, which is characterized by recurring or persistent abdominal pain with or without steatorrhea hereditary pancreatitis, pancreatic dysfunction.

Respiratory related syndromes, disorders or diseases include, but are not limited to, diseases of the respiratory tract or lung diseases such as asthma, bronchitis (acute or chronic), emphysema, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis.

The compounds of invention may be useful in the treatment of pruritus and related diseases including, but not limited to psoriatic pruritus, itch due to hemodyalisis, aguagenic pruritis, itching caused by skin disorders, allergic itch, insect bite itch, itch caused by hypersensitivity such as dry skin, acne, eczema, psoriasis or injury, itch caused by vulvar vestibulitis and the similar itch.

Allergic diseases: all forms of allergic reactions include but are not limited to angioneurotic edema, hay fever, insect bites, viral or bacterial diseases, allergic reactions to drugs, blood derivatives, contrast agents, delayed or immediate hypersensitivity, allergic rhinitis, contact dermatitis, conjunctivitis, allergic reactions associated with inflammatory diseases such as diseases of the joints, spondylitis, gout, vasculitis, Crohn's disease, inflammatory bowel disease (IBD), irritable bowel syndrome (IBS) or osteoporosis.

Autoimmune or inflammation related syndromes, disorders or diseases include, but are not limited to, psoriasis, lupus erythematosus, diseases of the connective tissue, Sjogren's syndrome, ankylosing spondylarthritis, rheumatoid arthritis, reactional arthritis, undifferentiated spondylarthritis, Behcet's disease, autoimmune hemolytic anaemias, multiple sclerosis, amyotrophic lateral sclerosis, amyloses, graft rejection or diseases affecting the plasma cell line.

Gastrointestinal diseases including, but not limited to inflammatory bowel diseases, irritable bowel syndrome, regional enteritis (Crohns disease), colitis ulcerosa, gastritis, or aphthous.

General Methods of Preparation

The compounds described herein may be prepared by techniques known in the art. In addition, the compounds described herein may be prepared by following the reaction sequence as depicted in Scheme-1 to Scheme-9. Further, in the following schemes, where specific bases, acids, reagents, solvents, coupling agents, etc. are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art are also within the scope of the present invention. All the isomers of the compounds in described in these schemes, unless otherwise specified, are also encompassed within the scope of this invention.

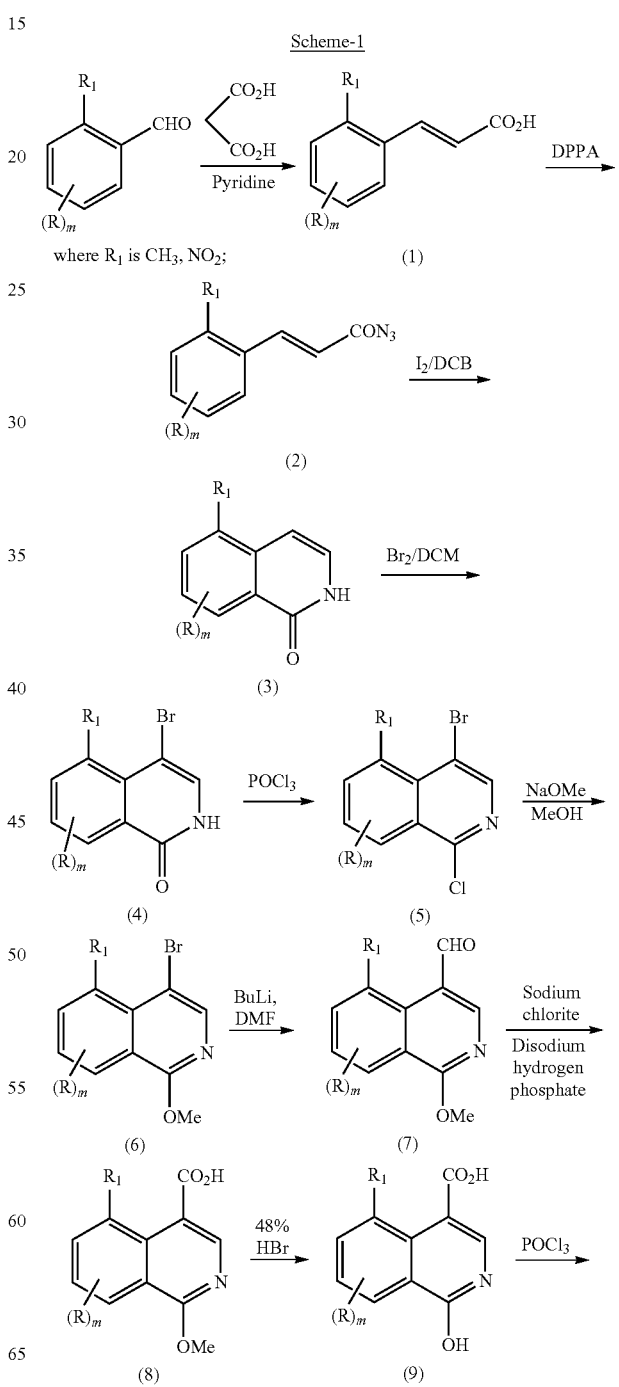

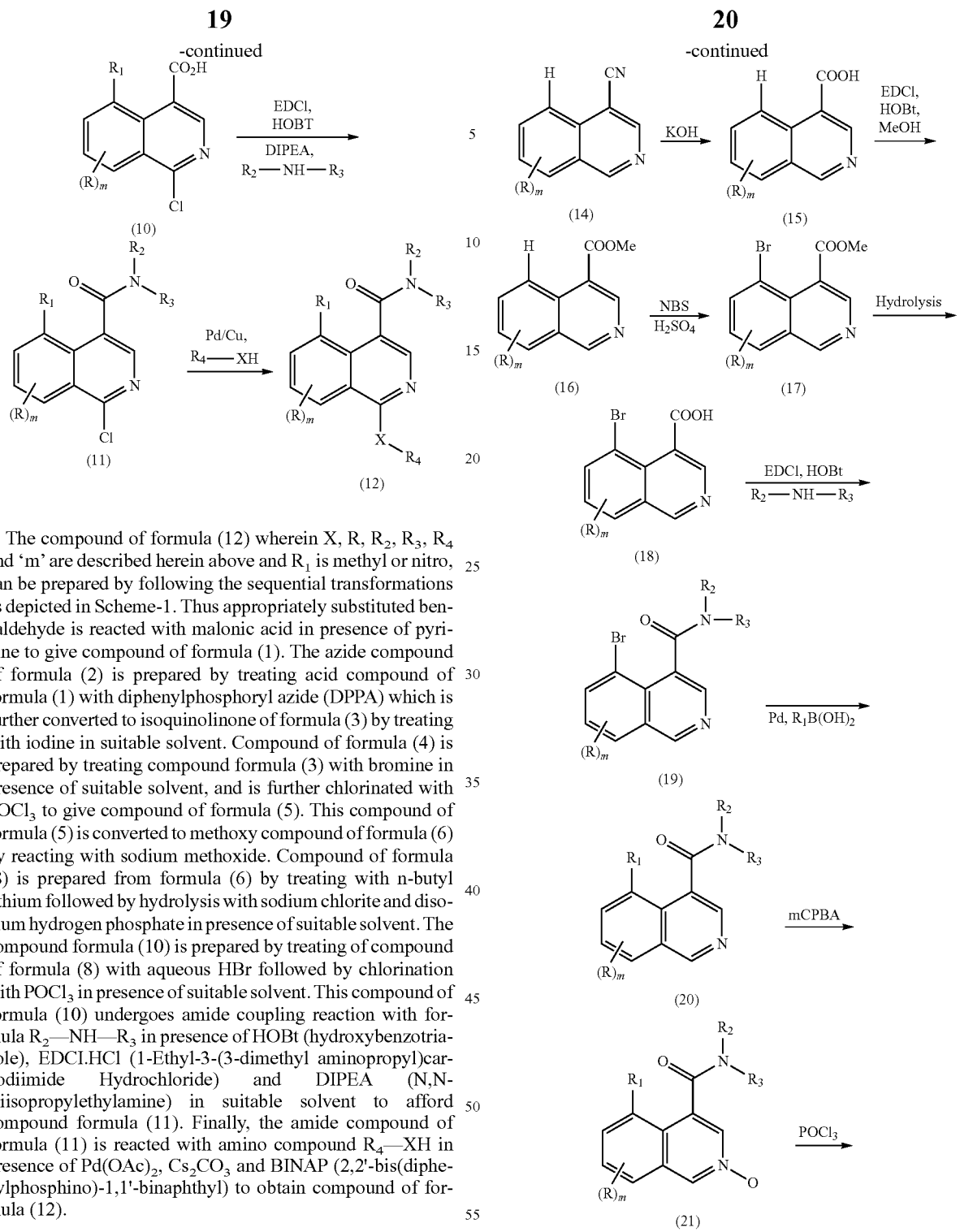

The compound of formula (12) wherein X, R, $R_2$, $R_3$, $R_4$ and 'm' are described herein above and $R_1$ is methyl or nitro, can be prepared by following the sequential transformations as depicted in Scheme-1. Thus appropriately substituted benzaldehyde is reacted with malonic acid in presence of pyridine to give compound of formula (1). The azide compound of formula (2) is prepared by treating acid compound of formula (1) with diphenylphosphoryl azide (DPPA) which is further converted to isoquinolinone of formula (3) by treating with iodine in suitable solvent. Compound of formula (4) is prepared by treating compound formula (3) with bromine in presence of suitable solvent, and is further chlorinated with $POCl_3$ to give compound of formula (5). This compound of formula (5) is converted to methoxy compound of formula (6) by reacting with sodium methoxide. Compound of formula (8) is prepared from formula (6) by treating with n-butyl lithium followed by hydrolysis with sodium chlorite and disodium hydrogen phosphate in presence of suitable solvent. The compound formula (10) is prepared by treating of compound of formula (8) with aqueous HBr followed by chlorination with $POCl_3$ in presence of suitable solvent. This compound of formula (10) undergoes amide coupling reaction with formula $R_2$—NH—$R_3$ in presence of HOBt (hydroxybenzotriazole), EDCI.HCl (1-Ethyl-3-(3-dimethyl aminopropyl)carbodiimide Hydrochloride) and DIPEA (N,N-Diisopropylethylamine) in suitable solvent to afford compound formula (11). Finally, the amide compound of formula (11) is reacted with amino compound $R_4$—XH in presence of $Pd(OAc)_2$, $Cs_2CO_3$ and BINAP (2,2'-bis(diphenylphosphino)-1,1'-binaphthyl) to obtain compound of formula (12).

Scheme-2

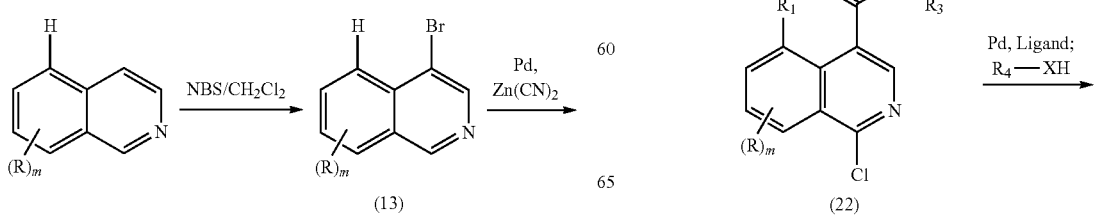

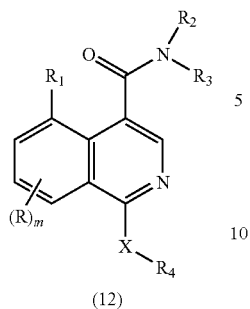

(12)

The compound of formula (12) wherein X, R, $R_2$, $R_3$, $R_4$ and 'm' are described herein above and $R_1$ is ethyl or cycloalkyl, can be prepared by following the sequential transformations as depicted in Scheme-2. The compound of formula (15) can be obtained from optionally substituted isoquinoline compound by following three sequential transformations. Thus, optionally substituted isoquinoline compound undergoes halogenation using NBS (N-bromosuccinimide) and dichloromethane followed by cyanation using palladium and $Zn(CN)_2$ to give cyano compound, which is further hydrolyzed to give compound of formula (15). This acid compound is alkylated in presence of EDCI, HOBt and methanol to give compound of formula (16). Compound of formula (16) is converted to halo compound of formula (17) in presence of NBS which again undergoes hydrolysis reaction to give acid compound of formula (18). This acid compound is coupled with $R_2$—NH—$R_3$ in presence of EDCI and HOBt and suitable solvent to obtain the compound of formula (19). The compound of formula (20) is obtained by reacting a compound of formula (19) with $R_1B(OH)_2$ in presence of palladium reagent. The compound of formula (20) is oxidized to give N-oxide compound of formula (21) in presence of mCPBA which further halogenated with $POCl_3$ to give compound of formula (22). Finally, this halo compound is converted to compound of formula (12) by reacting with $R_4$—XH in presence of a ligand and palladium.

Scheme-3

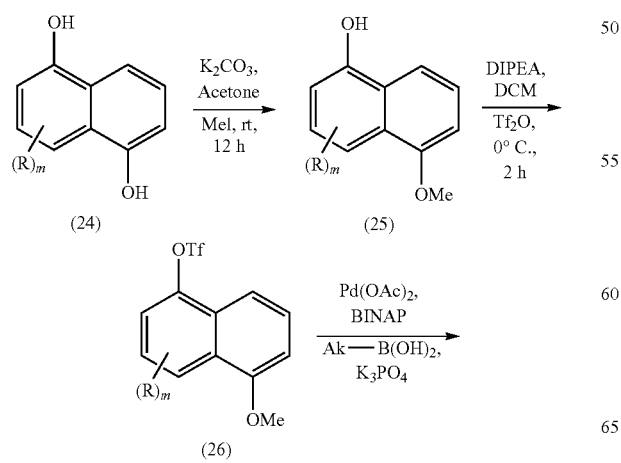

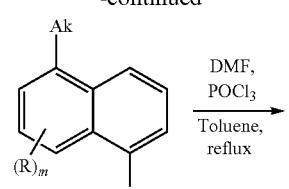

(27)

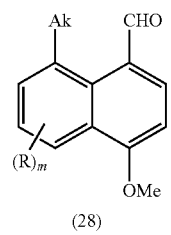

(28)

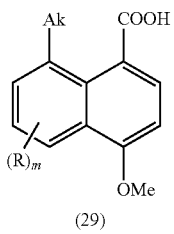

(29)

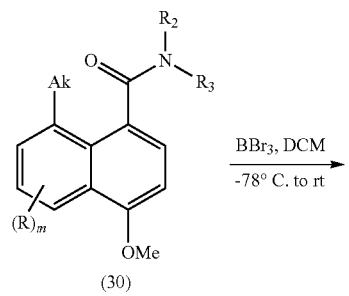

(30)

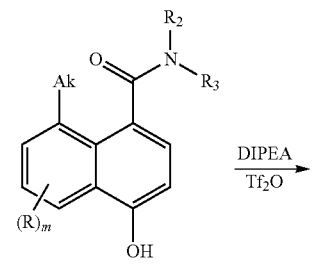

(31)

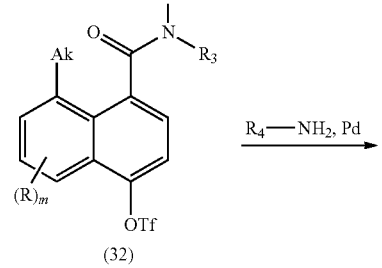

(32)

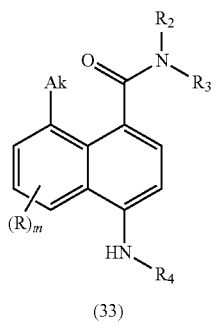

The compounds of formula (33), wherein R, R$_2$, R$_3$, R$_4$, and 'm' are as described herein above, can be prepared by following the sequential transformations as depicted in Scheme-3. Compound of formula (25) is prepared from compound of formula (24) by using suitable alkylating agent and base. Another hydroxyl group in compound of formula (25) is protected by using Tf$_2$O followed by alkylation using Ak-B(OH)$_2$ (where Ak is alkyl, cycloalkyl or haloalkyl etc.,) in presence of suitable reagent to afford compound of formula (27). Compound of formula (28) is obtained from compound of formula (27) in presence of POCl$_3$ and DMF which is further converted to acid compound of formula (29). This acid compound of formula (29) undergoes amide coupling reaction in presence of HOBt, EDCI and DIPEA in suitable solvent to give compound of formula (30). Methoxy group in compound of formula (30) undergoes hydrolysis in presence of BBr$_3$ to give compound of formula (31) further, which is protected by using Tf$_2$O to afford compound of formula (32). Finally compound of formula (32) is reacted with R$_4$—NH$_2$ in presence of Pd to give compound of formula (33).

The compounds of formula (38), wherein R, R$_2$, R$_3$, R$_4$ and 'm' are as described herein above, can be prepared by following the sequential transformations of compound formula (34) as depicted in Scheme-4. Thus, 1-amino-4-bromonaphthalene of formula (34) was converted to cyano compound of formula (35) by treating with Copper(I) cyanide and Copper (I) iodide in presence of suitable solvent. Coupling of compound of formula (35) with R$_4$-L where L is leaving group, in the presence of Palladium(II)acetate (Pd(OAc)$_2$) and cesium carbonate (Cs$_2$CO$_3$) in suitable solvent gives compound of formula (36). The compound of formula (36) undergoes hydrolysis to give acid compound of formula (37) in the presence of aqueous potassium hydroxide (KOH) solution. This acid compound of formula (37) further undergoes amide coupling reaction with an amine (R$_2$—NH—R$_3$) in the presence of hydroxybenzotriazole (HOBt), 1-ethyl-3-(3-dimethylaminopropyl)carbodiimide hydrochloride (EDC.HCl) and N,N-diisopropylethylamine (DIPEA) to afford compound of formula (38).

Scheme-5

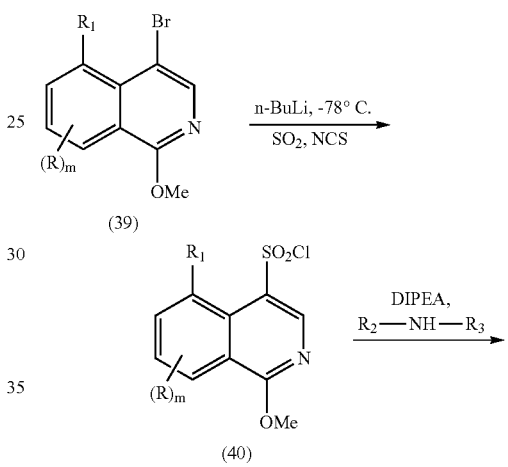

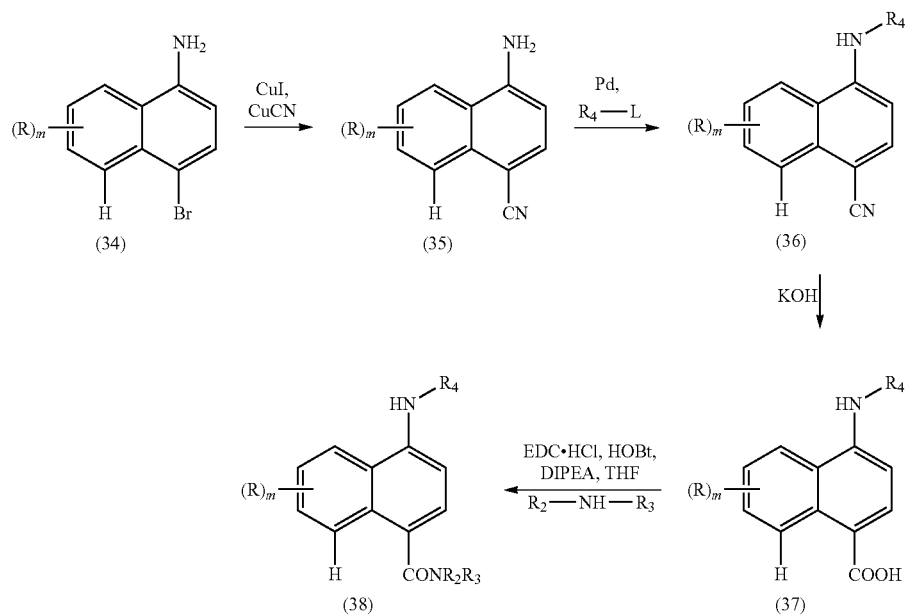

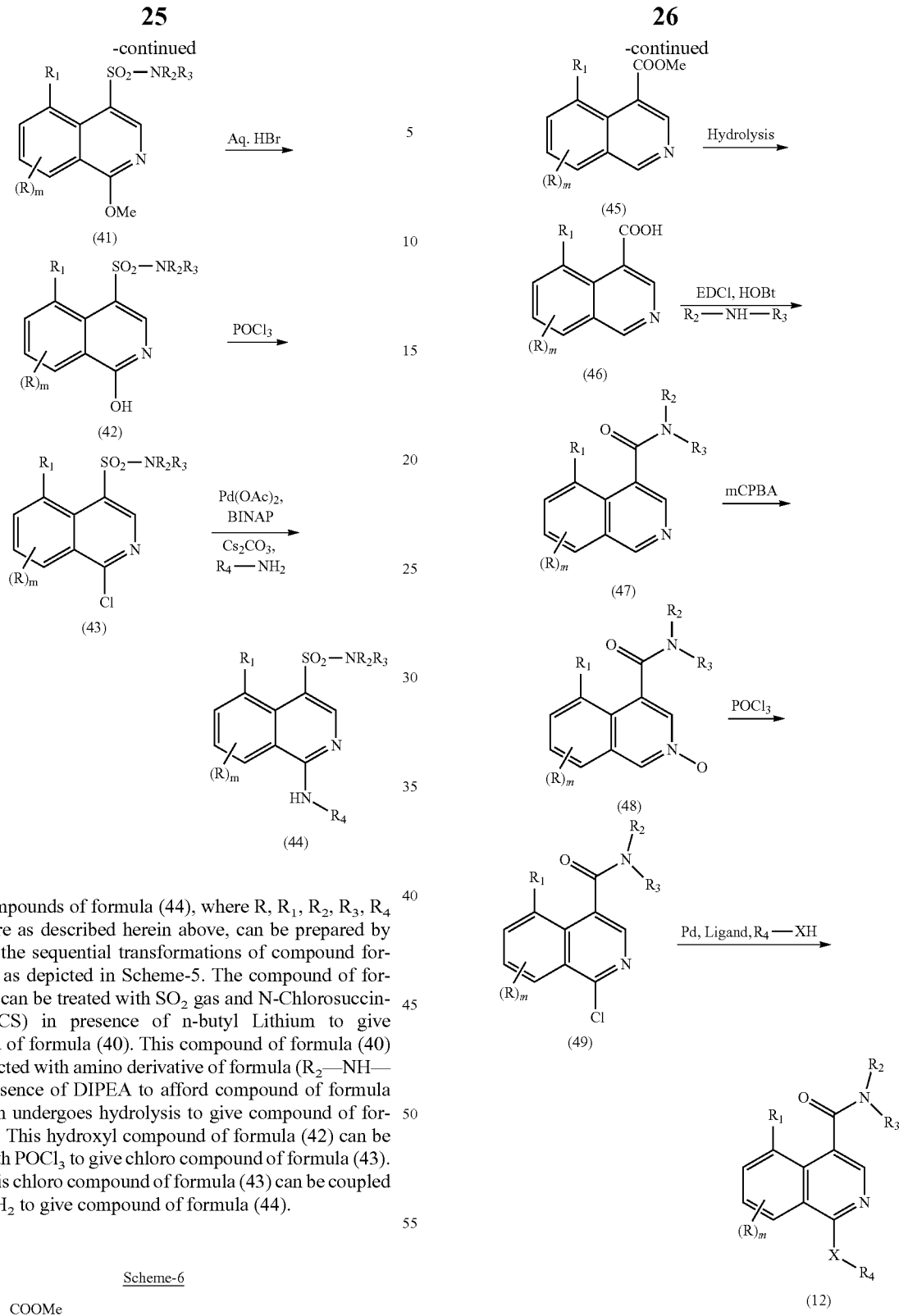

The compounds of formula (44), where R, $R_1$, $R_2$, $R_3$, $R_4$ and 'm' are as described herein above, can be prepared by following the sequential transformations of compound formula (39) as depicted in Scheme-5. The compound of formula (39) can be treated with $SO_2$ gas and N-Chlorosuccinimide (NCS) in presence of n-butyl Lithium to give compound of formula (40). This compound of formula (40) can be reacted with amino derivative of formula ($R_2$—NH—$R_3$) in presence of DIPEA to afford compound of formula (41) which undergoes hydrolysis to give compound of formula (42). This hydroxyl compound of formula (42) can be treated with $POCl_3$ to give chloro compound of formula (43). Finally, this chloro compound of formula (43) can be coupled with $R_4NH_2$ to give compound of formula (44).

Scheme-6

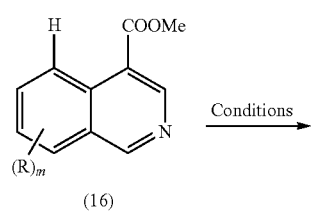

Compound of formula (12) wherein X, R, $R_2$, $R_3$, $R_4$ and 'm' are described herein above, can be prepared by following the sequential transformations as depicted in Scheme-6.

Compound of formula (45) is obtained where $R_1$ is halogen, from compound of formula (16) by treating with N-halosuccinimide. Additionally, Compound of formula (45) is obtained where $R_1$ is hydroxy, cyano, amino, alkoxy, haloalkoxy or cycloalkoxy, from compound of formula (16) in presence of suitable reagent(s) and conditions. Compound of formula (45) is hydrolyzed to give acid compound of formula (46) which further coupled with $R_2$—NH—$R_3$ in presence of EDCI and HOBt to give compound of formula (47). This compound of formula (47) is treated with mCPBA to give N-oxide compound of formula (48) which further converted to compound of formula (49). Finally, compound of formula (49) is reacted with $R_4$—XH in presence of palladium and ligand to give compound of formula (12).

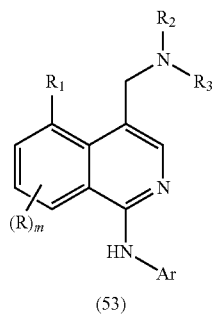

(53)

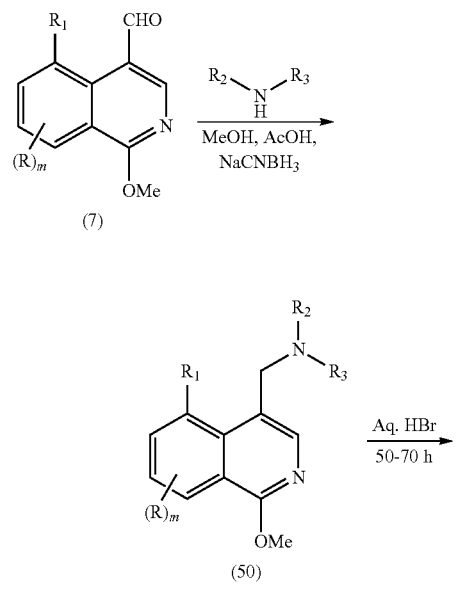

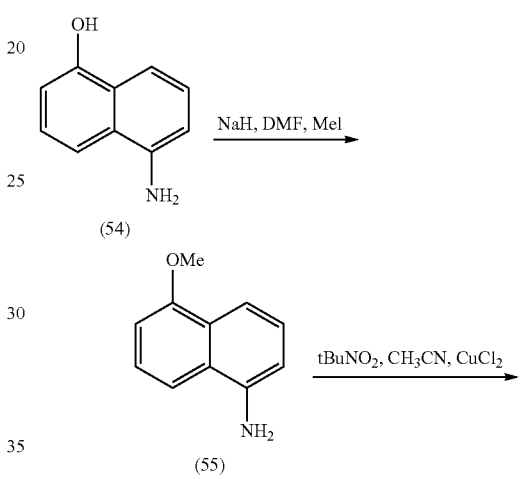

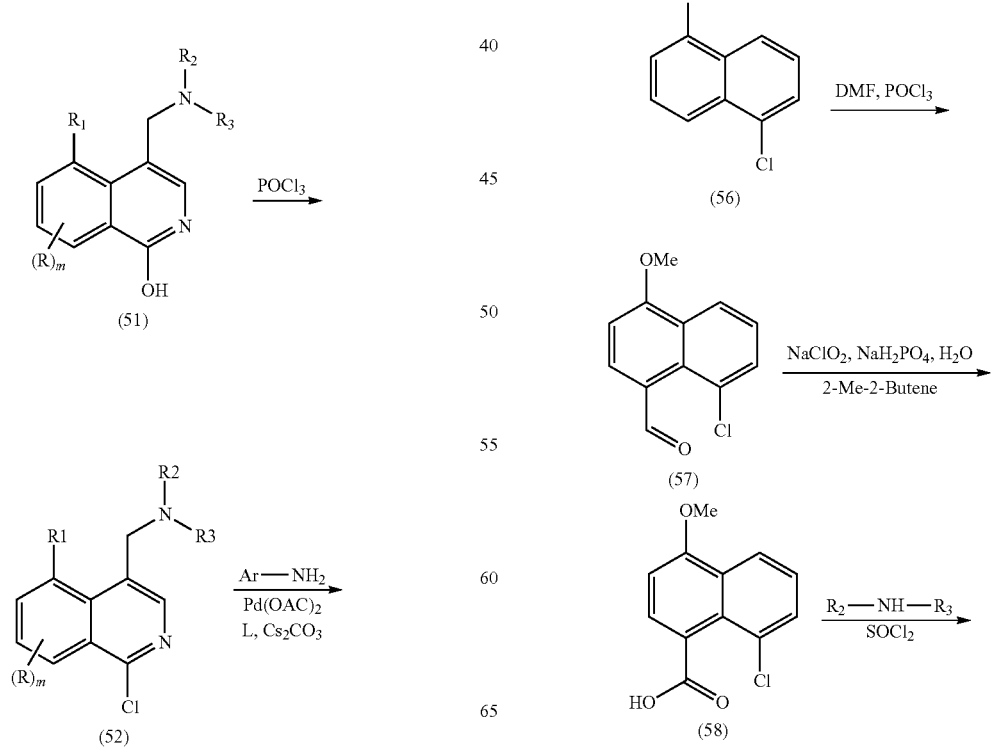

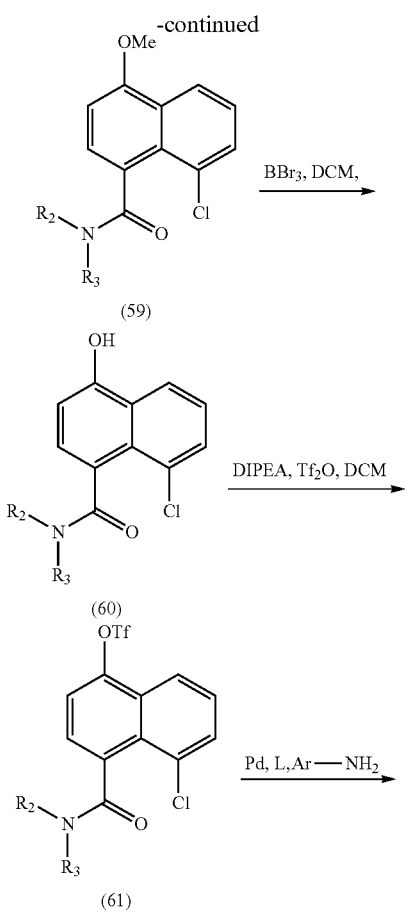

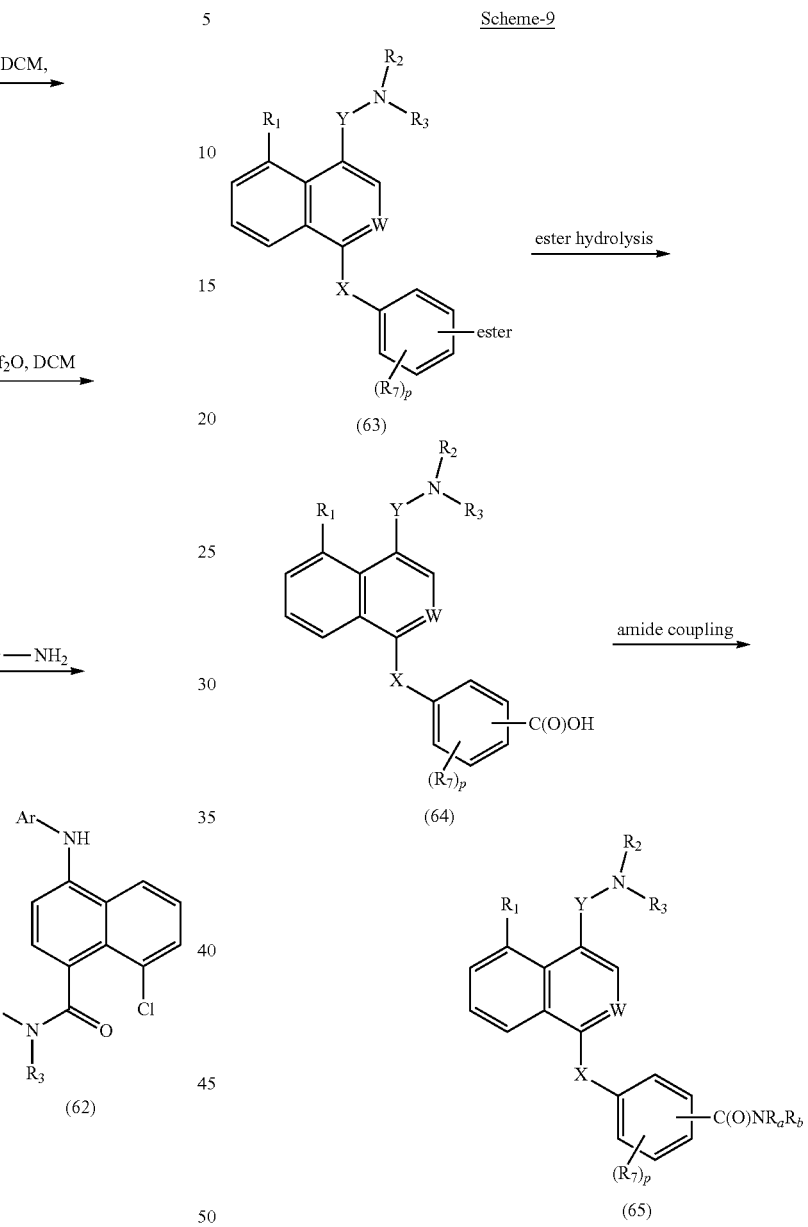

General Procedure for the Preparation of Acid Compound from Corresponding Ester:

Compound of formula (61) wherein Ar, $R_2$ and $R_3$ are as described herein above, can be prepared by following the sequential transformations as depicted in Scheme-6. Compound of formula (54) undergoes O-alkylation to give compound of formula (55) using suitable alkylating agent. The amino group in formula (55) undergoes halogenation to give compound of formula (56) which further converted to give compound of formula (58) through Vilsmeier-Haack reaction followed by oxidation as depicted in scheme-8. This compound of formula (58) undergoes amide coupling reaction with $R_2$—NH—$R_3$ in presence suitable reagent to give compound of formula (59). The compound of formula (59) is converted to compound of formula (61) through dealkylation followed by triflate reaction with $Tf_2O$ then coupling reaction with Ar—$NH_2$ in presence of suitable reagents.

To a well stirred solution of an ester intermediate (1 equiv) in $THF:H_2O$ (1:1) was added, LiOH (50 equiv) at RT and the reaction mixture was stirred overnight. After reaction completion (TLC) it was concentrated, acidified (pH~6.5) with 1N HCl and extracted with ethylacetate. This ethylacetate layer was concentrated to furnish the corresponding acid derivative.

This acid derivative of formula (64) was further coupled with suitable amine to give amide derivative of formula (65) by following the simple amide coupling procedure described herein.

In above scheme-8 where R1 is halogen, alkyl or cycloalkyl; W, X, Y, $R_a$, $R_b$, $R_2$, $R_3$, $R_7$ and 'p' are as defined herein above.

EXPERIMENTAL

Intermediates

Intermediate-1: o-Methylcinnamic acid

To a stirred solution of o-methylbenzaldehyde (50 g, 417 mmol) in pyridine (2 equiv, 65 mL) was added malonic acid (86.6 g, 834 mmol) and the mixture was refluxed for 4-5 h. The reaction mixture was then poured into ice-water followed by 1N HCl. The white solid precipitated out was filtered, washed with water and concentrated under high vacuum for 3-4 h to get the desired product (57 g, 87%).

Intermediate-2: o-Methylcinnamoyl azide

To a stirred solution of o-methylcinnamic acid (Intermediate-1) (30 g, 185 mmol) in dry THF (100 mL) was added TEA (51.5 mL, 37 mmol) and diphenylphosphoryl azide (DPPA) (56 g, 204 mmol) slowly under $N_2$ atmosphere and the mixture was stirred at room temperature for 2-3 h. It was quenched with cold water, extracted with EtOAc (3×200 mL), washed with water (2×200 mL), dried over $Na_2SO_4$, filtered and concentrated under reduced pressure to give the crude product. It was recrystallized from MeOH to obtain the desired compound (23 g, 66%).

Intermediate-3: 5-Methylisoquinolin-1(2H)-one

A stirred solution of o-methylcinnamoyl azide (Intermediate-2) (10 g, 53.5 mmol) in toluene (100 mL) was heated to 110° C. for 1 h. The solvent was removed, and charged 1,2-dichlorobenzene (DCB) (100 mL), $I_2$ (catalytic) and heated to 180° C. and maintained for overnight. The solvent was removed under reduced pressure and the product was recrystallized (EtOAc:Hexanes; 90:10) to furnish the desired compound (4 g, 45%).

Intermediate-4: 4-Bromo-5-methylisoquinolin-1(2H)-one

To a stirred solution of 5-methylisoquinolin-1(2H)-one (Intermediate-3) (10 g, 63 mmol) in $CH_2Cl_2$ (100 mL) was added, $Br_2$ (11.1 g, 69.3 mmol) drop wise and the mixture was stirred at RT (room temperature) overnight. $Et_2O$ (200 mL) was added to it, stirred for few min after which, a yellow solid precipitated out. It was filtered, washed with MeOH (10 mL), and dried to give desired intermediate (10 g, 67%) as white solid.

Intermediate-5: 4-Bromo-1-chloro-5-methylisoquinoline

A stirred solution of 4-bromo-5-methylisoquinolin-1(2H)-one (Intermediate-4) (10 g, 42 mmol) in $POCl_3$ (50 mL) was heated to 100° C. for 30 min. The reaction mixture was then poured into ice-water, extracted with $CH_2Cl_2$ (3×200 mL), washed with water (2×200 mL), dried over $Na_2SO_4$, filtered and concentrated to obtain desired compound (10 g, 92%).

Intermediate-6: 4-Bromo-1-methoxy-5-methylisoquinoline

To a stirred solution of 4-bromo-1-chloro-5-methylisoquinoline (Intermediate-5) (5.0 g, 19.5 mmol) in dry MeOH (100 mL) was added NaOMe (1.3 g, 23.4 mmol) and the reaction mixture was refluxed overnight. Solvent was removed and the resultant crude product was extracted with EtOAc (2×200 mL), washed with water (2×100 mL), dried over $Na_2SO_4$, filtered and concentrated under reduced pressure to furnished the title compound (4.5 g, 93%).

Intermediate-7: 1-Methoxy-5-methylisoquinolin-4-carbaldehyde

To a stirred solution of 4-bromo-1-methoxy-5-methylisoquinoline (Intermediate-6) (2 g, 7.9 mmol) in dry THF (20 mL) was added, n-BuLi (15 mL, 23.7 mmol) drop wise at −78° C. under $N_2$ atmosphere and stirred for 1 h. To this, dry DMF (3 mL) was added and the reaction mixture was stirred at −78° C. for another 1 h. Then it was quenched with saturated $NH_4Cl$ solution, extracted with EtOAc (3×100 mL), washed with water (1×200 mL), dried over $Na_2SO_4$, filtered and concentrated to afford the title compound (1.2 g, 78%).

Intermediate-8: 1-Methoxy-5-methylisoquinolin-4-carboxylic acid

To a stirred solution of 1-methoxy-5-methylisoquinolin-4-carbaldehyde (Intermediate-7) (2 g, 10 mmol) in ACN—$H_2O$ (120 mL, 1:1) was added, $NaClO_2$ (5.4 g, 59.7 mmol), $NaH_2PO_4$ (5.5 g, 40 mmol) and the mixture was stirred at RT overnight. It was then extracted with EtOAc (3×150 mL), dried over $Na_2SO_4$, filtered and concentrated to give the desired acid derivative (1.2 g, 56%).

Intermediate-9: 1-Hydroxy-5-methylisoquinolin-4-carboxylic acid

A solution of 1-methoxy-5-methylisoquinolin-4-carboxylic acid (Intermediate-8) (1.2 g, 5.5 mmol) in HBr (48% aq. solution, 20 mL) was stirred at RT for 24 h. After completion (TLC), the reaction mixture was poured into water, filtered, washed with water (4×25 mL), and then dried to afford title compound (600 mg, 52%).

Intermediate-10: 1-Chloro-5-methylisoquinolin-4-carboxylic acid

A stirred solution of 1-hydroxy-5-methylisoquinolin-4-carboxylic acid (Intermediate-9) (600 mg, 3 mmol) in $POCl_3$ (10 mL) was heated to 100° C. for 40-50 min. The reaction mixture was poured into ice-water, extracted with $CH_2Cl_2$ (2×100 mL), washed with water (2×100 mL), dried over $Na_2SO_4$, filtered and evaporated to give the desired compound (550 mg, 86%).

Intermediate-11a: 1-Chloro-5-methylisoquinolin-4-yl)(morpholino)methanone

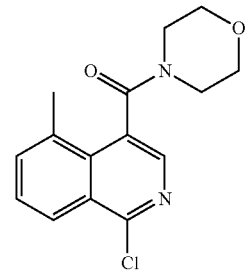 [SMILES: Cc1cccc2c(Cl)ncc(C(=O)N3CCOCC3)c12]

To a stirred solution of 1-chloro-5-methylisoquinolin-4-carboxylic acid (Intermediate-10) (100 mg) in THF was added morpholine (1.5 equiv), HOBt (1.5 equiv), EDCI (1.5 equiv) and DIPEA (2 equiv) under $N_2$ atmosphere. The reaction mixture was stirred at RT for overnight and then quenched with ice water. It was extracted with EtOAc (2×100 mL), washed with water (1×100 mL), dried over $Na_2SO_4$, filtered and concentrated to give the crude product which was purified by combiflash using EtOAc-Hexanes (1:1) to give the desired amide derivative.

Intermediate-11b: 1-Chloro-5-methyl-N-((tetrahydro-2H-pyran-4-yl)methyl)isoquinolin-4-carboxamide

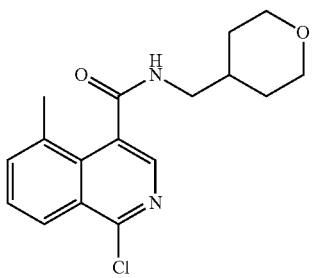 [SMILES: Cc1cccc2c(Cl)ncc(C(=O)NCC3CCOCC3)c12]

The title compound was prepared by using 1-chloro-5-methylisoquinolin-4-carboxylic acid (Intermediate-10) and (tetrahydro-2H-pyran-4-yl)methanamine by following the similar procedure as described for Intermediate-11a.

Intermediate-11c: N-(tert-Butyl)-1-chloro-5-methylisoquinolin-4-carboxamide

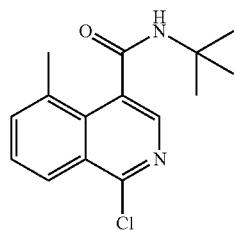 [SMILES: Cc1cccc2c(Cl)ncc(C(=O)NC(C)(C)C)c12]

This compound was prepared by using 1-chloro-5-methylisoquinolin-4-carboxylic acid (Intermediate-10) and tert-butylamine by following the similar procedure as described for Intermediate-11a.

Intermediate-11d: (1-Chloro-5-methylisoquinolin-4-yl)(piperidin-1-yl)methanone

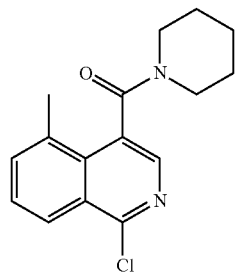 [SMILES: Cc1cccc2c(Cl)ncc(C(=O)N3CCCCC3)c12]

The title compound was prepared by using 1-chloro-5-methylisoquinolin-4-carboxylic acid (Intermediate-10) and piperidine by following the similar procedure as described for intermediate-11a.

Intermediate-11e: 6-Oxa-3-azabicyclo[3.1.1]heptan-3-yl(1-chloro-5-methylisoquinolin-4-yl)methanone

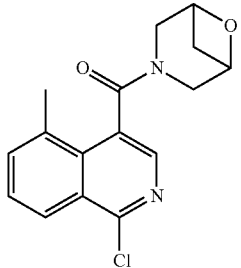 [SMILES: Cc1cccc2c(Cl)ncc(C(=O)N3CC4CC(C3)O4)c12]

The title compound was prepared by using 1-chloro-5-methylisoquinolin-4-carboxylic acid (Intermediate-10) and 6-oxa-3-azabicyclo[3.1.1]heptane by following the similar procedure as described for intermediate-11a.

Intermediate-11f: (1-Chloro-5-methylisoquinolin-4-yl)(2-oxa-6-azaspiro[3.3]heptan-6-yl)methanone

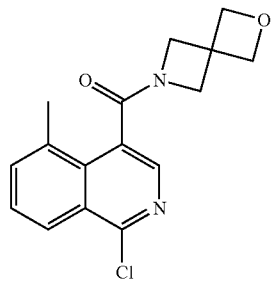 [SMILES: Cc1cccc2c(Cl)ncc(C(=O)N3CC4(COC4)C3)c12]

The title compound was prepared by using 1-chloro-5-methylisoquinolin-4-carboxylic acid (Intermediate-10) and 2-oxa-6-azaspiro[3.3]heptane by following the similar procedure as described for intermediate-11a.

Intermediate-11g: (1-Chloro-5-methylisoquinolin-4-yl)(2-oxa-6-azaspiro[3.5]nonan-6-yl)methanone

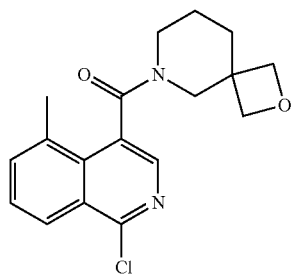 [SMILES: Cc1cccc2c(Cl)ncc(C(=O)N3CCCC4(COC4)C3)c12]

The title compound was prepared by using 1-chloro-5-methylisoquinolin-4-carboxylic acid (Intermediate-10) and 2-oxa-6-azaspiro[3.5]nonane by following the similar procedure as described for intermediate-11a.

Intermediate-11h: (1-Chloro-5-methylisoquinolin-4-yl)(3,5-dimethylpiperazin-1-yl)methanone

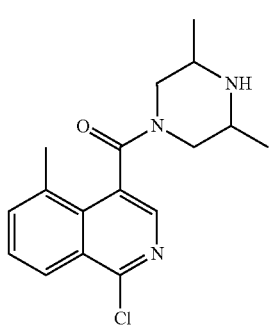 [SMILES: Cc1cccc2c(Cl)ncc(C(=O)N3CC(C)NC(C)C3)c12]

This compound was prepared by using 1-chloro-5-methylisoquinolin-4-carboxylic acid (Intermediate-10) and 2,6-dimethylpiperazine by following the similar procedure as described for intermediate-11a.

Intermediate-11i: 2-Oxa-5-azabicyclo[2.2.1]heptan-3-yl(1-chloro-5-methylisoquinolin-4-yl)methanone

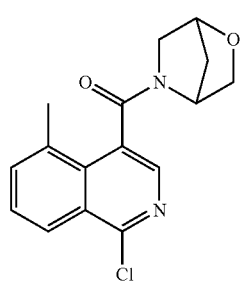 [SMILES: Cc1cccc2c(Cl)ncc(C(=O)N3CC4CC3CO4)c12]

The title compound was prepared by using 1-chloro-5-methylisoquinolin-4-carboxylic acid (Intermediate-10) and 2-oxa-5-azabicyclo[2.2.1]heptane by following the similar procedure as described for intermediate-11a.

Intermediate-11j: 3-Azabicyclo[3.1.0]hexan-3-yl(1-chloro-5-methylisoquinolin-4-yl)methanone

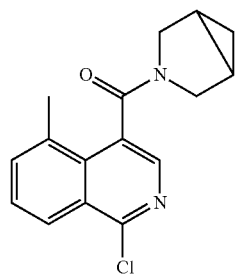 [SMILES: Cc1cccc2c(Cl)ncc(C(=O)N3CC4CC4C3)c12]

The title compound was prepared by using 1-chloro-5-methylisoquinolin-4-carboxylic acid (Intermediate-10) and 3-azabicyclo[3.1.0]hexane by following the similar procedure as described for intermediate-11a.

Intermediate-11k: 3-Oxa-9-azabicyclo[3.3.1]nonan-9-yl(1-chloro-5-methylisoquinolin-4-yl)methanone

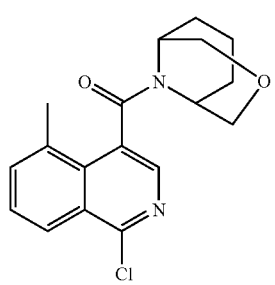 [SMILES: Cc1cccc2c(Cl)ncc(C(=O)N3C4CCCC3COC4)c12]

The title compound was prepared by using 1-chloro-5-methylisoquinolin-4-carboxylic acid (Intermediate-10) and 3-azabicyclo[3.1.0]hexane by following the similar procedure as described for intermediate-11a.

Intermediate-11l: (1-Chloro-5-methylisoquinolin-4-yl)(2-phenylmorpholino)methanone

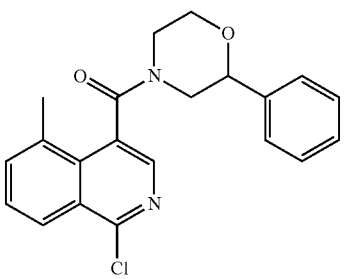 [SMILES: Cc1cccc2c(Cl)ncc(C(=O)N3CCOC(c4ccccc4)C3)c12]

The title compound was prepared by using 1-chloro-5-methylisoquinolin-4-carboxylic acid (Intermediate-10) and 2-phenylmorpholine by following the similar procedure as described for intermediate-11a.

Intermediate-11m: 1-Chloro-N-cyclohexyl-5-methyl-isoquinolin-4-carboxamide

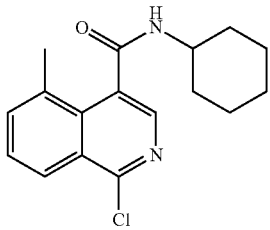 [SMILES: Cc1cccc2c(Cl)ncc(C(=O)NC3CCCCC3)c12]

This compound was prepared by using 1-chloro-5-methyl-isoquinolin-4-carboxylic acid (Intermediate-10) and cyclohexylamine by following the similar procedure as described for intermediate-11a.

Intermediate-11n: (1-Chloro-5-methylisoquinolin-4-yl)(pyrrolidin-1-yl)methanone

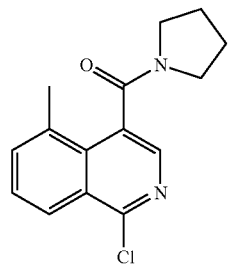 [SMILES: Cc1cccc2c(Cl)ncc(C(=O)N3CCCC3)c12]

The title compound was prepared by using 1-chloro-5-methylisoquinolin-4-carboxylic acid (Intermediate-10) and pyrrolidine by following the similar procedure as described for intermediate-11a.

Intermediate-11o: Azetidin-1-yl(1-chloro-5-methyl-isoquinolin-4-yl)methanone

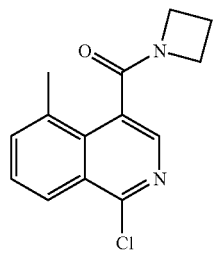 [SMILES: Cc1cccc2c(Cl)ncc(C(=O)N3CCC3)c12]

The title compound was prepared by using 1-chloro-5-methylisoquinolin-4-carboxylic acid (Intermediate-10) and azetidine by following the similar procedure as described for intermediate-11a.

Intermediate-11p: (1-Chloro-5-methylisoquinolin-4-yl)(2-oxa-7-azaspiro[3.5]nonan-7-yl)methanone

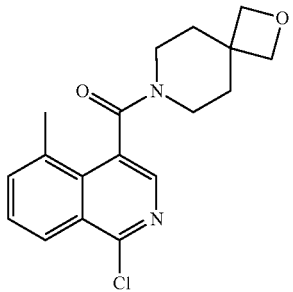 [SMILES: Cc1cccc2c(Cl)ncc(C(=O)N3CCC4(CC3)COC4)c12]

The title compound was prepared by using 1-chloro-5-methylisoquinolin-4-carboxylic acid (Intermediate-10) and 2-oxa-7-azaspiro[3.5]nonane by following the similar procedure as described for intermediate-11a.

Intermediate-11q: (1-Chloro-5-methylisoquinolin-4-yl)(1,1-dioxidothiomorpholino)methanone

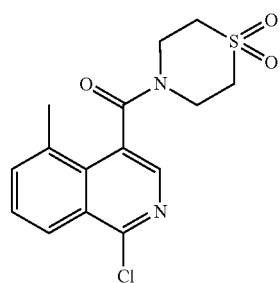 [SMILES: Cc1cccc2c(Cl)ncc(C(=O)N3CCS(=O)(=O)CC3)c12]

The title compound was prepared by using 1-chloro-5-methylisoquinolin-4-carboxylic acid (Intermediate-10) and 1,1-dioxidothiomorpholine by following the similar procedure as described for intermediate-11a.

Intermediate-11r: (1-Chloro-5-methylisoquinolin-4-yl)(4,4-difluoropiperidin-1-yl)methanone

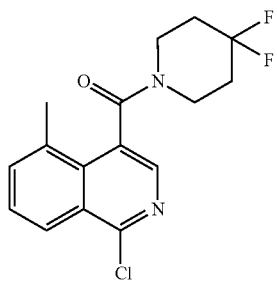 [SMILES: Cc1cccc2c(Cl)ncc(C(=O)N3CCC(F)(F)CC3)c12]

The title compound was prepared by using 1-chloro-5-methylisoquinolin-4-carboxylic acid (Intermediate-10) and 4,4-difluoropiperidine by following the similar procedure as described for intermediate-11a.

Intermediate-12: 3-Bromoisoquinoline

To a stirred solution of isoquinoline (24 g, 186 mmol) in AcOH (50 mL) was added NBS (36.2 g, 204.6 mmol) at RT and the reaction mixture was heated to 100° C. overnight. Then it was cooled to RT and concentrated under reduced pressure. The crude product obtained was purified by flash column chromatography (5% EtOAc:Hexanes) to furnish the title compound (9.2 g, 23.8%) as an oil.

Intermediate-13: Isoquinolin-4-carbonitrile

To a stirred solution of 3-bromoisoquinoline (Intermediate-12) (9.2 g, 44.2 mmol) in DMF (15 mL) were added, Pd(PPh$_3$)$_4$ (10.2 g, 8.84 mmol) and Zn(CN)$_2$ (10.34 g, 88.44 mmol, 2.0 eq) and the solution was degassed with N$_2$ for 20 min. It was then heated to 120° C. overnight. After the completion (TLC), reaction mixture was cooled to RT, filtered and concentrated under reduced pressure. The crude product obtained was purified by flash column chromatography (10% EtOAc:Hexanes) to afford the desired compound (3.4 g, 27.4%) as pale yellow solid.

Intermediate-14: Isoquinolin-4-carboxylic acid

To a stirred solution of isoquinolin-4-carbonitrile (Intermediate-13) (3.0 g, 19.45 mmol) in EtOH (30 mL) was added KOH (20 g in 20 mL water) and the mixture was refluxed overnight. It was then cooled to RT and concentrated under reduced pressure. The aqueous layer was washed with Et$_2$O and neutralized using 1N HCl. It was extracted with EtOAc and the organic layer was dried over Na$_2$SO$_4$, filtered, and concentrated to give the title compound (2 g, 59.3%) as an off white solid.

Intermediate-15: Methyl isoquinolin-4-carboxylate

To a stirred solution of isoquinolin-4-carboxylic acid (Intermediate-14) (1.2 g, 6.9 mmol) in CH$_2$Cl$_2$ (10 mL) was added, EDCI (1.3 g, 8.3 mmol), HOBt (1.12 g, 8.3 mmol), DMAP (84 mg, 0.7 mmol) and the mixture was stirred at RT for 20 min. To this, MeOH (0.33 g, 10.4 mmol) was added and the reaction mixture was further stirred at RT for overnight. It was diluted with CH$_2$Cl$_2$ (100 mL) and washed with water. The organic layer was separated, dried over Na$_2$SO$_4$, filtered and concentrated to give crude product that was purified by flash column chromatography (10% EtOAc:Hexanes) to give the desired product (700 mg, 54%) as pale yellow solid.

Intermediate-16: Methyl 5-bromoisoquinolin-4-carboxylate

To a mixture of conc. H$_2$SO$_4$ (16 mL) and methyl isoquinoline-4-carboxylate (Intermediate-15) (2.8 g, 15 mmol) at 0° C. was added, NBS (3.3 g, 18.7 mmol) slowly and the reaction mixture was allowed to come to RT and stirred overnight. After completion (TLC), it was quenched with ice, neutralized (NaHCO$_3$) and extracted with EtOAc (50 mL×3). The organic phase was separated, dried (Na$_2$SO$_4$) and concentrated to give dark brown oil (3.6 g) as crude product that was purified by flash column chromatography (25% EtOAc in Hexanes) to furnish the desired compound (1.4 g, 35%).

Intermediate-17: 5-Bromoisoquinolin-4-carboxylic acid

To a stirred solution of methyl 5-bromoisoquinolin-4-carboxylate (Intermediate-16) (10.1 g, 38.0 mmol) in MeOH (50 mL) was added, KOH (21.3 g, 380 mmol) dissolved in water (50 mL) and the reaction mixture was heated to 70° C. for 3 h. Then it was concentrated, diluted with water and washed with Et$_2$O (100 mL×3). The aqueous layer was acidified with 2N HCl (pH=3) and the white solid obtained was filtered to yield the desired acid derivative 6.0 g (62.7%).

Intermediate-18: 5-Bromoisoquinolin-4-carboxylic amide

To a stirred solution of 5-bromoisoquinoline-4-carboxylic acid (Intermediate-17) (1 equiv, 2.0 mmol) in dry THF (10.0 ml) were added, DIPEA (3 equiv), HOBT (1.5 equiv), EDC.HCl (1.5 equiv) at RT and the mixture was stirred for 10 min. To this, corresponding amine (1.2 equiv) was added and the reaction mixture was stirred overnight. After completion (TLC), it was concentrated under reduced pressure and the crude product was purified by flash column chromatography to furnish the corresponding amide derivative (60-80%).

Intermediate-19: 5-Alkylisoquinolin-4-carboxylic amide

In a 100 mL sealed tube, 5-bromoisoquinolin-4-carboxylic amide (Intermediate-18) (1 equiv), alkylboronic acid (2 equiv), K$_3$PO$_4$ (4 equiv), toluene (20 mL) and water (2 mL) were charged and the mixture was degassed for 30 min using N$_2$. Then, tricyclohexylphosphine (0.4 equiv), Pd(OAc)$_2$ (0.2 equiv) were added and the sealed tube was heated to 100° C. for 48 h. After completion (TLC), it was diluted with EtOAc (50 mL) and filtered through celite. The filtrate was collected and concentrated under vacuum to give the crude product that was purified by flash column chromatography to furnish the corresponding alkyl derivative (50-72%).

Intermediate-20: 5-Alkyl-2-oxideisoquinolin-4-carboxylic amide

In a 100 mL sealed tube, 5-alkylisoquinolin-4-carboxylic amide (Intermediate-19) (1 equiv) in CH$_2$Cl$_2$ (10 mL) was added, mCPBA (meta-Chloroperoxybenzoic acid) (2 equiv) at 0° C. and the reaction mixture was stirred overnight while allowing it to attain RT. After completion (TLC), it was diluted with CH$_2$Cl$_2$ (50 mL) and washed with saturated NaHCO$_3$ solution. The organic phase was separated, dried and concentrated to give the corresponding N-oxide derivative (85-95%).

Intermediate-21: 5-Alkyl-1-chloroisoquinolin-4-carboxylic amide

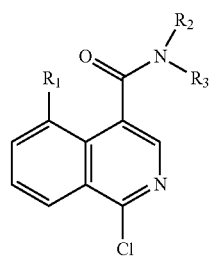

$R_1$ is alkyl or cycloalkyl; $R_2$ and $R_3$ is as defined in Formula (I)

To a stirred solution of 5-alkyl-2-oxideisoquinolin-4-carboxylic amide (Intermediate-20) (1 equiv) in CHCl$_3$ (20 mL)

was added, POCl₃ (10 equiv) and the reaction mixture was stirred for 2 h at 85° C. The crude product was then concentrated, diluted with water, extracted with CH₂Cl₂, dried and again concentrated. Finally it was purified by flash column chromatography to afford desired chloro compound (42-54%).

Intermediate-21a: (1-Chloro-5-cyclopropylisoquinolin-4-yl)(morpholino)methanone

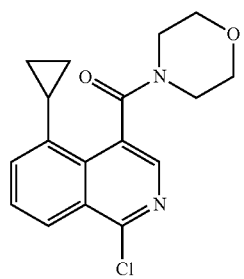 [SMILES: O=C(c1cnc(Cl)c2cccc(C3CC3)c12)N1CCOCC1]

This intermediate was prepared from the corresponding morpholine amide derivative and POCl₃ by using the similar procedure as described in Intermediate 21.

Intermediate-21b: (1-Chloro-5-cyclopropylisoquinolin-4-yl)(piperidin-1-yl)methanone

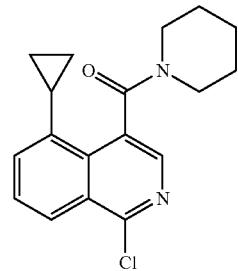 [SMILES: O=C(c1cnc(Cl)c2cccc(C3CC3)c12)N1CCCCC1]

This intermediate was prepared from the corresponding piperidine amide derivative and POCl₃ by using the similar procedure as described in Intermediate 21.

Intermediate-21c: (1-Chloro-5-ethylisoquinolin-4-yl)(morpholino)methanone

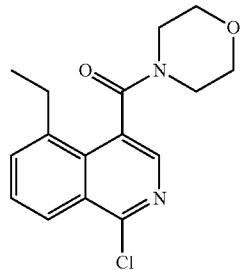 [SMILES: CCc1cccc2c(Cl)ncc(C(=O)N3CCOCC3)c12]

This intermediate was prepared from the corresponding morpholine amide derivative and POCl₃ by using the similar procedure as described in Intermediate 21.

Intermediate-21d: (1-Chloro-5-ethylisoquinolin-4-yl)(piperidin-1-yl)methanone

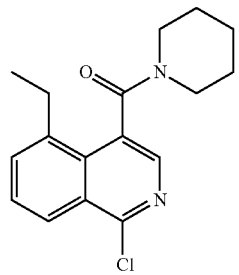 [SMILES: CCc1cccc2c(Cl)ncc(C(=O)N3CCCCC3)c12]

This intermediate was prepared from the corresponding piperidine amide derivative and POCl₃ by using the similar procedure as described in Intermediate 21.

Intermediate-22:
5-Methyl-4-(morpholin-4-carbonyl)naphthalen-1-yl trifluoromethane sulfonate

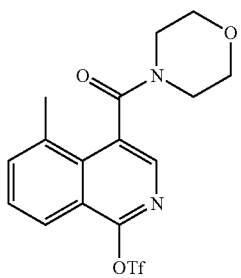 [SMILES: Cc1cccc2c(OS(=O)(=O)C(F)(F)F)ncc(C(=O)N3CCOCC3)c12]

Step-1: 5-Methoxynaphthalen-1-ol

To a stirred solution of 1,5-dihydroxy naphthalene (40 g, 0.25 mol) in dry acetone (200 mL) was added, K₂CO₃ (34.5 g, 0.25 mol) and the mixture was stirred at RT for 3 h, and then cooled to 0° C. To this, a solution of methyl iodide (124.5 mL, 2 mol) in dry acetone (100 mL) was added drop wise and the reaction mixture was stirred for 2 h at 0° C. and then for 10 h at RT. After completion (TLC), the mixture was filtered and washed with EtOAc. The solvent was removed under reduced pressure and the crude product was purified by column chromatography (8% EtOAc:Hexanes) to afford the desired compound (19.2 g, 44%) as a light green solid.

Step-2: 5-Methoxynaphthalen-1-yl trifluoromethanesulfonate

To a solution of 5-methoxynaphthalen-1-ol (above Step-1 intermediate) (19 g, 0.11 mol) in anhydrous dichloromethane (250 mL) at 0° C. was added, DIPEA (23 mL, 0.16 mol) and the mixture was stirred for 15 min. To this, Tf$_2$O (21.7 mL, 0.13 mol) was added slowly at 0° C. and the reaction mixture was stirred for 1.5 h and then quenched slowly with water (100 mL). The aqueous layer was extracted with CH$_2$Cl$_2$ (4×100 mL) and the combined organic layer was washed with water (100 mL), brine (100 mL), dried and filtered. The solvent was then evaporated and the crude product was purified by column chromatography (5% EtOAc:Hexanes) to furnish the desired compound (28.5 g, 85%) as a white solid.

Step-3: 1-Methoxy-5-methyl naphthalene

In a 500 mL 2-neck round bottom flask, toluene (300 mL) and deionized water (14 mL) were added and degassed under nitrogen for 20 minutes. Then, 5-methoxynaphthalen-1-yl trifluoromethanesulfonate (above Step-2 intermediate) (14 g, 45.75 mmol) was added to the above mixture. After stirring for 10 min at RT, K$_3$PO$_4$ (34 g, 160 mmol) and methylboronic acid (4.1 g, 68.6 mmol) were added followed by Pd(OAc)$_2$ (1.03 g, 4.6 mmol) and BINAP (5.7 g, 9.15 mmol) and the reaction mixture was stirred at RT for 15 min under nitrogen and then heated to 100° C. overnight. It was cooled and diluted with saturated NH$_4$Cl solution (150 mL). The aqueous layer was extracted with EtOAc (4×100 mL) and the combined organic layer was washed with water (100 mL), brine (100 mL), dried and filtered. After solvent removal, the crude product obtained was purified by column chromatography (5% EtOAc:Hexanes) to yield the desired compound (7 g, 87%) as a white solid.

Step-4: 4-Methoxy-8-methyl-1-naphthaldehyde

To a well stirred solution of 1-methoxy-5-methylnaphthalene (above Step-3 intermediate) (7.0 g, 40.7 mmol) in toluene (8 mL) and DMF (4.7 mL, 61 mmol) at 0° C. was added, POCl$_3$ (4.6 mL, 49.6 mmol) drop wise and the reaction mixture was stirred for 45 min at 0° C. and then refluxed for 2 h. The dark red solution was cooled to RT and poured into a mixture of ice (50 mL) and 10% aq. NaOH (100 mL) with stirring. The crude product was extracted with EtOAc (4×75 mL) and the combined organic layer was washed with 1 N HCl (3×50 mL), water (3×50 mL), brine, dried (Na$_2$SO$_4$) and filtered. The solvent was evaporated and the residue was washed with hexanes (2×15 mL) to afford the desired compound (6.4 g, 79%) as reddish brown solid.

Step-5: 4-Methoxy-8-methyl-1-naphthoic acid

To a solution of 4-methoxy-8-methyl-1-naphthaldehyde (above Step-4 intermediate) (4.4 g, 22 mmol) in $^t$BuOH (50 mL) and 2-methyl-2-butene (23.3 mL, 220 mmol) at 0° C. was added, a solution of NaClO$_2$ (6.0 g, 66 mmol) and NaH$_2$PO$_4$ (9.1 g, 66 mmol) in water (40 mL) drop wise and the reaction mixture was stirred at RT overnight. After completion (TLC), the solvent was evaporated and the residue was basified with 10% NaOH solution and washed with CH$_2$Cl$_2$ (2×50 mL). The aqueous layer was then acidified with 1 N HCl and extracted with EtOAc (4×100 mL). The combined organic layer was washed with water (100 mL), brine (100 mL), dried and filtered. After removal of solvent, the desired compound was obtained (4.5 g, 95%) as an off white solid.

Step-6: (4-Methoxy-8-methylnaphthalen-1-yl)(morpholino)methanone

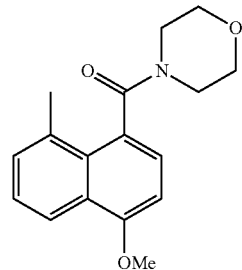 [SMILES: COc1ccc(C(=O)N2CCOCC2)c2c(C)cccc12]

To a mixture of 4-methoxy-8-methyl-1-naphthoic acid (above Step-5 intermediate) (1 equiv) in dry DMF (8 mL) was added, EDC.HCl (1.4 equiv) and HOBt (1.4 equiv) and the mixture was stirred for 10 min. To this, morpholine (1.5 equiv) and DIPEA (3 equiv) were added and the reaction mixture was stirred overnight. It was quenched with water (20 mL) and the aqueous layer was extracted with EtOAc (4×20 mL). The combined organic layer was washed with water (20 mL), 5% NaHCO$_3$ solution (20 mL), brine (25 mL), dried (Na$_2$SO$_4$) and filtered. The solvent was evaporated under reduced pressure and the crude product was purified by column chromatography to furnish the title compound.

Step-7: (4-Hydroxy-8-methylnaphthalen-1-yl)(morpholino)methanone

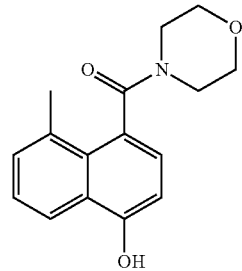 [SMILES: Cc1cccc2c(O)ccc(C(=O)N3CCOCC3)c12]

(4-Methoxy-8-methylnaphthalen-1-yl)(morpholino)methanone (above Step-6 intermediate) (1 equiv) was dissolved in dry CH$_2$Cl$_2$ (6 mL) and the solution was cooled to −78° C. To this, BBr$_3$ (3 equiv) dissolved in dry CH$_2$Cl$_2$ (3 mL) was added drop wise and the reaction mixture was allowed to stir at RT overnight. It was quenched slowly with brine solution (10 mL) and the aqueous layer was extracted with CH$_2$Cl$_2$ (4×10 mL). The combined organic layer was washed with water (10 mL), brine (10 mL), dried and filtered. The solvent was removed under reduced pressure to afford compound 7 that was used as such in the next step without any further purification.

Step-8: 5-Methyl-4-(morpholin-4-carbonyl)naphthalen-1-yl trifluoromethanesulfonate

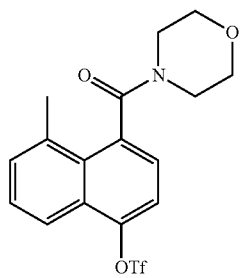 [SMILES: Cc1cccc2c(OS(=O)(=O)C(F)(F)F)ccc(C(=O)N3CCOCC3)c12]

To a solution of (4-hydroxy-8-methylnaphthalen-1-yl)(morpholino)methanone (above Step-7 intermediate) (1 equiv) in dry $CH_2Cl_2$ (4 mL) under nitrogen was added DIPEA (3 equiv) at 0° C. and the mixture was stirred for 10 min. To this, $Tf_2O$ (1.5 equiv) was added drop wise and the reaction mixture was stirred for another 1.5 h at 0° C. Then it was slowly quenched with water (10 mL) and the aqueous layer was extracted with $CH_2Cl_2$ (4×10 mL). The combined organic layer was washed with water (10 mL), brine (10 mL), dried ($Na_2SO_4$) and filtered. The solvent was removed under reduced pressure and the residue was purified by column to give the title compound.

Intermediate-22a: Preparation 5-alkyl-naphthalen-1-yl trifluoromethane sulfonate-4 carboxylic amide derivatives

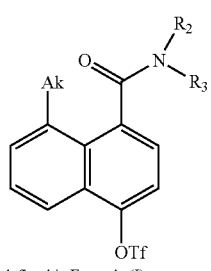

Ak is alkyl; $R_2$ and $R_3$ is as defined in Formula (I)

The amide derivatives of above formula were prepared by following the similar procedure as described in Step-6, step-7, step-8 of Intermediate-22 in a sequential manner by taking 4-methoxy-8-methyl-1-naphthoic acid and appropriate amine.

Intermediate-23: 5-Methyl-4-(piperidin-1-carbonyl)naphthalen-1-yl trifluoromethane sulfonate

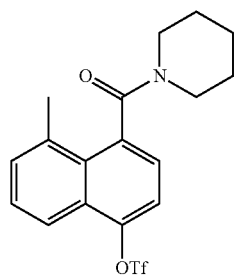 [SMILES: Cc1cccc2c(OS(=O)(=O)C(F)(F)F)ccc(C(=O)N3CCCCC3)c12]

The title compound was prepared in three steps as given below:

Step-1: (4-Methoxy-8-methylnaphthalen-1-yl)(piperidin-1-yl)methanone

4-Methoxy-8-methyl-1-naphthoic acid (Step-5 of Intermediate-22) was reacted with piperidine by following the similar procedure as described in Step-6 of Intermediate-22.

Step-2: (4-Hydroxy-8-methylnaphthalen-1-yl)(piperidin-1-yl)methanone

This compound was prepared by using (4-methoxy-8-methylnaphthalen-1-yl)(piperidin-1-yl)methanone (above step-1 intermediate) through the similar method as described in Step-7 of Intermediate-22.

Step-3: 5-Methyl-4-(piperidin-1-carbonyl)naphthalen-1-yl trifluoromethanesulfonate This compound was prepared by treating (4-hydroxy-8-methylnaphthalen-1-yl)(piperidin-1-yl)methanone (above step-2 intermediate) with $Tf_2O$ by following the similar procedure as described in Step-8 of Intermediate-22

Intermediate-24: 5-Methyl-4-(pyrrolidin-1-carbonyl)naphthalen-1-yl trifluoromethane sulfonate

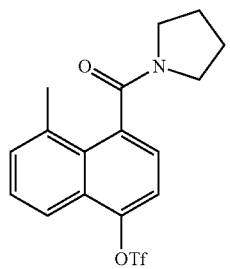 [SMILES: Cc1cccc2c(OS(=O)(=O)C(F)(F)F)ccc(C(=O)N3CCCC3)c12]

The title compound was prepared in three steps as given below:

Step-1: (4-Methoxy-8-methylnaphthalen-1-yl)(pyrrolidin-1-yl)methanone

4-Methoxy-8-methyl-1-naphthoic acid (Step-5 of Intermediate-22) was reacted with pyrrolidine by following the similar procedure as described in Step-6 of Intermediate-22.

Step-2: (4-Hydroxy-8-methylnaphthalen-1-yl)(pyrrolidin-1-yl)methanone

This compound was prepared by using (4-methoxy-8-methylnaphthalen-1-yl)(pyrrolidin-1-yl)methanone (above step-1 intermediate) through the similar procedure as described in Step-7 of Intermediate-22.

Step-3: 5-Methyl-4-(pyrrolidin-1-carbonyl)naphthalen-1-yl trifluoromethanesulfonate This compound was prepared by treating (4-hydroxy-8-methylnaphthalen-1-yl) (pyrrolidin-1-yl)methanone (above step-2 intermediate) with Tf₂O by following the similar procedure as described in Step-8 of Intermediate-22.

Intermediate-25: 4-(2-Oxa-5-azabicyclo[2.2.1]heptan-5-carbonyl)-5-methylnaphthalen-1-yl trifluoromethane sulfonate

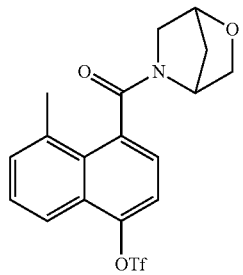 [SMILES: Cc1cccc2c(OS(=O)(=O)C(F)(F)F)ccc(C(=O)N3CC4CC3CO4)c12]

The title compound was prepared in three steps as given below:

Step-1: 2-Oxa-5-azabicyclo[2.2.1]heptan-5-yl(4-methoxy-8-methylnaphthalen-1-yl)methanone 4-Methoxy-8-methyl-1-naphthoic acid (Step-5 of Intermediate-22) was reacted with 2-oxa-5-azabicyclo[2.2.1]heptane by following the similar procedure as described in Step-6 of Intermediate-22.

Step-2: 2-Oxa-5-azabicyclo[2.2.1]heptan-5-yl(4-hydroxy-8-methylnaphthalen-1-yl)methanone This compound was prepared by using 2-oxa-5-azabicyclo[2.2.1]heptan-5-yl(4-methoxy-8-methylnaphthalen-1-yl)methanone (above step-1 intermediate) through the similar procedure as described in Step-7 of Intermediate-22.

Step-3: 4-(2-Oxa-5-azabicyclo[2.2.1]heptan-5-carbonyl)-5-methylnaphthalen-1-yl trifluoro methanesulfonate The title compound was prepared by treating 2-oxa-5-azabicyclo[2.2.1]heptan-5-yl(4-hydroxy-8-methylnaphthalen-1-yl)methanone (above step-2 intermediate) with Tf₂O using the similar procedure as described in Step-8 of Intermediate-22.

Intermediate-26: 4-(3-Azabicyclo[3.1.0]hexan-3-carbonyl)-5-methylnaphthalen-1-yl trifluoro methanesulfonate

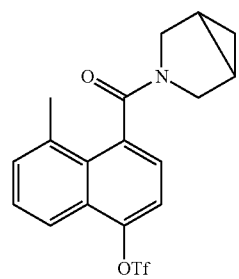 [SMILES: Cc1cccc2c(OS(=O)(=O)C(F)(F)F)ccc(C(=O)N3CC4CC4C3)c12]

The title compound was prepared in three steps as given below:

Step-1: 3-Azabicyclo[3.1.0]hexan-3-yl(4-methoxy-8-methylnaphthalen-1-yl)methanone 4-Methoxy-8-methyl-1-naphthoic acid (Step-5 of Intermediate-22) was reacted with 3-azabicyclo[3.1.0]hexane by following the similar procedure as described in Step-6 of Intermediate-22.

Step-2: 3-Azabicyclo[3.1.0]hexan-3-yl(4-hydroxy-8-methylnaphthalen-1-yl)methanone This compound was prepared by using 3-azabicyclo[3.1.0]hexan-3-yl(4-methoxy-8-methylnaphthalen-1-yl)methanone (above step-1 intermediate) through the similar method as described in Step-7 of Intermediate-22.

Step-3: 4-(3-Azabicyclo[3.1.0]hexan-3-carbonyl)-5-methylnaphthalen-1-yl trifluoromethane sulfonate The desired intermediate was prepared by treating 3-azabicyclo[3.1.0]hexan-3-yl(4-hydroxy-8-methylnaphthalen-1-yl)methanone (above step-2 intermediate) with Tf₂O using the similar procedure as described in Step-8 of Intermediate-22.

Intermediate-27: 4-(6-Oxa-3-azabicyclo[3.1.1]heptan-3-carbonyl)-5-methylnaphthalen-1-yl trifluoromethanesulfonate

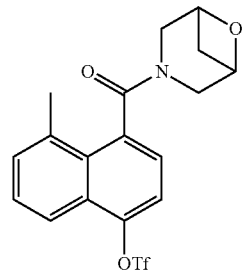 [SMILES: Cc1cccc2c(OS(=O)(=O)C(F)(F)F)ccc(C(=O)N3CC4CC(C3)O4)c12]

The title compound was prepared in three steps as given below:

Step-1: 6-Oxa-3-azabicyclo[3.1.1]heptan-3-yl(4-methoxy-8-methylnaphthalen-1-yl)methanone 4-Methoxy-8-methyl-1-naphthoic acid (Step-5 of Intermediate-22) was reacted with 6-oxa-3-azabicyclo[3.1.1]heptane by following the similar procedure as described in Step-6 of Intermediate-22.

Step-2: 6-Oxa-3-azabicyclo[3.1.1]heptan-3-yl(4-hydroxy-8-methylnaphthalen-1-yl)methanone This compound was prepared by using 6-oxa-3-azabicyclo[3.1.1]heptan-3-yl(4-methoxy-8-methylnaphthalen-1-yl)methanone (above step-1 intermediate) through the similar procedure as described in Step-7 of Intermediate-22.

Step-3: 4-(6-Oxa-3-azabicyclo[3.1.1]heptan-3-carbonyl)-5-methylnaphthalen-1-yl trifluoro methanesulfonate The title compound was prepared by treating 6-oxa-3-azabicyclo[3.1.1]heptan-3-yl(4-hydroxy-8-methylnaphthalen-1-yl)methanone (above step-2 intermediate) with Tf$_2$O using the similar procedure as described in Step-8 of Intermediate-22.

Intermediate-28: 5-Methyl-4-(2-oxa-6-azaspiro[3.3]heptan-6-carbonyl)naphthalen-1-yl trifluoro methanesulfonate

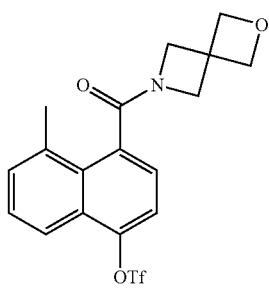 [SMILES: Cc1cccc2c(OS(=O)(=O)C(F)(F)F)ccc(C(=O)N3CC4(COC4)C3)c12]

The title compound was prepared in three steps as given below:

Step-1: (4-Methoxy-8-methylnaphthalen-1-yl)(2-oxa-6-azaspiro[3.3]heptan-6-yl)methanone 4-Methoxy-8-methyl-1-naphthoic acid (Step-5 of Intermediate-22) was reacted with 2-oxa-6-azaspiro[3.3]heptane by following the similar procedure as described in Step-6 of Intermediate-22.

Step-2: (4-Hydroxy-8-methylnaphthalen-1-yl)(2-oxa-6-azaspiro[3.3]heptan-6-yl)methanone This compound was prepared by using (4-methoxy-8-methylnaphthalen-1-yl)(2-oxa-6-azaspiro[3.3]heptan-6-yl)methanone (above step-1 intermediate) using similar procedure as described in Step-7 of Intermediate-22.

Step-3: 5-Methyl-4-(2-oxa-6-azaspiro[3.3]heptan-6-carbonyl)naphthalen-1-yl trifluoro methanesulfonate The title compound was prepared by treating (4-hydroxy-8-methylnaphthalen-1-yl)(2-oxa-6-azaspiro[3.3]heptan-6-yl)methanone (above step-2 intermediate) with Tf$_2$O using the similar procedure as described in Step-8 of Intermediate-22.

General Procedure A to Prepare Optionally Substituted 4-anilino-1-naphthoic acid

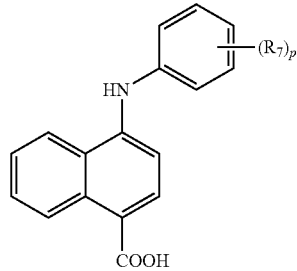

Step-1: 1-Amino-4-cyanonaphthalene

To a stirred solution of 1-amino-4-bromonaphthalene (5 g, 22.5 mmol) in DMF (30 mL) was added CuCN (10.1 g, 112.5 mmol), CuI (8.7 g, 45 mmol) and the mixture was heated to 120° C. in a sealed tube for 24 h. After completion of the reaction (TLC), the mixture was filtered and the filtrate was evaporated to give the crude product which was purified by column chromatography over silica gel (EtOAc in Hexanes, 5%) to furnish the desired compound.

Step-2: 4-((3-Chlorophenyl)amino)-1-naphthonitrile

To a stirred solution of 1-amino-4-cyanonaphthalene (1 equiv) in toluene (10 mL) was added the corresponding appropriately substituted iodobenzene (1.5 equiv), BINAP (0.25 equiv), Pd(OAc)$_2$ (0.2 equiv), Cs$_2$CO$_3$ (2 equiv) and the reaction mixture was heated in a sealed tube overnight. After completion of the reaction (TLC), mixture was filtered. The filtrate was evaporated to give the crude product that was purified by using combiflash (EtOAc in Hexanes, 4%) to afford the desired compound.

Step-3: 4-((optionally substituted phenyl)amino)-1-naphthoic acid

To a stirred solution of above Step-2 intermediate (1 equiv) in EtOH (40 mL) was added 50% aq. KOH solution (5 equiv) and the reaction mixture was refluxed for 1 day. The solvent was then removed under reduced pressure and to this, 1N HCl solution was added drop wise (pH~2) and extracted with EtOAc (3×200 mL), washed with water (50 mL), dried (Na$_2$SO$_4$), filtered and concentrated to give the corresponding acid derivative of the title compound.

The below Table-1, Intermediates 29 to 37 were prepared by using 1-amino-4-cyanonaphthalene by following the similar procedure as described in General procedure A

| Intermediate-29 | Intermediate-30 | Intermediate-31 |
|---|---|---|
| 4-((3-Chlorophenyl)amino)-1-naphthoic acid | 4-((3-Fluorophenyl)amino)-1-naphthoic acid | 4-((3,5-Difluorophenyl)amino)-1-naphthoic acid |

| Intermediate-32 | Intermediate-33 | Intermediate-34 |
|---|---|---|
| 4-((2,4-Difluorophenyl)amino)-1-naphthoic acid | 4-((2,4-Dichlorophenyl)amino)-1-naphthoic acid: | 4-((3-(Trifluoromethyl)phenyl)amino)-1-naphthoic acid |

| Intermediate-35 | Intermediate-36 | Intermediate-37 |
|---|---|---|
| 4-((4-Fluoro-3-(trifluoromethyl)phenyl)amino)-1-naphthoic acid | 4-((3-(Fluoromethyl)phenyl)amino)-1-naphthoic acid | 4-((3-(Difluoromethyl)phenyl)amino)-1-naphthoic acid |

Intermediate-38:
1-Methoxy-5-methylisoquinolin-4-sulfonylchloride

To a stirred solution of 4-bromo-1-methoxy-5-methylisoquinoline (3.5 g, 14 mmol) in dry THF was added, n-BuLi (17.5 mL, 28 mmol, 2 eq) dropwise at −78° C. and the mixture was stirred for 10 min. To this, dry $SO_2$ gas (excess) was purged and the mixture was stirred further at −78° C. for 30 min and then warmed to 0° C. Then, NCS (1.5 eq) was added and the reaction mixture was stirred for 10 min at 0° C. and then at RT for 1-1.5 h. It was quenched with saturated $NH_4Cl$ solution, extracted with EtOAc (3×100 mL), washed with water (1×200 mL), dried ($Na_2SO_4$), filtered and concentrated under reduced pressure to yield the desired compound (3.4 gm, 92%).

Intermediate-39:
1-Methoxy-5-methylisoquinolin-4-sulfonamide

To a solution of 1-methoxy-5-methylisoquinolin-4-sulfonylchloride (Intermediate-38) (1 equiv) in $CH_2Cl_2$ was added, DIPEA (2 equiv) and the corresponding amine (1.3 equiv) under $N_2$ and the mixture was stirred for 10 min at 0° C. and then at RT for 1 h. It was quenched with ice water, extracted with $CH_2Cl_2$ (2×100 mL), washed with water (1×100 mL), dried, filtered and concentrated under reduced pressure to furnish the product in 69-75% yield.

Intermediate-40: 1-Hydroxy-5-methylisoquinolin-4-sulfonamide

To a solution of 1-methoxy-5-methylisoquinolin-4-sulfonamide (Intermediate-39) (5 mmol) in DMF (5 mL) was added 47% aq. HBr (20 mL) and water (15 mL) at 0° C. and the reaction mixture was stirred at RT overnight. A white solid precipitated out that was filtered, washed with ice cold water, and dried under vacuum to afford the desired hydroxyl derivative in 75-80% yield.

Intermediate-41: 1-Chloro-5-methylisoquinolin-4-sulfonamide

A mixture of 1-hydroxy-5-methylisoquinolin-4-sulfonamide (Intermediate-40) (4 mmol) in $POCl_3$ (10 mL) was heated to 110° C. for 30 min. Then, it was poured into ice water to give precipitate that was filtered, washed with water, and dried to yield the desired compound in 80-86% yield.

Intermediate-41a: 4-((1-Chloro-5-methylisoquinolin-4-yl)sulfonyl)morpholine

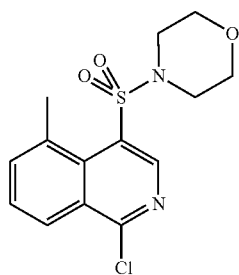 [SMILES: Cc1cccc2c(Cl)ncc(S(=O)(=O)N3CCOCC3)c12]

This intermediate was prepared from the corresponding morpholine amide derivative and $POCl_3$ by using the similar procedure as described in Intermediate-41.

Intermediate-41b: 1-Chloro-5-methyl-4-(piperidin-1-ylsulfonyl)isoquinoline

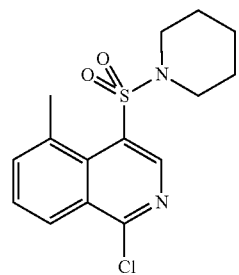 [SMILES: Cc1cccc2c(Cl)ncc(S(=O)(=O)N3CCCCC3)c12]

This intermediate was prepared from the corresponding piperidine amide derivative and $POCl_3$ by using the similar procedure as described in Intermediate-41.

Intermediate-42: Methyl 5-chloroisoquinolin-4-carboxylate

To a well stirred solution of conc. $H_2SO_4$ (28.5 mL) and methyl isoquinoline-4-carboxylate (5.0 g, 26.7 mmol) at 0° C. was added, NCS (35.7 g, 267 mmol) slowly and the reaction mixture was allowed to come to RT and then heated to 60° C. overnight. After completion (TLC), it was quenched with ice, neutralized ($NaHCO_3$) and extracted with EtOAc (100 mL×3). The organic phase was separated, dried ($Na_2SO_4$) and concentrated to give dark brown oil (4.6 g) as crude product that was purified by flash column chromatography (15% EtOAc in Hexanes) to furnish the desired compound (3.8 g, 64%) as pale yellow oil.

Intermediate-43: 1,5-Dichloroisoquinolin-4-carboxamide

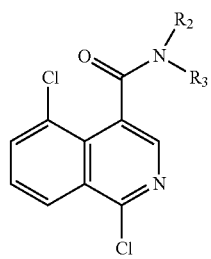

$R_2$ and $R_3$ is as defined in Formula (I)

This compound was obtained in 4 steps starting from Intermediate-42 as following:

Step-1: 5-Chloroisoquinolin-4-carboxylic acid

To a stirred solution of methyl 5-chloroisoquinolin-4-carboxylate (Intermediate-42) (3.8 g, 17.1 mmol) in MeOH (30 mL) was added, KOH (9.62 g, 171 mmol) solution in $H_2O$ (20 mL) and the reaction mixture was heated to 70° C. for 3 h. After completion (TLC), it was concentrated under vacuum to give crude product (3.5 g) that was diluted with water, acidified with 1N HCl (pH=3) and the aqueous phase was extracted with EtOAc, dried and concentrated under vacuum to afford the desired acid derivative (3 g, 84%) as an off white solid.

Step-2: 5-Chloroisoquinolin-4-carboxylic amide

A 100 mL RBF was charged with 5-chloroisoquinolin-4-carboxylic acid (1 equiv) in dry THF (20 mL), DIPEA (3 equiv), EDC.HCl (1.5 equiv), HOBT (1.5 equiv) under inert atmosphere and the mixture was stirred for 15 mins. To this, corresponding amine (1.2 equiv) was added dropwise and the reaction mixture was stirred overnight. After completion, it was diluted with EtOAc and water. The organic layer was then separated, dried and concentrated under reduced pressure to give the crude product that was purified by column chromatography using 100-200 silica gel (80% Ethyl acetate in Hexanes) to furnish the desired amide derivative in 70-84% yield.

Step-3: 5-Chloro-2-oxideisoquinolin-4-carboxylic amide

In a 100 mL sealed tube, 5-chloroisoquinolin-4-carboxylic amide (1 equiv) in $CH_2Cl_2$ (10 mL) was added, mCPBA (meta-Chloroperoxybenzoic acid) (2 equiv) at 0° C. and the reaction mixture was stirred overnight while allowing it to attain RT. After completion (TLC), it was diluted with $CH_2Cl_2$ (50 mL) and washed with 5% $NaHCO_3$ solution. The organic phase was separated, dried and concentrated to give the corresponding N-oxide derivative (80-92%).

Step-4: 1,5-Dichloroisoquinolin-4-carboxamide

A mixture of the corresponding 5-chloro-2-oxideisoquinolin-4-carboxamide (1 equiv) in POCl$_3$ (3 equiv) was heated to 110° C. for 30 min. Then, it was poured into ice water to give precipitate that was filtered, washed with water, dried and quickly filtered through silica gel to yield the desired title compound.

Intermediate-43a: (1,5-Dichloroisoquinolin-4-yl)(piperidin-1-yl)methanone

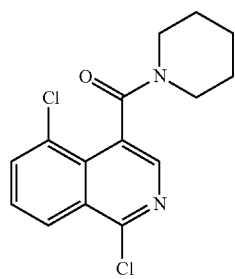 [SMILES: O=C(c1cnc(Cl)c2cccc(Cl)c12)N1CCCCC1]

A mixture of the corresponding 5-chloro-2-oxideisoquinolin-4-carboxamide (1 equiv) in POCl$_3$ (3 equiv) was heated to 110° C. for 30 min. Then, it was poured into ice water to give precipitate that was filtered, washed with water, dried and quickly filtered through silica gel to yield the desired compound.

Intermediate-43b: (1,5-Dichloroisoquinolin-4-yl)(morpholino)methanone

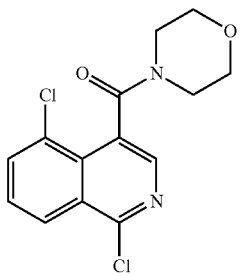 [SMILES: O=C(c1cnc(Cl)c2cccc(Cl)c12)N1CCOCC1]

This intermediate was prepared from the corresponding morpholine amide derivative and POCl$_3$ by using the similar procedure as described above. Intermediate-44: (5-Alkyl-1-methoxyisoquinolin-4-yl)methanamine To a stirred solution of 5-alkyl-1-methoxyisoquinolin-4-carboxyldehyde (Intermediate-7) (1 equiv) in MeOH was added, the corresponding amine (1.2 equiv) and AcOH (1.5 equiv) at RT. The mixture was heated to 70-75° C. for 30 min. and then cooled to RT again. To this, NaCNBH$_3$ (2 equiv) was added slowly and the reaction mixture was heated to 70-75° C. for 16 h. The solvent was removed under reduced pressure and the reaction mixture was diluted with aq. NaHCO$_3$ solution, extracted with EtOAc (3×100 mL), washed with water (1×200 mL), dried (Na$_2$SO$_4$), filtered and concentrated under vacuum to give the crude product that was purified by combiflash to furnish the corresponding methanamine in 50-60% yield.

Intermediate-45: (5-Alkyl-1-hydroxyisoquinolin-4-yl)methanamine

A well stirred solution of (5-alkyl-1-methoxyisoquinolin-4-yl)methanamine (Intermediate-44) (1 equiv) in DMF (5 mL) was cooled to 0° C. and to this, 47% aq. HBr (20 mL) and ice cold water (15 mL) were added. The reaction mixture was then stirred at RT for 2 days. After neutralization, a white solid precipitated out that was filtered, washed with cold water, and dried under high vacuum to get the desired hydroxy derivative in 70-75% yield.

Intermediate-46: (5-Alkyl-1-chloroisoquinolin-4-yl)methanamine

A mixture of the corresponding (5-alkyl-1-hydroxyisoquinolin-4-yl)methanamine (Intermediate-45) (1 equiv) in POCl$_3$ (3 equiv) was heated to 110° C. for 30 min. Then, it was poured into ice water to give precipitate that was filtered, washed with water, and dried under vacuum to afford the desired compound in 80-86% yield.

Intermediate-46a: 4-(1-Chloro-5-methylisoquinolin-4-yl)methyl)morpholine

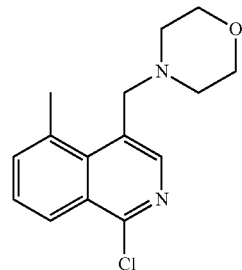 [SMILES: Cc1cccc2c(Cl)ncc(CN3CCOCC3)c12]

This intermediate was prepared from the corresponding morpholine derivative and POCl$_3$ by using the similar procedure as described for Intermediate-46.

Intermediate-46b: 1-Chloro-5-methyl-4-(piperidin-1-ylmethyl)isoquinoline

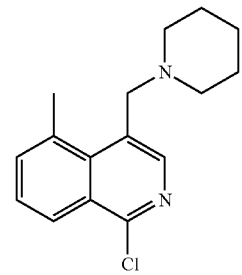 [SMILES: Cc1cccc2c(Cl)ncc(CN3CCCCC3)c12]

This intermediate was prepared from the corresponding piperidine derivative and POCl$_3$ by using the similar procedure as described for Intermediate-46.

EXAMPLES

The present invention is further illustrated by the following examples, which are not to be construed in any way as imposing limitations upon the scope of this disclosure, but rather are intended to be illustrative only.

Example-1

(1-((3-Chlorophenyl)amino)-5-methylisoquinolin-4-yl)(morpholino)methanone

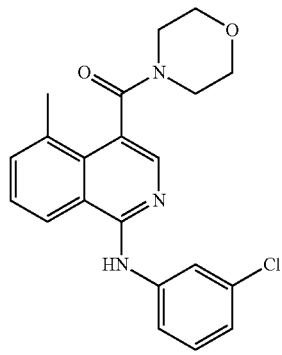 [SMILES: Cc1cccc2c(Nc3cccc(Cl)c3)ncc(C(=O)N3CCOCC3)c12]

To a stirred solution of Intermediate-11a (100 mg, 0.3 mmol) in toluene was added 3-chloroaniline (1.5 equiv), BINAP (0.25 equiv), Pd(OAc)$_2$ (0.2 equiv), CS$_2$CO$_3$ (2 equiv) and the reaction mixture was heated in a sealed tube for 6-7 h. After the completion of reaction (TLC), the inorganic solids were filtered through celite bed and the filtrate was evaporated to give the crude product which was purified by combiflash using EtOAc:Hexane (1:1) to furnish the title compound. $^1$H NMR (400 MHz, CDCl$_3$) δ 2.58 (s, 3H), 3.25-4.14 (m, 8H), 7.04-7.06 (m, 1H), 7.28-7.30 (d, 1H, J=8.0 Hz), 7.36 (s, 1H), 7.46-7.52 (m, 3H), 7.82-7.85 (m, 2H), 7.95 (s, 1H); MS m/z 382 (M+1).

Example-2

(1-((3-Fluorophenyl)amino)-5-methylisoquinolin-4-yl)(morpholino)methanone

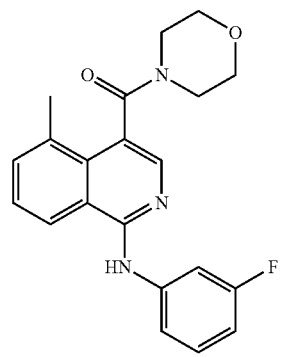 [SMILES: Cc1cccc2c(Nc3cccc(F)c3)ncc(C(=O)N3CCOCC3)c12]

The title compound was prepared by using Intermediate-11a and 3-fluoroaniline by following the similar procedure as described in Example-1; $^1$H NMR (400 MHz, CDCl$_3$) δ 2.57 (s, 3H), 3.25-4.15 (m, 8H), 6.74-6.79 (m, 1H), 7.27-7.32 (m, 2H), 7.45-7.51 (m, 3H), 7.66-7.70 (m, 1H), 7.83-7.86 (m, 1H), 7.95 (s, 1H); MS m/z 366 (M+1).

Example-3

(1-((3,5-Difluorophenyl)amino)-5-methylisoquinolin-4-yl)(morpholino)methanone

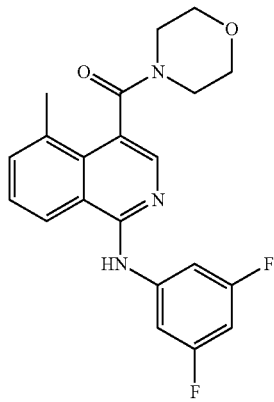 [SMILES: Cc1cccc2c(Nc3cc(F)cc(F)c3)ncc(C(=O)N3CCOCC3)c12]

The title compound was prepared by using Intermediate-11a and 3,5-difluoroaniline by following the similar procedure as described in Example-1; $^1$H NMR (400 MHz, CDCl$_3$) δ 2.58 (s, 3H), 3.25-4.15 (m, 8H), 6.49-6.54 (m, 1H), 7.31-7.34 (m, 2H), 7.43 (s, 1H), 7.50-7.53 (m, 2H), 7.81-7.83 (dd, 1H, J=8.0 Hz, 2.0 Hz), 7.97 (s, 1H); MS m/z 384 (M+1).

Example-4

(5-Methyl-1-((3-(trifluoromethyl)phenyl)amino)isoquinolin-4-yl)(morpholino)methanone

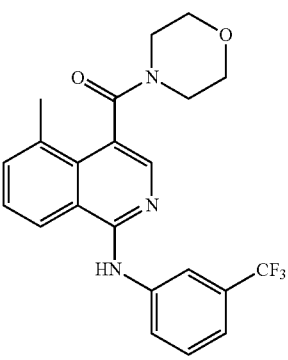 [SMILES: Cc1cccc2c(Nc3cccc(C(F)(F)F)c3)ncc(C(=O)N3CCOCC3)c12]

The title compound was prepared by using Intermediate-11a and 3-(trifluoromethyl)aniline by following the similar procedure as described in Example-1; $^1$H NMR (400 MHz, CDCl$_3$) δ 2.56 (s, 3H), 3.27-4.14 (m, 8H), 7.30-7.32 (d, 1H, J=8.0 Hz), 7.44-7.5 (m, 4H), 7.83-7.88 (m, 2H), 7.93 (s, 1H), 7.96 (s, 1H); MS m/z 416 (M+1).

Example-5

(1-((4-Fluorophenyl)amino)-5-methylisoquinolin-4-yl)(morpholino)methanone

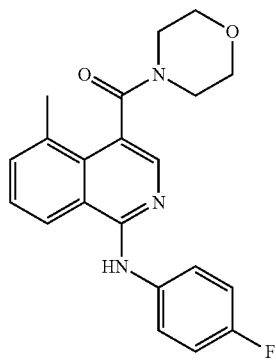 [SMILES: Cc1cccc2c(Nc3ccc(F)cc3)ncc(C(=O)N3CCOCC3)c12]

This compound was prepared by using Intermediate-11a and 4-fluoroaniline by following the similar procedure as described in Example-1; $^1$H NMR (400 MHz, CDCl$_3$) δ 2.62 (s, 3H), 3.28-4.16 (m, 8H), 7.09-7.13 (m, 2H), 7.19 (s, 1H), 7.51-7.61 (m, 4H), 7.86-7.88 (m, 1H), 7.95 (s, 1H); MS m/z 366 (M+1).

Example-6

(1-((4-Fluoro-3-(trifluoromethyl)phenyl)amino)-5-methylisoquinolin-4-yl)(morpholino)methanone

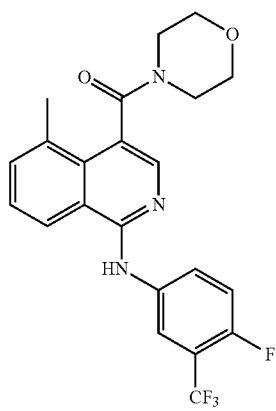 [SMILES: Cc1cccc2c(Nc3ccc(F)c(C(F)(F)F)c3)ncc(C(=O)N3CCOCC3)c12]

The title compound was prepared by using Intermediate-11a and 4-fluoro-3-(trifluoromethyl)aniline by following the similar procedure as described in Example-1; $^1$H NMR (400 MHz, CDCl$_3$) δ 2.56 (s, 3H), 3.25-4.14 (m, 8H), 7.17-7.22 (t, 1H, J=9.2 Hz), 7.45-7.51 (m, 3H), 7.81-7.92 (m, 4H); MS m/z 434 (M+1).

Example-7

(1-((2,4-Difluorophenyl)amino)-5-methylisoquinolin-4-yl)(morpholino)methanone

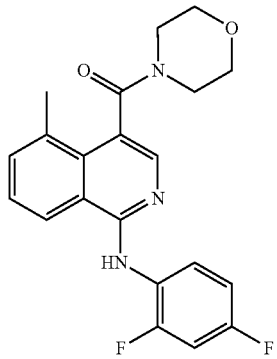

This compound was prepared by using Intermediate-11a and 2,4-difluoroaniline by following the similar procedure as described in Example-1; $^1$H NMR (400 MHz, CDCl$_3$) δ 2.6 (s, 3H), 3.25-4.14 (m, 8H), 6.91-6.97 (m, 2H), 7.3 (s, 1H), 7.52-7.56 (m, 2H), 7.87-7.89 (m, 1H), 7.95 (s, 1H), 8.35-8.38 (m, 1H); MS m/z 384 (M+1)

Example-8

(1-((3,4-Difluorophenyl)amino)-5-methylisoquinolin-4-yl)(morpholino)methanone

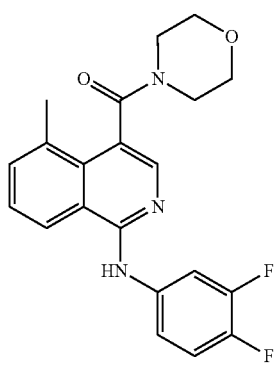

This compound was prepared by using Intermediate-11a and 3,4-difluoroaniline by following the similar procedure as described in Example-1; $^1$H NMR (400 MHz, CDCl$_3$) δ 2.57 (s, 3H), 3.26-4.14 (m, 8H), 7.12-7.2 (m, 2H), 7.29 (s, 1H), 7.47-7.53 (m, 2H), 7.76-7.83 (m, 2H), 7.95 (s, 1H); MS m/z 384 (M+1).

Example-9

(1-((2,3-Difluorophenyl)amino)-5-methylisoquinolin-4-yl)(morpholino)methanone

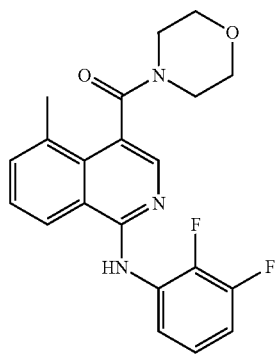

The title compound was prepared by using Intermediate-11a and 2,3-difluoroaniline by following the similar procedure as described in Example-1; $^1$H NMR (400 MHz, CDCl$_3$) δ 2.63 (s, 3H), 3.27-4.17 (m, 8H), 6.85-6.92 (m, 1H), 7.09-7.16 (m, 1H), 7.48-7.49 (m, 1H), 7.55-7.58 (m, 2H), 7.91-7.93 (m, 1H), 8.01 (s, 1H), 8.24-8.26 (m, 1H); MS m/z 384 (M+1).

Example-10

(1-((3-Chloro-2-fluorophenyl)amino)-5-methylisoquinolin-4-yl)(morpholino)methanone

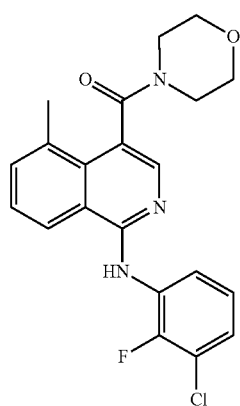

This compound was prepared by using Intermediate-11a and 3-chloro-2-fluoroaniline by following the similar procedure as described in Example-1; $^1$H NMR (400 MHz, CDCl$_3$) δ 2.61 (s, 3H), 3.27-4.14 (m, 8H), 7.05-7.12 (m, 2H), 7.48-7.49 (m, 1H), 7.53-7.57 (m, 2H), 7.88-7.91 (m, 1H), 7.99 (s, 1H), 7.40-7.44 (m, 1H); MS m/z 400 (M+1).

Example-11

(1-((3-Chloro-4-fluorophenyl)amino)-5-methylisoquinolin-4-yl)(morpholino)methanone

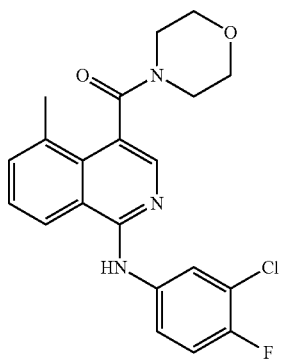

This compound was prepared by using Intermediate-11a and 3-chloro-4-fluoroaniline by following the similar procedure as described in Example-1; $^1$H NMR (400 MHz, CDCl$_3$) δ 2.59 (s, 3H), 3.27-4.16 (m, 8H), 7.12-7.17 (s, 1H, J=8.8 Hz), 7.31 (s, 1H), 7.43-7.54 (m, 3H), 7.83-7.87 (m, 2H), 7.95 (s, 1H); MS m/z 400 (M+1).

Example-12

(1-(((3-Fluoromethyl)phenyl)amino)-5-methylisoquinolin-4-yl)(morpholino)methanone

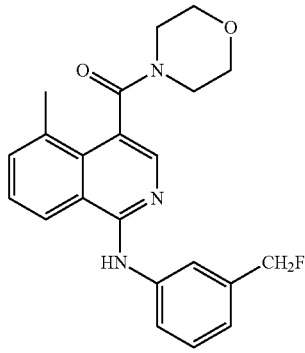

The title compound was prepared by using Intermediate-11a and 3-(fluoromethyl)aniline by following the similar procedure as described in Example-1; $^1$H NMR (400 MHz, CDCl$_3$) δ 2.61 (s, 3H), 3.27-4.16 (m, 8H), 5.37-5.49 (d, 2H, J=48.0 Hz), 7.11-7.13 (d, 1H, J=7.2 Hz), 7.32 (s, 1H), 7.40-7.44 (t, 1H, J=7.6 Hz), 7.51-7.56 (m, 2H), 7.64-7.67 (d, 1H, J=7.2 Hz), 7.73-7.74 (m, 1H), 7.87-7.89 (m, 1H), 8.0 (s, 1H); MS m/z 380 (M+1).

Example-13

(1-(((3-Difluoromethyl)phenyl)amino)-5-methylisoquinolin-4-yl)(morpholino)methanone

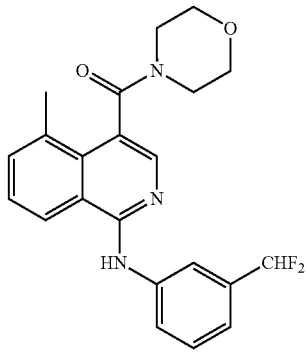 [SMILES: Cc1cccc2c(Nc3cccc(C(F)F)c3)ncc(C(=O)N3CCOCC3)c12]

The title compound was prepared by using Intermediate-11a and 3-(difluoromethyl)aniline by following the similar procedure as described in Example-1; $^1$H NMR (400 MHz, CDCl$_3$) δ 2.59 (s, 3H), 3.26-4.14 (m, 8H), 6.53-6.82 (t, 2H, J=56.8 Hz), 7.21-7.23 (m, 1H), 7.38 (s, 1H), 7.44-7.54 (m, 3H), 7.76-7.78 (m, 1H), 7.85-7.87 (m, 2H), 7.97 (s, 1H); MS m/z 398 (M+1).

Example-14

1-((3-Chlorophenyl)amino)-5-methyl-N-((tetrahydro-2H-pyran-4-yl)methyl)isoquinolin-4-carboxamide

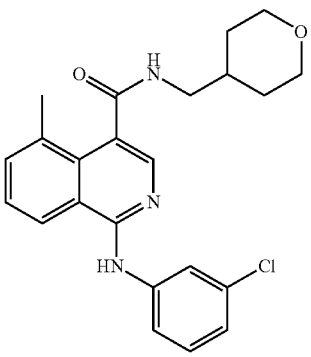 [SMILES: Cc1cccc2c(Nc3cccc(Cl)c3)ncc(C(=O)NCC3CCOCC3)c12]

The title compound was prepared by using Intermediate-11b and 3-chloroaniline by following the similar procedure as described in Example-1; $^1$H NMR (400 MHz, CDCl$_3$) δ 1.40-1.46 (m, 2H), 1.70-1.74 (m, 2H), 1.93-1.94 (m, 1H), 2.64 (s, 3H), 3.38-3.45 (m, 4H), 4.00-4.03 (dd, 2H, J=11.0 Hz, 4.0 Hz), 5.85 (s, 1H), 6.15 (s, 1H), 6.82-6.93 (m, 1H), 7.04-7.06 (m, 1H), 7.14-7.29 (m, 2H), 7.43-7.53 (m, 3H), 7.78-7.83 (m, 2H), 8.08 (s, 1H); MS m/z 410 (M+1).

Example-15

1-((3,5-Difluorophenyl)amino)-5-methyl-N-((tetrahydro-2H-pyran-4-yl)methyl)isoquinolin-4-carboxamide

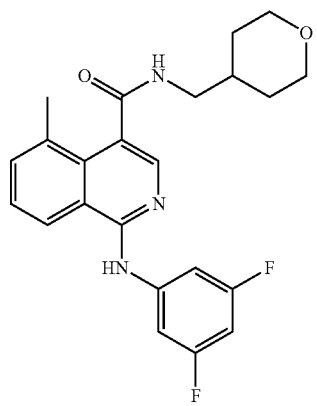 [SMILES: Cc1cccc2c(Nc3cc(F)cc(F)c3)ncc(C(=O)NCC3CCOCC3)c12]

The title compound was prepared by using Intermediate-11b and 3,5-difluoroaniline by following the similar procedure as described in Example-1; $^1$H NMR (400 MHz, CDCl$_3$) δ 1.40-1.47 (m, 2H), 1.71-1.75 (m, 2H), 1.92-1.98 (m, 1H), 2.63 (s, 3H), 3.39-3.45 (m, 4H), 4.00-4.03 (dd, 2H, J=11.0 Hz, 4.0 Hz), 6.08 (s, 1H), 6.48-6.52 (m, 1H), 7.30-7.33 (m, 2H), 7.44-7.52 (m, 3H), 7.76-7.78 (d, 1H, J=7.6 Hz), 8.08 (s, 1H); MS m/z 412 (M+1).

Example-16

1-((3-Fluorophenyl)amino)-5-methyl-N-((tetrahydro-2H-pyran-4-yl)methyl)isoquinolin-4-carboxamide

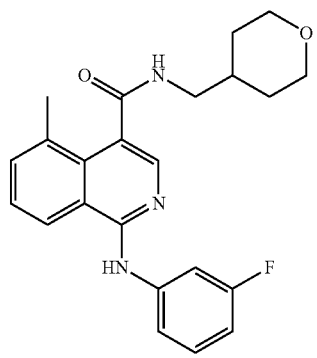 [SMILES: Cc1cccc2c(Nc3cccc(F)c3)ncc(C(=O)NCC3CCOCC3)c12]

The title compound was prepared by using Intermediate-11b and 3-fluoroaniline by following the similar procedure as described in Example-1; $^1$H NMR (400 MHz, CDCl$_3$) δ 1.45-1.49 (m, 2H), 1.73-1.77 (m, 2H), 1.96-1.98 (m, 1H), 2.67 (s, 3H), 3.41-3.47 (m, 4H), 4.02-4.06 (dd, 2H, J=11.0 Hz, 4.0 Hz), 6.14 (s, 1H), 6.80-6.81 (m, 1H), 7.26-7.36 (m, 3H), 7.49-7.56 (m, 2H), 7.70-7.73 (m, 2H), 8.08 (s, 1H); MS m/z 394 (M+1).

Example-17

1-((4-Fluorophenyl)amino)-5-methyl-N-((tetrahydro-2H-pyran-4-yl)methyl)isoquinolin-4-carboxamide

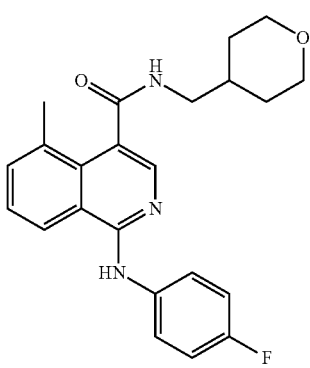 [SMILES: Cc1cccc2c(Nc3ccc(F)cc3)ncc(C(=O)NCC3CCOCC3)c12]

The title compound was prepared by using Intermediate-11b and 4-fluoroaniline by following the similar procedure as described in Example-1; $^1$H NMR (400 MHz, CDCl$_3$) δ 1.40-1.47 (m, 2H), 1.71-1.75 (m, 2H), 1.94-1.95 (m, 1H), 2.66 (s, 3H), 3.39-3.46 (m, 4H), 4.01-4.04 (dd, 2H, J=11.0 Hz, 4.0 Hz), 6.11 (s, 1H), 7.07-7.11 (m, 2H), 7.23 (s, 1H), 7.48-7.59 (m, 4H), 7.81-7.83 (d, 1H, J=8.0 Hz), 8.06 (s, 1H); MS m/z 394 (M+1).

Example-18

N-(tert-Butyl)-1-((3-chlorophenyl)amino)-5-methyl-isoquinolin-4-carboxamide

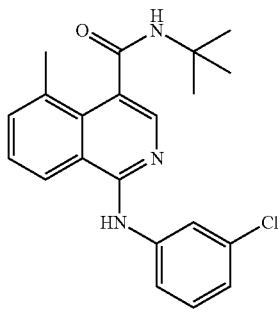 [SMILES: Cc1cccc2c(Nc3cccc(Cl)c3)ncc(C(=O)NC(C)(C)C)c12]

The title compound was prepared by using Intermediate-11c and 3-chloroaniline by following the similar procedure as described in Example-1; $^1$H NMR (400 MHz, DMSO-d$_6$) δ 1.40 (s, 9H), 2.64 (s, 3H), 7.01-7.04 (m, 1H), 7.32-7.36 (t, 1H, J=8.0 Hz), 7.55-7.61 (m, 2H), 7.75-7.78 (m, 1H), 7.92 (s, 1H), 8.07-8.08 (t, 1H, J=2.0 Hz), 8.15 (s, 1H), 8.39-8.42 (m, 1H), 9.40 (s, 1H); MS m/z 368 (M+1).

Example-19

N-(tert-Butyl)-1-((3-fluorophenyl)amino)-5-methyl-isoquinolin-4-carboxamide

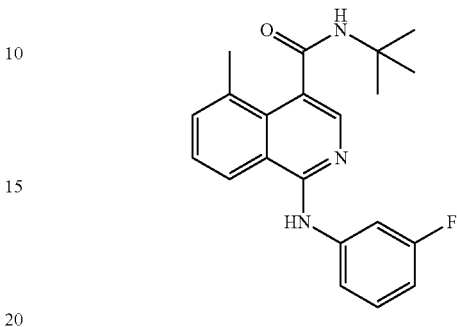

The title compound was prepared by using Intermediate-11c and 3-fluoroaniline by following the similar procedure as described in Example-1; $^1$H NMR (400 MHz, DMSO-d$_6$) δ 1.40 (s, 9H), 2.64 (s, 3H), 6.76-6.81 (m, 1H), 7.30-7.36 (q, 1H, J=8.0 Hz), 7.55-7.63 (m, 3H), 7.88-7.92 (m, 2H), 8.15 (s, 1H), 8.40-8.42 (dd, 1H, J=8.0 Hz, 2.0 Hz), 9.42 (s, 1H); MS m/z 352 (M+1).

Example-20

N-(tert-Butyl)-1-((3,5-difluorophenyl)amino)-5-methylisoquinolin-4-carboxamide

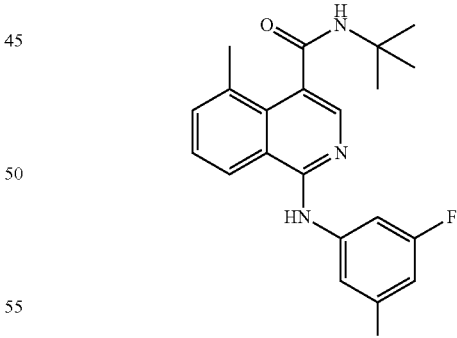

The title compound was prepared by using Intermediate-11c and 3,5-difluoroaniline by following the similar procedure as described in Example-1; $^1$H NMR (400 MHz, DMSO-d$_6$) δ 1.40 (s, 9H), 2.64 (s, 3H), 6.75-6.79 (m, 1H), 7.57-7.71 (m, 4H), 7.96 (s, 1H), 8.16 (s, 1H), 8.38-8.40 (dd, 1H, J=8.0 Hz, 2.0 Hz), 9.57 (s, 1H); MS m/z 370 (M+1).

Example-21

(1-((3-Fluorophenyl)amino)-5-methylisoquinolin-4-yl)(piperidino)methanone

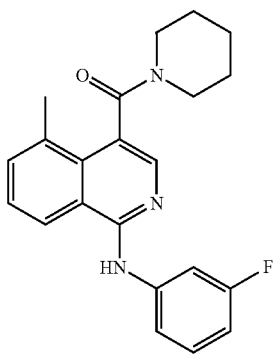

The title compound was prepared by using Intermediate-11d and 3-fluoroaniline by following the similar procedure as described in Example-1; $^1$H NMR (400 MHz, CDCl$_3$) δ 1.49-1.78 (m, 6H), 2.59 (s, 3H), 3.12-3.2 (m, 1H), 3.40-3.49 (m, 2H), 4.15-4.18 (m, 1H), 6.76-6.8 (m, 1H), 7.25-7.32 (m, 3H), 7.46-7.51 (m, 2H), 7.66-7.7 (m, 1H), 7.83-7.85 (dd, 1H, J=7.6 Hz, 1.6 Hz), 7.96 (s, 1H); MS m/z 364 (M+1).

Example-22

(1-((3-Chlorophenyl)amino)-5-methylisoquinolin-4-yl)(piperidin-1-yl)methanone

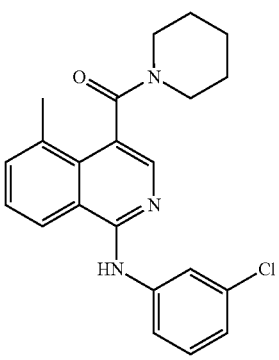

The title compound was prepared by using Intermediate-11d and 3-chloroaniline by following the similar procedure as described in Example-1; $^1$H NMR (400 MHz, CDCl$_3$) δ 1.49-1.76 (m, 6H), 2.59 (s, 3H), 3.12-3.19 (m, 1H), 3.40-3.49 (m, 2H), 4.15-4.18 (m, 1H), 7.02-7.04 (d, 1H, J=7.6 Hz), 7.24-7.29 (m, 2H), 7.45-7.50 (m, 3H), 7.81-7.84 (m, 2H), 7.96 (s, 1H); MS m/z 380 (M+1).

Example-23

(5-Methyl-1-(((3-trifluoromethyl)phenyl)amino)isoquinolin-4-yl)(piperidin-1-yl)methanone

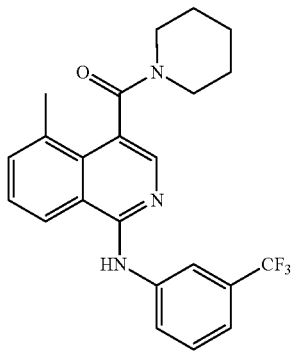

This compound was prepared by using Intermediate-11d and 3-(trifluoromethyl)aniline by following the similar procedure as described in Example-1; $^1$H NMR (400 MHz, CDCl$_3$) δ 1.50-1.78 (m, 6H), 2.57 (s, 3H), 3.15-3.19 (m, 1H), 3.40-3.50 (m, 2H), 4.15-4.18 (m, 1H), 7.29-7.31 (d, 1H, J=7.6 Hz), 7.43-7.48 (m, 3H), 7.51 (s, 1H), 7.84-7.90 (m, 2H), 7.93 (s, 1H), 7.97 (s, 1H); MS m/z 414 (M+1).

Example-24

(1-((3,5-Difluorophenyl)amino)-5-methylisoquinolin-4-yl)(piperidin-1-yl)methanone

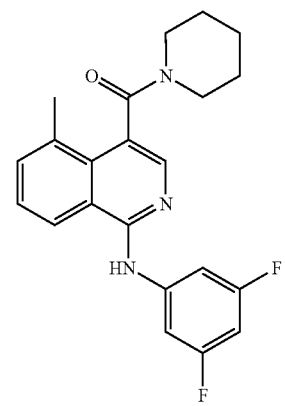

The title compound was prepared by using Intermediate-11d and 3,5-difluoroaniline by following the similar procedure as described in Example-1; $^1$H NMR (400 MHz, CDCl$_3$) δ 1.49-1.78 (m, 6H), 2.56 (s, 3H), 3.14-3.19 (m, 1H), 3.40-3.51 (m, 2H), 4.16-4.19 (m, 1H), 6.45-6.51 (m, 1H), 7.30-7.34 (m, 2H), 7.43-7.48 (m, 2H), 7.56 (s, 1H), 7.79-7.81 (m, 1H), 7.92 (s, 1H); MS m/z 382 (M+1).

Example-25

(1-((2,4-Dichlorophenyl)amino)-5-methylisoquinolin-4-yl)(piperidin-1-yl)methanone

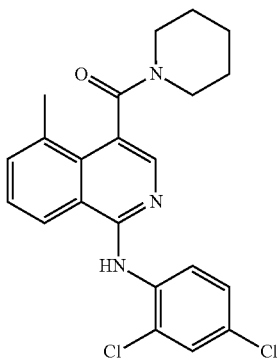 [SMILES: Cc1cccc2c(Nc3ccc(Cl)cc3Cl)ncc(C(=O)N3CCCCC3)c12]

This compound was prepared by using Intermediate-11d and 2,4-dichloroaniline by following the similar procedure as described in Example-1; $^1$H NMR (400 MHz, CDCl$_3$) δ 1.48-1.81 (m, 6H), 2.62 (s, 3H), 3.15-3.21 (m, 1H), 3.43-3.50 (m, 2H), 4.19-4.22 (m, 1H), 7.47-7.55 (m, 2H), 7.60-7.64 (t, 1H, J=7.6 Hz), 7.82-7.83 (m, 1H), 7.90-7.92 (d, 1H, J=8.8 Hz), 8.02 (s, 1H), 8.78-8.79 (d, 1H, J=7.6 Hz); MS m/z 414 (M+1).

Example-26

(1-((4-Fluorophenyl)amino)-5-methylisoquinolin-4-yl)(piperidin-1-yl)methanone

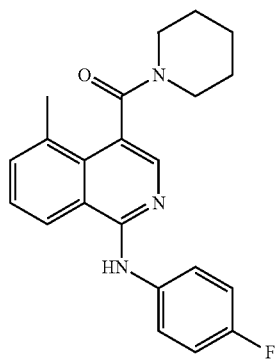

The title compound was prepared by using Intermediate-11d and 4-fluoroaniline by following the similar procedure as described in Example-1; $^1$H NMR (400 MHz, CDCl$_3$) δ 1.49-1.78 (m, 6H), 2.59 (s, 3H), 3.12-3.19 (m, 1H), 3.40-3.49 (m, 2H), 4.12-4.17 (m, 1H), 7.05-7.09 (m, 2H), 7.18 (s, 1H), 7.45-7.58 (m, 4H), 7.83-7.85 (m, 1H), 7.91 (s, 1H); MS m/z 364 (M+1).

Example-27

(1-((4-Fluoro-3-(trifluoromethyl)phenyl)amino)-5-methylisoquinolin-4-yl)(piperidin-1-yl)methanone

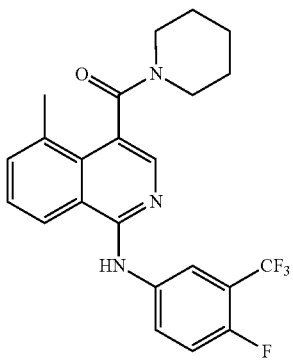

This compound was prepared by using Intermediate-11d and 4-fluoro-3-(trifluoromethyl)aniline by following the similar procedure as described in Example-1; $^1$H NMR (400 MHz, CDCl$_3$) δ 1.50-1.78 (m, 6H), 2.58 (s, 3H), 3.13-3.19 (m, 1H), 3.40-3.50 (m, 2H), 4.15-4.18 (m, 1H), 7.17-7.22 (t, 1H, J=9.2 Hz), 7.36 (s, 1H), 7.47-7.49 (m, 2H), 7.82-7.90 (m, 4H); MS m/z 432 (M+1).

Example-28

(1-((2,4,5-Trifluorophenyl)amino)-5-methylisoquinolin-4-yl)(piperidin-1-yl)methanone

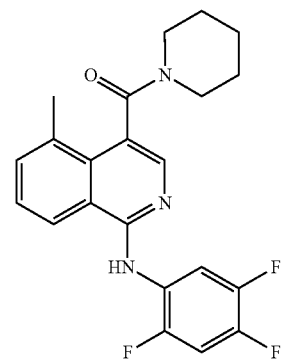

The title compound was prepared by using Intermediate-11d and 2,4,5-trifluoroaniline by following the similar procedure as described in Example-1; $^1$H NMR (400 MHz, CDCl$_3$) δ 1.50-1.78 (m, 6H), 2.61 (s, 3H), 3.13-3.18 (m, 1H), 3.38-3.49 (m, 2H), 4.15-4.18 (m, 1H), 6.99-7.07 (m, 1H), 7.39 (s, 1H), 7.51-7.54 (m, 2H), 7.83-7.85 (m, 1H), 7.99 (s, 1H), 8.61-8.66 (m, 1H); MS m/z 400 (M+1).

Example-29

(1-((2,4-Difluorophenyl)amino)-5-methylisoquinolin-4-yl)(piperidin-1-yl)methanone

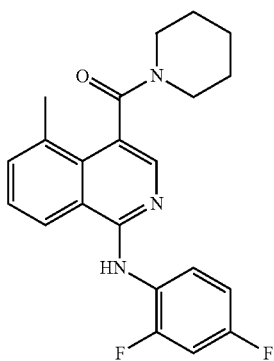

This compound was prepared by using Intermediate-11d and 2,4-difluoroaniline by following the similar procedure as described in Example-1; $^1$H NMR (400 MHz, CDCl$_3$) δ 1.52-1.78 (m, 6H), 2.63 (s, 3H), 3.14-3.20 (m, 1H), 3.41-3.51 (m, 2H), 4.15-4.20 (m, 1H), 6.94-6.99 (m, 2H), 7.30-7.31 (m, 1H), 7.52-7.56 (m, 2H), 7.88-7.91 (m, 1H), 7.97 (s, 1H), 8.38-8.44 (m, 1H); MS m/z 382 (M+1).

Example-30

(1-((3,4-Difluorophenyl)amino)-5-methylisoquinolin-4-yl)(piperidin-1-yl)methanone

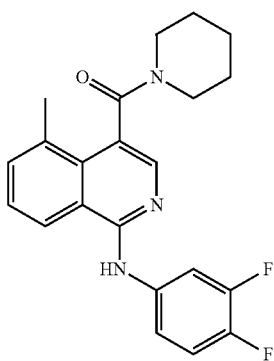

The above compound was prepared by using Intermediate-11d and 3,4-difluoroaniline by following the similar procedure as described in Example-1; $^1$H NMR (400 MHz, CDCl$_3$) δ 1.49-1.78 (m, 6H), 2.58 (s, 3H), 3.12-3.19 (m, 1H), 3.40-3.49 (m, 2H), 4.13-4.18 (m, 1H), 7.13-7.20 (m, 3H), 7.45-7.51 (m, 2H), 7.75-7.82 (m, 2H), 7.96 (s, 1H); MS m/z 382 (M+1).

Example-31

(5-Methyl-1-(((4-trifluoromethyl)phenyl)amino)isoquinolin-4-yl)(piperidin-1-yl)methanone

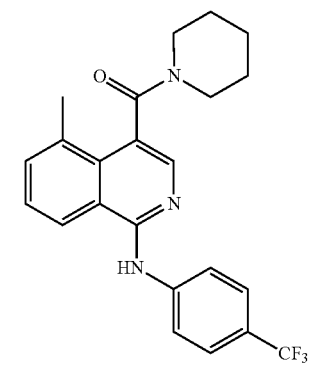 [SMILES: Cc1cccc2c(Nc3ccc(C(F)(F)F)cc3)ncc(C(=O)N3CCCCC3)c12]

This compound was prepared by using Intermediate-11d and 4-(trifluoromethyl)aniline by following the similar procedure as described in Example-1; $^1$H NMR (400 MHz, CDCl$_3$) δ 1.49-1.76 (m, 6H), 2.59 (s, 3H), 3.12-3.18 (m, 1H), 3.38-3.49 (m, 2H), 4.13-4.18 (m, 1H), 7.40 (s, 1H), 7.47-7.52 (m, 2H), 7.59-7.61 (d, 2H, J=8.4 Hz), 7.75-7.77 (d, 2H, J=8.4 Hz), 7.85-7.87 (m, 1H), 7.96 (s, 1H); MS m/z 414 (M+1).

Example-32

(1-((2-Chloro-4-(trifluoromethyl)phenyl)amino)-5-methylisoquinolin-4-yl)(piperidin-1-yl)methanone The title compound was prepared by using Intermediate-11d and 2-chloro-4-(trifluoromethyl)aniline by following the similar procedure as described in Example-1; $^1$H NMR (400 MHz, CDCl$_3$) δ 1.51-1.82 (m, 6H), 2.63 (s, 3H), 3.16-3.23 (m, 1H), 3.41-3.52 (m, 2H), 4.17-4.22 (m, 1H), 7.57-7.78 (m, 4H), 8.06-8.14 (m, 3H), 8.82-8.84 (m, 1H); MS m/z 448 (M+1).

Example-33

(1-((2,3-Difluorophenyl)amino)-5-methylisoquinolin-4-yl)(piperidin-1-yl)methanone

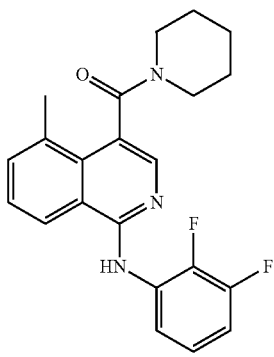

The above compound was prepared by using Intermediate-11d and 2,3-difluoroaniline by following the similar procedure as described in Example-1; $^1$H NMR (400 MHz, CDCl$_3$) δ 1.49-1.76 (m, 6H), 2.62 (s, 3H), 3.12-3.18 (m, 1H), 3.38-3.49 (m, 2H), 4.15-4.19 (m, 1H), 6.84-6.88 (m, 1H), 7.09-7.12 (m, 1H), 7.42-7.43 (m, 1H), 7.52-7.55 (m, 2H), 7.89-7.91 (m, 1H), 7.99 (s, 1H), 8.24-8.28 (m, 1H); MS m/z 382 (M+1).

Example-34

(1-((2,5-Difluorophenyl)amino)-5-methylisoquinolin-4-yl)(piperidin-1-yl)methanone

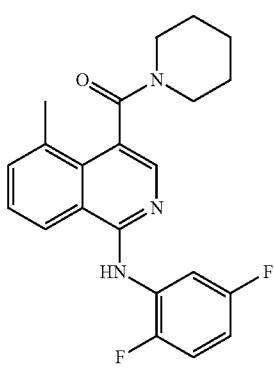 [SMILES: Cc1cccc2c(Nc3cc(F)ccc3F)ncc(C(=O)N3CCCCC3)c12]

This compound was prepared by using Intermediate-11d and 2,5-difluoroaniline by following the similar procedure as described in Example-1; $^1$H NMR (400 MHz, CDCl$_3$) δ 1.49-1.78 (m, 6H), 2.62 (s, 3H), 3.12-3.19 (m, 1H), 3.39-3.50 (m, 2H), 4.15-4.18 (m, 1H), 6.64-6.69 (m, 1H), 7.05-7.12 (m, 1H), 7.53-7.57 (m, 3H), 7.86-7.88 (m, 1H), 8.02 (s, 1H), 8.51-8.55 (m, 1H); MS m/z 382 (M+1).

Example-35

(1-((4-Chlorophenyl)amino)-5-methylisoquinolin-4-yl)(piperidin-1-yl)methanone

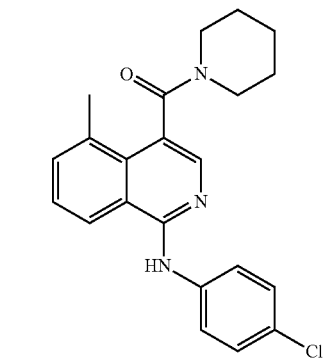

The above compound was prepared by using Intermediate-11d and 4-chloroaniline by following the similar procedure as described in Example-1; $^1$H NMR (400 MHz, CDCl$_3$) δ 1.48-1.78 (m, 6H), 2.57 (s, 3H), 3.12-3.18 (m, 1H), 3.39-3.49 (m, 2H), 4.09-4.18 (m, 1H), 7.29-7.32 (m, 3H), 7.43-7.48 (m, 2H), 7.57-7.61 (m, 2H), 7.82-7.84 (m, 1H), 7.90 (s, 1H); MS m/z 380 (M+1).

Example-36

(1-((3-Chloro-4-fluorophenyl)amino)-5-methylisoquinolin-4-yl)(Piperidin-1-yl)methanone

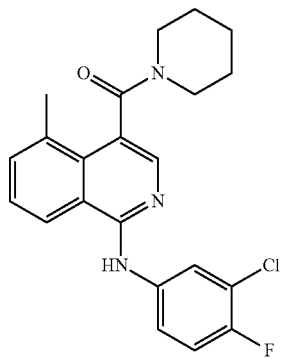

The title compound was prepared by using Intermediate-11d and 3-chloro-4-fluoroaniline by following the similar procedure as described in Example-1; $^1$H NMR (400 MHz, CDCl$_3$) δ 1.51-1.79 (m, 6H), 2.59 (s, 3H), 3.14-3.20 (m, 1H), 3.41-3.51 (m, 2H), 4.15-4.18 (m, 1H), 7.12-7.16 (t, 2H, J=8.8 Hz), 7.43-7.52 (m, 3H), 7.82-7.86 (m, 2H), 7.93 (s, 1H); MS m/z 398 (M+1).

Example-37

(1-((3-(Fluoromethyl)phenyl)amino)-5-methylisoquinolin-4-yl)(piperidin-1-yl)methanone

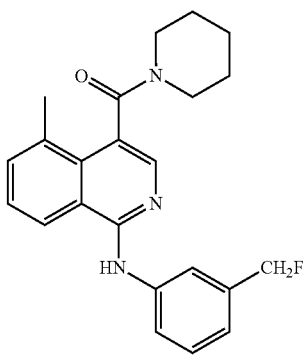 [SMILES: Cc1cccc2c(Nc3cccc(C(F)F)c3)ncc(C(=O)N3CCCCC3)c12]

This compound was prepared by using Intermediate-11d and 3-(fluoromethyl)aniline by following the similar procedure as described in Example-1; ¹H NMR (400 MHz, CDCl₃) δ 1.49-1.78 (m, 6H), 2.60 (s, 3H), 3.12-3.19 (m, 1H), 3.40-3.49 (m, 2H), 4.11-4.18 (m, 1H), 5.35-5.47 (d, 2H, J=47.6 Hz), 7.08-7.01 (m, 1H), 7.24 (s, 1H), 7.38-7.41 (m, 1H), 7.47-7.52 (m, 2H), 7.62-7.64 (m, 1H), 7.70 (s, 1H), 7.84-7.86 (m, 1H), 7.96 (s, 1H); MS m/z 378 (M+1).

Example-38

(1-((3-(Difluoromethyl)phenyl)amino)-5-methylisoquinolin-4-yl)(piperidin-1-yl)methanone

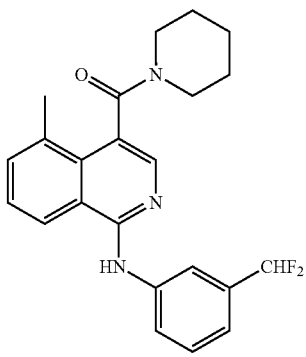

The above compound was prepared by using Intermediate-11d and 3-(difluoromethyl)aniline by following the similar procedure as described in Example-1; ¹H NMR (400 MHz, CDCl₃) δ 1.49-1.76 (m, 6H), 2.59 (s, 3H), 3.12-3.18 (m, 1H), 3.39-3.49 (m, 2H), 4.14-4.17 (m, 1H), 6.52-6.80 (t, 1H, J=56.8 Hz), 7.19-7.21 (m, 1H), 7.31 (s, 1H), 7.42-7.51 (m, 3H), 7.75-7.77 (m, 1H), 7.84-7.86 (m, 2H), 7.95 (s, 1H); MS m/z 396 (M+1).

Example-39

6-Oxa-3-azabicyclo[3.1.1]heptan-3-yl(1-((3-chlorophenyl)amino)-5-methylisoquinolin-4-yl)methanone

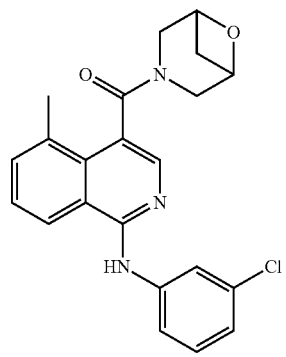

This compound was prepared by using Intermediate-11e and 3-chloroaniline by following the similar procedure as described in Example-1; ¹H NMR (400 MHz, CDCl₃) δ (as mixture of isomers) 1.87-2.0 (m, 2H), 2.59 (s, 3H), 3.22-5.3 (m, 6H), 7.03-7.06 (m, 1H), 7.27-7.51 (m, 5H), 7.80-7.84 (m, 2H), 7.86-8.0 (m, 1H); MS m/z 394 (M+1).

Example-40

6-Oxa-3-azabicyclo[3.1.1]heptan-3-yl(5-methyl-1-((3-(trifluoromethyl)phenyl)amino)isoquinolin-4-yl)methanone

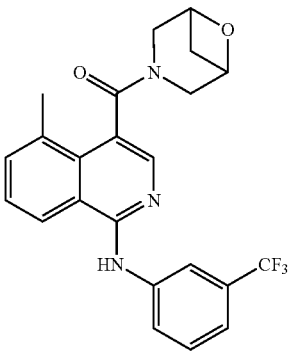

The title compound was prepared by using Intermediate-11e and 3-(trifluoromethyl)aniline by following the similar procedure as described in Example-1; ¹H NMR (400 MHz, CDCl₃) δ (as mixture of isomers) 1.85-2.05 (m, 2H), 2.54 (s, 3H), 3.23-5.29 (m, 6H), 7.30-7.37 (m, 1H), 7.43-7.65 (m, 4H), 7.83-8.02 (m, 4H); MS m/z 428 (M+1).

Example-41

(5-Methyl-1-((3-(trifluoromethyl)phenyl)amino)isoquinolin-4-yl)(2-oxa-6-azaspiro[3.3]heptan-6-yl)methanone

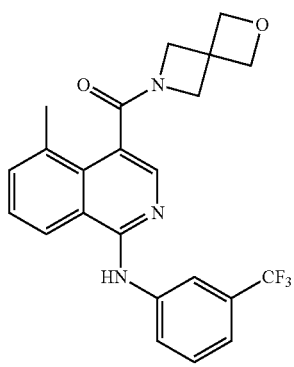 [SMILES: Cc1cccc2c(Nc3cccc(C(F)(F)F)c3)ncc(C(=O)N3CC4(COC4)C3)c12]

The title compound was prepared by using Intermediate-11f and 3-(trifluoromethyl)aniline by following the similar procedure as described in Example-1; $^1$H NMR (400 MHz, CDCl$_3$) δ 2.57 (s, 3H), 4.11 (s, 2H), 4.39 (s, 2H), 4.75-4.77 (m, 2H), 4.86-4.88 (m, 2H), 7.33-7.35 (m, 1H), 7.46-7.55 (m, 4H), 7.85-7.87 (m, 2H), 7.99 (s, 2H); MS m/z 428 (M+1).

Example-42

(5-Methyl-1-((3-chlorophenyl)amino)isoquinolin-4-yl)(2-oxa-6-azaspiro[3.3]heptan-6-yl)methanone

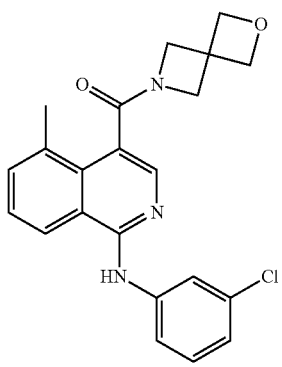 [SMILES: Cc1cccc2c(Nc3cccc(Cl)c3)ncc(C(=O)N3CC4(COC4)C3)c12]

This compound was prepared by using Intermediate-11f and 3-chloroaniline by following the similar procedure as described in Example-1; $^1$H NMR (400 MHz, CDCl$_3$) δ 2.56 (s, 3H), 4.08 (s, 2H), 4.39 (s, 2H), 4.74-4.76 (m, 2H), 4.85-4.87 (m, 2H), 7.05-7.07 (m, 1H), 7.25-7.3 (m, 2H), 7.39-7.53 (m, 3H), 7.82-7.84 (m, 2H), 8.01 (s, 1H); MS m/z 394 (M+1).

Example-43

(5-Methyl-1-((2,4,5-trifluorophenyl)amino)isoquinolin-4-yl)(2-oxa-6-azaspiro[3.3]heptan-6-yl)methanone

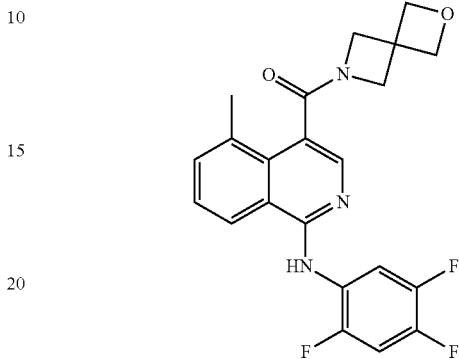

The title compound was prepared by using Intermediate-11f and 2,4,5-trifluoroaniline by following the similar procedure as described in Example-1; $^1$H NMR (400 MHz, CDCl$_3$) δ 2.60 (s, 3H), 4.09 (bs, 2H), 4.41 (s, 2H), 4.77 (d, 2H, 6.8 Hz), 4.88 (d, 2H, 7.2 Hz), 7.02-7.09 (m, 1H), 7.46 (bs, 1H), 7.53-7.58 (m, 2H), 7.84-7.87 (m, 1H), 8.03 (s, 1H), 8.62-8.69 (m, 1H); MS m/z 414 (M+1).

Example-44

(1-((4-Fluoro-3-(trifluoromethyl)phenyl)amino)-5-methylisoquinolin-4-yl)(2-oxa-6-azaspiro[3.3]heptan-6-yl)methanone

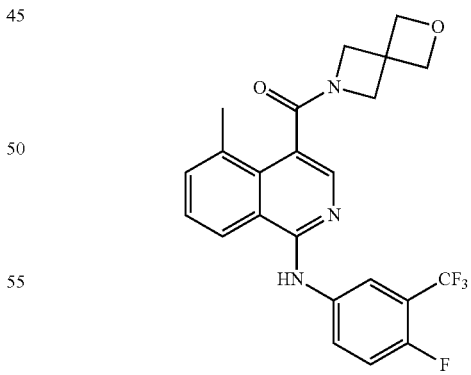

The above compound was prepared by using Intermediate-11f and 4-fluoro-3-(trifluoro methyl)aniline by following the similar procedure as described in Example-1; $^1$H NMR (400 MHz, CDCl$_3$) δ 2.55 (s, 3H), 4.09 (bs, 2H), 4.39 (bs, 2H), 4.75 (d, 2H, J=6.8 Hz), 4.87 (d, 2H, J=6.8 Hz), 7.18-7.26 (m, 1H), 7.36 (bs, 1H), 7.48-7.54 (m, 2H), 7.82-7.86 (m, 2H), 7.91-7.94 (m, 2H); MS m/z 446 (M+1).

Example-45

(5-Methyl-1-((3-fluorophenyl)amino)isoquinolin-4-yl)(2-oxa-6-azaspiro[3.3]heptan-6-yl)methanone

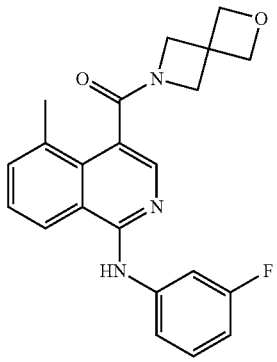 [SMILES: Cc1cccc2c(Nc3cccc(F)c3)ncc(C(=O)N3CC4(COC4)C3)c12]

This compound was prepared by using Intermediate-11f and 3-fluoroaniline by following the similar procedure as described in Example-1; $^1$H NMR (400 MHz, CDCl$_3$) δ 2.57 (s, 3H), 4.08 (bs, 2H), 4.39 (s, 2H), 4.75 (d, 2H, J=7.2 Hz), 4.86 (d, 2H, J=6.8 Hz), 6.76-6.80 (m, 1H), 7.25-7.33 (m, 2H), 7.39 (bs, 1H), 7.47-7.53 (m, 2H), 7.69-7.72 (m, 1H)), 7.83 (d, 1H, J=7.2 Hz), 7.98 (s, 1H); MS m/z 378 (M+1).

Example-46

(5-Methyl-1-((2,3-difluorophenyl)amino)isoquinolin-4-yl)(2-oxa-6-azaspiro[3.3]heptan-6-yl)methanone

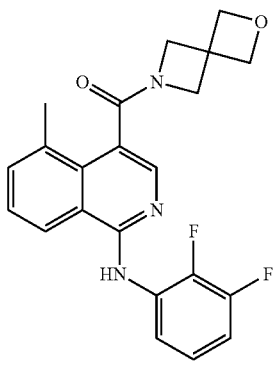 [SMILES: Cc1cccc2c(Nc3cccc(F)c3F)ncc(C(=O)N3CC4(COC4)C3)c12]

The title compound was prepared by using Intermediate-11f and 2,3-difluoroaniline by following the similar procedure as described in Example-1; $^1$H NMR (400 MHz, CDCl$_3$) δ 2.59 (s, 3H), 4.07 (bs, 2H), 4.39 (s, 2H), 4.75 (d, 2H, J=6.8 Hz), 4.86 (d, 2H, J=7.2 Hz), 6.84-6.91 (m, 1H), 7.08-7.14 (m, 1H), 7.48 (bs, 1H), 7.56-7.57 (m, 2H), 7.88-7.91 (m, 1H)), 8.02 (s, 1H), 8.26 (t, 1H); MS m/z 396 (M+1).

Example-47

(5-Methyl-1-((4-fluorophenyl)amino)isoquinolin-4-yl)(2-oxa-6-azaspiro[3.3]heptan-6-yl)methanone

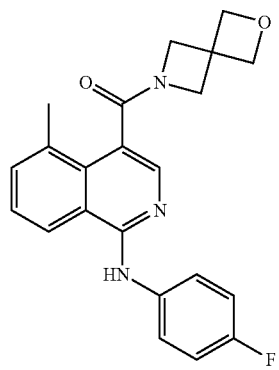 [SMILES: Cc1cccc2c(Nc3ccc(F)cc3)ncc(C(=O)N3CC4(COC4)C3)c12]

This compound was prepared by using Intermediate-11f and 4-fluoroaniline by following the similar procedure as described in Example-1; $^1$H NMR (400 MHz, CDCl$_3$) δ 2.58 (s, 3H), 4.07-4.12 (m, 2H), 4.38 (s, 2H), 4.74 (d, 2H, J=6.8 Hz), 4.86 (d, 2H, J=6.8 Hz), 7.06-7.11 (m, 2H), 7.19 (bs, 1H), 7.48-7.59 (m, 4H), 7.84 (d, 1H, J=6.8 Hz), 7.94 (s, 1H); MS m/z 378 (M+1).

Example-48

(5-Methyl-1-((2,4-difluorophenyl)amino)isoquinolin-4-yl)(2-oxa-6-azaspiro[3.3]heptan-6-yl)methanone

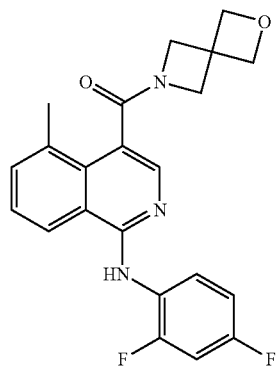 [SMILES: Cc1cccc2c(Nc3ccc(F)cc3F)ncc(C(=O)N3CC4(COC4)C3)c12]

This compound was prepared by using Intermediate-11f and 2,4-difluoroaniline by following the similar procedure as described in Example-1; $^1$H NMR (400 MHz, CD$_3$OD) δ 2.57 (s, 3H), 4.38 (bs, 2H), 4.78 (d, 2H, 7.2 Hz), 4.84-4.89 (m, 4H), 7.0-7.11 (m, 2H), 7.54-7.60 (m, 2H), 7.63-7.70 (m, 1H), 7.76 (s, 1H), 8.26 (d, 1H, 8 Hz); MS m/z 396 (M+1).

Example-49

(5-Methyl-1-((3,5-difluorophenyl)amino)isoquinolin-4-yl)(2-oxa-6-azaspiro[3.3]heptan-6-yl)methanone

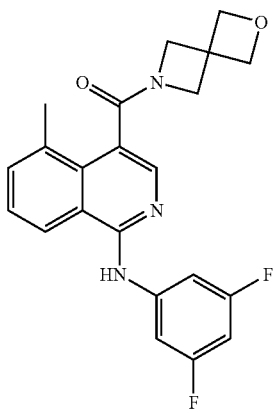 [SMILES: Cc1cccc2c(Nc3cc(F)cc(F)c3)ncc(C(=O)N3CC4(COC4)C3)c12]

This compound was prepared by using Intermediate-11f and 3,5-difluoroaniline by following the similar procedure as described in Example-1; $^1$H NMR (400 MHz, CD$_3$OD) δ 2.59 (s, 3H), 4.40-4.44 (m, 2H), 4.61 (s, 2H), 4.78-4.89 (m, 4H), 6.57-6.62 (m, 1H), 7.47-7.53 (m, 2H), 7.58-7.66 (m, 2H), 8.0 (s, 1H), 8.30 (d, 1H, J=8.4 Hz); MS m/z 396 (M+1).

Example-50

(1-((3-Chlorophenyl)amino)-5-methylisoquinolin-4-yl)(2-oxa-6-azaspiro[3.5]nonan-6-yl)methanone

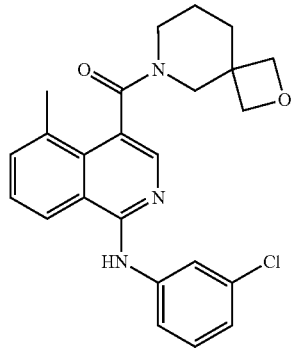 [SMILES: Cc1cccc2c(Nc3cccc(Cl)c3)ncc(C(=O)N3CCCC4(COC4)C3)c12]

This compound was prepared by using Intermediate-11g and 3-chloroaniline by following the similar procedure as described in Example-1; $^1$H NMR (400 MHz, CDCl$_3$) δ 1.50-2.07 (m, 4H), 2.57 (s, 3H), 2.85-4.29 (m, 4H), 4.36-4.63 (m, 4H), 7.06-7.08 (m, 1H), 7.29-7.32 (m, 1H), 7.47-7.55 (m, 3H), 7.83-8.0 (m, 4H); MS m/z 422 (M+1).

Example-51

(5-Methyl-1-((3-(trifluoromethyl)phenyl)amino)isoquinolin-4-yl)(2-oxa-6-azaspiro[3.5]nonan-6-yl)methanone

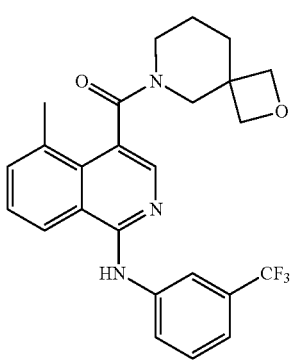 [SMILES: Cc1cccc2c(Nc3cccc(C(F)(F)F)c3)ncc(C(=O)N3CCCC4(COC4)C3)c12]

The title compound was prepared by using Intermediate-11g and 3-(trifluoromethyl)aniline by following the similar procedure as described in Example-1; $^1$H NMR (400 MHz, CDCl$_3$) δ 1.50-2.10 (m, 4H), 2.57 (s, 3H), 2.85-4.29 (m, 4H), 4.36-4.58 (m, 4H), 7.33-7.35 (m, 1H), 7.43-7.55 (m, 4H), 7.86-7.88 (m, 2H), 7.92-8.0 (m, 2H); MS m/z 456 (M+1).

Example-52

(3,5-Dimethylpiperazin-1-yl)(5-methyl-1-((3-(trifluoromethyl)phenyl)amino)isoquinolin-4-yl)methanone

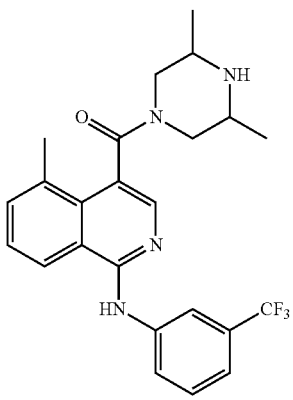 [SMILES: Cc1cccc2c(Nc3cccc(C(F)(F)F)c3)ncc(C(=O)N3CC(C)NC(C)C3)c12]

The above compound was prepared by using Intermediate-11h and 3-(trifluoromethyl)aniline by following the similar procedure as described in Example-1; $^1$H NMR (400 MHz, CDCl$_3$) δ 0.91-0.93 (m, 3H), 1.17-1.25 (m, 3H), 2.36-2.42 (m, 1H), 2.49 (s, 3H), 2.69-2.71 (m, 1H), 2.71-2.99 (m, 2H), 3.43-3.46 (m, 1H), 4.71-4.74 (m, 1H), 7.25-7.27 (m, 1H), 7.38-7.40 (m, 2H), 7.46-7.52 (m, 2H), 7.87-7.90 (m, 2H), 7.95-7.98 (m, 1H); MS m/z 443 (M+1).

Example-53

(3,5-Dimethylpiperazin-1-yl)(5-methyl-1-((3-chlorophenyl)amino)isoquinolin-4-yl)methanone

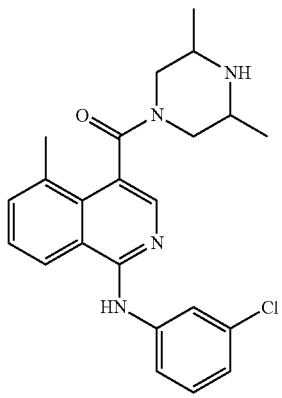 [SMILES: Cc1cccc2c(Nc3cccc(Cl)c3)ncc(C(=O)N3CC(C)NC(C)C3)c12]

The above compound was prepared by using Intermediate-11h and 3-chloroaniline by following the similar procedure as described in Example-1; $^1$H NMR (400 MHz, CDCl$_3$) δ 0.916 (d, 3H, J=6 Hz), 1.17 (d, 3H, J=5.6 Hz), 2.36-2.46 (m, 1H), 2.51 (s, 3H), 2.69 (s, 1H), 2.74-2.97 (m, 2H), 3.43-3.48 (m, 1H), 4.71-4.83 (m, 1H), 7.05 (d, 1H, J=7.6 Hz) 7.25-7.28 (m, 1H), 7.47-7.51 (m, 3H), 7.82-7.85 (m, 2H), 7.97 (s, 1H); MS m/z 409 (M+1).

Example-54

(1-(4-Fluorophenoxy)-5-methylisoquinolin-4-yl)(morpholino)methanone

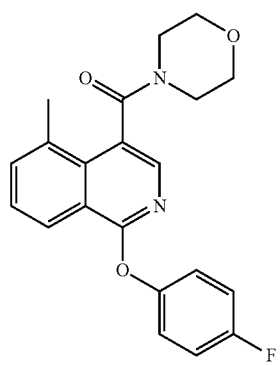 [SMILES: Cc1cccc2c(Oc3ccc(F)cc3)ncc(C(=O)N3CCOCC3)c12]

To a stirred solution of (1-chloro-5-methylisoquinolin-4-yl)(morpholino)methanone Intermediate-11a (1 equiv) in dry DMF (5 mL) was added, 4-fluorophenol (1.1 equiv), CuI (1.1 equiv) and K$_2$CO$_3$ (2 equiv) in a sealed tube. The reaction mixture was degassed for 20 min and then stirred at 150° C. for 2 h. It was allowed to reach RT and then diluted with EtOAc. The slurry was filtered through celite, and then washed with EtOAc. The solvent was then removed, and the residue was purified by column chromatography (15% EtOAc:Hexane) to afford the title compound; $^1$H NMR (400 MHz, CDCl$_3$) δ 2.61 (s, 3H), 3.23-4.13 (m, 8H), 7.15-7.20 (m, 4H), 7.55-7.61 (m, 2H), 7.82 (s, 1H), 8.39-8.41 (m, 1H); MS m/z 367 (M+1).

Example-55

(1-(3,4-Difluorophenoxy)-5-methylisoquinolin-4-yl)(morpholino)methanone

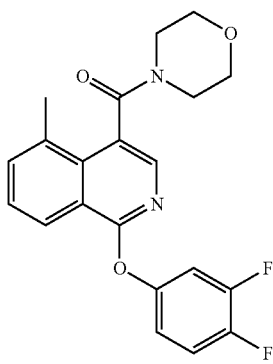

The title compound was prepared by using Intermediate-11a and 3,4-difluorophenol by following the similar procedure as described in Example-54; $^1$H NMR (400 MHz, CDCl$_3$) δ 2.63 (s, 3H), 3.24-4.10 (m, 8H), 6.96-7.27 (m, 3H), 7.57-7.63 (m, 2H), 7.83 (s, 1H), 8.36-8.38 (m, 1H); MS m/z 385 (M+1).

Example-56

(1-(2-Chloro-4-fluorophenoxy)-5-methylisoquinolin-4-yl)(morpholino)methanone

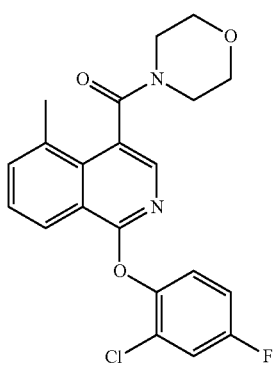

The title compound was prepared by using Intermediate-11a and 2-chloro-4-fluorophenol by following the similar procedure as described in Example-54; $^1$H NMR (400 MHz, CD$_3$OD) δ 2.63 (s, 3H), 3.50-4.06 (m, 8H), 7.22-7.25 (m, 1H), 7.40-7.43 (m, 2H), 7.69-7.77 (m, 2H), 7.80 (s, 1H), 8.47-8.49 (m, 1H); MS m/z 401 (M+1).

Example-57

(1-(4-Fluorophenoxy)-5-methylisoquinolin-4-yl)(piperidin-1-yl)methanone

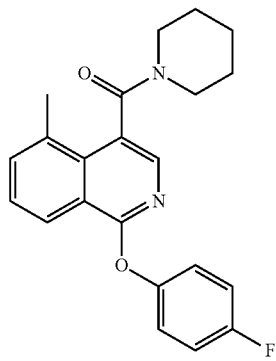 [SMILES: Cc1cccc2c(Oc3ccc(F)cc3)ncc(C(=O)N3CCCCC3)c12]

The title compound was prepared by using Intermediate-11d and 4-fluorophenol by following the similar procedure as described in Example-54; $^1$H NMR (400 MHz, CDCl$_3$) δ 1.43-1.75 (m, 6H), 2.63 (s, 3H), 3.09-3.16 (m, 1H), 3.33-3.49 (m, 2H), 4.11-4.17 (m, 1H), 7.15-7.21 (m, 4H), 7.25-7.60 (m, 2H), 7.82 (s, 1H), 8.38-8.41 (m, 1H); MS m/z 365 (M+1).

Example-58

(1-(3,4-Difluorophenoxy)-5-methylisoquinolin-4-yl)(piperidin-1-yl)methanone

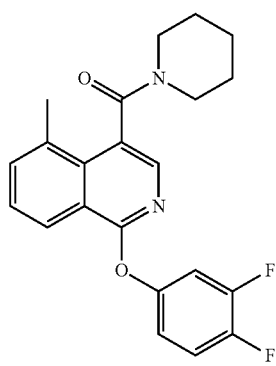 [SMILES: Cc1cccc2c(Oc3ccc(F)c(F)c3)ncc(C(=O)N3CCCCC3)c12]

The title compound was prepared by using Intermediate-11d and 3,4-difluorophenol by following the similar procedure as described in Example-54; $^1$H NMR (400 MHz, CDCl$_3$) δ 1.42-1.76 (m, 6H), 2.62 (s, 3H), 3.11-3.16 (m, 1H), 3.33-3.49 (m, 2H), 4.11-4.17 (m, 1H), 6.96-7.26 (m, 3H), 7.55-7.61 (m, 2H), 7.82 (s, 1H), 8.34-8.37 (m, 1H); MS m/z 383 (M+1).

Example-59

(1-(2-Chloro-4-fluorophenoxy)-5-methylisoquinolin-4-yl)(piperidin-1-yl)methanone

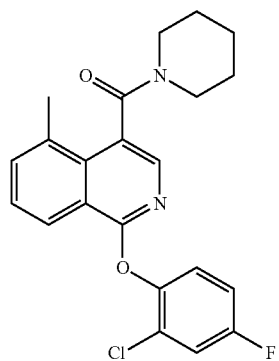 [SMILES: Cc1cccc2c(Oc3ccc(F)cc3Cl)ncc(C(=O)N3CCCCC3)c12]

This compound was prepared by using Intermediate-11d and 2-chloro-4-fluorophenol by following the similar procedure as described in Example-54; $^1$H NMR (400 MHz, CDCl$_3$) δ 1.46-1.76 (m, 6H), 2.63 (s, 3H), 3.11-3.16 (m, 1H), 3.33-3.50 (m, 2H), 4.09-4.14 (m, 1H), 7.06-7.30 (m, 3H), 7.56-7.61 (m, 2H), 7.79 (s, 1H), 8.43-8.45 (m, 1H); MS m/z 399 (M+1).

Example-60

6-Oxa-3-azabicyclo[3.1.1]heptan-3-yl(1-((3-chloro-4-fluorophenyl)amino)-5-methylisoquinolin-4-yl)methanone

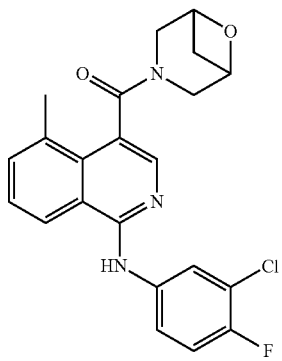 [SMILES: Cc1cccc2c(Nc3ccc(F)c(Cl)c3)ncc(C(=O)N3CC4CC(C3)O4)c12]

The title compound was prepared by using Intermediate-11e and 3-chloro-4-fluoroaniline by following the similar procedure as described in Example-1; $^1$H NMR (400 MHz, CDCl$_3$) δ (as mixture of isomers) 1.89-2.06 (m, 2H), 2.61 (s, 3H), 3.24-5.16 (m, 6H), 7.13-7.18 (m, 1H), 7.45-7.55 (m, 4H), 7.82-8.0 (m, 3H); MS m/z 412 (M+1).

Example-61

6-Oxa-3-azabicyclo[3.1.1]heptan-3-yl(1-((3-chloro-2-fluorophenyl)amino)-5-methyl isoquinolin-4-yl)methanone

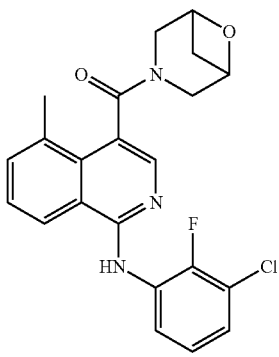 [SMILES: Cc1cccc2c(Nc3cccc(Cl)c3F)ncc(C(=O)N3CC4CC(C3)O4)c12]

This compound was prepared by using Intermediate-11e and 3-chloro-2-fluoroaniline by following the similar procedure as described in Example-1; $^1$H NMR (400 MHz, CDCl$_3$) δ (as mixture of isomers) 1.88-2.02 (m, 2H), 2.68 (s, 3H), 3.24-5.15 (m, 6H), 7.08-7.13 (m, 2H), 7.54-8.05 (m, 5H), 8.38-8.4 (m, 1H); MS m/z 412 (M+1).

Example-62

6-Oxa-3-azabicyclo[3.1.1]heptan-3-yl(1-((3-fluorophenyl)amino)-5-methylisoquinolin-4-yl)methanone

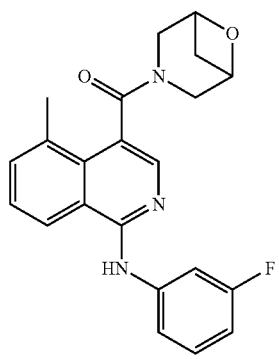 [SMILES: Cc1cccc2c(Nc3cccc(F)c3)ncc(C(=O)N3CC4CC(C3)O4)c12]

This compound was prepared by using Intermediate-11e and 3-fluoroaniline by following the similar procedure as described in Example-1; $^1$H NMR (400 MHz, CDCl$_3$) δ (as mixture of isomers) 1.89-2.06 (m, 2H), 2.65 (s, 3H), 3.27-5.16 (m, 6H), 6.76-6.81 (m, 1H), 7.30-7.52 (m, 5H), 7.67-8.0 (m, 3H); MS m/z 378 (M+1).

Example-63

6-Oxa-3-azabicyclo[3.1.1]heptan-3-yl(1-((3-methylphenyl)amino)-5-methylisoquinolin-4-yl)methanone

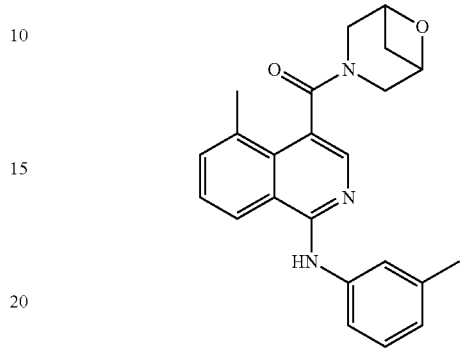

This compound was prepared by using Intermediate-11e and m-toluidine by following the similar procedure as described in Example-1; $^1$H NMR (400 MHz, CDCl$_3$) δ (as mixture of isomers) 1.87-2.03 (m, 2H), 2.38 (s, 3H), 2.59 (s, 3H), 3.26-5.13 (m, 6H), 6.91-6.94 (m, 1H), 7.24-7.29 (m, 3H), 7.43-7.54 (m, 3H), 7.83-7.99 (m, 2H); MS m/z 374 (M+1).

Example-64

6-Oxa-3-azabicyclo[3.1.1]heptan-3-yl(1-((3-fluoro-2-methylphenyl)amino)-5-methylisoquinolin-4-yl)methanone

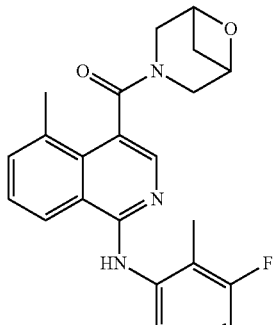

This compound was prepared by using Intermediate-11e and 3-fluoro-2-methylaniline by following the similar procedure as described in Example-1; $^1$H NMR (400 MHz, CDCl$_3$) δ (as mixture of isomers) 1.88-2.06 (m, 2H), 2.24 (s, 3H), 2.62 (s, 3H), 3.27-5.14 (m, 6H), 6.88-6.94 (m, 1H), 7.04 (s, 1H), 7.20-7.23 (m, 1H), 7.48-7.58 (m, 3H), 7.87-7.97 (m, 2H); MS m/z 392 (M+1).

Example-65

6-Oxa-3-azabicyclo[3.1.1]heptan-3-yl(1-((3-chloro-2-methylphenyl)amino)-5-methyl isoquinolin-4-yl)methanone

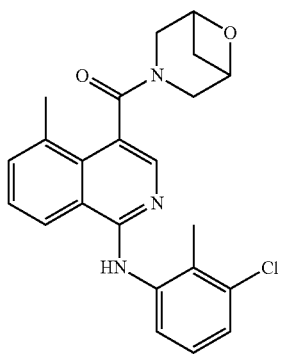 [SMILES: Cc1c(Cl)cccc1Nc1ncc(C(=O)N2CC3CC(C2)O3)c2c(C)cccc12]

This compound was prepared by using Intermediate-11e and 3-chloro-2-methylaniline by following the similar procedure as described in Example-1; $^1$H NMR (400 MHz, CDCl$_3$) δ (as mixture of isomers) 1.88-2.06 (m, 2H), 2.37 (s, 3H), 2.61 (s, 3H), 3.27-5.14 (m, 6H), 7.04 (s, 1H), 7.18-7.27 (m, 2H), 7.51-7.58 (m, 3H), 7.87-7.95 (m, 2H); MS m/z 408 (M+1).

Example-66

6-Oxa-3-azabicyclo[3.1.1]heptan-3-yl(1-((5-chloro-2-methylphenyl)amino)-5-methyl isoquinolin-4-yl)methanone

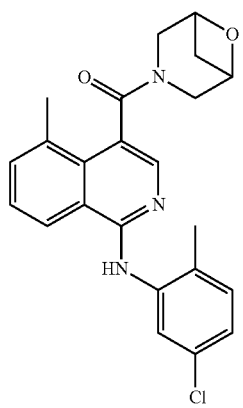 [SMILES: Cc1ccc(Cl)cc1Nc1ncc(C(=O)N2CC3CC(C2)O3)c2c(C)cccc12]

The title compound was prepared by using Intermediate-11e and 5-chloro-2-methyl aniline by following the similar procedure as described in Example-1; $^1$H NMR (400 MHz, CDCl$_3$) δ (as mixture of isomers) 1.89-2.06 (m, 2H), 2.32 (s, 3H), 2.62 (s, 3H), 3.28-5.15 (m, 6H), 7.05-7.09 (m, 2H), 7.18-7.21 (m, 1H), 7.53-7.59 (m, 2H), 7.84-8.0 (m, 3H); MS m/z 408 (M+1).

Example-67

6-Oxa-3-azabicyclo[3.1.1]heptan-3-yl(1-((2-fluoro-3-methylphenyl)amino)-5-methylisoquinolin-4-yl)methanone

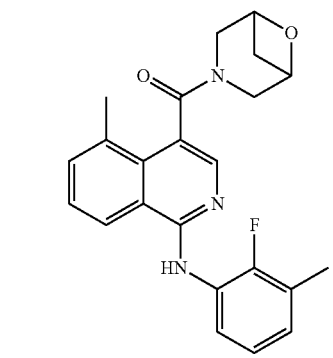 [SMILES: Cc1cccc(Nc2ncc(C(=O)N3CC4CC(C3)O4)c3c(C)cccc23)c1F]

This compound was prepared by using Intermediate-11e and 2-fluoro-3-methylaniline by following the similar procedure as described in Example-1; $^1$H NMR (400 MHz, CDCl$_3$) δ (as mixture of isomers) 1.89-2.05 (m, 2H), 2.34 (s, 3H), 2.62 (s, 3H), 3.26-5.16 (m, 6H), 6.90-6.91 (m, 1H), 7.08-7.11 (m, 1H), 7.53-7.57 (m, 3H), 7.89-8.26 (m, 3H); MS m/z 392 (M+1).

Example-68

6-Oxa-3-azabicyclo[3.1.1]heptan-3-yl(1-((2,3-difluorophenyl)amino)-5-methylisoquinolin-4-yl)methanone

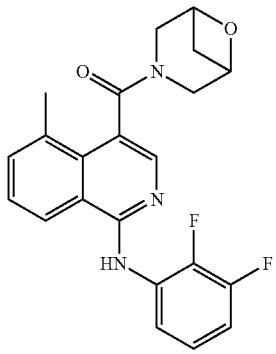 [SMILES: Cc1cccc2c(Nc3cccc(F)c3F)ncc(C(=O)N3CC4CC(C3)O4)c12]

The desired compound was prepared by using Intermediate-11e and 2,3-difluoroaniline by following the similar procedure as described in Example-1; $^1$H NMR (400 MHz, CDCl$_3$) δ (as mixture of isomers) 1.90-2.06 (m, 2H), 2.63 (s, 3H), 3.26-5.17 (m, 6H), 6.86-6.06 (m, 1H), 7.10-7.14 (m, 1H), 7.49 (s, 1H), 7.55-7.6 (m, 2H), 7.90-8.26 (m, 3H); MS m/z 396 (M+1).

Example-69

6-Oxa-3-azabicyclo[3.1.1]heptan-3-yl(1-((3,5-difluorophenyl)amino)-5-methylisoquinolin-4-yl)methanone

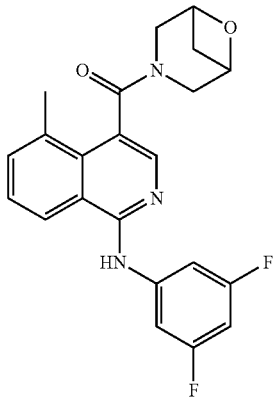 [SMILES: Cc1cccc2c(Nc3cc(F)cc(F)c3)ncc(C(=O)N3CC4CC(C3)O4)c12]

The desired compound was prepared by using Intermediate-11e and 3,5-difluoroaniline by following the similar procedure as described in Example-1; ¹H NMR (400 MHz, CDCl₃) δ (as mixture of isomers) 1.90-2.07 (m, 2H), 2.58 (s, 3H), 3.27-5.17 (m, 6H), 6.50-6.55 (m, 1H), 7.32-7.36 (m, 2H), 7.49-7.56 (m, 3H), 7.82-8.01 (m, 2H); MS m/z 396 (M+1).

Example-70

2-Oxa-5-azabicyclo[2.2.1]heptan-5-yl(1-((3-chlorophenyl)amino)-5-methylisoquinolin-4-yl)methanone

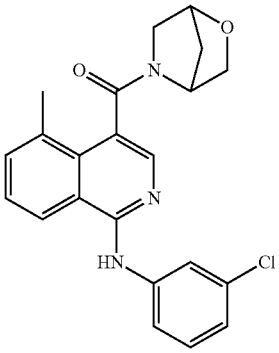 [SMILES: Cc1cccc2c(Nc3cccc(Cl)c3)ncc(C(=O)N3CC4CC3CO4)c12]

This compound was prepared by using Intermediate-11i and 3-chloroaniline by following the similar procedure as described in Example-1; ¹H NMR (400 MHz, CDCl₃) δ (as mixture of isomers) 1.89-2.06 (m, 2H), 2.61 (s, 3H), 3.27-5.16 (m, 6H), 7.06-7.09 (m, 1H), 7.27-7.33 (m, 2H), 7.46-7.55 (m, 3H), 7.82-7.88 (m, 2H), 7.99-8.02 (m, 1H); MS m/z 394 (M+1).

Example-71

2-Oxa-5-azabicyclo[2.2.1]heptan-5-yl(1-((3-(trifluoromethyl)phenyl)amino)-5-methyl isoquinolin-4-yl) methanone

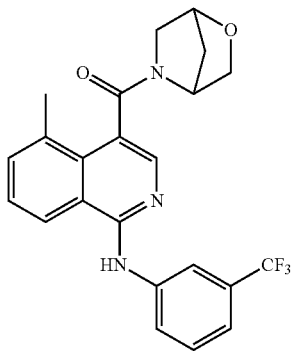 [SMILES: Cc1cccc2c(Nc3cccc(C(F)(F)F)c3)ncc(C(=O)N3CC4CC3CO4)c12]

The desired compound was prepared by using Intermediate-11i and 3-(trifluoromethyl)aniline by following the similar procedure as described in Example-1; ¹H NMR (400 MHz, CDCl₃) δ (as mixture of isomers) 1.85-2.04 (m, 2H), 2.60 (s, 3H), 3.23-5.15 (m, 6H), 7.32-7.35 (m, 1H), 7.44-7.56 (m, 4H), 7.83-8.02 (m, 4H); MS m/z 428 (M+1).

Example-72

2-Oxa-5-azabicyclo[2.2.1]heptan-5-yl(1-((3-chloro-2-fluorophenyl)amino)-5-methylisoquinolin-4-yl) methanone

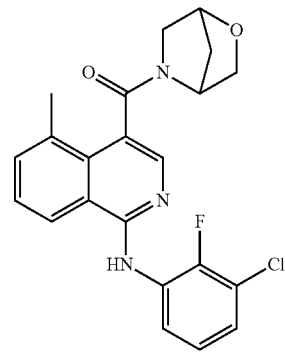 [SMILES: Cc1cccc2c(Nc3cccc(Cl)c3F)ncc(C(=O)N3CC4CC3CO4)c12]

This compound was prepared by using Intermediate-11i and 3-chloro-2-fluoroaniline by following the similar procedure as described in Example-1; ¹H NMR (400 MHz, CDCl₃) δ (as mixture of isomers) 1.87-2.06 (m, 2H), 2.63 (s, 3H), 3.26-5.16 (m, 6H), 7.13-7.17 (m, 2H), 7.53-7.6 (m, 3H), 7.91-8.02 (m, 2H), 8.36 (s, 1H); MS m/z 412 (M+1).

Example-73

2-Oxa-5-azabicyclo[2.2.1]heptan-5-yl(1-((3-chloro-4-fluorophenyl)amino)-5-methylisoquinolin-4-yl)methanone

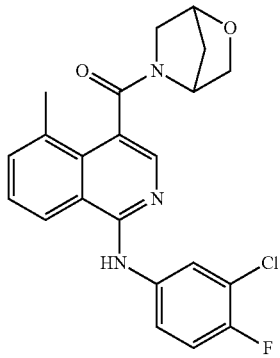 [SMILES: Cc1cccc2c(Nc3ccc(F)c(Cl)c3)ncc(C(=O)N3CC4CC3CO4)c12]

This compound was prepared by using Intermediate-11i and 3-chloro-4-fluoroaniline by following the similar procedure as described in Example-1; $^1$H NMR (400 MHz, CDCl$_3$) δ (as mixture of isomers) 1.90-2.06 (m, 2H), 2.61 (s, 3H), 3.25-5.15 (m, 6H), 7.13-7.19 (m, 1H), 7.43-7.58 (m, 3H), 7.60-7.96 (m, 4H); MS m/z 412 (M+1).

Example-74

2-Oxa-5-azabicyclo[2.2.1]heptan-5-yl(1-((3-methylphenyl)amino)-5-methylisoquinolin-4-yl)methanone

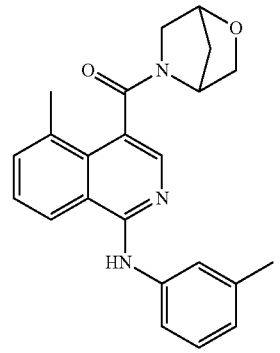 [SMILES: Cc1cccc(Nc2ncc(C(=O)N3CC4CC3CO4)c3c(C)cccc23)c1]

This compound was prepared by using Intermediate-11i and m-toluidine by following the similar procedure as described in Example-1; $^1$H NMR (400 MHz, CDCl$_3$) δ (as mixture of isomers) 1.86-2.08 (m, 2H), 2.39 (s, 3H), 2.61 (s, 3H), 3.10-5.25 (m, 6H), 6.94-6.96 (m, 1H), 7.27-7.57 (m, 6H), 7.86-7.99 (m, 2H); MS m/z 374 (M+1).

Example-75

3-Azabicyclo[3.1.0]hexan-3-yl(1-((3-chlorophenyl)amino)-5-methylisoquinolin-4-yl)methanone

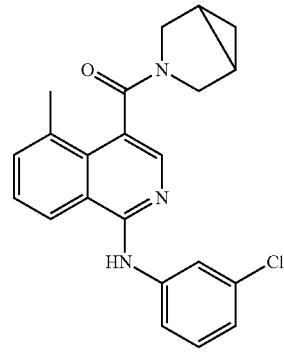 [SMILES: Cc1cccc2c(Nc3cccc(Cl)c3)ncc(C(=O)N3CC4CC4C3)c12]

This compound was prepared by using Intermediate-11j and 3-chloroaniline by following the similar procedure as described in Example-1; $^1$H NMR (400 MHz, CDCl$_3$) δ 0.22-0.35 (m, 1H), 0.77-0.82 (m, 1H), 1.46-1.69 (m, 2H), 2.58 (s, 3H), 3.25-4.15 (m, 4H), 7.05-7.07 (d, 1H, J=8.0 Hz), 7.24-7.32 (m, 2H), 7.47-7.53 (m, 3H), 7.82-7.99 (m, 3H); MS m/z 378 (M+1).

Example-76

3-Azabicyclo[3.1.0]hexan-3-yl(1-((3-(trifluoromethyl)phenyl)amino)-5-methylisoquinolin-4-yl)methanone

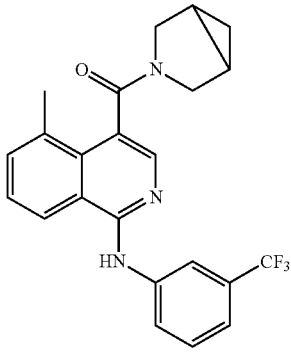 [SMILES: Cc1cccc2c(Nc3cccc(C(F)(F)F)c3)ncc(C(=O)N3CC4CC4C3)c12]

The desired compound was prepared by using Intermediate-11j and 3-(trifluoromethyl)aniline by following the similar procedure as described in Example-1; $^1$H NMR (400 MHz, CDCl$_3$) δ 0.22-0.35 (m, 1H), 0.77-0.83 (m, 1H), 1.46-1.68 (m, 2H), 2.55 (s, 3H), 3.24-4.15 (m, 4H), 7.31-7.33 (m, 1H), 7.45-7.56 (m, 4H), 7.83-7.96 (m, 4H); MS m/z 412 (M+1).

Example-77

3-Azabicyclo[3.1.0]hexan-3-yl(1-((3-fluoro-2-methylphenyl)amino)-5-methylisoquinolin-4-yl)methanone

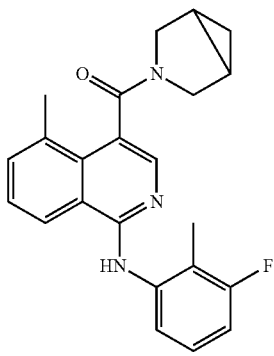 [SMILES: Cc1c(F)cccc1Nc1ncc(C(=O)N2CC3CC3C2)c2c(C)cccc12]

This compound was prepared by using Intermediate-11j and 3-fluoro-2-methylaniline by following the similar procedure as described in Example-1; ¹H NMR (400 MHz, CDCl₃) δ 0.27-0.31 (m, 1H), 0.80-0.81 (m, 1H), 1.49-1.7 (m, 2H), 2.6 (s, 3H), 2.74 (s, 3H), 3.21-4.2 (m, 4H), 7.12-7.18 (m, 2H), 7.53-7.65 (m, 4H), 7.96-8.07 (s, 1H), 8.84-8.86 (m, 1H); MS m/z 376 (M+1).

Example-78

3-Oxa-9-azabicyclo[3.3.1]nonan-9-yl(1-((3-chlorophenyl)amino)-5-methylisoquinolin-4-yl)methanone

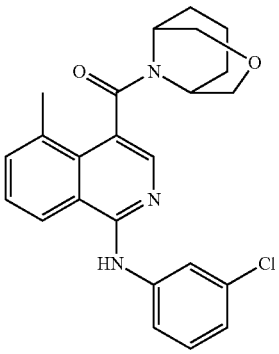 [SMILES: Cc1cccc2c(Nc3cccc(Cl)c3)ncc(C(=O)N3C4CCCC3COC4)c12]

This compound was prepared by using Intermediate-11k and 3-chloroaniline by following the similar procedure as described in Example-1; ¹H NMR (400 MHz, CDCl₃) δ (as mixture of isomers) 1.68-2.17 (m, 4H), 2.55-2.7 (m, 2H), 2.76 (s, 3H), 3.60-4.14 (m, 6H), 4.82 (s, 1H), 7.07-7.1 (d, 1H, J=8.0 Hz), 7.30-7.33 (m, 1H), 7.47-7.56 (m, 3H), 7.82-7.88 (m, 2H), 8.03-8.07 (m, 1H); MS m/z 422 (M+1).

Example-79

3-Oxa-9-azabicyclo[3.3.1]nonan-9-yl(1-((3-(trifluoromethyl)phenyl)amino)-5-methyl isoquinolin-4-yl)methanone

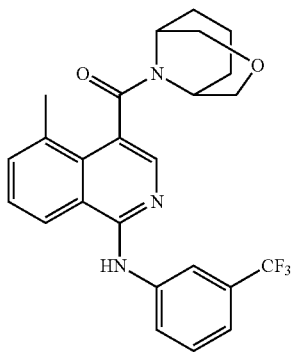 [SMILES: Cc1cccc2c(Nc3cccc(C(F)(F)F)c3)ncc(C(=O)N3C4CCCC3COC4)c12]

The desired compound was prepared by using Intermediate-11k and 3-(trifluoromethyl)aniline by following the similar procedure as described in Example-1; ¹H NMR (400 MHz, CDCl₃) δ (as mixture of isomers) 1.78-2.1 (m, 4H), 2.58-2.68 (m, 2H), 2.76 (s, 3H), 3.60-4.09 (m, 6H), 4.83 (s, 1H), 7.33-7.35 (d, 1H, J=7.6 Hz), 7.42 (s, 1H), 7.48-7.55 (m, 3H), 7.88-8.06 (m, 3H); MS m/z 456 (M+1).

Example-80

3-Oxa-9-azabicyclo[3.3.1]nonan-9-yl(1-((3-fluoro-2-methylphenyl)amino)-5-methylisoquinolin-4-yl)methanone

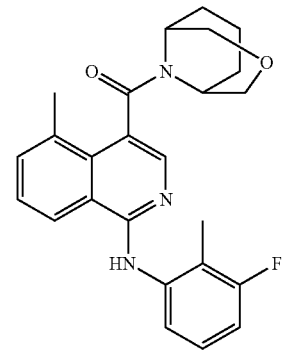 [SMILES: Cc1c(F)cccc1Nc1ncc(C(=O)N2C3CCCC2COC3)c2c(C)cccc12]

The title compound was prepared by using Intermediate-11k and 3-fluoro-2-methyl aniline by following the similar procedure as described in Example-1; ¹H NMR (400 MHz, CDCl₃) δ (as mixture of isomers) 1.71-2.07 (m, 4H), 2.24 (s, 3H), 2.60-2.63 (m, 2H), 2.77 (s, 3H), 3.50-4.07 (m, 6H), 4.81 (s, 1H), 6.90-6.94 (t, 1H, J=8.8 Hz), 7.19-7.24 (m, 1H), 7.45-7.59 (m, 3H), 7.88-8.0 (m, 2H); MS m/z 420 (M+1).

Example-81

(5-Methyl-1-(m-tolylamino)isoquinolin-4-yl)(morpholino)methanone

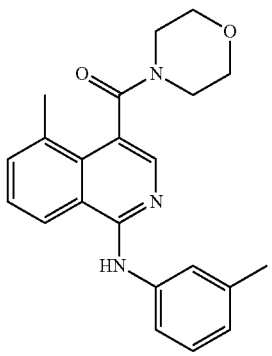 [SMILES: Cc1cccc(Nc2ncc(C(=O)N3CCOCC3)c3c(C)cccc23)c1]

This compound was prepared by using Intermediate-11a and m-toluidine by following the similar procedure as described in Example-1; $^1$H NMR (400 MHz, CDCl$_3$) δ 2.37 (s, 3H), 2.58 (s, 3H), 3.24-4.13 (m, 8H), 6.90-6.92 (d, 1H, J=7.6 Hz), 7.19 (s, 1H), 7.25-7.27 (m, 1H), 7.41-7.52 (m, 4H), 7.84-7.85 (d, 1H, J=7.2 Hz), 7.95 (s, 1H); MS m/z 362 (M+1).

Example-82

(1-((3-Fluoro-4-methylphenyl)amino)-5-methylisoquinolin-4-yl)(morpholino)methanone

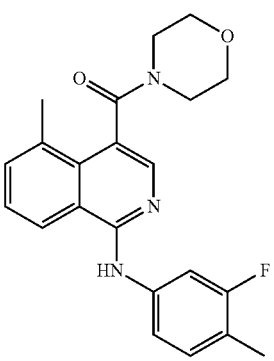 [SMILES: Cc1ccc(Nc2ncc(C(=O)N3CCOCC3)c3c(C)cccc23)cc1F]

The desired compound was prepared by using Intermediate-11a and 3-fluoro-4-methylaniline by following the similar procedure as described in Example-1; $^1$H NMR (400 MHz, CDCl$_3$) δ 2.24 (s, 3H), 2.57 (s, 3H), 3.25-4.12 (m, 8H), 7.12-7.14 (m, 2H), 7.23-7.24 (m, 1H), 7.45-7.57 (m, 3H), 7.81-7.83 (m, 1H), 7.93 (s, 1H); MS m/z 380 (M+1).

Example-83

(1-((3-Fluoro-2-methylphenyl)amino)-5-methylisoquinolin-4-yl)(morpholino)methanone

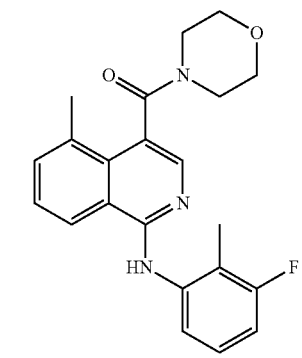 [SMILES: Cc1c(F)cccc1Nc1ncc(C(=O)N2CCOCC2)c2c(C)cccc12]

This compound was prepared by using Intermediate-11a and 3-fluoro-2-methylaniline by following the similar procedure as described in Example-1; $^1$H NMR (400 MHz, CDCl$_3$) δ 2.24 (s, 3H), 2.62 (s, 3H), 3.27-4.14 (m, 8H), 6.89-6.93 (t, 1H, J=8.8 Hz), 7.01 (s, 1H), 7.19-7.25 (m, 1H), 7.50-7.58 (m, 3H), 7.88-7.9 (m, 1H), 7.95 (s, 1H); MS m/z 380 (M+1).

Example-84

(1-((2-Fluoro-3-methylphenyl)amino)-5-methylisoquinolin-4-yl)(morpholino)methanone

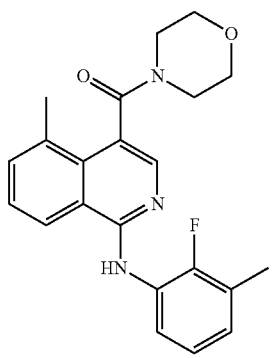 [SMILES: Cc1cccc(Nc2ncc(C(=O)N3CCOCC3)c3c(C)cccc23)c1F]

This compound was prepared by using Intermediate-11a and 2-fluoro-3-methylaniline by following the similar procedure as described in Example-1; $^1$H NMR (400 MHz, CDCl$_3$) δ 2.35 (s, 3H), 2.62 (s, 3H), 3.27-4.17 (m, 8H), 6.98-6.93 (t, 1H, J=7.6 Hz), 7.07-7.11 (t, 1H, J=7.6 Hz), 7.53-7.65 (m, 3H), 7.89-7.93 (m, 1H), 7.99 (s, 1H), 8.3 (s, 1H); MS m/z 380 (M+1).

Example-85

(1-((4-Fluoro-3-methylphenyl)amino)-5-methyliso-quinolin-4-yl)(morpholino)methanone

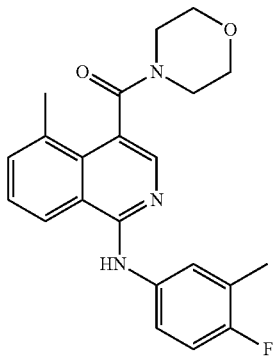 [SMILES: Cc1cc(Nc2ncc(C(=O)N3CCOCC3)c3c(C)cccc23)ccc1F]

This compound was prepared by using Intermediate-11a and 4-fluoro-3-methylaniline by following the similar procedure as described in Example-1; $^1$H NMR (400 MHz, CDCl$_3$) δ 2.29 (s, 3H), 2.57 (s, 3H), 3.24-4.11 (m, 8H), 6.98-7.02 (t, 1H, J=8.8 Hz), 7.31-7.53 (m, 5H), 7.82-7.84 (d, 1H, J=8.0 Hz), 7.92 (s, 1H); MS m/z 380 (M+1).

Example-86

(1-((2-Chloro-5-methylphenyl)amino)-5-methyliso-quinolin-4-yl)(morpholino)methanone

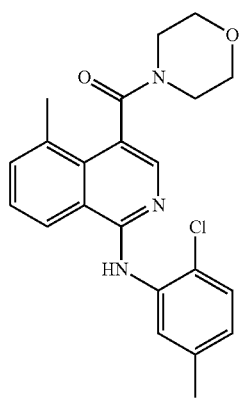 [SMILES: Cc1ccc(Cl)c(Nc2ncc(C(=O)N3CCOCC3)c3c(C)cccc23)c1]

The title compound was prepared by using Intermediate-11a and 2-chloro-5-methylaniline by following the similar procedure as described in Example-1; $^1$H NMR (400 MHz, CDCl$_3$) δ 2.41 (s, 3H), 2.63 (s, 3H), 3.26-4.16 (m, 8H), 6.83-6.85 (d, 1H, J=7.6 Hz), 7.31-7.33 (d, 1H, J=8.0 Hz), 7.56-7.57 (m, 2H), 7.88 (s, 1H), 7.94-7.97 (m, 1H), 8.03 (s, 1H), 8.44 (s, 1H); MS m/z 396 (M+1).

Example-87

(1-((3-Chloro-2-methylphenyl)amino)-5-methyliso-quinolin-4-yl)(morpholino)methanone

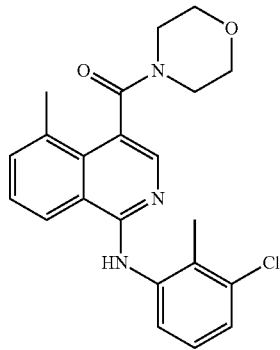 [SMILES: Cc1c(Cl)cccc1Nc1ncc(C(=O)N2CCOCC2)c2c(C)cccc12]

This compound was prepared by using Intermediate-11a and 3-chloro-2-methylaniline by following the similar procedure as described in Example-1; $^1$H NMR (400 MHz, CDCl$_3$) δ 2.37 (s, 3H), 2.62 (s, 3H), 3.27-4.14 (m, 8H), 7.0-7.01 (m, 1H), 7.19-7.27 (m, 2H), 7.53-7.56 (m, 3H), 7.88-7.9 (d, 1H, J=7.6 Hz), 7.92 (s, 1H); MS m/z 396 (M+1).

Example-88

(1-((5-Chloro-2-methylphenyl)amino)-5-methyliso-quinolin-4-yl)(morpholino)methanone

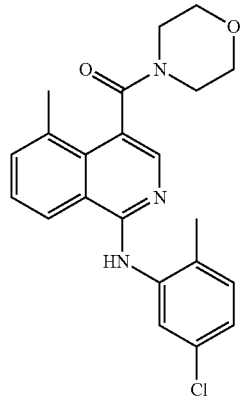 [SMILES: Cc1ccc(Cl)cc1Nc1ncc(C(=O)N2CCOCC2)c2c(C)cccc12]

The title compound was prepared by using Intermediate-11a and 5-chloro-2-methyl aniline by following the similar procedure as described in Example-1; $^1$H NMR (400 MHz, CDCl$_3$) δ 2.32 (s, 3H), 2.62 (s, 3H), 3.27-4.15 (m, 8H), 7.06-7.08 (m, 2H), 7.18-7.2 (d, 1H, J=8.0 Hz), 7.51-7.57 (m, 2H), 7.85-7.87 (d, 1H, J=7.6 Hz), 7.94-7.95 (m, 2H); MS m/z 396 (M+1).

Example-89

(1-((3-Chloro-4-methylphenyl)amino)-5-methylisoquinolin-4-yl)(morpholino)methanone

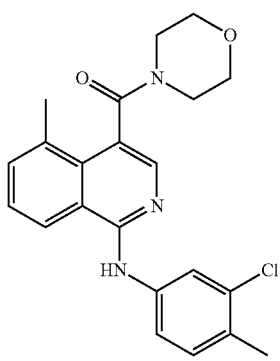 [SMILES: Cc1ccc(Nc2ncc(C(=O)N3CCOCC3)c3c(C)cccc23)cc1Cl]

This compound was prepared by using Intermediate-11a and 3-chloro-4-methylaniline by following the similar procedure as described in Example-1; ¹H NMR (400 MHz, CDCl₃) δ 2.37 (s, 3H), 2.6 (s, 3H), 3.27-4.16 (m, 8H), 7.21-7.27 (m, 2H), 7.38-7.41 (m, 1H), 7.48-7.54 (m, 2H), 7.77-7.78 (m, 1H), 7.84-7.86 (d, 1H, J=7.6 Hz), 7.98 (s, 1H); MS m/z 396 (M+1).

Example-90

(1-((2,4-Dichlorophenyl)amino)-5-methylisoquinolin-4-yl)(morpholino)methanone

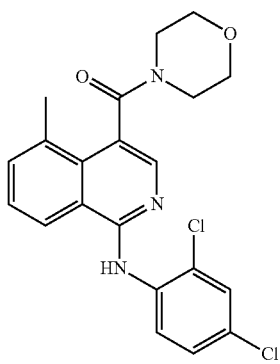 [SMILES: Cc1cccc2c(Nc3ccc(Cl)cc3Cl)ncc(C(=O)N3CCOCC3)c12]

The desired compound was prepared by using Intermediate-11a and 2,4-dichloroaniline by following the similar procedure as described in Example-1; ¹H NMR (400 MHz, CDCl₃) δ 2.6 (s, 3H), 3.22-4.14 (m, 8H), 7.28-7.31 (m, 1H), 7.43-7.44 (m, 1H), 7.55-7.56 (m, 2H), 7.85 (s, 1H), 7.9-7.92 (m, 1H), 7.98 (s, 1H), 8.61-8.63 (m, 1H); MS m/z 416 (M+1).

Example-91

(5-Methyl-1-(m-tolylamino)isoquinolin-4-yl)(piperidin-1-yl)methanone

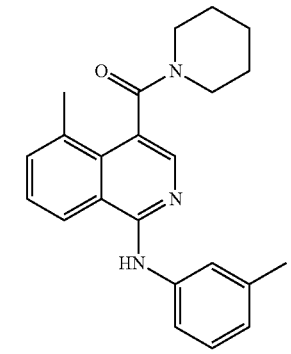 [SMILES: Cc1cccc(Nc2ncc(C(=O)N3CCCCC3)c3c(C)cccc23)c1]

This compound was prepared by using Intermediate-11d and m-toluidine by following the similar procedure as described in Example-1; ¹H NMR (400 MHz, CDCl₃) δ 1.48-1.75 (m, 6H), 2.36 (s, 3H), 2.58 (s, 3H), 3.11-3.18 (m, 1H), 3.39-3.47 (m, 2H), 4.11-4.16 (m, 1H), 6.89-6.9 (d, 1H, J=7.6 Hz), 7.16 (s, 1H), 7.22-7.26 (m, 1H), 7.41-7.5 (m, 4H), 7.83-7.84 (d, 1H, J=7.2 Hz), 7.94 (s, 1H); MS m/z 360 (M+1).

Example-92

(1-((3-Chloro-4-methylphenyl)amino)-5-methylisoquinolin-4-yl)(piperidin-1-yl)methanone

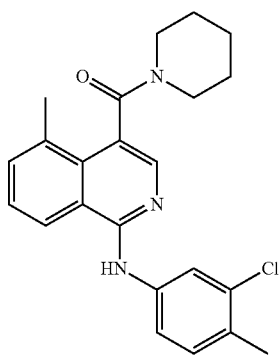 [SMILES: Cc1ccc(Nc2ncc(C(=O)N3CCCCC3)c3c(C)cccc23)cc1Cl]

The desired compound was prepared by using Intermediate-11d and 3-chloro-4-methyl aniline by following the similar procedure as described in Example-1; ¹H NMR (400 MHz, CDCl₃) δ 1.51-1.77 (m, 6H), 2.37 (s, 3H), 2.61 (s, 3H), 3.15-3.19 (m, 1H), 3.43-3.49 (m, 2H), 4.12-4.18 (m, 1H), 7.19-7.2 (m, 1H), 7.22 (s, 1H), 7.38-7.41 (m, 1H), 7.47-7.53 (m, 2H), 7.76-7.77 (m, 1H), 7.83-7.85 (d, 1H, J=7.6 Hz), 7.96 (s, 1H); MS m/z 394 (M+1).

Example-93

(1-((2-Chloro-5-methylphenyl)amino)-5-methylisoquinolin-4-yl)(piperidin-1-yl)methanone

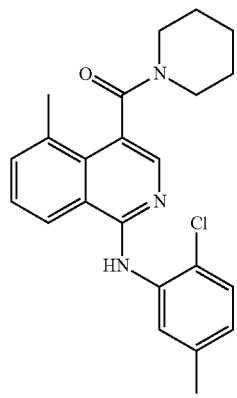 [SMILES: Cc1ccc(Cl)c(Nc2ncc(C(=O)N3CCCCC3)c3c(C)cccc23)c1]

This compound was prepared by using Intermediate-11d and 2-chloro-5-methylaniline by following the similar procedure as described in Example-1; $^1$H NMR (400 MHz, CDCl$_3$) δ 1.53-1.81 (m, 6H), 2.6 (s, 3H), 2.63 (s, 3H), 3.15-3.21 (m, 1H), 3.40-3.51 (m, 2H), 4.2-4.24 (m, 1H), 7.25-7.27 (m, 1H), 7.52-7.72 (m, 4H), 7.8 (s, 1H), 8.1 (s, 1H), 8.81-8.83 (d, 1H, J=7.6 Hz); MS m/z 394 (M+1).

Example-94

(1-((4-Fluoro-3-methylphenyl)amino)-5-methylisoquinolin-4-yl)(piperidin-1-yl)methanone

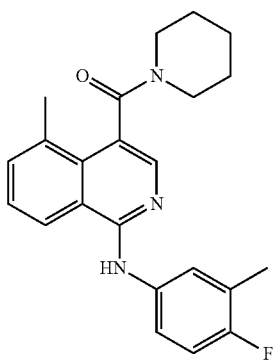 [SMILES: Cc1cc(Nc2ncc(C(=O)N3CCCCC3)c3c(C)cccc23)ccc1F]

The desired compound was prepared by using Intermediate-11d and 4-fluoro-3-methyl aniline by following the similar procedure as described in Example-1; $^1$H NMR (400 MHz, CDCl$_3$) δ 1.48-1.74 (m, 6H), 2.28 (s, 3H), 2.58 (s, 3H), 3.12-3.18 (m, 1H), 3.40-3.48 (m, 2H), 4.11-4.15 (m, 1H), 6.98-7.02 (m, 1H), 7.31-7.52 (m, 5H), 7.82-7.84 (m, 1H), 7.88 (s, 1H); MS m/z 378 (M+1).

Example-95

(1-((3-Fluoro-4-methylphenyl)amino)-5-methylisoquinolin-4-yl)(piperidin-1-yl)methanone

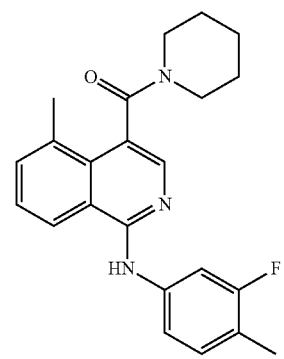 [SMILES: Cc1ccc(Nc2ncc(C(=O)N3CCCCC3)c3c(C)cccc23)cc1F]

This compound was prepared by using Intermediate-11d and 3-fluoro-4-methylaniline by following the similar procedure as described in Example-1; $^1$H NMR (400 MHz, CDCl$_3$) δ 1.49-1.79 (m, 6H), 2.25 (s, 3H), 2.59 (s, 3H), 3.12-3.19 (m, 1H), 3.40-3.5 (m, 2H), 4.15-4.18 (m, 1H), 7.11-7.23 (m, 3H), 7.45-7.59 (m, 3H), 7.82-7.83 (m, 1H), 7.84 (s, 1H); MS m/z 378 (M+1).

Example-96

(1-((3-Fluoro-2-methylphenyl)amino)-5-methylisoquinolin-4-yl)(piperidin-1-yl)methanone

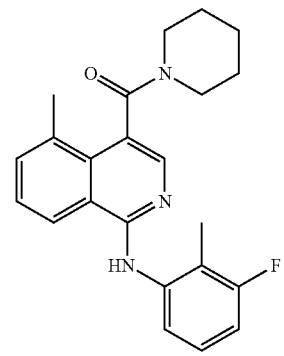 [SMILES: Cc1c(F)cccc1Nc1ncc(C(=O)N2CCCCC2)c2c(C)cccc12]

This compound was prepared by using Intermediate-11d and 3-fluoro-2-methylaniline by following the similar procedure as described in Example-1; $^1$H NMR (400 MHz, CDCl$_3$) δ 1.50-1.76 (m, 6H), 2.24 (s, 3H), 2.62 (s, 3H), 3.18-3.19 (m, 1H), 3.42-3.5 (m, 2H), 4.13-4.18 (m, 1H), 6.87-7.0 (m, 2H), 7.20-7.24 (m, 1H), 7.49-7.54 (m, 3H), 7.87-7.93 (m, 2H); MS m/z 378 (M+1).

Example-97

(1-((2-Fluoro-3-methylphenyl)amino)-5-methylisoquinolin-4-yl)(piperidin-1-yl)methanone

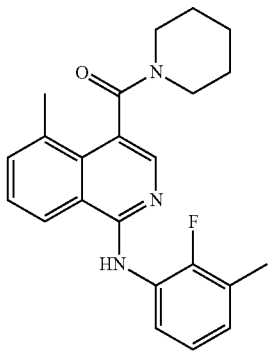 [SMILES: Cc1cccc(Nc2ncc(C(=O)N3CCCCC3)c3c(C)cccc23)c1F]

The title compound was prepared by using Intermediate-11d and 2-fluoro-3-methylaniline by following the similar procedure as described in Example-1; ¹H NMR (400 MHz, CDCl₃) δ 1.50-1.77 (m, 6H), 2.34 (s, 3H), 2.62 (s, 3H), 3.13-3.2 (m, 1H), 3.41-3.5 (m, 2H), 4.15-4.19 (m, 1H), 6.87-6.9 (t, 1H, J=7.2 Hz), 7.06-7.1 (t, 1H, J=7.6 Hz), 7.51-7.55 (m, 3H), 7.90-7.92 (m, 1H), 7.99 (s, 1H), 8.3 (s, 1H); MS m/z 378 (M+1).

Example-98

(1-(Benzhydrylamino)-5-methylisoquinolin-4-yl)(piperidin-1-yl)methanone

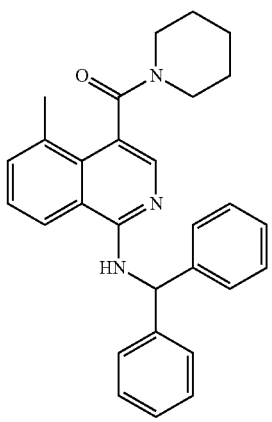 [SMILES: Cc1cccc2c(NC(c3ccccc3)c3ccccc3)ncc(C(=O)N3CCCCC3)c12]

The title compound was prepared by using Intermediate-11d and diphenylmethanamine by following the similar procedure as described in Example-1; ¹H NMR (400 MHz, CDCl₃) δ 1.47-1.76 (m, 6H), 2.55 (s, 3H), 3.14-3.2 (m, 1H), 3.40-3.48 (m, 2H), 4.04-4.07 (m, 1H), 5.83 (s, 1H), 6.63 (s, 1H), 7.23-7.51 (m, 12H), 7.72-7.74 (d, 1H, J=8.0 Hz), 7.81 (s, 1H); MS m/z 436 (M+1).

Example-99

(5-Methyl-1-((3-(trifluoromethyl)phenyl)amino)isoquinolin-4-yl)(2-phenylmorpholino)methanone

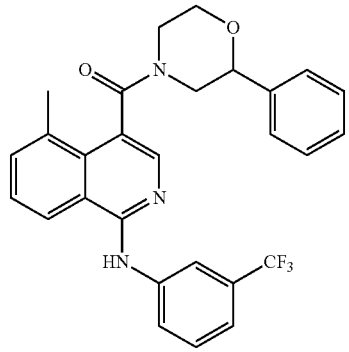 [SMILES: Cc1cccc2c(Nc3cccc(C(F)(F)F)c3)ncc(C(=O)N3CCOC(c4ccccc4)C3)c12]

The title compound was prepared by using Intermediate-11l and 3-(trifluoromethyl)aniline by following the similar procedure as described in Example-1; ¹H NMR (400 MHz, CDCl₃) δ 2.48 (s, 3H), 2.88-4.91 (m, 7H), 7.18-7.25 (m, 2H), 7.30-7.51 (m, 8H), 7.83-8.1 (m, 4H); MS m/z 492 (M+1).

Example-100

N-Cyclohexyl-1-((3-fluorophenyl)amino)-5-methylisoquinolin-4-carboxamide

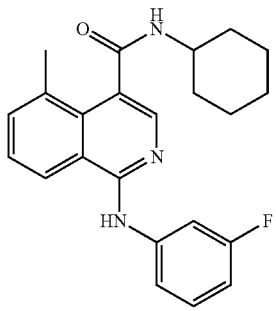 [SMILES: Cc1cccc2c(Nc3cccc(F)c3)ncc(C(=O)NC3CCCCC3)c12]

This compound was prepared by using Intermediate-11m and 3-fluoroaniline by following the similar procedure as described in Example-1; ¹H NMR (400 MHz, DMSO-d6) δ 1.1-1.98 (m, 10H), 2.59 (s, 3H), 3.76-3.77 (m, 1H), 6.78-6.82 (m, 1H), 7.31-7.37 (m, 1H), 7.56-7.63 (m, 3H), 7.86-7.91 (m, 2H), 8.31-8.44 (m, 2H), 9.44 (s, 1H); MS m/z 378 (M+1).

Example-101

N-Cyclohexyl-1-((3,5-difluorophenyl)amino)-5-methylisoquinolin-4-carboxamide

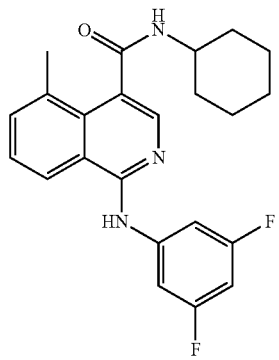 [SMILES: Cc1cccc2c(Nc3cc(F)cc(F)c3)ncc(C(=O)NC3CCCCC3)c12]

This compound was prepared by using Intermediate-11m and 3,5-difluoroaniline by following the similar procedure as described in Example-1; $^1$H NMR (400 MHz, DMSO-d6) δ 1.21-2.13 (m, 10H), 2.69 (s, 3H), 4.02-4.09 (m, 1H), 5.84-5.86 (m, 1H), 6.48-6.53 (m, 1H), 7.30-7.37 (m, 3H), 7.47-7.54 (m, 2H), 7.78-7.8 (d, 1H, J=8.0 Hz), 8.1 (s, 1H); MS m/z 396 (M+1).

Example-102

(1-((3-Chlorophenyl)amino)-5-methylisoquinolin-4-yl)(pyrrolidin-1-yl)methanone

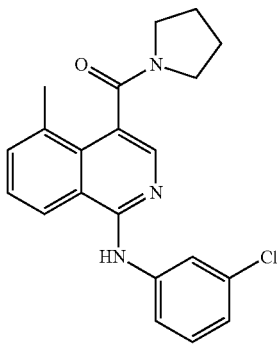 [SMILES: Cc1cccc2c(Nc3cccc(Cl)c3)ncc(C(=O)N3CCCC3)c12]

This compound was prepared by using Intermediate-11n and 3-chloroaniline by following the similar procedure as described in Example-1; $^1$H NMR (400 MHz, DMSO-d6) δ 1.79-1.93 (m, 4H), 2.44 (s, 3H), 3.02-3.57 (m, 4H), 7.03-7.06 (m, 1H), 7.33-7.37 (t, 1H, J=8.0 Hz), 7.58-7.64 (m, 2H), 7.78-7.81 (m, 1H), 7.91 (s, 1H), 8.05-8.06 (m, 1H), 8.43-8.45 (m, 1H), 9.44 (s, 1H); MS m/z 366 (M+1).

Example-103

(1-((3-Fluorophenyl)amino)-5-methylisoquinolin-4-yl)(pyrrolidin-1-yl)methanone

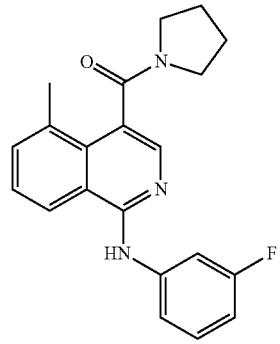 [SMILES: Cc1cccc2c(Nc3cccc(F)c3)ncc(C(=O)N3CCCC3)c12]

This compound was prepared by using Intermediate-11n and 3-fluoroaniline by following the similar procedure as described in Example-1; $^1$H NMR (400 MHz, DMSO-d6) δ 1.78-1.94 (m, 4H), 2.44 (s, 3H), 2.99-4.03 (m, 4H), 6.78-6.83 (m, 1H), 7.31-7.37 (m, 1H), 7.57-7.63 (m, 3H), 7.85-7.9 (m, 2H), 8.43-8.45 (m, 1H), 9.45 (s, 1H); MS m/z 350 (M+1).

Example-104

(1-((3,5-Difluorophenyl)amino)-5-methylisoquinolin-4-yl)(pyrrolidin-1-yl)methanone

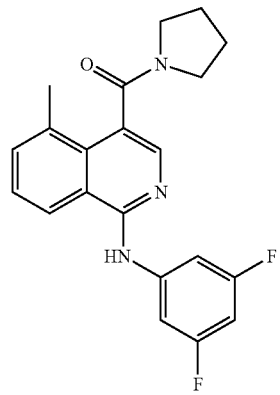 [SMILES: Cc1cccc2c(Nc3cc(F)cc(F)c3)ncc(C(=O)N3CCCC3)c12]

The desired compound was prepared by using Intermediate-11n and 3,5-difluoroaniline by following the similar procedure as described in Example-1; $^1$H NMR (400 MHz, DMSO-d6) δ 1.77-1.98 (m, 4H), 2.45 (s, 3H), 2.99-3.57 (m, 4H), 6.77-6.81 (m, 1H), 7.60-7.72 (m, 4H), 7.96 (s, 1H), 8.41-8.44 (m, 1H), 9.6 (s, 1H); MS m/z 368 (M+1).

Example-105

(1-((2,4-Difluorophenyl)amino)-5-methylisoquinolin-4-yl)(pyrrolidin-1-yl)methanone

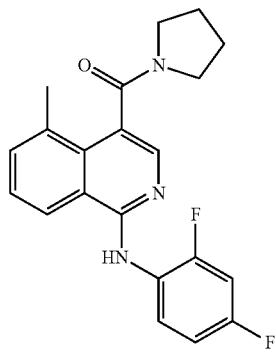 [SMILES: Cc1cccc2c(Nc3ccc(F)cc3F)ncc(C(=O)N3CCCC3)c12]

The desired compound was prepared by using Intermediate-11n and 2,4-difluoroaniline by following the similar procedure as described in Example-1; $^1$H NMR (400 MHz, DMSO-d6) δ 1.77-1.9 (m, 4H), 2.46 (s, 3H), 3.01-3.52 (m, 4H), 7.10-7.11 (m, 1H), 7.29-7.35 (m, 1H), 7.47-7.61 (m, 3H), 7.7 (s, 1H), 8.32-8.35 (m, 1H), 9.16 (s, 1H); MS m/z 368 (M+1).

Example-106

Azetidin-1-yl(1-((3,5-difluorophenyl)amino)-5-methylisoquinolin-4-yl)methanone

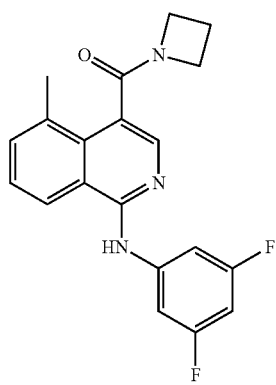 [SMILES: Cc1cccc2c(Nc3cc(F)cc(F)c3)ncc(C(=O)N3CCC3)c12]

This compound was prepared by using Intermediate-11o and 3,5-difluoroaniline by following the similar procedure as described in Example-1; $^1$H NMR (400 MHz, DMSO-d6) δ 2.24-2.28 (m, 2H), 2.59 (s, 3H), 3.91-4.1 (m, 4H), 6.78-6.84 (m, 1H), 7.61-7.74 (m, 4H), 7.99 (s, 1H), 8.41-8.43 (m, 1H), 9.63 (s, 1H); MS m/z 354 (M+1).

Example-107

Azetidin-1-yl(1-((4-fluorophenyl)amino)-5-methylisoquinolin-4-yl)methanone

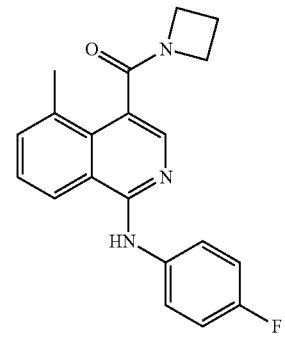 [SMILES: Cc1cccc2c(Nc3ccc(F)cc3)ncc(C(=O)N3CCC3)c12]

The desired compound was prepared by using Intermediate-11o and 4-fluoroaniline by following the similar procedure as described in Example-1; $^1$H NMR (400 MHz, DMSO-d6) δ 2.20-2.27 (m, 2H), 2.6 (s, 3H), 3.88-4.07 (m, 4H), 7.15-7.19 (m, 2H), 7.54-7.62 (m, 2H), 7.77-7.8 (m, 2H), 7.82 (s, 1H), 8.39-8.41 (m, 1H), 9.33 (s, 1H); MS m/z 336 (M+1).

Example-108

(1-((3-Chloro-2-methylphenyl)amino)-5-methylisoquinolin-4-yl)(piperidin-1-yl)methanone

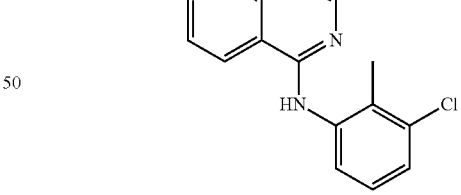

This compound was prepared by using Intermediate-11d and 3-chloro-2-methylaniline by following the similar procedure as described in Example-1; $^1$H NMR (400 MHz, CDCl$_3$) δ 1.44-1.81 (m, 6H), 2.54 (s, 3H), 2.74 (s, 3H), 3.15-3.21 (m, 1H), 3.40-3.51 (m, 2H), 3.90-4.1 (m, 1H), 6.54 (s, 1H), 7.45-7.47 (d, 1H, J=8.0 Hz), 7.63-7.7 (m, 2H), 8.2-8.22 (d, 1H, J=8.0 Hz), 8.63 (s, 1H), 8.69-8.71 (m, 1H), 8.85 (s, 1H); MS m/z 394 (M+1).

Example-109

(1-((5-Chloro-2-methylphenyl)amino)-5-methylisoquinolin-4-yl)(piperidin-1-yl)methanone

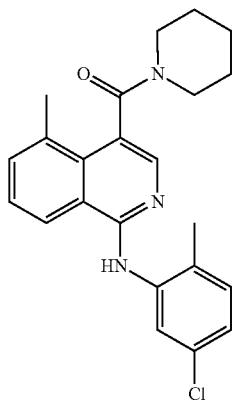 [SMILES: Cc1ccc(Cl)cc1Nc1ncc(C(=O)N2CCCCC2)c2c(C)cccc12]

The desired compound was prepared by using Intermediate-11d and 5-chloro-2-methylaniline by following the similar procedure as described in Example-1; ¹H NMR (400 MHz, CDCl₃) δ 1.51-1.78 (m, 6H), 2.33 (s, 3H), 2.62 (s, 3H), 3.15-3.21 (m, 1H), 3.42-3.51 (m, 2H), 4.14-4.17 (m, 1H), 7.0 (s, 1H), 7.01-7.06 (m, 1H), 7.17-7.19 (d, 1H, J=8.0 Hz), 7.49-7.55 (m, 2H), 7.84-7.86 (m, 1H), 7.95-7.99 (m, 2H); MS m/z 394 (M+1).

Example-110

(5-Methyl-1-((3-(trifluoromethyl)phenyl)amino)isoquinolin-4-yl)(2-oxa-7-azaspiro[3.5]nonan-7-yl)methanone

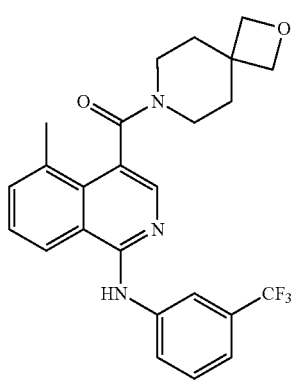 [SMILES: Cc1cccc2c(Nc3cccc(C(F)(F)F)c3)ncc(C(=O)N3CCC4(CC3)COC4)c12]

This compound was prepared by using Intermediate-11p and 3-(trifluoromethyl)aniline by following the similar procedure as described in Example-1; ¹H NMR (400 MHz, CDCl₃) δ 1.78-2.12 (m, 4H), 2.54 (s, 3H), 3.09-3.15 (m, 1H), 3.36-3.46 (m, 2H), 4.15-4.19 (m, 1H), 4.43-4.55 (m, 4H), 7.31-7.33 (m, 1H), 7.43-7.52 (m, 4H), 7.84-7.88 (m, 2H), 7.92 (s, 1H), 7.99 (s, 1H); MS m/z 456 (M+1).

Example-111

(1-((3-Fluorophenyl)amino)-5-methylisoquinolin-4-yl)(2-oxa-7-azaspiro[3.5]nonan-7-yl)methanone

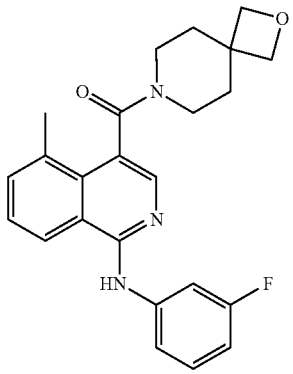 [SMILES: Cc1cccc2c(Nc3cccc(F)c3)ncc(C(=O)N3CCC4(CC3)COC4)c12]

The title compound was prepared by using Intermediate-11p and 3-fluoroaniline by following the similar procedure as described in Example-1; ¹H NMR (400 MHz, CDCl₃) δ 1.79-2.1 (m, 4H), 2.57 (s, 3H), 3.13-3.16 (m, 1H), 3.37-3.46 (m, 2H), 4.16-4.22 (m, 1H), 4.44-4.55 (m, 4H), 6.77-6.81 (m, 1H), 7.27-7.35 (m, 3H), 7.51-7.53 (m, 2H), 7.69-7.73 (m, 1H), 7.85-7.88 (m, 1H), 7.99 (s, 1H); MS m/z 406 (M+1).

Example-112

(1-((3-Chlorophenyl)amino)-5-methylisoquinolin-4-yl)(2-oxa-7-azaspiro[3.5]nonan-7-yl)methanone

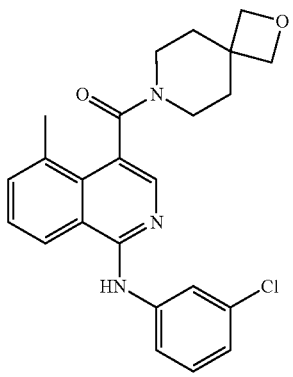 [SMILES: Cc1cccc2c(Nc3cccc(Cl)c3)ncc(C(=O)N3CCC4(CC3)COC4)c12]

This compound was prepared by using Intermediate-11p and 3-chloroaniline by following the similar procedure as described in Example-1; ¹H NMR (400 MHz, CDCl₃) δ 1.79-2.1 (m, 4H), 2.56 (s, 3H), 3.13-3.16 (m, 1H), 3.37-3.47 (m, 2H), 4.16-4.22 (m, 1H), 4.44-4.55 (m, 4H), 7.05-7.08 (m, 1H), 7.27-7.32 (m, 2H), 7.47-7.53 (m, 3H), 7.84-7.87 (m, 2H), 7.99 (s, 1H); MS m/z 422 (M+1).

General Procedure B:
5-Alkyl-1-(arylamino)isoquinolin-4-carboxylic amide

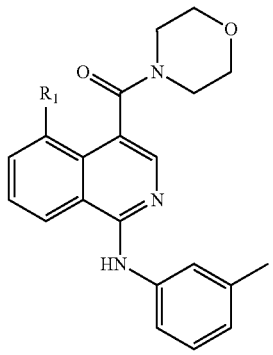

5-Alkyl-1-chloroisoquinolin-4-carboxylic amide (Intermediate-21) (1 equiv), toluene (2.0 mL), $Cs_2CO_3$ (3 equiv) were charged in a sealed tube and degassed for 30 min. To this mixture, BINAP (0.2 equiv), $PdOAc_2$ (0.1 equiv) and the corresponding aniline (1.2 equiv) were added and the reaction mixture was heated to 110° C. overnight. After completion (TLC) and cooling to RT, it was diluted with EtOAc and filtered through celite. The filtrate was collected and concentrated to give crude product that was purified by flash column chromatography to furnish the desired compounds (40-50%).

Example-113

(5-Cyclopropyl-1-(m-tolylamino)isoquinolin-4-yl)(morpholino)methanone

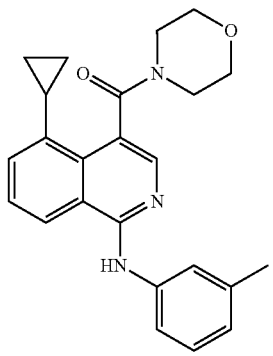 [SMILES: Cc1cccc(Nc2ncc(C(=O)N3CCOCC3)c3c(C4CC4)cccc23)c1]

This compound was prepared by using Intermediate-21a and m-toluidine by following the general procedure B; $^1$H NMR (400 MHz, $CDCl_3$) δ 0.49-0.52 (m, 1H), 0.85-0.95 (m, 2H), 1.0-1.01 (m, 1H), 2.4 (s, 3H), 2.46-2.48 (m, 1H), 3.31-3.34 (m, 1H), 3.38-3.41 (m, 1H), 3.59-3.64 (m, 2H), 3.71-3.77 (m, 2H), 3.92-3.95 (m, 1H), 4.31-4.35 (m, 1H), 6.93-6.95 (d, 1H, J=7.2 Hz), 7.2 (s, 1H), 7.27-7.3 (m, 2H), 7.44-7.45 (m, 2H), 7.5-7.53 (m, 1H), 7.57-7.58 (d, 1H), 7.86-7.88 (d, 1H, J=8.4 Hz), 8.0 (s, 1H); MS m/z 388 (M+1).

Example-114

(1-((3-Chlorophenyl)amino)-5-cyclopropylisoquinolin-4-yl)(morpholino)methanone

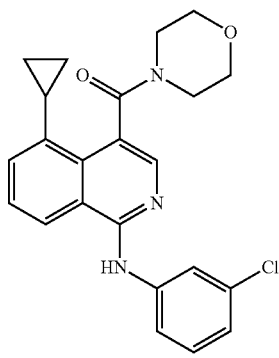 [SMILES: O=C(c1cnc(Nc2cccc(Cl)c2)c2cccc(C3CC3)c12)N1CCOCC1]

This compound was prepared by using Intermediate-21a and m-chloroaniline by following the general procedure B; $^1$H NMR (400 MHz, $CDCl_3$) δ 0.49-0.51 (m, 1H), 0.86-0.94 (m, 2H), 0.99-1.01 (m, 1H), 2.46 (m, 1H), 3.31 (m, 1H), 3.4 (m, 1H), 3.57-3.65 (m, 2H), 3.71-3.75 (m, 2H), 3.93-3.96 (m, 1H), 4.32-4.35 (d, 1H), 7.06-7.08 (m, 1H), 7.27-7.34 (m, 2H), 7.47-7.57 (m, 3H), 7.82-7.86 (m, 2H), 8.05 (s, 1H); MS m/z 408 (M+1).

Example-115

(5-Cyclopropyl-1-(2-fluoro-3-methylphenyl)amino)isoquinolin-4-yl)(morpholino)methanone

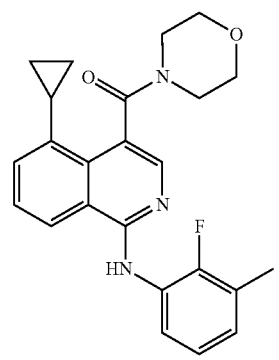 [SMILES: Cc1cccc(Nc2ncc(C(=O)N3CCOCC3)c3c(C4CC4)cccc23)c1F]

This compound was prepared by using Intermediate-21a and 2-fluoro-3-methylaniline by following the general procedure B; $^1$H NMR (400 MHz, $CDCl_3$) δ 0.51-0.53 (m, 1H), 0.86-0.91 (m, 2H), 0.92-1.02 (m, 1H), 2.35 (s, 3H), 2.47 (m, 1H), 3.33-3.3 (m, 1H), 3.39 (m, 1H), 3.56-3.64 (m, 2H), 3.69-3.77 (m, 2H), 3.93-3.95 (m, 1H), 4.32-4.35 (d, 1H), 6.88-6.92 (t, 1H), 7.07-7.11 (m, 1H), 7.4-7.5 (d, 1H), 7.53-7.6 (m, 2H), 7.9-7.92 (dd, 1H), 8.06 (s, 1H), 8.27-8.31 (t, 1H); MS m/z 406 (M+1).

Example-116

(5-Cyclopropyl-1-(2,3-difluorophenyl)amino)isoquinolin-4-yl)(morpholino)methanone

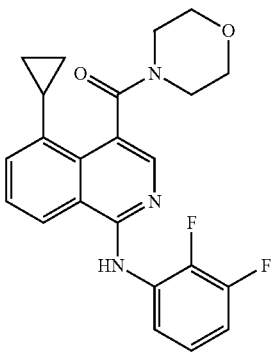 [SMILES: O=C(c1cnc(Nc2cccc(F)c2F)c2cccc(C3CC3)c12)N1CCOCC1]

The desired compound was prepared by using Intermediate-21a and 2,3-difluoroaniline by following the general procedure B; $^1$H NMR (400 MHz, CDCl$_3$) δ 0.52-0.55 (m, 1H), 0.88-0.97 (m, 2H), 1.02-1.03 (m, 1H), 2.46-2.48 (m, 1H), 3.3-3.34 (m, 1H), 3.39-3.42 (m, 1H), 3.54-3.63 (m, 2H), 3.7-3.77 (m, 2H), 3.93-3.96 (m, 1H), 4.32-4.35 (m, 1H), 6.88-6.92 (m, 1H), 7.11-7.15 (m, 1H), 7.46-7.47 (m, 1H), 7.56-7.62 (m, 2H), 7.91-7.93 (dd, 1H), 8.07 (s, 1H), 8.25-8.27 (m, 1H); MS m/z 410 (M+1).

Example-117

(5-Cyclopropyl-1-(2,3,6-trifluorophenyl)amino)isoquinolin-4-yl)(morpholino)methanone

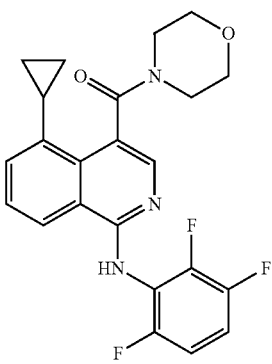 [SMILES: O=C(c1cnc(Nc2c(F)ccc(F)c2F)c2cccc(C3CC3)c12)N1CCOCC1]

This compound was prepared by using Intermediate-21a and 2,3,6-trifluoroaniline by following the general procedure B; $^1$H NMR (400 MHz, CDCl$_3$) δ 0.51-0.54 (m, 1H), 0.87-0.96 (m, 2H), 1.01-1.02 (m, 1H), 2.47 (m, 1H), 3.3-3.33 (m, 1H), 3.39-3.41 (m, 1H), 3.5-3.62 (m, 2H), 3.7-3.91 (m, 2H), 3.91-3.94 (m, 1H), 4.29-4.32 (d, 1H), 6.75 (bs, 1H), 6.95-7.08 (m, 2H), 7.53-7.63 (m, 2H), 7.98-7.99 (t, 2H); MS m/z 428 (M+1).

Example-118

(5-Cyclopropyl-1-((3-(trifluoromethyl)phenyl)amino)isoquinolin-4-yl)(morpholino)methanone

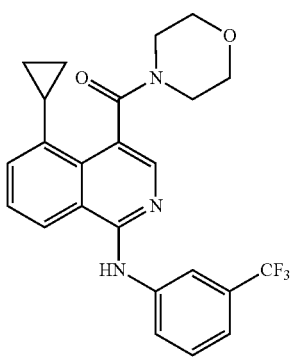 [SMILES: O=C(c1cnc(Nc2cccc(C(F)(F)F)c2)c2cccc(C3CC3)c12)N1CCOCC1]

The desired compound was prepared by using Intermediate-21a and 3-(trifluoromethyl)aniline by following the general procedure B; $^1$H NMR (400 MHz, CDCl$_3$) δ 0.47-0.5 (m, 1H), 0.85-0.94 (m, 2H), 0.97-1.01 (m, 1H), 2.44-2.46 (m, 1H), 3.29-3.35 (m, 1H), 3.38-3.44 (m, 1H), 3.58-3.66 (m, 2H), 3.71-3.78 (m, 2H), 3.93-3.96 (m, 1H), 4.32-4.35 (d, 1H), 7.33-7.35 (d, 1H), 7.47-7.56 (m, 4H), 7.86-7.91 (t, 2H), 7.98-8.01 (d, 2H); MS m/z 442 (M+1).

Example-119

(5-Cyclopropyl-1-((2-fluoro-3-(trifluoromethyl)phenyl)amino)isoquinolin-4-yl)(morpholino)methanone

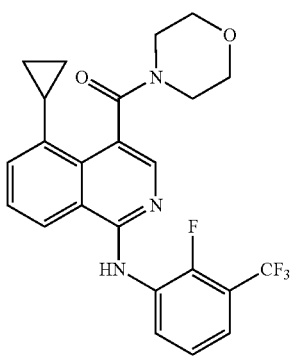 [SMILES: O=C(c1cnc(Nc2cccc(C(F)(F)F)c2F)c2cccc(C3CC3)c12)N1CCOCC1]

This compound was prepared by using Intermediate-21a and 2-fluoro-3-(trifluoromethyl)aniline by following the general procedure B; $^1$H NMR (400 MHz, CDCl$_3$) δ 0.53-0.55 (m, 1H), 0.89-1.02 (m, 2H), 1.03-1.26 (m, 1H), 2.43-2.5 (m, 1H), 3.27-3.33 (m, 1H), 3.34-3.44 (m, 1H), 3.53-3.64 (m, 2H), 3.7-3.74 (m, 2H), 3.93-3.96 (m, 1H), 4.32-4.36 (d, 1H), 7.27-7.32 (m, 2H), 7.57-7.63 (m, 3H), 7.91-7.93 (d, 1H), 8.07 (s, 1H), 8.76-8.8 (m, 1H); MS m/z 460 (M+1).

Example-120

(1-((3-Chlorophenyl)amino)-5-cyclopropylisoquinolin-4-yl)(piperidin-1-yl)methanone

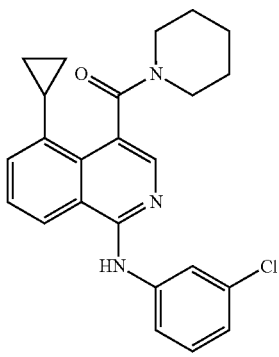 [SMILES: O=C(c1cnc(Nc2cccc(Cl)c2)c2cccc(C3CC3)c12)N1CCCCC1]

The title compound was prepared by using Intermediate-21b and m-chloroaniline by following the general procedure B; ¹H NMR (400 MHz, CDCl₃) δ 0.49-0.52 (m, 1H), 0.84-1.01 (m, 4H), 1.26-1.3 (m, 2H), 1.68-1.7 (m, 1H), 1.76-1.77 (m, 2H), 1.86-1.87 (m, 1H), 2.48-2.52 (m, 1H), 3.07-3.13 (m, 2H), 3.62-3.65 (d, 1H), 7.05-7.07 (dd, 1H), 7.27-7.31 (t, 1H), 7.47-7.56 (m, 4H), 7.81-7.86 (m, 2H), 8.05 (s, 1H); MS m/z 406 (M+1).

Example-121

(1-((3-Chloro-2-fluorophenyl)amino)-5-cyclopropylisoquinolin-4-yl)(piperidin-1-yl)methanone

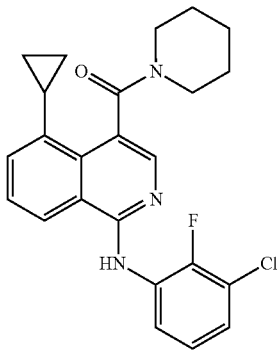 [SMILES: O=C(c1cnc(Nc2cccc(Cl)c2F)c2cccc(C3CC3)c12)N1CCCCC1]

This compound was prepared by using Intermediate-21b and 3-chloro-2-fluoroaniline by following the general procedure B; ¹H NMR (400 MHz, CDCl₃) δ 0.53-0.55 (m, 1H), 0.84-1.01 (m, 5H), 1.25-1.31 (m, 2H), 1.67-1.68 (m, 1H), 1.7-1.72 (m, 1H), 2.48-2.52 (m, 1H), 3.07-3.13 (m, 2H), 3.59-3.62 (m, 1H), 4.47-4.51 (m, 1H), 7.07-7.16 (m, 2H), 7.47 (brs, 1H), 7.54-7.59 (m, 2H), 7.89-7.91 (dd, 1H), 8.06 (s, 1H), 8.42-8.45 (t, 1H); MS m/z 424 (M+1).

Example-122

(1-((2,3-Difluorophenyl)amino)-5-cyclopropylisoquinolin-4-yl)(piperidin-1-yl)methanone

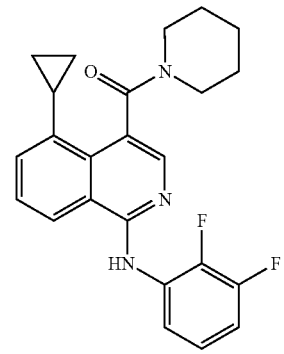 [SMILES: O=C(c1cnc(Nc2cccc(F)c2F)c2cccc(C3CC3)c12)N1CCCCC1]

This compound was prepared by using Intermediate-21b and 2,3-difluoroaniline by following the general procedure B; ¹H NMR (400 MHz, CDCl₃) δ 0.52-0.55 (m, 1H), 0.85-1.01 (m, 4H), 1.59-1.61 (m, 2H), 1.69-1.72 (m, 1H), 1.76-1.8 (m, 1H), 1.86-1.88 (m, 1H), 2.47-2.52 (m, 1H), 3.05-3.13 (m, 2H), 3.59-3.62 (m, 1H), 4.46-4.52 (m, 1H), 6.85-6.9 (m, 1H), 7.09-7.13 (m, 1H), 7.44-7.45 (m, 1H), 7.54-7.59 (m, 2H), 7.9-7.92 (dd, 1H), 8.07 (s, 1H), 8.24-8.27 (m, 1H); MS m/z 408 (M+1).

Example-123

(1-((2,3-Difluorophenyl)amino)-5-ethylisoquinolin-4-yl)(morpholino)methanone

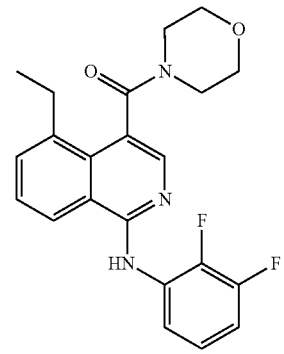

The desired compound was prepared by using Intermediate-21c and 2,3-difluoroaniline by following the general procedure B; ¹H NMR (400 MHz, CDCl₃) δ 1.29-1.3 (t, 3H), 2.86-2.9 (m, 1H), 3.12-3.16 (m, 1H), 3.3-3.33 (m, 1H), 3.41-3.42 ((m, 1H), 3.6-3.67 (m, 3H), 3.7-3.71 (m, 1H), 3.79-3.82 (m, 1H), 4.11-4.12 (m, 1H), 6.91-6.93 (m, 1H), 7.1-7.16 (m, 1H), 7.51-7.53 (m, 1H), 7.62-7.68 (m, 2H), 7.92-7.94 (m, 1H), 8.0 (s, 1H), 8.22-8.26 (t, 1H); MS m/z 398 (M+1).

Example-124

(1-((2,3-Difluorophenyl)amino)-5-ethylisoquinolin-4-yl)(piperidin-1-yl)methanone

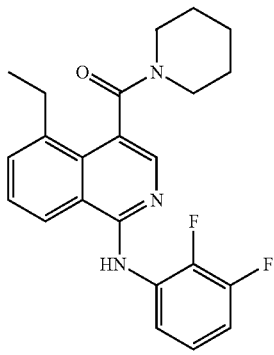 [SMILES: CCc1cccc2c(Nc3cccc(F)c3F)ncc(C(=O)N3CCCCC3)c12]

The title compound was prepared by using Intermediate-21d and 2,3-difluoroaniline by following the general procedure B; $^1$H NMR (400 MHz, CDCl$_3$) δ 1.27-1.37 (m, 5H), 1.51-1.52 (m, 3H), 1.74-1.76 (m, 2H), 2.02-2.06 (m, 1H), 2.84-2.92 (m, 1H), 3.13-3.19 (m, 2H), 3.42-3.52 (m, 2H), 4.16-4.19 (m, 1H), 6.83-6.9 (m, 1H), 7.06-7.12 (m, 1H), 7.45 (s, 1H), 7.6-7.66 (m, 2H), 7.91-7.93 (d, 1H, J=7.2 Hz), 7.99 (s, 1H), 8.23-8.27 (t, 1H); MS m/z 396 (M+1).

Example-125

(1-((2,4-Difluorophenyl)amino)-5-ethylisoquinolin-4-yl)(piperidin-1-yl)methanone

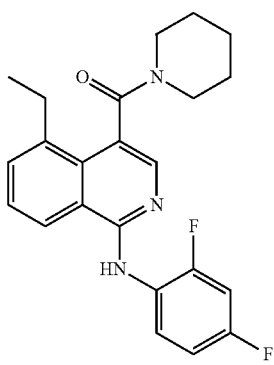 [SMILES: CCc1cccc2c(Nc3ccc(F)cc3F)ncc(C(=O)N3CCCCC3)c12]

This compound was prepared by using Intermediate-21d and 2,4-difluoroaniline by following the general procedure B; $^1$H NMR (400 MHz, CDCl$_3$) δ 1.32-1.36 (t, 3H), 1.49-1.52 (m, 2H), 1.61-1.78 (m, 4H), 2.85-2.91 (m, 1H), 3.13-3.21 (m, 2H), 3.41-3.52 (m, 2H), 4.15-4.18 (m, 1H), 6.92-6.98 (m, 2H), 7.27-7.3 (m, 1H), 7.58-7.64 (m, 2H), 7.88-7.95 (m, 2H), 8.38-8.39 (m, 1H); MS m/z 396 (M+1).

Example-126

(1-((3,5-Difluorophenyl)amino)-5-ethylisoquinolin-4-yl)(piperidin-1-yl)methanone

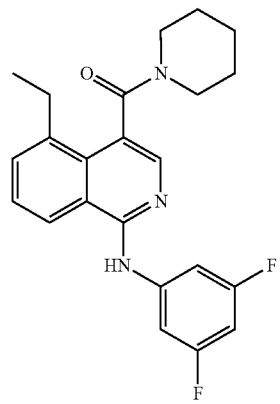

The desired compound was prepared by using Intermediate-21d and 3,5-difluoroaniline by following the general procedure B; $^1$H NMR (400 MHz, CDCl$_3$) δ 1.26-1.31 (t, 3H), 1.52-1.56 (m, 2H), 1.59-1.81 (m, 4H), 2.81-2.87 (m, 1H), 3.09-3.18 (m, 1H), 3.2-3.23 (m, 1H), 3.46-3.54 (m, 2H), 4.18-4.22 (m, 1H), 6.49-6.52 (m, 1H), 7.32-7.35 (dd, 2H), 7.5-7.57 (m, 2H), 7.62 (s, 1H), 7.8-7.82 (m, 1H), 7.92 (s, 1H); MS m/z 396 (M+1).

Example-127

(1-((3-Chlorophenyl)amino)-5-ethylisoquinolin-4-yl)(piperidin-1-yl)methanone

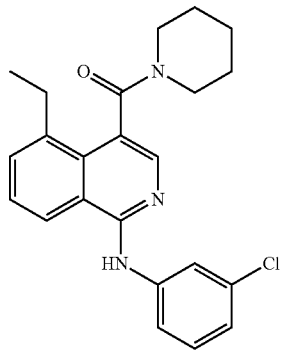

This compound was prepared by using Intermediate-21d and 3-chloroaniline by following the general procedure B; $^1$H NMR (400 MHz, CDCl$_3$) δ 1.28-1.33 (t, 3H), 1.5-1.54 (m, 2H), 1.62-1.79 (m, 4H), 2.82-2.88 (m, 1H), 3.1-3.23 (m, 2H), 3.45-3.52 (m, 2H), 4.16-4.2 (m, 1H), 7.03-7.05 (m, 1H), 7.26-7.3 (m, 1H), 7.42 (s, 1H), 7.48-7.58 (m, 3H), 7.81-7.85 (m, 2H), 7.93 (s, 1H); MS m/z 394 (M+1).

Example-128

(1-((3-Chloro-2-fluorophenyl)amino)-5-ethylisoquinolin-4-yl)(piperidin-1-yl)methanone

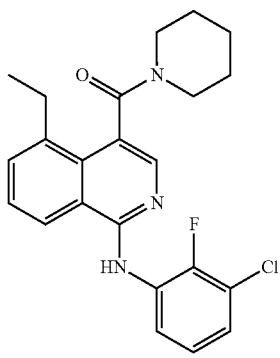

This compound was prepared by using Intermediate-21d and 3-chloro-2-fluoroaniline by following the general procedure B; $^1$H NMR (400 MHz, CDCl$_3$) δ 1.33-1.37 (t, 3H), 1.49-1.52 (m, 2H), 1.59-1.79 (m, 4H), 2.86-2.92 (m, 1H), 3.14-3.2 (m, 2H), 3.4-3.53 (m, 2H), 4.14-4.19 (m, 1H), 7.07-7.15 (m, 2H), 7.48 (brs, 1H), 7.6-7.66 (m, 2H), 7.9-7.92 (d, 1H), 7.99 (s, 1H), 8.14-8.45 (m, 1H); MS m/z 412 (M+1).

Example-129

(5-Ethyl-1-((2-Fluoro-3-(trifluoromethyl)phenyl)amino)isoquinolin-4-yl)(piperidin-1-yl)methanone

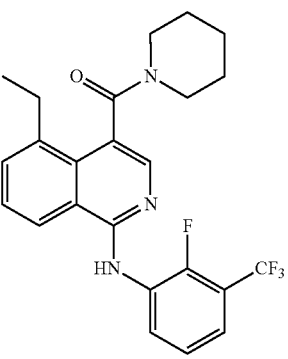

This compound was prepared by using Intermediate-21d and 2-fluoro-3-(trifluoromethyl)aniline by following the general procedure B; $^1$H NMR (400 MHz, CDCl$_3$) δ 1.27-1.37 (t, 3H), 1.51-1.65 (m, 4H), 1.67-1.76 (m, 2H), 2.87-2.94 (m, 1H), 3.15-3.21 (m, 2H), 3.41-3.53 (m, 2H), 4.16-4.19 (m, 1H), 7.27-7.29 (m, 2H), 7.58-7.67 (m, 3H), 7.91-7.93 (d, 1H), 8.0 (s, 1H), 8.76-8.79 (m, 1H); MS m/z 446 (M+1).

Example-130

(1-((3-Fluoro-2-methylphenyl)amino)-5-ethylisoquinolin-4-yl)(piperidin-1-yl)methanone

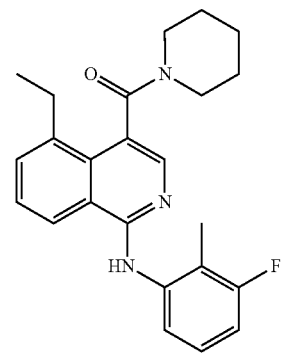

This compound was prepared by using Intermediate-21d and 3-fluoro-2-methylaniline by following the general procedure B; $^1$H NMR (400 MHz, CDCl$_3$) δ 1.22-1.36 (t, 3H), 1.48-1.51 (m, 2H), 1.59-1.77 (m, 4H), 2.24 (s, 3H), 2.87-2.91 (m, 1H), 3.13-3.19 (m, 2H), 3.44-3.52 (m, 2H), 4.12-4.16 (m, 1H), 6.87-6.91 (t, 1H), 6.99 (br s, 1H), 7.17-7.23 (m, 1H), 7.49-7.51 (d, 1H), 7.56-7.64 (m, 2H), 7.88-7.92 (m, 2H); MS m/z 392 (M+1).

Example-131

(1-((3-Chloro-2-methylphenyl)amino)-5-ethylisoquinolin-4-yl)(piperidin-1-yl)methanone

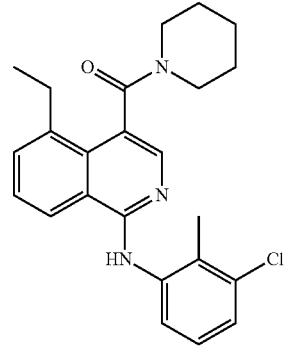

The title compound was prepared by using Intermediate-21d and 3-chloro-2-methyl aniline by following the general procedure B; $^1$H NMR (400 MHz, CDCl$_3$) δ 1.27-1.36 (t, 3H), 1.47-1.52 (m, 2H), 1.6-1.78 (m, 4H), 2.36 (s, 3H), 2.85-2.91 (m, 1H), 3.12-3.23 (m, 2H), 3.42-3.53 (m, 2H), 4.1-4.14 (m, 1H), 7.03 (s, 1H), 7.17-7.19 (t, 1H), 7.22-7.24 (d, 1H), 7.51-7.58 (m, 2H), 7.62-7.63 (d, 1H), 7.88-7.89 (m, 2H); MS m/z 408 (M+1).

Example-132

(4-((3-Chlorophenyl)amino)-8-methylnaphthalen-1-yl)(morpholino)methanone

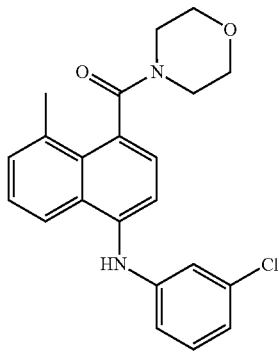 [SMILES: Cc1cccc2c(Nc3cccc(Cl)c3)ccc(C(=O)N3CCCCC3)c12]

In a sealed tube, Pd(OAc)$_2$ (0.1 equiv) and BINAP (0.2 equiv) were dissolved in dry toluene and the mixture was degassed for 30 min. To this, intermediate-22 (1 equiv) was added and the mixture was stirred for 10 minutes. Then, Cs$_2$CO$_3$ (3.0 equiv) and 3-chloroaniline (1.2 equiv) were added to the above mixture while stirring at RT for 15 min and then the reaction mixture was heated to 100° C. overnight. After completion (TLC), it was cooled, filtered and washed with EtOAc. The solvent was evaporated under reduced pressure and the crude product was purified by column chromatography (8% EtOAc:Hexanes) to furnish the desired compound in 68% yield; $^1$H NMR (400 MHz, CDCl$_3$) δ 7.94-7.92 (m, 1H), 7.41-7.31 (m, 3H), 7.24 (s, 1H), 7.16 (t, 1H), 6.95 (t, 1H), 6.88-6.86 (m, 2H), 6.11 (s, 1H), 4.15-4.10 (m, 1H), 3.92-3.87 (m, 1H), 3.80-3.74 (m, 1H), 3.68-3.62 (m, 2H), 3.59-3.54 (m, 1H), 3.28-3.20 (m, 2H), 2.66 (s, 3H); MS m/z 381 (M+1).

Example-133

(4-((3-Fluorophenyl)amino)-8-methylnaphthalen-1-yl)(morpholino)methanone

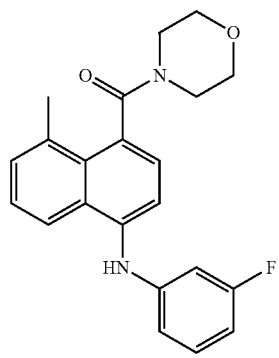 [SMILES: Cc1cccc2c(Nc3cccc(F)c3)ccc(C(=O)N3CCCCC3)c12]

The title compound was prepared by using Intermediate-22 and 3-fluoroaniline using the similar procedure as described for Example-132; $^1$H NMR (400 MHz, CDCl$_3$) δ 7.97-7.95 (m, 1H), 7.52-7.37 (m, 3H), 7.28 (s, 1H), 7.23-7.17 (m, 1H), 6.74-6.72 (m, 1H), 6.68-6.64 (m, 2H), 6.07 (s, 1H), 4.15-4.11 (m, 1H), 3.93-3.88 (m, 1H), 3.80-3.75 (m, 1H), 3.69-3.62 (m, 2H), 3.59-3.53 (m, 1H), 3.30-3.18 (m, 2H), 2.67 (s, 3H); MS m/z 365 (M+1).

Example-134

(8-Methyl-4-((3-trifluoromethyl)phenyl)amino)naphthalen-1-yl)(morpholino)methanone

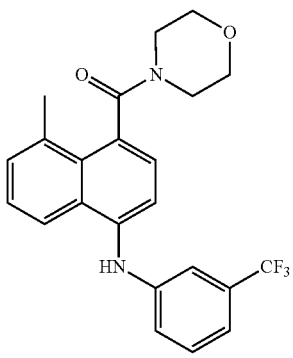 [SMILES: Cc1cccc2c(Nc3cccc(C(F)(F)F)c3)ccc(C(=O)N3CCCCC3)c12]

The title compound was prepared by using Intermediate-22 and 3-(trifluoromethyl)aniline by following the similar procedure as described in Example-132; $^1$H NMR (400 MHz, CDCl$_3$) δ 7.96-7.94 (m, 1H), 7.42-7.38 (m, 2H), 7.34-7.32 (m, 2H), 7.27 (s, 1H), 7.21 (brs, 1H), 7.15-7.07 (m, 2H), 6.19 (s, 1H), 4.15-4.11 (m, 1H), 3.92-3.88 (m, 1H), 3.80-3.75 (m, 1H), 3.68-3.62 (m, 2H), 3.59-3.54 (m, 1H), 3.31-3.21 (m, 2H), 2.67 (s, 3H); MS m/z 415 (M+1).

Example-135

(4-((2,3-Difluorophenyl)amino)-8-methylnaphthalen-1-yl)(morpholino)methanone

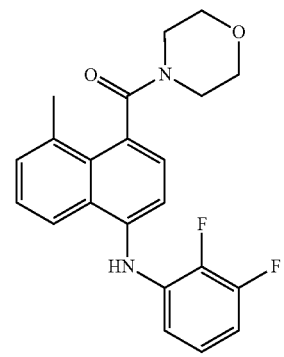 [SMILES: Cc1cccc2c(Nc3cccc(F)c3F)ccc(C(=O)N3CCCCC3)c12]

The title compound was prepared by using Intermediate-22 and 2,3-difluoroaniline by following the similar procedure as described in Example-132; $^1$H NMR (400 MHz, CDCl$_3$) δ 8.00-7.98 (m, 1H), 7.46-7.36 (m, 3H), 7.30-7.28 (m, 1H), 6.88-6.84 (m, 1H), 6.72-6.68 (m, 2H), 6.12 (s, 1H), 4.12-4.11 (m, 1H), 3.92-3.87 (m, 1H), 3.80-3.74 (m, 1H), 3.67-3.63 (m, 2H), 3.58-3.53 (m, 1H), 3.26-3.20 (m, 2H), 2.67 (s, 3H); MS m/z 383 (M+1).

Example-136

(4-((3,4-Difluorophenyl)amino)-8-methylnaphthalen-1-yl)(morpholino)methanone

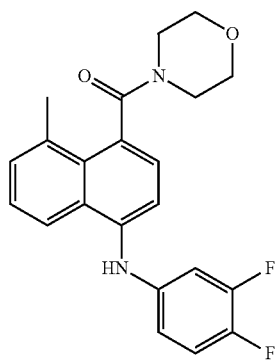 [SMILES: Cc1cccc2c(Nc3ccc(F)c(F)c3)ccc(C(=O)N3CCCCC3)c12]

The title compound was prepared by using Intermediate-22 and 3,4-difluoroaniline by following the similar procedure as described in Example-132; $^1$H NMR (400 MHz, CDCl$_3$) δ 7.92 (dd, J=1.6 Hz, 7.6 Hz, 1H), 7.43-7.38 (m, 2H), 7.24 (s, 2H), 7.06 (q, J=8.8 Hz, 1H), 6.82-6.77 (m, 1H), 6.70-6.67 (m, 1H), 6.01 (s, 1H), 4.14-4.09 (m, 1H), 3.91-3.87 (m, 1H), 3.80-3.74 (m, 1H), 3.67-3.61 (m, 2H), 3.58-3.52 (m, 1H), 3.27-3.17 (m, 2H), 2.66 (s, 3H); MS m/z 383 (M+1).

Example-137

(4-((2,4-Difluorophenyl)amino)-8-methylnaphthalen-1-yl)(morpholino)methanone

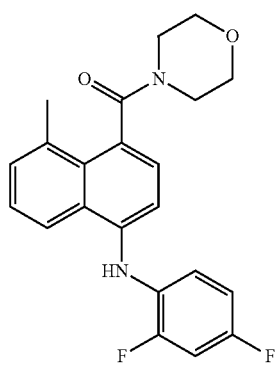 [SMILES: Cc1cccc2c(Nc3ccc(F)cc3F)ccc(C(=O)N3CCCCC3)c12]

The title compound was prepared by using Intermediate-22 and 2,4-difluoroaniline by following the similar procedure as described for Example-132; $^1$H NMR (400 MHz, CDCl$_3$) δ 7.99-7.97 (m, 1H), 7.46-7.39 (m, 2H), 7.25-7.23 (m, 1H), 7.17-7.15 (m, 1H), 7.07-7.03 (m, 1H), 6.96-6.92 (m, 1H), 6.79-6.78 (m, 1H), 5.97 (s, 1H), 4.13-4.09 (m, 1H), 3.91-3.87 (m, 1H), 3.79-3.73 (m, 1H), 3.67-3.61 (m, 2H), 3.57-3.48 (m, 1H), 3.29-3.17 (m, 2H), 2.66 (s, 3H); MS m/z 383 (M+1).

Example-138

(4-((3,5-Difluorophenyl)amino)-8-methylnaphthalen-1-yl)(morpholino)methanone

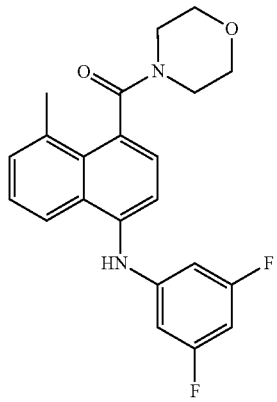 [SMILES: Cc1cccc2c(Nc3cc(F)cc(F)c3)ccc(C(=O)N3CCCCC3)c12]

The title compound was prepared by using Intermediate-22 and 3,5-difluoroaniline by following the similar procedure as described in Example-132; $^1$H NMR (400 MHz, CDCl$_3$) δ 7.88-7.86 (m, 1H), 7.37-7.33 (m, 2H), 7.21 (q, J=8.0 Hz, 2H), 6.53 (brs, 1H), 6.40-6.37 (m, 2H), 6.29-6.25 (m, 1H), 4.16-4.11 (m, 1H), 3.93-3.89 (m, 1H), 3.82-3.76 (m, 1H), 3.70-63 (m, 2H), 3.59-3.54 (m, 1H), 3.26-3.19 (m, 2H), 2.65 (s, 3H); MS m/z 383 (M+1).

Example-139

(4-((3-Chloro-4-fluorophenyl)amino)-8-methylnaphthalen-1-yl)(morpholino)methanone

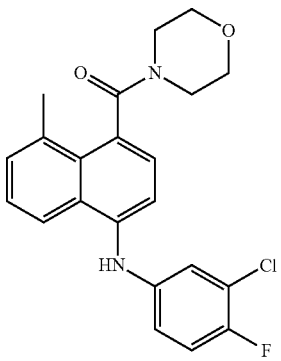

The title compound was prepared by using Intermediate-22 and 3-chloro-4-fluoroaniline by following the similar procedure as described in Example-132; $^1$H NMR (400 MHz, CDCl$_3$) δ 7.92-7.90 (m, 1H), 7.42-7.37 (m, 2H), 7.21 (q, J=7.6 Hz, 2H), 7.06-7.01 (m, 2H), 6.86-6.83 (m, 1H), 6.05 (s, 1H), 4.15-4.10 (m, 1H), 3.91-3.87 (m, 1H), 3.80-3.74 (m, 1H), 3.68-3.62 (m, 2H), 3.58-3.53 (m, 1H), 3.28-3.20 (m, 2H), 2.66 (s, 3H); MS m/z 399 (M+1).

Example-140

(4-((4-Fluoro-3-(trifluoromethyl)phenyl)amino)-8-methylnaphthalen-1-yl)(morpholino)methanone

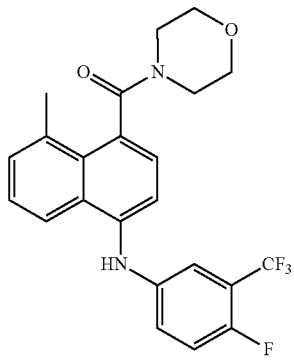

The title compound was prepared by using Intermediate-22 and 4-fluoro-3-(trifluoromethyl)aniline by following the similar procedure as described in Example-132; ¹H NMR (400 MHz, CDCl₃) δ 7.91-7.89 (m, 1H), 7.40-7.35 (m, 2H), 7.22-7.19 (m, 2H), 7.15 (d, J=7.6 Hz, 1H), 7.09-7.07 (m, 2H), 6.27 (s, 1H), 4.15-4.10 (m, 1H), 3.93-3.88 (m, 1H), 3.80-3.75 (m, 1H), 3.69-3.62 (m, 2H), 3.58-3.53 (m, 1H), 3.28-3.20 (m, 2H), 2.65 (m, 3H); MS m/z 433 (M+1).

Example-141

(4-((3-Chlorophenyl)amino)-8-methylnaphthalen-1-yl)(piperidin-1-yl)methanone

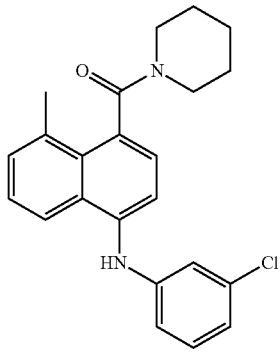

The title compound was prepared by using Intermediate-23 and 3-chloroaniline by following the similar procedure as described in Example-132; ¹H NMR (400 MHz, CDCl₃) δ 7.93-7.91 (m, 1H), 7.38-7.29 (m, 3H), 7.22 (d, J=7.6 Hz, 1H), 7.14 (t, J=8.0 Hz, 1H), 6.93 (t, J=2.0 Hz, 1H), 6.85-6.79 (m, 2H), 6.14 (s, 1H), 4.20-4.15 (m, 1H), 3.49-3.43 (m, 1H), 3.33-3.27 (m, 1H), 3.10-3.04 (m, 1H), 2.66 (s, 3H), 1.78-1.42 (m, 6H); MS m/z 379 (M+1).

Example-142

(4-((3-Fluorophenyl)amino)-8-methylnaphthalen-1-yl)(piperidin-1-yl)methanone

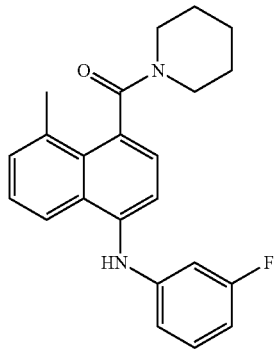

The title compound was prepared by using Intermediate-23 and 3-fluoroaniline by following the similar procedure as described in Example-132; ¹H NMR (400 MHz, CDCl₃) δ 7.96-7.94 (m, 1H), 7.52-7.36 (m, 3H), 7.26-7.25 (m, 1H), 7.21-7.15 (m, 1H), 6.72-6.70 (m, 1H), 6.65-6.61 (m, 2H), 6.06 (s, 1H), 4.19-4.15 (m, 1H), 3.49-3.43 (m, 1H), 3.33-3.28 (m, 1H), 3.11-3.06 (m, 1H), 2.67 (s, 3H), 1.78-1.60 (m, 4H), 1.51-1.47 (m, 2H); MS m/z 363 (M+1).

Example-143

(8-Methyl-4-((3-trifluoromethyl)phenyl)amino)naphthalen-1-yl)(piperidin-1-yl)methanone

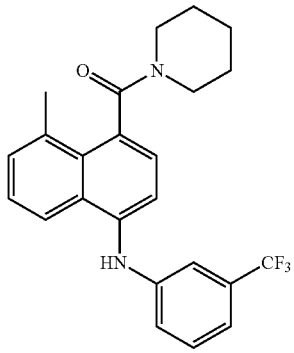

The title compound was prepared by using Intermediate-23 and 3-(trifluoromethyl)aniline by following the similar procedure as described in Example-132; ¹H NMR (400 MHz, CDCl₃) δ 7.94-7.92 (m, 1H), 7.40-7.29 (m, 4H), 7.26-7.24 (m, 1H), 7.19 (bs, 1H), 7.12-7.05 (m, 2H), 6.15 (brs, 1H), 4.19-4.10 (m, 1H), 3.49-3.43 (m, 1H), 3.33-3.27 (m, 1H), 3.11-3.04 (m, 1H), 2.66 (s, 3H), 1.76-1.60 (m, 4H), 1.59-1.48 (m, 2H); MS m/z 413 (M+1).

Example-144

(4-((2,3-Difluorophenyl)amino)-8-methylnaphthalen-1-yl)(piperidin-1-yl)methanone

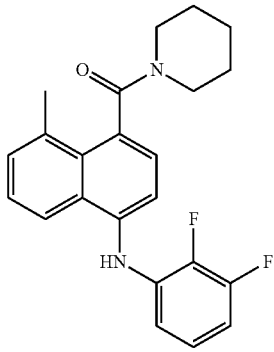

The title compound was prepared by using Intermediate-23 and 2,3-difluoroaniline by following the similar procedure as described in Example-132; $^1$H NMR (400 MHz, CDCl$_3$) δ 7.98-7.97 (m, 1H), 7.44-7.37 (m, 3H), 7.29-7.27 (m, 1H), 6.88-6.82 (m, 1H), 6.68-6.62 (m, 2H), 6.09 (s, 1H), 4.20-4.17 (m, 1H), 3.49-3.42 (m, 1H), 3.32-3.26 (m, 1H), 3.10-3.03 (m, 1H), 2.67 (s, 3H), 1.77-1.47 (m, 6H); MS m/z 381 (M+1).

Example-145

(4-((3,4-Difluorophenyl)amino)-8-methylnaphthalen-1-yl)(piperidin-1-yl)methanone

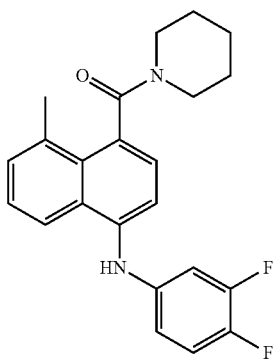

The title compound was prepared by using Intermediate-23 and 3,4-difluoroaniline by following the similar procedure as described in Example-132; $^1$H NMR (400 MHz, CDCl$_3$) δ 7.90-7.88 (m, 1H), 7.38-7.33 (m, 2H), 7.20 (s, 2H), 7.02 (q, J=8.8 Hz, 1H), 6.78-6.73 (m, 1H), 6.66-6.65 (m, 1H), 6.06 (s, 1H), 4.19-4.16 (m, 1H), 3.48-3.42 (m, 1H), 3.31-3.26 (m, 1H), 3.09-3.04 (m, 1H), 2.65 (s, 3H), 1.77-1.65 (m, 4H), 1.49-1.45 (m, 2H); MS m/z 381 (M+1).

Example-146

(4-((2,4-Difluorophenyl)amino)-8-methylnaphthalen-1-yl)(piperidin-1-yl)methanone

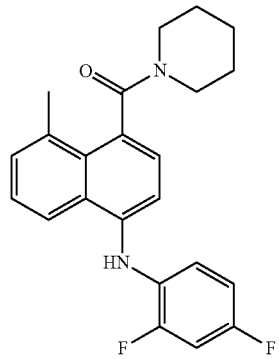

The title compound was prepared by using Intermediate-23 and 2,4-difluoroaniline by following the similar procedure as described in Example-132; $^1$H NMR (400 MHz, CDCl$_3$) δ 8.00 (d, J=8.0 Hz, 1H), 7.57-7.40 (m, 2H), 7.27-7.20 (m, 2H), 7.06-6.93 (m, 2H), 6.79 (t, J=8.4 Hz, 1H), 5.95 (s, 1H), 4.21-4.16 (m, 1H), 3.50-3.48 (m, 1H), 3.34-3.30 (m, 1H), 3.12-3.09 (m, 1H), 2.69 (s, 3H), 1.71-148 (m, 6H); MS m/z 381 (M+1).

Example-147

(4-((3,5-Difluorophenyl)amino)-8-methylnaphthalen-1-yl)(piperidin-1-yl)methanone

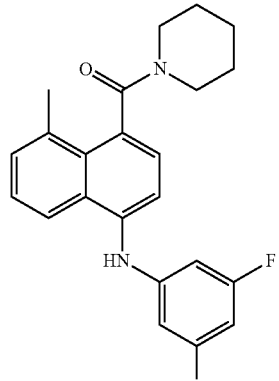

The title compound was prepared by using Intermediate-23 and 3,5-difluoroaniline by following the similar procedure as described in Example-132; $^1$H NMR (400 MHz, CDCl$_3$) δ 7.90-7.88 (m, 1H), 7.37-7.31 (m, 3H), 7.23 (s, 1H), 6.37-6.36 (m, 2H), 6.35-6.27 (m, 2H), 4.21-4.17 (m, 1H), 3.49-3.44 (m, 1H), 3.30-3.26 (m, 1H), 3.10-3.03 (m, 1H), 2.66 (s, 3H), 1.77-1.55 (m, 6H); MS m/z 381 (M+1).

Example-148

(4-((3-Chloro-4-fluorophenyl)amino)-8-methylnaphthalen-1-yl)(piperidin-1-yl)methanone

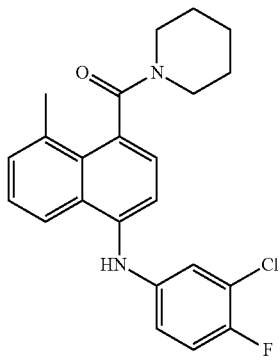 [SMILES: Cc1cccc2c(Nc3ccc(F)c(Cl)c3)ccc(C(=O)N3CCCCC3)c12]

The title compound was prepared by using Intermediate-23 and 3-chloro-4-fluoroaniline by following the similar procedure as described in Example-132; $^1$H NMR (400 MHz, CDCl$_3$) δ 7.92-7.90 (m, 1H), 7.40-7.35 (m, 2H), 7.23-7.21 (m, 2H), 7.06-7.00 (m, 2H), 6.85-6.81 (m, 1H), 4.21-4.13 (m, 1H), 3.50-3.45 (m, 1H), 3.34-3.29 (m, 1H), 3.12-3.06 (m, 1H), 2.67 (s, 3H), 1.78-1.49 (m, 6H); MS m/z 397 (M+1).

Example-149

(4-((4-Fluoro-3-(trifluoromethyl)phenyl)amino)-8-methylnaphthalen-1-yl)(piperidin-1-yl)methanone

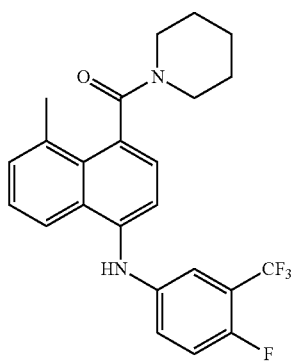 [SMILES: Cc1cccc2c(Nc3ccc(F)c(C(F)(F)F)c3)ccc(C(=O)N3CCCCC3)c12]

The title compound was prepared by using Intermediate-23 and 4-fluoro-3-(trifluoromethyl)aniline by following the similar procedure as described in Example-132; $^1$H NMR (400 MHz, CDCl$_3$) δ 7.90-7.86 (m, 1H), 7.37-7.35 (m, 2H), 7.22-7.16 (m, 3H), 7.07-7.05 (m, 2H), 6.20 (s, 1H), 4.20-4.17 (m, 1H), 3.49-3.46 (m, 1H), 3.31-3.28 (m, 1H), 3.11-3.05 (m, 1H), 2.66 (s, 3H), 1.78-1.60 (m, 4H), 1.50-1.46 (m, 2H); MS m/z 431 (M+1).

Example-150

(8-Methyl-4-(m-tolylamino)naphthalen-1-yl)(morpholino)methanone

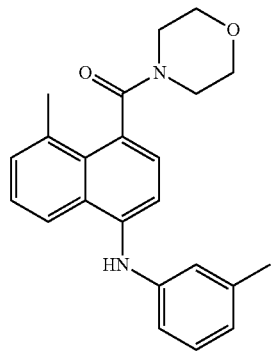 [SMILES: Cc1cccc(Nc2ccc(C(=O)N3CCOCC3)c3c(C)cccc23)c1]

This compound was prepared by using Intermediate-22 and m-toluidine using the similar procedure as described for Example-132; $^1$H NMR (400 MHz, CDCl$_3$) δ 2.33 (s, 3H), 2.85 (s, 3H), 3.21-3.25 (m, 1H), 3.28-3.3 (m, 1H), 3.54-3.68 (m, 3H), 3.75-3.81 (m, 1H), 3.88-3.92 (m, 1H), 4.11-4.15 (m, 1H), 6.80-6.82 (m. 1H), 6.86-6.88 (m, 2H), 7.17-7.26 (m, 3H), 7.33-7.35 (m, 1H), 7.39-7.44 (m, 2H), 7.98-8.0 (m, 1H); MS m/z 361 (M+1).

Example-151

(4-((4-Fluoro-3-methylphenyl)amino)-8-methylnaphthalen-1-yl)(morpholino)methanone

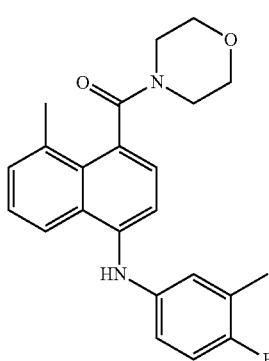

The desired compound was prepared by using Intermediate-22 and 4-fluoro-3-methyl aniline using the similar procedure as described for Example-132; $^1$H NMR (400 MHz, CDCl$_3$) δ 2.33 (s, 3H), 2.85 (s, 3H), 3.21-3.25 (m, 1H), 3.28-3.3 (m, 1H), 3.54-3.68 (m, 3H), 3.75-3.81 (m, 1H), 3.88-3.92 (m, 1H), 4.11-4.15 (m, 1H), 6.80-6.82 (m. 1H), 6.86-6.88 (m, 2H), 7.17-7.26 (m, 3H), 7.33-7.35 (m, 1H), 7.39-7.44 (m, 2H), 7.98-8.0 (m, 1H); MS m/z 379 (M+1).

Example-152

(4-((3-Fluoro-4-methylphenyl)amino)-8-methyl-naphthalen-1-yl)(morpholino)methanone

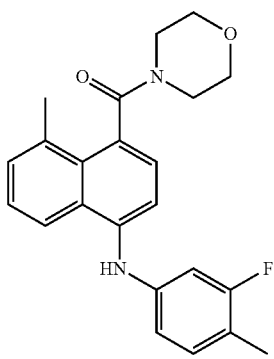 [SMILES: Cc1ccc(Nc2ccc(C(=O)N3CCOCC3)c3c(C)cccc23)cc1F]

The desired compound was prepared by using Intermediate-22 and 3-fluoro-4-methyl aniline using the similar procedure as described for Example-132; $^1$H NMR (400 MHz, CDCl$_3$) δ 2.42 (s, 3H), 2.68 (s, 3H), 3.22-3.30 (m, 2H), 3.57-3.6 (m, 1H), 3.64-3.69 (m, 2H), 3.78-3.8 (m, 1H), 3.89-3.9 (m, 1H), 4.13-4.14 (m, 1H), 5.99 (brs, 1H), 6.69-6.72 (m, 2H), 7.08 (t, 1H, J=8.0 Hz), 7.25-7.33 (m, 2H), 7.41-7.45 (m, 2H), 7.96-7.98 (m, 1H); MS m/z 379 (M+1).

Example-153

(4-((3-Fluoro-2-methylphenyl)amino)-8-methyl-naphthalen-1-yl)(morpholino)methanone

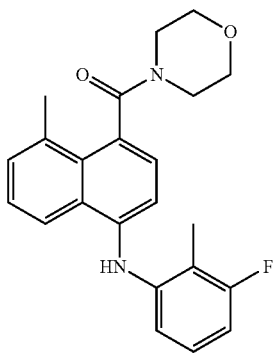 [SMILES: Cc1c(F)cccc1Nc1ccc(C(=O)N2CCOCC2)c2c(C)cccc12]

The desired compound was prepared by using Intermediate-22 and 3-fluoro-2-methyl aniline using the similar procedure as described for Example-132; $^1$H NMR (400 MHz, CDCl$_3$) δ 2.20 (s, 3H), 2.68 (s, 3H), 3.20-3.29 (m, 2H), 3.53-3.59 (m, 1H), 3.63-3.69 (m, 2H), 3.75-3.81 (m, 1H), 3.88-3.93 (m, 1H), 4.11-4.15 (m, 1H), 5.86 (s, 1H), 6.74-6.78 (m, 2H), 7.0-7.07 (m, 2H), 7.23-7.25 (m, 1H), 7.42-7.46 (m, 2H), 7.97-7.99 (m, 1H); MS m/z 379 (M+1).

Example-154

(4-((3-Chloro-4-methylphenyl)amino)-8-methyl-naphthalen-1-yl)(morpholino)methanone

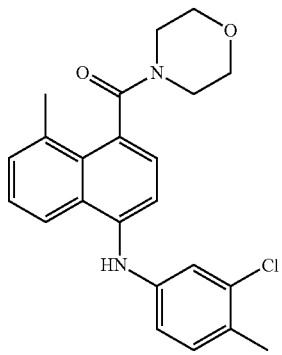 [SMILES: Cc1ccc(Nc2ccc(C(=O)N3CCOCC3)c3c(C)cccc23)cc1Cl]

The desired compound was prepared by using Intermediate-22 and 3-chloro-4-methyl aniline using the similar procedure as described for Example-132; $^1$H NMR (400 MHz, CDCl$_3$) δ 2.32 (s, 3H), 2.65 (s, 3H), 3.20-3.28 (m, 2H), 3.55-3.67 (m, 3H), 3.74-3.80 (m, 1H), 3.87-3.91 (m, 1H), 4.09-4.14 (m, 1H), 5.97 (brs, 1H), 6.82 (dd, J=2.4 Hz, 8.0 Hz, 1H), 7.04 (d, J=2.4 Hz, 1H), 7.11 (d, J=8.0 Hz, 1H), 7.23-7.29 (m, 2H), 7.37-7.43 (m, 2H), 7.93-7.95 (m, 1H); MS m/z 395 (M+1).

Example-155

(4-((3-Chloro-2-methylphenyl)amino)-8-methyl-naphthalen-1-yl)(morpholino)methanone This compound was prepared by using Intermediate-22 and 3-chloro-2-methylaniline using the similar procedure as described for Example-132; $^1$H NMR (400 MHz, CDCl$_3$) δ 2.36 (s, 3H), 2.68 (s, 3H), 3.22-3.30 (m, 2H), 3.52-3.58 (m, 1H), 3.63-3.69 (m, 2H), 3.75-3.80 (m, 1H), 3.88-3.90 (m, 1H), 4.11-4.14 (m, 1H), 5.89 (brs, 1H), 6.87-6.92 (m, 2H), 7.01-7.07 (m, 1H), 7.11-7.15 (m, 1H), 7.22-7.25 (m, 1H), 7.43-7.46 (m, 2H), 7.93-7.96 (m, 1H); MS m/z 395 (M+1).

Example-156

(4-((3-(Fluoromethyl)phenyl)amino)-8-methylnaphthalen-1-yl)(morpholino)methanone

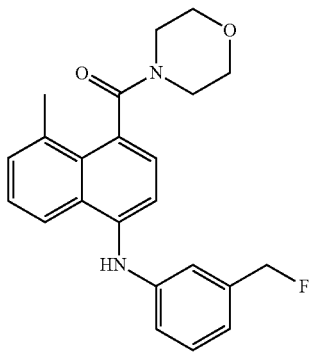 [SMILES: Cc1cccc2c(Nc3cccc(CF)c3)ccc(C(=O)N3CCOCC3)c12]

The desired compound was prepared by using Intermediate-22 and 3-(fluoromethyl)aniline using the similar procedure as described for Example-132; $^1$H NMR (400 MHz, CDCl$_3$) δ 7.98-7.97 (m, 1H), 7.43-7.38 (m, 2H), 7.34-7.25 (m, 3H), 7.03-6.94 (m, 3H), 6.07 (s, 1H), 5.33 (d, 2H, J=48.0 Hz), 4.15-4.10 (m, 1H), 3.92-3.87 (m, 1H), 3.80-3.75 (m, 1H), 3.68-3.62 (m, 2H), 3.59-3.53 (m, 1H), 3.28-3.18 (m, 2H), 2.67 (s, 3H); MS m/z 379 (M+1).

Example-157

(4-((3-(Difluoromethyl)phenyl)amino)-8-methylnaphthalen-1-yl)(morpholino)methanone

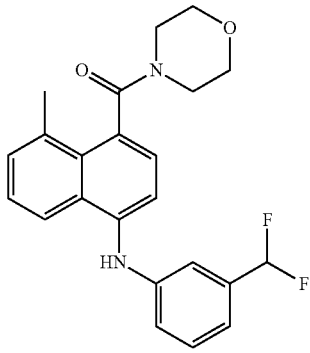 [SMILES: Cc1cccc2c(Nc3cccc(C(F)F)c3)ccc(C(=O)N3CCOCC3)c12]

The title compound was prepared by using Intermediate-22 and 3-(difluoromethyl)aniline using the similar procedure as described for Example-132; $^1$H NMR (400 MHz, CDCl$_3$) δ 7.98-7.96 (m, 1H), 7.44-7.40 (m, 2H), 7.37-7.33 (m, 2H), 7.28 (s, 1H), 7.13 (brs, 1H), 7.07-7.04 (m, 2H), 6.57 (t, 1H, J=56.4 Hz), 6.09 (s, 1H), 4.15-4.11 (m, 1H), 3.92-3.88 (m, 1H), 3.80-3.74 (m, 1H), 3.68-3.62 (m, 2H), 3.59-3.54 (m, 1H), 3.29-3.20 (m, 2H), 2.67 (s, 3H); MS m/z 397 (M+1).

Example-158

(4-((4-Chlorophenyl)amino)-8-methylnaphthalen-1-yl)(piperidin-1-yl)methanone

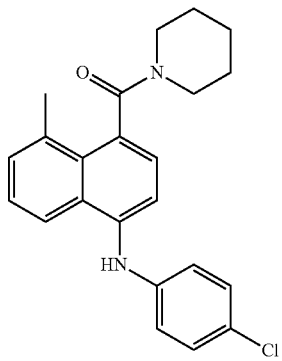 [SMILES: Cc1cccc2c(Nc3ccc(Cl)cc3)ccc(C(=O)N3CCCCC3)c12]

This compound was prepared by using Intermediate-23 and 4-chloroaniline by following the similar procedure as described in Example-132; $^1$H NMR (400 MHz, CDCl$_3$) δ 7.94-7.92 (m, 1H), 7.39-7.34 (m, 2H), 7.24 (s, 1H), 7.23-7.18 (m, 3H), 6.92-6.88 (m, 2H), 6.08 (brs, 1H), 4.19-4.16 (m, 1H), 3.49-3.43 (m, 1H), 3.32-3.27 (m, 1H), 3.10-3.04 (m, 1H), 2.66 (s, 3H), 1.76-1.25 (m, 6H); MS m/z 379 (M+1).

Example-159

(4-((4-Fluorophenyl)amino)-8-methylnaphthalen-1-yl)(piperidin-1-yl)methanone

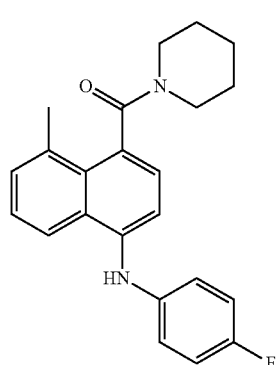

The title compound was prepared by using Intermediate-23 and 4-fluoroaniline by following the similar procedure as described in Example-132; $^1$H NMR (400 MHz, CDCl$_3$) δ 7.95-7.93 (m, 1H), 7.40-7.35 (m, 2H), 7.17 (q, J=7.6 Hz, 2H), 7.0-6.98 (m, 4H), 5.98 (s, 1H), 4.18-4.15 (m, 1H), 3.48-3.42 (m, 1H), 3.31-3.27 (m, 1H), 3.10-3.04 (m, 1H), 2.65 (s, 3H), 1.75-1.42 (m, 6H); MS m/z 363 (M+1).

Example-160

(4-((3-(Difluoromethyl)phenyl)amino)-8-methyl-naphthalen-1-yl)(piperidin-1-yl)methanone

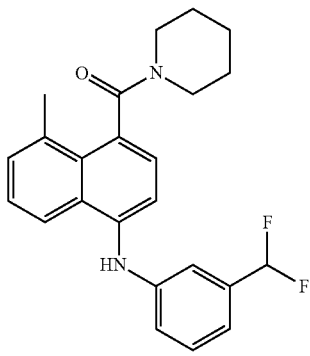 [SMILES: Cc1cccc2c(Nc3cccc(C(F)F)c3)ccc(C(=O)N3CCCCC3)c12]

The desired compound was prepared by using Intermediate-23 and 3-(difluoromethyl)aniline by following the similar procedure as described in Example-132; ¹H NMR (400 MHz, CDCl₃) δ 7.95-7.94 (m, 1H), 7.40-7.29 (m, 4H), 7.25-7.23 (m, 1H), 7.1 (brs, 1H), 7.04-7.01 (m, 2H), 6.56 (t, J=56.4 Hz, 1H), 6.16 (s, 1H), 4.2-4.17 (m, 1H), 3.5-3.43 (m, 1H), 3.33-3.28 (m, 1H), 3.11-3.05 (m, 1H), 2.67 (s, 3H), 1.77-1.57 (m, 4H), 1.50-1.46 (m, 2H); MS m/z 395 (M+1).

Example-161

(4-((3-Methoxyphenyl)amino)-8-methylnaphthalen-1-yl)(piperidin-1-yl)methanone

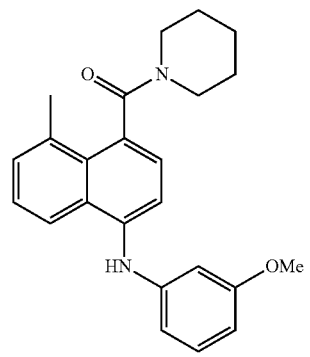 [SMILES: COc1cccc(Nc2ccc(C(=O)N3CCCCC3)c3c(C)cccc23)c1]

This compound was prepared by using Intermediate-23 and 3-methoxyaniline by following the similar procedure as described in Example-132; ¹H NMR (400 MHz, CDCl₃) δ 7.98-7.96 (m, 1H), 7.4-7.34 (m, 3H), 7.24-7.22 (m, 1H), 7.17 (t, J=8.0 Hz, 1H), 6.61-6.55 (m, 2H), 6.51-6.5 (m, 1H), 6.0 (s, 1H), 4.19-4.15 (m, 1H), 3.77 (s, 3H), 3.47-3.45 (m, 1H), 3.31-3.28 (m, 1H), 3.1-3.05 (m, 1H), 2.66 (s, 3H), 1.76-1.46 (m, 6H); MS m/z 375 (M+1).

Example-162

(4-((3-(Trifluoromethyl)phenyl)amino)-8-methyl-naphthalen-1-yl)(pyrrolidin-1-yl)methanone

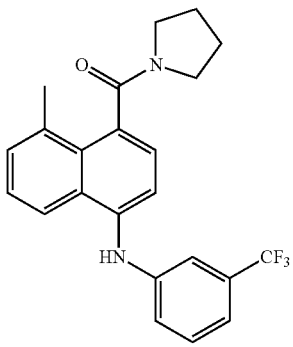 [SMILES: Cc1cccc2c(Nc3cccc(C(F)(F)F)c3)ccc(C(=O)N3CCCC3)c12]

The desired compound was prepared by using Intermediate-24 and 3-(trifluoromethyl)aniline by following the similar procedure as described in Example-132; ¹H NMR (400 MHz, CDCl₃) δ 7.96-7.95 (m, 1H), 7.40-7.37 (m, 2H), 7.35-7.3 (m, 3H), 7.19 (brs, 1H), 7.13-7.05 (m, 2H), 6.19 (s, 1H), 3.76-75 (m, 1H), 3.70-3.64 (m, 1H), 3.18-3.05 (m, 2H), 2.65 (s, 3H), 2.04-1.98 (m, 2H), 1.92-1.85 (m, 2H); MS m/z 399 (M+1).

Example-163

2-Oxa-5-azabicyclo[2.2.1]heptan-5-yl(4-((2,3-difluorophenyl)amino)-8-methylnaphthalen-1-yl)methanone

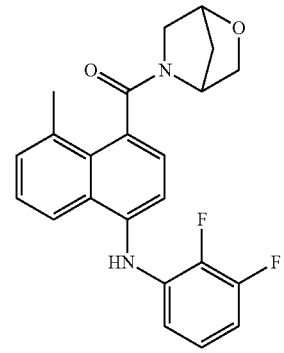 [SMILES: Cc1cccc2c(Nc3cccc(F)c3F)ccc(C(=O)N3CC4CC3CO4)c12]

This compound was prepared by using Intermediate-25 and 2,3-difluoroaniline by following the similar procedure as described in Example-132; ¹H NMR (400 MHz, CDCl₃) (as mixture of isomers) δ 1.93-2.04 (m, 2H), 2.69 (s, 3H), 3.00-3.19 (m, 1H), 3.63-4.77 (m, 5H), 6.12 (s, 1H), 6.13 (m, 1H), 6.67-6.72 (m, 2H), 6.85-6.89 (m, 1H), 7.30-7.37 (m, 2H), 7.39-7.42 (m, 1H), 7.51-7.52 (m, 1H), 7.96-7.98 (m, 1H); MS m/z 395 (M+1).

Example-164

2-Oxa-5-azabicyclo[2.2.1]heptan-5-yl(4-((3-(difluoromethyl)phenyl)amino)-8-methyl naphthalen-1-yl)methanone

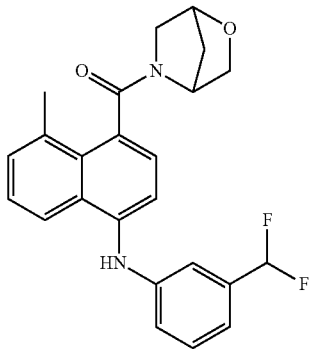 [SMILES: Cc1cccc2c(Nc3cccc(C(F)F)c3)ccc(C(=O)N3CC4CC3CO4)c12]

This compound was prepared by using Intermediate-25 and 3-(difluoromethyl)aniline by following the similar procedure as described in Example-132; $^1$H NMR (400 MHz, CDCl$_3$) (as mixture of isomers) δ 1.87-2.04 (m, 2H), 2.68 (s, 3H), 3.0-3.21 (m, 1H), 3.57-4.77 (m, 5H), 6.08-6.10 (m, 2H), 6.58 (t, 1H), 7.03-7.17 (m, 3H), 7.30-7.43 (m, 4H), 7.95-7.97 (m, 1H); MS m/z 409 (M+1).

Example-165

3-Azabicyclo[3.1.0]hexan-3-yl(4-((3-fluorophenyl)amino)-8-methylnaphthalen-1-yl)methanone

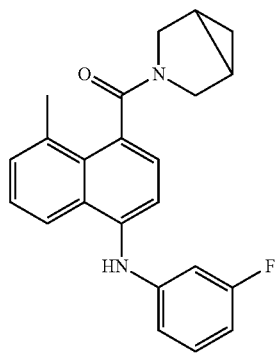 [SMILES: Cc1cccc2c(Nc3cccc(F)c3)ccc(C(=O)N3CC4CC4C3)c12]

The desired compound was prepared by using Intermediate-26 and 3-fluoroaniline by following the similar procedure as described in Example-132; $^1$H NMR (400 MHz, CDCl$_3$) (as mixture of isomers) δ 0.31-0.32 (m, 1H), 0.76-0.80 (m, 1H), 1.46-1.68 (m, 2H), 2.66 (s, 3H), 3.12-3.24 (m, 1H), 3.51-3.58 (m, 2H), 4.06-4.17 (m, 1H), 6.07 (s, 1H), 6.58-6.74 (m, 3H), 7.17-7.24 (m, 2H), 7.36-7.41 (m, 3H), 7.96-7.98 (m, 1H); MS m/z 361 (M+1).

Example-166

3-Azabicyclo[3.1.0]hexan-3-yl(4-((2,3-difluorophenyl)amino)-8-methylnaphthalen-1-yl)methanone

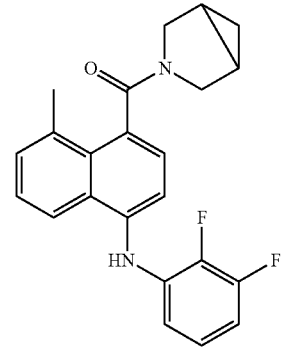 [SMILES: Cc1cccc2c(Nc3cccc(F)c3F)ccc(C(=O)N3CC4CC4C3)c12]

The desired compound was prepared by using Intermediate-26 and 2,3-difluoroaniline by following the similar procedure as described in Example-132; $^1$H NMR (400 MHz, CDCl$_3$) (as mixture of isomers) δ 0.26-0.32 (m, 1H), 0.77-0.78 (m, 1H), 1.44-1.68 (m, 2H), 2.67 (s, 3H), 3.11-3.23 (m, 1H), 3.51-3.75 (m, 2H), 4.06-4.17 (m, 1H), 6.11 (s, 1H), 6.67-6.71 (m, 2H), 6.84-7.01 (m, 1H), 7.21-7.32 (m, 2H), 7.37-7.46 (m, 2H), 7.99-8.00 (m, 1H); MS m/z 379 (M+1).

Example-167

3-Azabicyclo[3.1.0]hexan-3-yl(4-((3-(difluoromethyl)phenyl)amino)-8-methylnaphthalen-1-yl)methanone

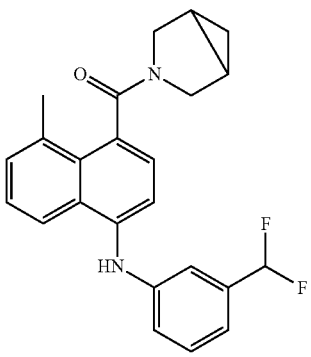 [SMILES: Cc1cccc2c(Nc3cccc(C(F)F)c3)ccc(C(=O)N3CC4CC4C3)c12]

This compound was prepared by using Intermediate-26 and 3-(difluoromethyl)aniline by following the similar procedure as described in Example-132; $^1$H NMR (400 MHz, CDCl$_3$) (as mixture of isomers) δ 0.26-0.33 (m, 1H), 0.77-0.8 (m, 1H), 1.45-1.68 (m, 2H), 2.66 (s, 3H), 3.16-3.24 (m, 1H), 3.53-3.58 (m, 2H), 4.01-4.17 (m, 1H), 6.14 (s, 1H), 6.58 (t, 1H, J=56.4 Hz), 7.04-7.11 (m, 3H), 7.21-7.24 (m, 1H), 7.31-7.42 (m, 4H), 7.95-7.98 (m, 1H); MS m/z 393 (M+1).

Example-168

3-Azabicyclo[3.1.0]hexan-3-yl(8-methyl-4-(m-tolylamino)naphthalen-1-yl)methanone

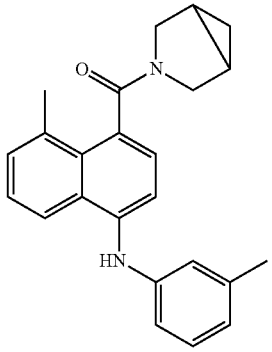 [SMILES: Cc1cccc(Nc2ccc(C(=O)N3CC4CC4C3)c3c(C)cccc23)c1]

The title compound was prepared by using Intermediate-26 and m-toluidine by following the similar procedure as described in Example-132; $^1$H NMR (400 MHz, CDCl$_3$) (as mixture of isomers) δ 0.26-0.32 (m, 1H), 0.75-0.76 (m, 1H), 1.43-1.66 (m, 2H), 2.32 (s, 3H), 2.65 (s, 3H), 3.13-3.25 (m, 1H), 3.52-3.57 (m, 2H), 4.05-4.17 (m, 1H), 5.97 (s, 1H), 6.78-6.86 (m, 3H), 7.01-7.24 (m, 2H), 7.31-7.54 (m, 3H), 7.97-7.98 (m, 1H); MS m/z 357 (M+1).

Example-169

3-Azabicyclo[3.1.0]hexan-3-yl(4-((3-chlorophenyl)amino)-8-methylnaphthalen-1-yl)methanone

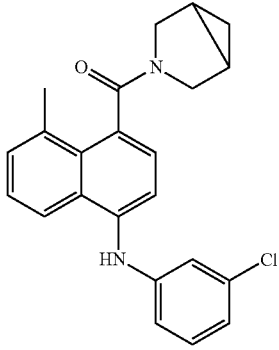 [SMILES: Cc1cccc2c(Nc3cccc(Cl)c3)ccc(C(=O)N3CC4CC4C3)c12]

The desired compound was prepared by using Intermediate-26 and 3-chloroaniline by following the similar procedure as described in Example-132; $^1$H NMR (400 MHz, CDCl$_3$) (as mixture of isomers) δ 0.26-0.33 (m, 1H), 0.75-0.76 (m, 1H), 1.41-1.66 (m, 2H), 2.65 (s, 3H), 3.12-3.24 (m, 1H), 3.51-3.75 (m, 2H), 4.05-4.09 (m, 1H), 6.07 (s, 1H), 6.83-6.89 (m, 2H), 6.94-6.95 (m, 1H), 7.15-7.24 (m, 2H), 7.32-7.42 (m, 3H), 7.93-7.96 (m, 1H); MS m/z 377 (M+1).

Example-170

3-Azabicyclo[3.1.0]hexan-3-yl(4-((3-fluoro-2-methylphenyl)amino)-8-methylnaphthalen-1-yl)methanone

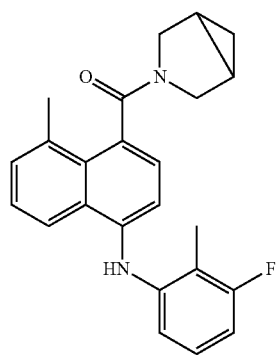 [SMILES: Cc1c(F)cccc1Nc1ccc(C(=O)N2CC3CC3C2)c2c(C)cccc12]

The desired compound was prepared by using Intermediate-26 and 3-fluoro-2-methyl aniline by following the similar procedure as described in Example-132; $^1$H NMR (400 MHz, CDCl$_3$) (as mixture of isomers) δ 0.26-0.33 (m, 1H), 0.74-0.76 (m, 1H), 1.43-1.66 (m, 2H), 2.22 (s, 3H), 2.66 (s, 3H), 3.11-3.24 (m, 1H), 3.53-3.75 (m, 2H), 4.05-4.16 (m, 1H), 5.83 (s, 1H), 6.72-6.75 (m, 2H), 7.02-7.06 (m, 2H), 7.19-7.24 (m, 1H), 7.40-7.43 (m, 2H), 7.94-7.96 (m, 1H); MS m/z 375 (M+1).

Example-171

3-Azabicyclo[3.1.0]hexan-3-yl(4-((3-fluoro-4-methylphenyl)amino)-8-methylnaphthalen-1-yl)methanone

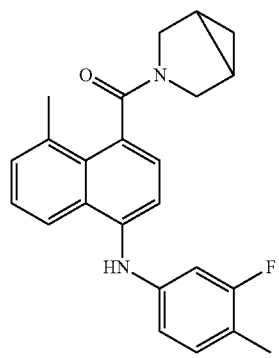 [SMILES: Cc1ccc(Nc2ccc(C(=O)N3CC4CC4C3)c3c(C)cccc23)cc1F]

This compound was prepared by using Intermediate-26 and 3-fluoro-4-methylaniline by following the similar procedure as described in Example-132; $^1$H NMR (400 MHz, CDCl$_3$) (as mixture of isomers) δ 0.27-0.32 (m, 1H), 0.72-0.76 (m, 1H), 1.43-1.63 (m, 2H), 2.23 (s, 3H), 2.65 (s, 3H), 3.11-3.24 (m, 1H), 3.51-3.74 (m, 2H), 4.05-4.13 (m, 1H), 5.98 (s, 1H), 6.62-6.7 (m, 2H), 7.05-7.2 (m, 1H), 7.22-7.25 (m, 1H), 7.29-7.42 (m, 3H), 7.94-7.97 (m, 1H); MS m/z 375 (M+1).

Example-172

6-Oxa-3-azabicyclo[3.1.1]heptan-3-yl(4-((2,3-difluorophenyl)amino)-8-methylnaphthalen-1-yl)methanone

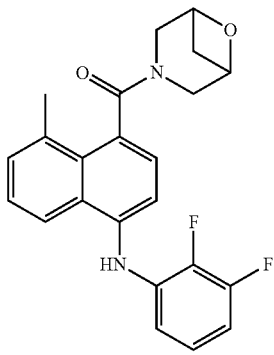 [SMILES: Cc1cccc2c(Nc3cccc(F)c3F)ccc(C(=O)N3CC4CC(C3)O4)c12]

The desired compound was prepared by using Intermediate-27 and 2,3-difluoroaniline by following the similar procedure as described in Example-132; $^1$H NMR (400 MHz, CDCl$_3$) (as mixture of isomers) δ 1.24-1.26 (m, 1H), 1.90-1.94 (m, 1H), 2.65 (s, 3H), 3.22-3.29 (m, 1H), 3.78-3.89 (m, 3H), 4.10-4.37 (m, 1H), 4.73-4.77 (m, 1H), 6.16 (s, 1H), 6.26 (t, 1H, J=8.4 Hz), 6.69-6.78 (m, 2H), 6.89-6.91 (m, 1H), 7.31-7.47 (m, 3H), 8.0-8.03 (m, 1H); MS m/z 395 (M+1).

Example-173

6-Oxa-3-azabicyclo[3.1.1]heptan-3-yl(4-((3-fluoro-2-methylphenyl)amino)-8-methylnaphthalen-1-yl)methanone

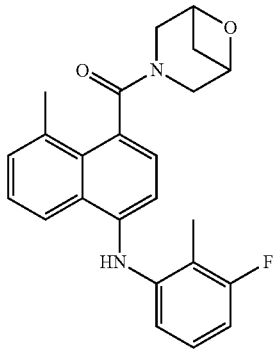 [SMILES: Cc1c(F)cccc1Nc1ccc(C(=O)N2CC3CC(C2)O3)c2c(C)cccc12]

The desired compound was prepared by using Intermediate-27 and 3-fluoro-2-methyl aniline by following the similar procedure as described in Example-132; $^1$H NMR (400 MHz, CDCl$_3$) (as mixture of isomers) δ 1.26-1.28 (m, 1H), 1.90-1.95 (m, 1H), 2.22 (s, 3H), 2.71 (s, 3H), 3.24-3.29 (m, 1H), 3.86-4.21 (m, 3H), 4.45-4.46 (m, 1H), 4.78-4.80 (m, 1H), 5.87 (s, 1H), 6.76 (t, 2H, J=8.4 Hz), 7.03-7.09 (m, 2H), 7.30-7.32 (m, 1H), 7.41-7.45 (m, 2H), 7.98-8.0 (m, 1H); MS m/z 391 (M+1).

Example-174

6-Oxa-3-azabicyclo[3.1.1]heptan-3-yl(4-((3-chlorophenyl)amino)-8-methylnaphthalene-1-yl)methanone

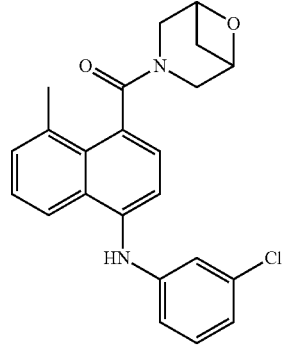 [SMILES: Cc1cccc2c(Nc3cccc(Cl)c3)ccc(C(=O)N3CC4CC(C3)O4)c12]

This compound was prepared by using Intermediate-27 and 3-chloroaniline by following the similar procedure as described in Example-132; $^1$H NMR (400 MHz, CDCl$_3$) (as mixture of isomers) δ 1.57-2.02 (m, 2H), 2.72 (s, 3H), 3.26-3.31 (m, 1H), 3.44-4.22 (m, 3H), 4.48-4.5 (m, 1H), 4.79-4.81 (m, 1H), 6.03 (s, 1H), 6.91-6.96 (m, 2H), 6.97-7.01 (m, 1H), 7.19 (t, 1H, J=8.0 Hz), 7.33-7.53 (m, 4H), 7.97-7.99 (m, 1H); MS m/z 393 (M+1).

Example-175

6-Oxa-3-azabicyclo[3.1.1]heptan-3-yl(4-((3-(trifluoromethyl)phenyl)amino)-8-methyl naphthalene-1-yl)methanone

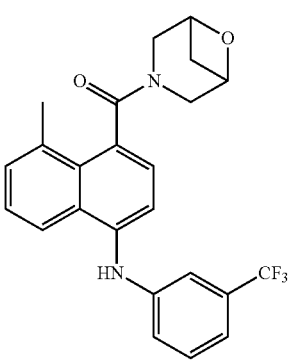 [SMILES: Cc1cccc2c(Nc3cccc(C(F)(F)F)c3)ccc(C(=O)N3CC4CC(C3)O4)c12]

The title compound was prepared by using Intermediate-27 and 3-(trifluoromethyl)aniline by following the similar procedure as described in Example-132; $^1$H NMR (400 MHz, CDCl$_3$) (as mixture of isomers) δ 1.22-1.29 (m, 1H), 1.89-1.99 (m, 1H), 2.71 (s, 3H), 3.26-3.34 (m, 1H), 3.45-4.22 (m, 3H), 4.46-4.48 (m, 1H), 4.81-4.82 (m, 1H), 6.22 (s, 1H), 7.01-7.17 (m, 2H), 7.22-7.28 (m, 2H), 7.32-7.46 (m, 4H), 7.98-8.0 (m, 1H); MS m/z 427 (M+1).

Example-176

6-Oxa-3-azabicyclo[3.1.1]heptan-3-yl(4-((3-chloro-2-fluorophenyl)amino)-8-methylnaphthalen-1-yl)methanone

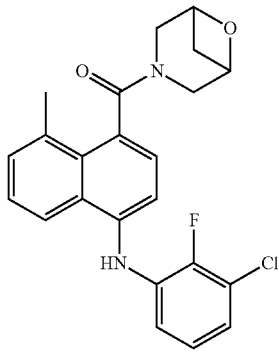 [SMILES: Cc1cccc2c(Nc3cccc(Cl)c3F)ccc(C(=O)N3CC4CC(C3)O4)c12]

This compound was prepared by using Intermediate-27 and 3-chloro-2-fluoro aniline by following the similar procedure as described in Example-132; $^1$H NMR (400 MHz, CDCl$_3$) (as mixture of isomers) δ 1.28-1.35 (m, 1H), 1.89-1.98 (m, 1H), 2.73 (s, 3H), 3.24-3.39 (m, 1H), 3.44-4.22 (m, 3H), 4.45-4.50 (m, 1H), 4.79-4.81 (m, 1H), 6.13 (s, 1H), 6.73-7.01 (m, 4H), 7.30-7.54 (m, 3H), 7.98-8.0 (m, 1H); MS m/z 411 (M+1).

Example-177

6-Oxa-3-azabicyclo[3.1.1]heptan-3-yl(4-((3-chloro-4-fluorophenyl)amino)-8-methylnaphthalen-1-yl)methanone

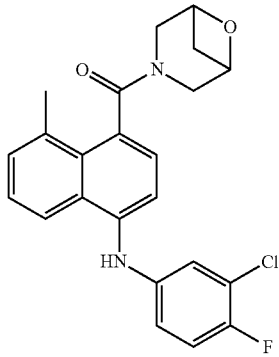 [SMILES: Cc1cccc2c(Nc3ccc(F)c(Cl)c3)ccc(C(=O)N3CC4CC(C3)O4)c12]

This compound was prepared by using Intermediate-27 and 3-chloro-4-fluoroaniline by following the similar procedure as described in Example-132; $^1$H NMR (400 MHz, CDCl$_3$) (as mixture of isomers) δ 1.54-1.57 (m, 1H), 1.89-1.98 (m, 1H), 2.72 (s, 3H), 3.25-3.31 (m, 1H), 3.44-4.22 (m, 3H), 4.46-4.50 (m, 1H), 4.79-4.80 (m, 1H), 5.96 (s, 1H), 6.86-6.88 (m, 1H), 7.01-7.09 (m, 2H), 7.28-7.54 (m, 4H), 7.95-7.97 (m, 1H); MS m/z 411 (M+1).

Example-178

(4-((2,3-Difluorophenyl)amino)-8-methylnaphthalen-1-yl)(2-oxa-6-azaspiro[3.3]heptan-6-yl)methanone

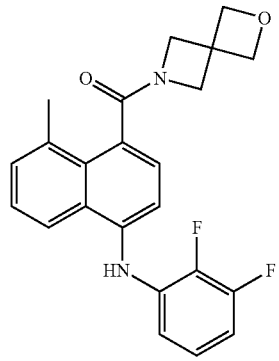 [SMILES: Cc1cccc2c(Nc3cccc(F)c3F)ccc(C(=O)N3CC4(COC4)C3)c12]

The desired compound was prepared by using Intermediate-28 and 2,3-difluoroaniline by following the similar procedure as described in Example-132; $^1$H NMR (400 MHz, CDCl$_3$) δ 2.63 (s, 3H), 3.95 (brs, 2H), 4.38 (s, 2H), 4.73 (d, 2H, J=6.8 Hz), 4.85 (d, 2H, J=6.8 Hz), 6.13 (s, 1H), 6.69-6.72 (m, 2H), 6.84-6.90 (m, 1H), 7.3-7.35 (m, 2H), 7.39-7.45 (m, 2H), 7.98 (d, 1H, J=7.6 Hz); MS m/z 395 (M+1).

Example-179

(4-((3-Chlorophenyl)amino)naphthalen-1-yl)(morpholino)methanone

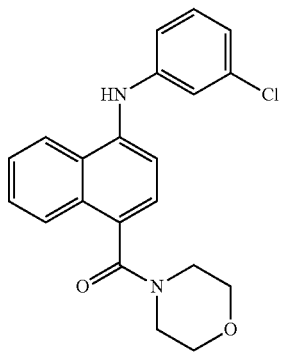 [SMILES: O=C(c1ccc(Nc2cccc(Cl)c2)c2ccccc12)N1CCOCC1]

To a stirred solution of acid Intermediate-29 (1 equiv) in dry THF (5 mL) was added, morpholine (1.5 equiv), HOBt (1.5 equiv), EDC.HCl (1.5 equiv) and DIPEA (2 equiv) under inert atmosphere and the reaction mixture was stirred at RT overnight. Then it was quenched with ice water, extracted with EtOAc (2×100 mL), washed with water (1×200 mL), dried over Na$_2$SO$_4$, filtered and concentrated under reduced pressure to give the crude product which was purified by combiflash using (EtOAc in Hexanes, 10%) to yield the title compound; $^1$H NMR (400 MHz, CDCl$_3$) δ 3.27 (bs, 2H), 3.56 (bs, 2H), 3.85-4.0 (m, 4H), 6.11 (s, 1H), 6.87-6.92 (m, 2H), 7.01-7.02 (t, 1H), 7.16-7.20 (t, 1H), 7.34 (s, 2H), 7.50-7.59 (m, 2H), 7.87-7.89 (d, 1H, J=8.0 Hz), 8.01-8.03 (d, 1H, J=7.6 Hz); MS m/z 367 (M+1).

Example-180

4-((3-Chlorophenyl)amino)-N-((tetrahydro-2H-pyran-4-yl)methyl)-1-naphthamide

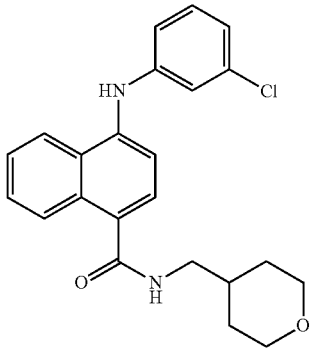 [SMILES: O=C(NCC1CCOCC1)c1ccc(Nc2cccc(Cl)c2)c2ccccc12]

This compound was prepared by using Intermediate-29 and (tetrahydro-2H-pyran-4-yl)methanamine by following the similar procedure as described in Example-179; $^1$H NMR (400 MHz, CDCl$_3$) δ 1.39-1.48 (m, 2H), 1.70-1.74 (m, 2H), 1.91-1.95 (m, 1H), 3.39-3.46 (m, 4H), 4.0-4.03 (dd, 2H, J=11.5 Hz, 4.0 Hz), 6.06 (s, 1H), 6.16 (s, 1H), 6.89-6.93 (t, 2H, J=8.0 Hz), 7.02 (s, 1H), 7.17-7.21 (t, 1H, J=8.0 Hz), 7.28-7.30 (d, 1H, J=7.6 Hz), 7.52-7.58 (m, 3H), 7.99-8.01 (d, 1H, J=8.4 Hz), 8.39-8.41 (d, 1H, J=8.4 Hz); MS m/z 395 (M+1).

Example-181

4-((3-Chlorophenyl)amino)-N-(pyridin-4-ylmethyl)-1-naphthamide

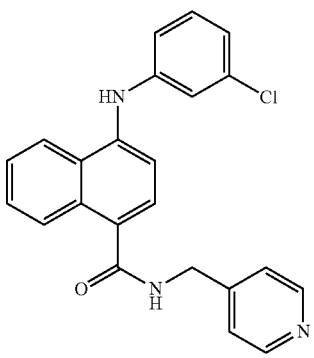 [SMILES: O=C(NCc1ccncc1)c1ccc(Nc2cccc(Cl)c2)c2ccccc12]

The title compound was prepared by using Intermediate-29 and pyridin-4-ylmethanamine by following the same procedure as described in Example-179; $^1$H NMR (400 MHz, CDCl$_3$) δ 4.74-4.75 (d, 2H, J=6.4 Hz), 6.18 (s, 1H), 6.41 (s, 1H), 6.92-6.95 (t, 2H, J=7.2 Hz), 7.05 (s, 1H), 7.19-7.23 (m, 1H), 7.30-7.33 (m, 3H), 7.55-7.62 (m, 3H), 8.01-8.03 (d, 1H, J=8.8 Hz), 8.45-8.48 (d, 1H, J=8.4 Hz), 8.60 (s, 2H); MS m/z 388 (M+1).

Example-182

N-Butyl-4-((3-chlorophenyl)amino)-1-naphthamide

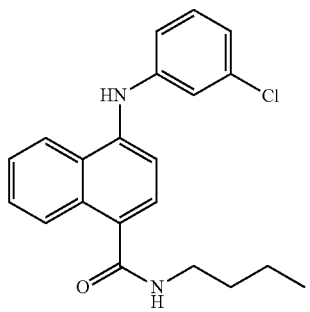 [SMILES: CCCCNC(=O)c1ccc(Nc2cccc(Cl)c2)c2ccccc12]

This compound was prepared by using Intermediate-29 and n-butylamine by following the similar procedure as described in Example-179; $^1$H NMR (400 MHz, CDCl$_3$) δ 1.54 (s, 9H), 5.81 (s, 1H), 6.18 (s, 1H), 6.86-6.90 (t, 2H, J=8.0 Hz), 6.98 (s, 1H), 7.15-7.19 (t, 2H, J=8.0 Hz), 7.45-7.58 (m, 3H), 7.97-7.99 (d, 1H, J=8.4 Hz), 8.33-8.35 (d, 1H, J=8.0 Hz); MS m/z 353 (M+1).

Example-183

(4-((3-Fluorophenyl)amino)naphthalen-1-yl)(morpholino)methanone

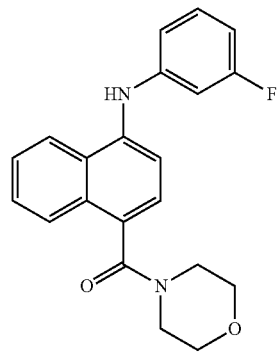 [SMILES: O=C(c1ccc(Nc2cccc(F)c2)c2ccccc12)N1CCOCC1]

This compound was prepared by using Intermediate-30 and morpholine by following the similar procedure as described in Example-179; $^1$H NMR (400 MHz, CDCl$_3$) δ 3.27 (bs, 2H), 3.55 (bs, 2H), 3.85-3.99 (m, 4H), 6.1 (bs, 1H), 6.60-6.65 (m, 1H), 6.69-6.78 (m, 2H), 7.18-7.22 (m, 1H), 7.34-7.39 (m, 2H), 7.51-7.57 (m, 2H), 7.87-7.90 (d, 1H, J=8.4 Hz), 8.02-8.04 (d, 1H, J=8.0 Hz); MS m/z 351 (M+1).

Example-184

4-((3-Fluorophenyl)amino)-N-((tetrahydro-2H-pyran-4-yl)methyl)-1-naphthamide

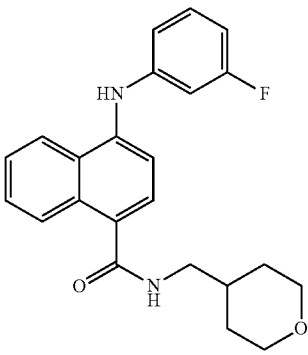 [SMILES: O=C(NCC1CCOCC1)c1ccc(Nc2cccc(F)c2)c2ccccc12]

This compound was prepared by using Intermediate-30 and (tetrahydro-2H-pyran-4-yl)methanamine by following the similar procedure described in Example-179; $^1$H NMR (400 MHz, CDCl$_3$) δ 1.42-1.51 (m, 2H), 1.73-1.77 (m, 2H), 1.95-1.97 (m, 1H), 3.41-3.49 (m, 4H), 4.02-4.06 (m, 2H), 6.10 (brs, 1H), 6.21 (s, 1H), 6.65-6.69 (m, 1H), 6.74-6.83 (m, 2H), 7.22-7.26 (m, 1H), 7.34-7.36 (d, 1H, J=7.6 Hz), 7.53-7.63 (m, 3H), 8.03-8.05 (d, 1H, J=8.4 Hz), 8.42-8.44 (d, 1H, J=8.0 Hz); MS m/z 379 (M+1).

Example-185

4-((3-Fluorophenyl)amino)-N-(pyridin-4-ylmethyl)-1-naphthamide

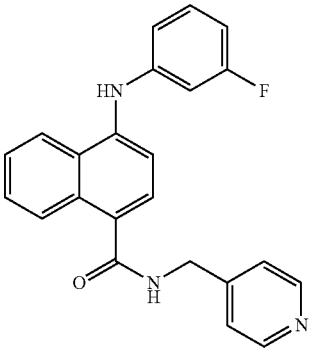 [SMILES: O=C(NCc1ccncc1)c1ccc(Nc2cccc(F)c2)c2ccccc12]

The title compound was prepared by using Intermediate-30 and pyridin-4-ylmethanamine by following the similar procedure as described in Example-179; $^1$H NMR (400 MHz, CDCl$_3$) δ 4.54-4.55 (d, 2H, J=6.0 Hz), 6.65-6.68 (m, 1H), 6.82-6.90 (m, 2H), 7.24-7.30 (m, 1H), 7.38-7.41 (m, 3H), 7.54-7.61 (m, 2H), 7.68-7.70 (d, 1H, J=8.0 Hz), 8.21-8.23 (m, 1H), 8.33-8.35 (m, 1H), 8.54 (bs, 2H), 8.70 (s, 1H), 9.07-9.10 (t, 1H, J=6.0 Hz); MS m/z 372 (M+1).

Example-186

N-Butyl-4-((3-fluorophenyl)amino)-1-naphthamide

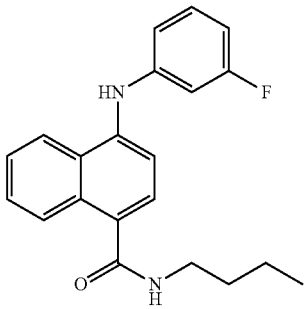 [SMILES: CCCCNC(=O)c1ccc(Nc2cccc(F)c2)c2ccccc12]

This compound was prepared by using Intermediate-30 and n-butylamine by following the similar procedure as described in Example-179; $^1$H NMR (400 MHz, CDCl$_3$) δ 1.42 (s, 9H), 6.57-6.62 (m, 1H), 6.72-6.76 (m, 1H), 6.84-6.87 (m, 1H), 7.21-7.26 (m, 1H), 7.34-7.36 (d, 1H, J=7.6 Hz), 7.45-7.47 (d, 1H, J=8.0 Hz), 8.03-8.05 (m, 1H), 7.51-7.60 (m, 2H), 8.00 (s, 1H), 8.14-8.20 (m, 2H), 8.56 (s, 1H); MS m/z 337 (M+1).

Example-187

(4-((3,5-Difluorophenyl)amino)naphthalen-1-yl)(morpholino)methanone

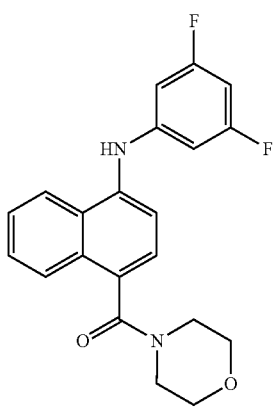 [SMILES: O=C(c1ccc(Nc2cc(F)cc(F)c2)c2ccccc12)N1CCOCC1]

This compound was prepared by using Intermediate-31 and morpholine by following the similar procedure as described in Example-179; $^1$H NMR (400 MHz, CDCl$_3$) δ 3.25 (bs, 2H), 3.55 (bs, 2H), 3.86-4.01 (m, 4H), 6.27-6.32 (t, 1H, J=9.0 Hz), 6.41-6.47 (m, 3H), 7.27-7.29 (m, 2H), 7.45-7.54 (m, 2H), 7.82-7.84 (d, 1H, J=8.4 Hz), 7.93-7.96 (d, 1H, J=8.4 Hz); MS m/z 369 (M+1).

Example-188

4-((3,5-Difluorophenyl)amino)-N-((tetrahydro-2H-pyran-4-yl)methyl)-1-naphthamide

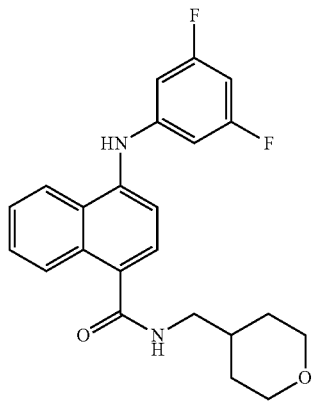 [SMILES: O=C(NCC1CCOCC1)c1ccc(Nc2cc(F)cc(F)c2)c2ccccc12]

The above compound was prepared by using Intermediate-31 and (tetrahydro-2H-pyran-4-yl)methanamine by following the similar procedure as described in Example-179; $^1$H NMR (400 MHz, CDCl$_3$) δ 1.42-1.49 (m, 2H), 1.71-1.74 (m, 2H), 1.94 (m, 1H), 3.39-3.48 (m, 4H), 4.00-4.04 (dd, 2H, J=11.5 Hz, 4.0 Hz), 6.06 (s, 1H), 6.20 (s, 1H), 6.34 (t, 1H, J=8.0 Hz), 6.43-6.45 (d, 2H, J=7.6 Hz), 7.34-7.36 (d, 1H, J=8.0 Hz), 7.51-7.59 (m, 3H), 7.98-8.00 (d, 1H, J=8.4 Hz), 8.36-8.39 (d, 1H, J=8.4 Hz); MS m/z 397 (M+1).

Example-189

4-((3,5-Difluorophenyl)amino)-N-(pyridin-4-ylmethyl)-1-naphthamide

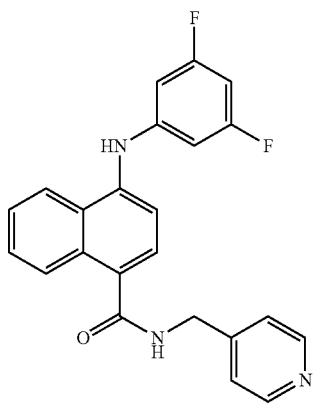 [SMILES: O=C(NCc1ccncc1)c1ccc(Nc2cc(F)cc(F)c2)c2ccccc12]

The title compound was prepared by using Intermediate-31 and pyridin-4-ylmethanamine by following the similar procedure as described in Example-179; $^1$H NMR (400 MHz, CDCl$_3$) δ 4.75-4.77 (d, 2H, J=6.4 Hz), 6.28 (s, 1H), 6.36-6.49 (m, 4H), 7.33-7.37 (m, 3H), 7.55-7.63 (m, 3H), 8.0-8.1 (d, 1H, J=8.4 Hz), 8.42-8.44 (d, 1H, J=8.4 Hz), 8.6-8.62 (d, 2H, J=4.8 Hz); MS m/z 390 (M+1).

Example-190

(4-((3,5-Difluorophenyl)amino)naphthalen-1-yl)(3,5-dimethylmorpholino)methanone

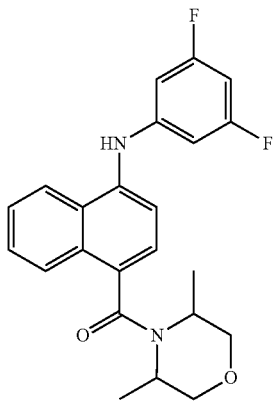 [SMILES: CC1COCC(C)N1C(=O)c1ccc(Nc2cc(F)cc(F)c2)c2ccccc12]

This compound was prepared by using Intermediate-31 and 3,5-dimethylmorpholine by following the similar procedure as described in Example-179; $^1$H NMR (400 MHz, CDCl$_3$) δ 1.01-1.02 (d, 3H, J=6.0 Hz), 1.31-1.33 (d, 3H, J=6.0 Hz), 2.64-2.84 (m, 2H), 3.20-3.25 (t, 1H, J=12.8 Hz), 3.44-3.77 (m, 2H), 3.77-3.83 (t, 1H, J=12.8 Hz), 6.27-6.33 (m, 1H), 6.44-6.49 (m, 2H), 7.21-7.25 (m, 1H), 7.29-7.31 (m, 1H), 7.45-7.54 (m, 2H), 7.69-7.71 (m, 1H), 7.89-7.99 (m, 2H); MS m/z 397 (M+1).

Example-191

(4-((3,5-Difluorophenyl)amino)naphthalen-1-yl)(piperidin-1-yl)methanone

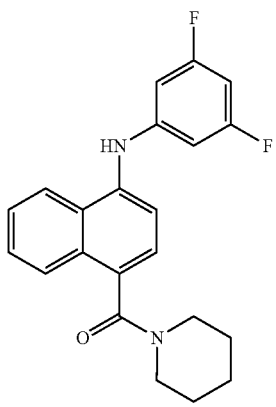 [SMILES: O=C(c1ccc(Nc2cc(F)cc(F)c2)c2ccccc12)N1CCCCC1]

The title compound was prepared by using Intermediate-31 and piperidine by following the similar procedure as described in Example-179; $^1$H NMR (400 MHz, CDCl$_3$) δ 1.43-1.76 (m, 6H), 3.17-3.19 (m, 2H), 3.88-3.90 (m, 2H), 6.30-6.31 (m, 1H), 6.40-6.47 (m, 3H), 7.22-7.27 (m, 2H), 7.43-7.51 (m, 2H), 7.81-7.83 (d, 1H, J=8.0 Hz), 7.92-7.94 (d, 1H, J=8.0 Hz); MS m/z 367 (M+1).

Example-192

(4-((2,4-Difluorophenyl)amino)naphthalen-1-yl)(morpholino)methanone

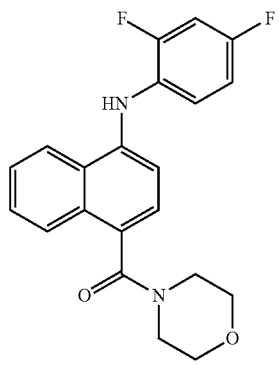 [SMILES: O=C(c1ccc(Nc2ccc(F)cc2F)c2ccccc12)N1CCOCC1]

This compound was prepared by using Intermediate-32 and morpholine by following the similar procedure as described in Example-179; $^1$H NMR (400 MHz, CDCl$_3$) δ 3.27 (bs, 2H), 3.54 (bs, 2H), 3.85-3.99 (m, 4H), 6.1 (s, 1H), 6.82-6.84 (m, 1H), 6.93-6.98 (m, 1H), 7.09-7.16 (m, 2H), 7.33-7.31 (d, 1H, J=7.6 Hz), 7.53-7.60 (m, 2H), 7.88-7.90 (m, 1H), 8.05-8.07 (m, 1H); MS m/z 369 (M+1).

Example-193

4-((2,4-Difluorophenyl)amino)-N-((tetrahydro-2H-pyran-4-yl)methyl)-1-naphthamide

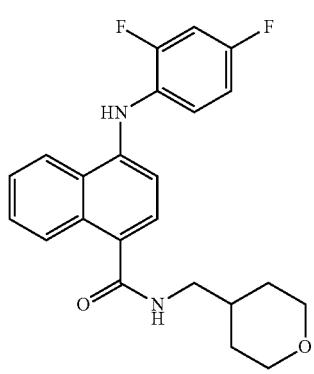 [SMILES: O=C(NCC1CCOCC1)c1ccc(Nc2ccc(F)cc2F)c2ccccc12]

This compound was prepared by using Intermediate-32 and (tetrahydro-2H-pyran-4-yl)methanamine by following the similar procedure as described in Example-179; $^1$H NMR (400 MHz, CDCl$_3$) δ 1.37-1.47 (m, 2H), 1.69-1.73 (m, 2H), 1.90-1.96 (m, 1H), 3.37-3.45 (m, 4H), 3.99-4.02 (m, 2H), 6.10 (m, 2H), 6.81-6.84 (m, 1H), 6.92-6.98 (m, 1H), 7.05-7.07 (d, 1H, J=7.6 Hz), 7.11-7.17 (m, 1H), 7.49-7.51 (d, 1H, J=7.6 Hz), 7.53-7.62 (m, 2H), 8.03-8.05 (d, 1H, J=7.6 Hz), 8.40-8.42 (d, 1H, J=8.0 Hz); MS m/z 397 (M+1).

Example-194

4-((2,4-Difluorophenyl)amino)-N-(pyridin-4-ylmethyl)-1-naphthamide

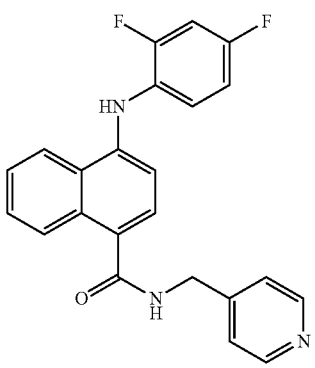 [SMILES: O=C(NCc1ccncc1)c1ccc(Nc2ccc(F)cc2F)c2ccccc12]

The title compound was prepared by using Intermediate-32 and pyridin-4-ylmethanamine by following the similar procedure as described in Example-179; $^1$H NMR (400 MHz, CDCl$_3$) δ 4.73-4.75 (d, 2H, J=6.0 Hz), 6.11 (s, 1H), 6.36-6.38 (m, 1H), 6.81-6.87 (m, 1H), 6.94-6.99 (m, 1H), 7.05-7.07 (d, 1H, J=8.0 Hz), 7.15-7.21 (m, 1H), 7.31-7.33 (m, 1H), 7.56-7.64 (m, 3H), 8.04-8.07 (m, 1H), 8.47-8.50 (m, 1H), 8.59-8.60 (m, 2H); MS m/z 390 (M+1).

Example-195

N-Butyl-4-((2,4-difluorophenyl)amino)-1-naphthamide

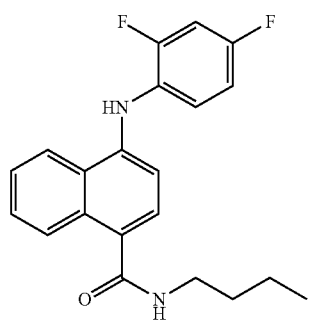 [SMILES: CCCCNC(=O)c1ccc(Nc2ccc(F)cc2F)c2ccccc12]

The above compound was prepared by using Intermediate-32 and n-butylamine by following the similar procedure as described for Example-179; $^1$H NMR (400 MHz, CDCl$_3$) δ 1.55 (s, 9H), 5.81 (s, 1H), 6.04 (s, 1H), 6.80-6.84 (m, 1H), 6.95-7.0 (m, 1H), 7.08-7.14 (m, 2H), 7.48-7.51 (m, 1H), 7.54-7.63 (m, 2H), 8.04-8.06 (d, 1H, J=8.4 Hz), 8.39-8.41 (d, 1H, J=8.4 Hz); MS m/z 355 (M+1).

Example-196

(4-((2,4-Difluorophenyl)amino)naphthalen-1-yl)(piperidin-1-yl)methanone

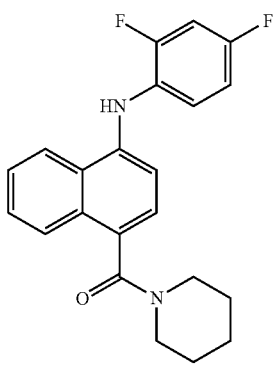 [SMILES: O=C(c1ccc(Nc2ccc(F)cc2F)c2ccccc12)N1CCCCC1]

This compound was prepared by using Intermediate-32 and piperidine by following the similar procedure as described in Example-179; $^1$H NMR (400 MHz, CDCl$_3$) δ 1.40-1.74 (m, 6H), 3.18-3.20 (m, 2H), 3.81-3.90 (m, 2H), 5.97 (s, 1H), 6.76-7.18 (m, 4H), 7.29-7.31 (m, 1H), 7.51-7.57 (m, 2H), 7.87-7.89 (m, 1H), 8.02-8.10 (m, 1H); MS m/z 367 (M+1).

Example-197

(4-((2,4-Dichlorophenyl)amino)naphthalen-1-yl)(morpholino)methanone

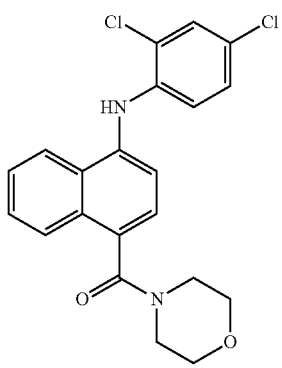 [SMILES: O=C(c1ccc(Nc2ccc(Cl)cc2Cl)c2ccccc12)N1CCOCC1]

This compound was prepared by using Intermediate-33 and morpholine by following the similar procedure as described in Example-179; $^1$H NMR (400 MHz, CDCl$_3$) 3.1 (bs, 2H), 3.5 (bs, 2H), 3.7-3.9 (m, 4H), 6.83-6.85 (d, 1H, J=8.0 Hz), 6.97-6.98 (d, 1H, J=8.0 Hz), 7.23-7.26 (dd, 1H, J=8.8 Hz, 2.4 Hz), 7.36-7.38 (d, 1H, J=8.0 Hz), 7.53-7.63 (m, 3H), 7.81-7.83 (m, 1H), 8.09-8.11 (m, 1H), 8.14 (s, 1H); MS m/z 401 (M+1).

Example-198

4-((2,4-Dichlorophenyl)amino)-N-((tetrahydro-2H-pyran-4-yl)methyl)-1-naphthamide

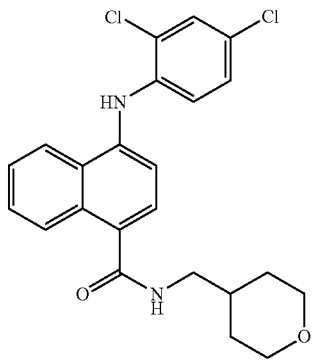 [SMILES: O=C(NCC1CCOCC1)c1ccc(Nc2ccc(Cl)cc2Cl)c2ccccc12]

This compound was prepared by using Intermediate-33 and (tetrahydro-2H-pyran-4-yl)methanamine by following the similar procedure as described in Example-179; $^1$H NMR (400 MHz, CDCl$_3$) δ 1.19-1.29 (m, 2H), 1.64-1.67 (m, 2H), 1.82 (m, 1H), 3.31-3.32 (m, 4H), 3.86-3.88 (d, 2H, J=9.2 Hz), 6.77-6.80 (d, 1H, J=8.8 Hz), 6.91-6.93 (d, 1H, J=8.0 Hz), 7.24-7.26 (d, 1H, J=8.0 Hz), 7.51-7.63 (m, 3H), 8.06-8.09 (d, 1H, J=8.0 Hz), 8.18 (s, 1H), 8.26-8.28 (d, 1H, J=8.0 Hz), 8.47-8.50 (t, 1H, J=5.2 Hz); MS m/z 429 (M+1).

Example-199

4-((2,4-Dichlorophenyl)amino)-N-(pyridin-4-ylmethyl)-1-naphthamide

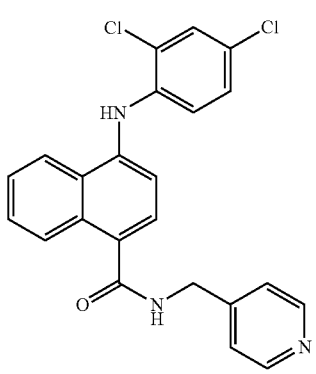 [SMILES: O=C(NCc1ccncc1)c1ccc(Nc2ccc(Cl)cc2Cl)c2ccccc12]

The title compound was prepared by using Intermediate-33 and pyridin-4-ylmethanamine by following the similar procedure as described in Example-179; $^1$H NMR (400 MHz, CDCl$_3$) δ 4.53-4.55 (d, 2H, J=6.0 Hz), 6.87-6.90 (m, 2H), 7.27-7.30 (dd, 1H, J=8.4, 2.4 Hz), 7.37-7.39 (d, 1H, J=5.2 Hz), 7.52-7.60 (m, 2H), 7.64-7.66 (m, 2H), 8.12-8.14 (d, 1H, J=8.0 Hz), 8.26 (s, 1H), 8.32-8.34 (m, 1H), 8.54 (bs, 2H), 9.07-9.10 (t, 1H, J=6.0 Hz); MS m/z 422 (M+1).

Example-200

N-Butyl-4-((2,4-dichlorophenyl)amino)-1-naphthamide

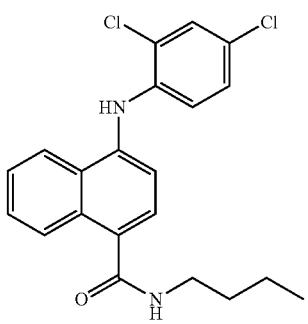 [SMILES: CCCCNC(=O)c1ccc(Nc2ccc(Cl)cc2Cl)c2ccccc12]

The above compound was prepared by using Intermediate-33 and n-butylamine by following the similar procedure as described in Example-179; ¹H NMR (400 MHz, CDCl₃) δ 1.43 (s, 9H), 6.70-6.72 (d, 1H, J=8.8 Hz), 6.95-6.97 (d, 1H, J=7.6 Hz), 7.22-7.25 (dd, 1H, J=8.8, 2.4 Hz), 7.44-7.46 (d, 1H, J=7.6 Hz), 7.50-7.62 (m, 3H), 8.03-8.05 (m, 1H), 8.12 (s, 1H), 8.18-8.20 (m, 1H); MS m/z 387 (M+1).

Example-201

Morpholino(4-((3-(trifluoromethyl)phenyl)amino)naphthalen-1-yl)methanone

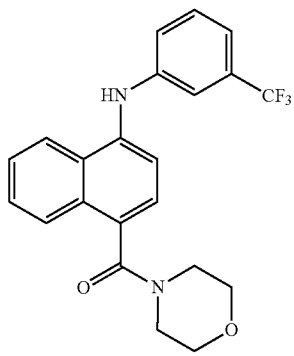 [SMILES: O=C(c1ccc(Nc2cccc(C(F)(F)F)c2)c2ccccc12)N1CCOCC1]

This compound was prepared by using Intermediate-34 and morpholine by following the similar procedure as described in Example-179; ¹H NMR (400 MHz, CDCl₃) δ 3.27 (brs, 2H), 3.56 (brs, 2H), 3.86-4.02 (m, 4H), 6.48 (s, 1H), 7.15-7.16 (m, 2H), 7.22-7.24 (m, 1H), 7.27-7.29 (m, 2H), 7.33-7.37 (t, 1H, J=8.0 Hz), 7.46-7.55 (m, 2H), 7.83-7.86 (m, 1H), 7.99-8.01 (m, 1H); MS m/z 401 (M+1).

Example-202

Piperidin-1-yl(4-((3-(trifluoromethyl)phenyl)amino)naphthalen-1-yl)methanone

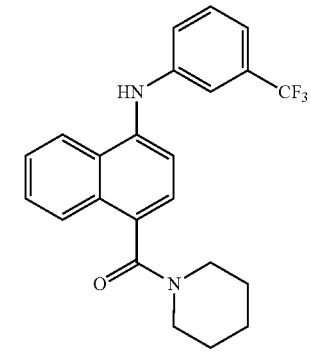 [SMILES: O=C(c1ccc(Nc2cccc(C(F)(F)F)c2)c2ccccc12)N1CCCCC1]

The above compound was prepared by using Intermediate-34 and piperidine by following the similar procedure as described in Example-179; ¹H NMR (400 MHz, CDCl₃) δ 1.43-1.76 (m, 6H), 3.19-3.21 (m, 2H), 3.88-3.90 (m, 2H), 6.45 (s, 1H), 7.12-7.14 (m, 2H), 7.22-7.27 (m, 3H), 7.31-7.35 (t, 1H, J=8.0 Hz), 7.44-7.52 (m, 2H), 7.82-7.84 (d, 1H, J=8.0 Hz), 7.97-7.99 (d, 1H, J=8.0 Hz); MS m/z 399 (M+1).

Example-203

(4-((4-Fluoro-3-(trifluoromethyl)phenyl)amino)naphthalen-1-yl)(morpholino)methanone

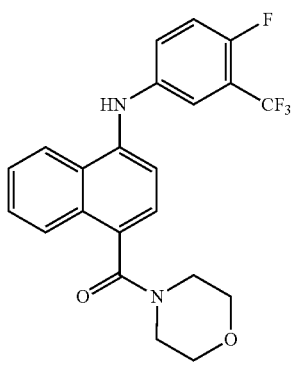 [SMILES: O=C(c1ccc(Nc2ccc(F)c(C(F)(F)F)c2)c2ccccc12)N1CCOCC1]

This compound was prepared by using Intermediate-35 and morpholine by following the similar procedure as described in Example-179; ¹H NMR (400 MHz, CDCl₃) δ 3.27 (brs, 2H), 3.55 (brs, 2H), 3.86-4.02 (m, 4H), 6.38 (s, 1H), 7.12-7.17 (m, 3H), 7.24 (s, 1H), 7.27-7.28 (m, 1H), 7.46-7.56 (m, 2H), 7.83-7.85 (m, 1H), 7.96-7.97 (m, 1H); MS m/z 419 (M+1).

Example-204

(4-((4-Fluoro-3-(trifluoromethyl)phenyl)amino)naphthalen-1-yl)(piperidin-1-yl)methanone

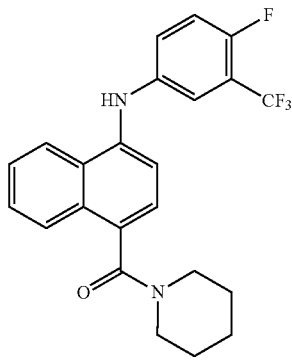 [SMILES: O=C(c1ccc(Nc2ccc(F)c(C(F)(F)F)c2)c2ccccc12)N1CCCCC1]

This compound was prepared by using Intermediate-35 and piperidine by following the similar procedure as described in Example-179; $^1$H NMR (400 MHz, CD$_3$OD) δ 1.46-1.75 (m, 6H), 3.19-3.21 (m, 2H), 3.85-3.87 (m, 2H), 7.19-7.23 (t, 2H, J=10.0 Hz), 7.30-7.36 (m, 4H), 7.54-7.62 (m, 2H), 7.80-7.82 (d, 1H, J=8.0 Hz), 8.19-8.21 (d, 1H, J=8.0 Hz); MS m/z 417 (M+1).

Example-205

Morpholino(4-((3-(fluoromethyl)phenyl)amino)naphthalen-1-yl)methanone

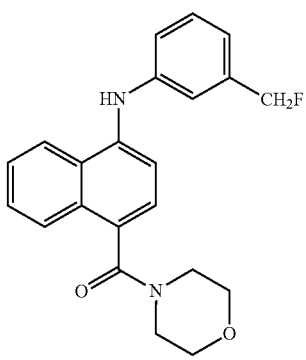

This compound was prepared by using Intermediate-36 and morpholine by following the similar procedure as described in Example-179; $^1$H NMR (400 MHz, CDCl$_3$) δ 3.28 (brs, 2H), 3.55 (brs, 2H), 3.84-3.99 (m, 4H), 5.27-5.39 (d, 2H, J=48.0 Hz), 6.11 (s, 1H), 6.95-6.99 (m, 1H), 7.03-7.08 (m, 2H), 7.27-7.30 (m, 1H), 7.31-7.33 (m, 2H), 7.50-7.59 (m, 2H), 7.87-8.90 (m, 1H), 8.03-8.05 (m, 1H); MS m/z 365 (M+1).

Example-206

(4-((3-(Fluoromethyl)phenyl)amino)naphthalen-1-yl)(piperidin-1-yl)methanone

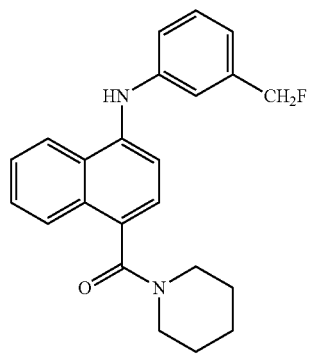

The title compound was prepared by using Intermediate-36 and piperidine by following the similar procedure as described in Example-179; $^1$H NMR (400 MHz, CDCl$_3$) δ 1.44-1.75 (m, 6H), 3.21-3.23 (m, 2H), 3.88 (brs, 2H), 5.28-5.40 (d, 2H, J=48.0 Hz), 6.10-6.20 (brs, 2H), 6.94-7.06 (m, 3H), 7.28-7.36 (m, 2H), 7.48-7.57 (m, 2H), 7.87-7.89 (m, 1H), 8.03-8.04 (m, 1H); MS m/z 363 (M+1).

Example-207

(4-((3-(Difluoromethyl)phenyl)amino)naphthalen-1-yl)(morpholino)methanone

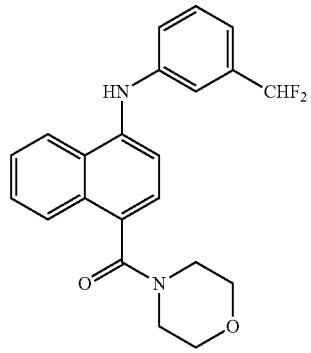 [SMILES: O=C(c1ccc(Nc2cccc(C(F)F)c2)c2ccccc12)N1CCOCC1]

This compound was prepared by using Intermediate-37 and morpholine by following the similar procedure as described in Example-179; $^1$H NMR (400 MHz, CDCl$_3$) δ 3.28 (brs, 2H), 3.55 (brs, 2H), 3.85-3.99 (m, 4H), 6.20 (s, 1H), 6.44-6.72 (t, 1H, J=56.4 Hz), 7.06-7.12 (m, 2H), 7.17 (s, 1H), 7.33-7.36 (m, 3H), 7.49-7.58 (m, 2H), 7.87-7.89 (m, 1H), 8.02-8.04 (m, 1H); MS m/z 383 (M+1).

Example-208

(4-((3-(Difluoromethyl)phenyl)amino)naphthalen-1-yl)(piperidin-1-yl)methanone

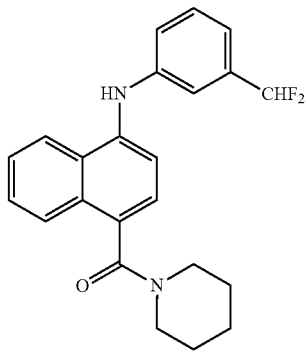 [SMILES: O=C(c1ccc(Nc2cccc(C(F)F)c2)c2ccccc12)N1CCCCC1]

The title compound was prepared by using Intermediate-37 and piperidine by following the similar procedure as described in Example-179; $^1$H NMR (400 MHz, CDCl$_3$) δ 1.43-1.7 (m, 6H), 3.19-3.22 (m, 2H), 3.87-3.88 (m, 2H), 6.24 (s, 1H), 6.43-6.71 (t, 1H, J=56.4 Hz), 7.03-7.10 (m, 2H), 7.15 (s, 1H), 7.30-7.34 (m, 3H), 7.46-7.54 (m, 2H), 7.85-7.87 (m, 1H), 8.0-8.02 (m, 1H); MS m/z 381 (M+1).

Example-209

N-(3-chlorophenyl)-5-methyl-4-(morpholinosulfonyl)isoquinolin-1-amine

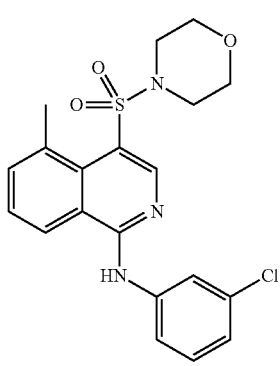 [SMILES: Cc1cccc2c(Nc3cccc(Cl)c3)ncc(S(=O)(=O)N3CCOCC3)c12]

The title compound was prepared by using Intermediate-41a and 3-chloroaniline by following the general procedure B; $^1$H NMR (400 MHz, DMSO-d$_6$) δ 3.01 (s, 3H), 3.31-3.42 (m, 4H), 3.64-3.71 (m, 4H), 7.15-7.17 (m, 1H), 7.38-7.42 (t, 1H, J=8.0 Hz), 7.66-8.01 (m, 4H), 8.47-8.52 (m, 2H), 9.88 (s, 1H); MS m/z 418 (M+1).

Example-210

5-Methyl-4-(morpholinosulfonyl)-N-(3-(trifluoromethyl)phenyl)isoquinolin-1-amine

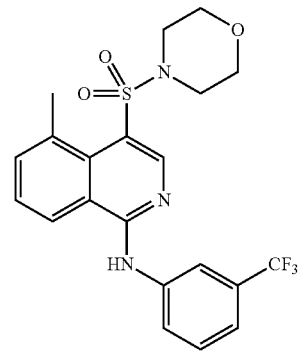 [SMILES: Cc1cccc2c(Nc3cccc(C(F)(F)F)c3)ncc(S(=O)(=O)N3CCOCC3)c12]

The title compound was prepared by using Intermediate-41a and 3-(trifluoromethyl)aniline by following the general procedure B; $^1$H NMR (400 MHz, CDCl$_3$) δ 3.11 (s, 3H), 3.46-3.48 (m, 4H), 3.79-3.81 (m, 4H), 7.4-7.42 (d, 1H, J=8.0 Hz), 7.51-7.7 (m, 4H), 7.88-7.9 (d, 2H, J=8.0 Hz), 7.99 (s, 1H), 8.57 (s, 1H); MS m/z 452 (M+1).

Example-211

N-(2,3-Difluorophenyl)-5-methyl-4-(morpholinosulfonyl)isoquinolin-1-amine

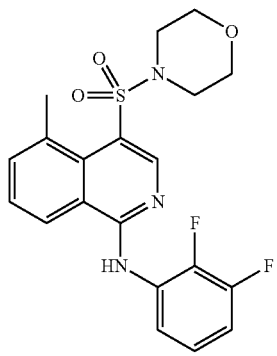 [SMILES: Cc1cccc2c(Nc3cccc(F)c3F)ncc(S(=O)(=O)N3CCOCC3)c12]

The title compound was prepared by using Intermediate-41a and 2,3-difluoroaniline by following the general procedure B; $^1$H NMR (400 MHz, DMSO-d$_6$) δ 2.99 (s, 3H), 3.28-3.33 (m, 4H), 3.36-3.65 (m, 4H), 7.24-7.35 (m, 3H), 7.66-7.7 (t, 1H, J=7.6 Hz), 7.76-7.78 (d, 1H, J=7.2 Hz), 8.37 (s, 1H), 8.42-8.44 (d, 1H, J=8.0 Hz), 9.93 (s, 1H); MS m/z 420 (M+1).

Example-212

N-(4-Fluoro-3-(trifluoromethyl)phenyl)-5-methyl-4-(morpholinosulfonyl)isoquinolin-1-amine

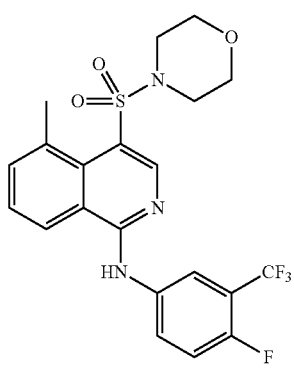

The title compound was prepared by using Intermediate-41a and 4-fluoro-3-(trifluoro methyl)aniline by following the general procedure B; $^1$H NMR (400 MHz, CDCl$_3$) δ 3.11 (s, 3H), 3.45-3.48 (m, 4H), 3.78-3.81 (m, 4H), 7.23-7.28 (m, 1H), 7.45 (s, 1H), 7.57-7.61 (m, 1H), 7.69-7.71 (d, 1H, J=7.2 Hz), 7.84-7.92 (m, 3H), 8.53 (s, 1H); MS m/z 470 (M+1).

Example-213

N-(3-Chlorophenyl)-5-methyl-4-(piperidin-1-ylsulfonyl)isoquinolin-1-amine

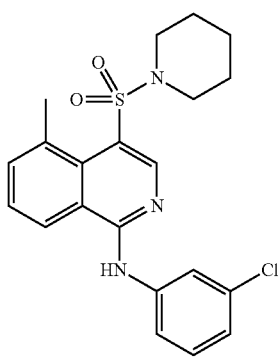 [SMILES: Cc1cccc2c(Nc3cccc(Cl)c3)ncc(S(=O)(=O)N3CCCCC3)c12]

The title compound was prepared by using Intermediate-41b and 3-chloroaniline by following the general procedure B; NMR (400 MHz, CDCl$_3$) δ 1.68-1.69 (m, 6H), 3.12 (s, 3H), 3.45-3.46 (m, 4H), 7.12-7.14 (m, 1H), 7.3-7.34 (t, 1H, J=8.0 Hz), 7.44-7.49 (m, 2H), 7.53-7.57 (t, 1H, J=8.0 Hz), 7.66-7.68 (m, 1H), 7.84-7.87 (m, 2H), 8.46 (s, 1H); MS m/z 416 (M+1).

Example-214

5-Methyl-4-(piperidin-1-ylsulfonyl)-N-(3-(trifluoromethyl)phenyl)isoquinolin-1-amine

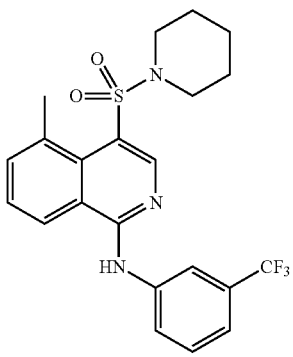 [SMILES: Cc1cccc2c(Nc3cccc(C(F)(F)F)c3)ncc(S(=O)(=O)N3CCCCC3)c12]

The title compound was prepared by using Intermediate-41b and 3-(trifluoromethyl)aniline by following the general procedure B; $^1$H NMR (400 MHz, CDCl$_3$) δ 1.67-1.69 (m, 6H), 3.11 (s, 3H), 3.42-3.45 (m, 4H), 7.38-7.4 (d, 1H, J=8.0 Hz), 7.49-7.56 (m, 3H), 7.65-7.66 (m, 1H), 7.85-7.87 (d, 2H, J=8.0 Hz), 7.99 (s, 1H), 8.45 (s, 1H); MS m/z 450 (M+1).

Example-215

N-(2,3-Difluorophenyl)-5-methyl-4-(piperidin-1-ylsulfonyl)isoquinolin-1-amine

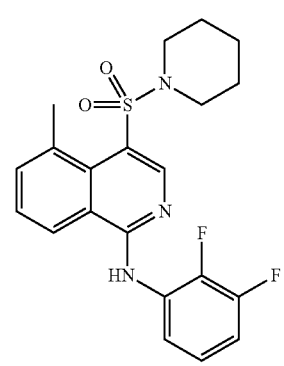 [SMILES: Cc1cccc2c(Nc3cccc(F)c3F)ncc(S(=O)(=O)N3CCCCC3)c12]

The title compound was prepared by using Intermediate-41b and 2,3-difluoroaniline by following the general procedure B; $^1$H NMR (400 MHz, DMSO-d$_6$) δ 1.69-1.72 (m, 6H), 3.15 (s, 3H), 3.44-3.46 (m, 4H), 6.94-6.98 (m, 1H), 7.12-7.19 (m, 1H), 7.59-7.72 (m, 3H), 7.91-7.93 (d, 1H, J=8.0 Hz), 8.20-8.25 (m, 1H), 8.5 (s, 1H); MS m/z 418 (M+1).

Example-216

N-(4-Fluoro-3-(trifluoromethyl)phenyl)-5-methyl-4-(piperidin-1-ylsulfonyl)isoquinolin-1-amine

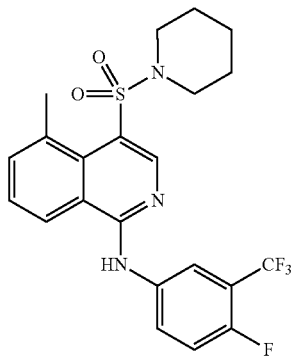 [SMILES: Cc1cccc2c(Nc3ccc(F)c(C(F)(F)F)c3)ncc(S(=O)(=O)N3CCCCC3)c12]

The title compound was prepared by using Intermediate-41b and 4-fluoro-3-(trifluoro methyl)aniline by following the general procedure B; ¹H NMR (400 MHz, CDCl₃) δ 1.68-1.7 (m, 6H), 3.12 (s, 3H), 3.43-3.45 (m, 4H), 7.22-7.24 (m, 1H), 7.42 (s, 1H), 7.54-7.57 (m, 1H), 7.67-7.68 (d, 1H, J=7.2 Hz), 7.82-7.92 (m, 3H), 8.42 (s, 1H); MS m/z 468 (M+1).

Example-217

N-(4-Fluorophenyl)-5-methyl-4-(piperidin-1-ylsulfonyl)isoquinolin-1-amine

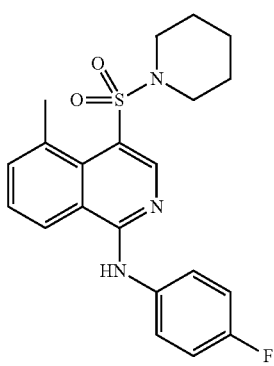 [SMILES: Cc1cccc2c(Nc3ccc(F)cc3)ncc(S(=O)(=O)N3CCCCC3)c12]

The title compound was prepared by using Intermediate-41b and 4-fluoroaniline by following the general procedure B; ¹H NMR (400 MHz, CDCl₃) δ 1.65-1.68 (m, 6H), 3.1 (s, 3H), 3.4-3.42 (m, 4H), 7.08-7.12 (m, 2H), 7.36 (s, 1H), 7.5-7.58 (m, 3H), 7.64-7.66 (d, 1H, J=8.0 Hz), 7.83-7.85 (d, 1H, J=8.0 Hz), 8.41 (s, 1H); MS m/z 400 (M+1).

Example-218

(5-Chloro-1-((3-chlorophenyl)amino)isoquinolin-4-yl)(piperidin-1-yl)methanone

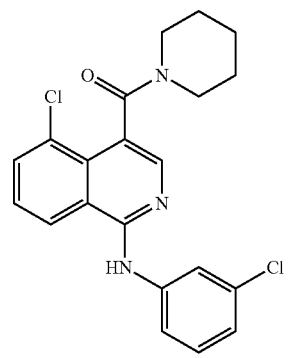

The title compound was prepared by using Intermediate-43a and 3-chloroaniline by following the general procedure B; ¹H NMR (400 MHz, CDCl₃) δ 1.26-1.52 (m, 3H), 1.72-1.82 (m, 3H), 3.17-3.24 (m, 1H), 3.38-3.42 (m, 1H), 3.49-3.56 (m, 1H), 4.14-4.18 (m, 1H), 7.03-7.05 (dd, 1H), 7.36-7.4 (t, 1H), 7.52-7.54 (dd, 1H), 7.58-7.6 (d, 1H), 7.82-7.84 (m, 2H), 7.89-7.91 (d, 1H), 8.09 (s, 1H); MS m/z 400 (M+1).

Example-219

(5-Chloro-1-((3-fluoro-2-methylphenyl)amino)isoquinolin-4-yl)(piperidin-1-yl)methanone

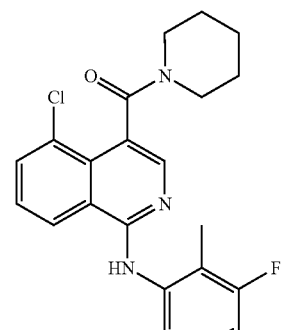

The title compound was prepared by using Intermediate-43a and 3-fluoro-2-methylaniline by following the general procedure B; ¹H NMR (400 MHz, CDCl₃) δ 1.26-1.29 (m, 1H), 1.46-1.52 (m, 2H), 1.63-1.83 (m, 3H), 2.74 (s, 3H), 3.21-3.26 (m, 1H), 3.37-3.5 (m, 2H), 4.18-4.21 (m, 1H), 7.19-7.22 (t, 1H), 7.53-7.67 (m, 2H), 7.74-7.74 (m, 2H), 8.14 (s, 1H), 8.91-8.94 (d, 1H); MS m/z 398 (M+1).

Example-220

(5-Chloro-1-((2,3-difluorophenyl)amino)isoquinolin-4-yl)(piperidin-1-yl)methanone

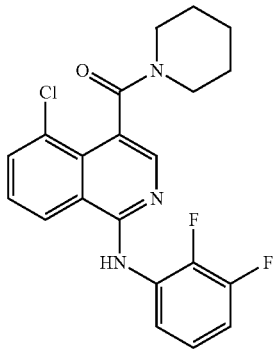

This compound was prepared by using Intermediate-43a and 2,3-difluoroaniline by following the general procedure B; $^1$H NMR (400 MHz, CDCl$_3$) δ 0.87-0.94 (m, 1H), 1.26-1.28 (m, 3H), 1.77-1.79 (m, 2H), 3.15-3.21 (m, 1H), 3.34-3.39 (m, 1H), 3.43-3.5 (m, 1H), 4.12-4.18 (m, 1H), 6.87-6.94 (m, 1H), 7.10-7.16 (m, 1H), 7.43-7.45 (m, 1H), 7.53-7.61 (m, 1H), 7.82-7.84 (dd, 1H), 7.98-8.0 (d, 1H), 8.07 (s, 1H), 8.22-8.26 (m, 1H); MS m/z 402 (M+1).

Example-221

(5-Chloro-1-((3-chlorophenyl)amino)isoquinolin-4-yl)(morpholino)methanone

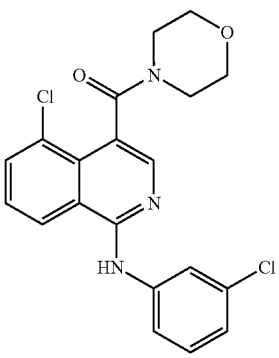

The desired compound was prepared by using Intermediate-43b and 3-chloroaniline by following the general procedure B; $^1$H NMR (400 MHz, CDCl$_3$) δ 3.30-3.40 (m, 2H), 3.56-3.61 (m, 1H), 3.64-3.81 (m, 3H), 3.92-3.97 (m, 1H), 4.09-4.14 (m, 1H), 7.07-7.09 (m, 1H), 7.30-7.32 (m, 1H), 7.45-7.52 (m, 2H), 7.69-7.71 (m, 2H), 7.82-7.83 (t, 1H), 7.91-7.94 (m, 2H); MS m/z 402 (M+1).

Example-222

(5-Chloro-1-((3-fluoro-2-methylphenyl)amino)isoquinolin-4-yl)(morpholino)methanone

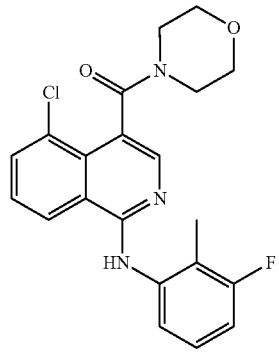

The title compound was prepared by using Intermediate-43b and 3-fluoro-2-methylaniline by following the general procedure B; $^1$H NMR (400 MHz, CDCl$_3$) δ 2.23 (s, 3H), 3.31-3.39 (m, 2H), 3.5-3.66 (m, 2H), 3.7-3.77 (m, 2H), 3.9-3.95 (m, 1H), 4.07-4.12 (m, 1H), 6.92-6.96 (t, 1H), 7.01-7.02 (m, 1H), 7.20-7.26 (m, 1H), 7.44-7.48 (m, 1H), 7.53-7.58 (t, 1H), 7.81-7.83 (dd, 1H), 7.95-7.98 (d, 1H), 8.0 (s, 1H); MS m/z 400 (M+1).

Example-223

(5-Chloro-1-((2,3-difluorophenyl)amino)isoquinolin-4-yl)(morpholino)methanone

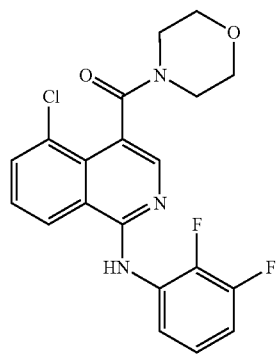

This compound was prepared by using Intermediate-43b and 2,3-difluoroaniline by following the general procedure B; $^1$H NMR (400 MHz, CDCl$_3$) δ 3.31-3.34 (m, 2H), 3.54-3.67 (m, 2H), 3.71-3.79 (m, 2H), 3.91-3.96 (m, 1H), 4.08-4.14 (m, 1H), 6.89-6.95 (m, 1H), 7.11-7.17 (m, 1H), 7.49-7.50 (d, 1H), 7.58-7.62 (t, 1H), 7.83-7.85 (dd, 1H), 7.99-8.01 (d, 1H), 8.08 (s, 1H), 8.21-8.24 (m, 1H); MS m/z 404 (M+1).

Example-224

5-Methyl-4-(morpholinomethyl)-N-(3-(trifluoromethyl)phenyl)isoquinolin-1-amine

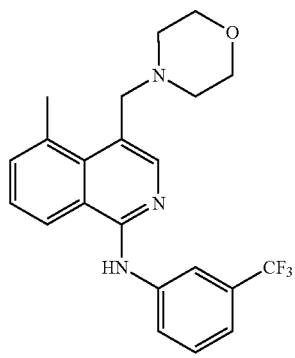

This compound was prepared by using Intermediate-46a and 3-(trifluoromethyl)aniline by following the general procedure B; $^1$H NMR (400 MHz, CDCl$_3$) δ 2.49 (s, 4H), 3.09 (s, 3H), 3.66 (s, 4H), 3.8 (s, 2H), 7.19 (s, 1H), 7.22-7.31 (m, 1H), 7.37-7.56 (m, 3H), 7.83-7.88 (m, 2H), 7.95-7.97 (m, 2H); MS m/z 402 (M+1).

Example-225

N-(3,5-difluorophenyl)-5-methyl-4-(morpholinomethyl)isoquinolin-1-amine

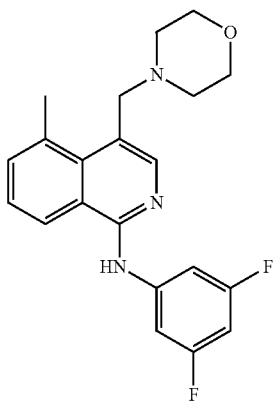 [SMILES: Cc1cccc2c(Nc3cc(F)cc(F)c3)ncc(CN3CCOCC3)c12]

This compound was prepared by using Intermediate-46a and 3,5-difluoroaniline by following the general procedure B; $^1$H NMR (400 MHz, CDCl$_3$) δ 2.49 (s, 4H), 3.09 (s, 3H), 3.66 (s, 4H), 3.81 (s, 2H), 6.46-6.51 (m, 1H), 7.16 (s, 1H), 7.26-7.3 (m, 2H), 7.47-7.56 (m, 2H), 7.81-7.83 (d, 1H, J=8.4 Hz), 7.97 (s, 1H); MS m/z 370 (M+1).

Example-226

N-(2,3-difluorophenyl)-5-methyl-4-(morpholinomethyl)isoquinolin-1-amine

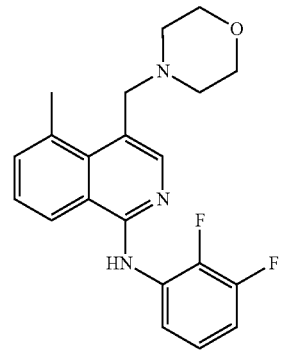 [SMILES: Cc1cccc2c(Nc3cccc(F)c3F)ncc(CN3CCOCC3)c12]

This compound was prepared by using Intermediate-46a and 2,3-difluoroaniline by following the general procedure B; $^1$H NMR (400 MHz, CDCl$_3$) δ 2.48 (s, 4H), 3.09 (s, 3H), 3.66 (s, 4H), 3.80 (s, 2H), 6.80-6.87 (m, 1H), 7.07-7.13 (m, 1H), 7.33-7.34 (m, 1H), 7.49-7.56 (m, 2H), 7.89-7.91 (d, 1H, J=8.0 Hz), 7.95 (s, 1H), 8.22-8.26 (m, 1H); MS m/z 370 (M+1).

Example-227

N-(5-chloro-2-fluorophenyl)-5-methyl-4-(morpholinomethyl)isoquinolin-1-amine

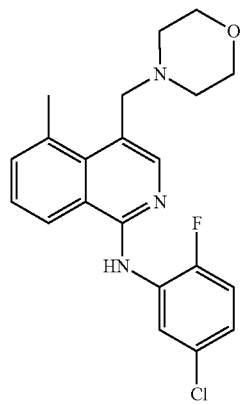 [SMILES: Cc1cccc2c(Nc3cc(Cl)ccc3F)ncc(CN3CCOCC3)c12]

This compound was prepared by using Intermediate-46a and 5-chloro-2-fluoroaniline by following the general procedure B; $^1$H NMR (400 MHz, CDCl$_3$) δ 2.49 (s, 4H), 3.09 (s, 3H), 3.67 (s, 4H), 3.81 (s, 2H), 6.91-6.95 (m, 1H), 7.05-7.1 (m, 1H), 7.40-7.41 (m, 1H), 7.48-7.56 (m, 2H), 7.85-7.87 (d, 1H, J=8.0 Hz), 7.99 (s, 1H), 8.71-8.73 (m, 1H); MS m/z 386 (M+1).

Example-228

N-(3,5-difluorophenyl)-5-methyl-4-(piperidin-1-ylmethyl)isoquinolin-1-amine

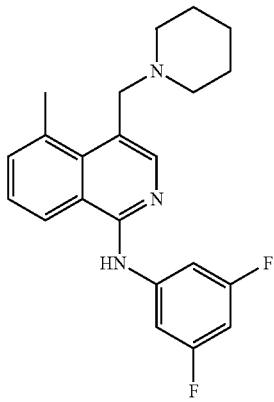 [SMILES: Cc1cccc2c(Nc3cc(F)cc(F)c3)ncc(CN3CCCCC3)c12]

This compound was prepared by using Intermediate-46b and 3,5-difluoroaniline by following the general procedure B; ¹H NMR (400 MHz, CDCl₃) δ 1.44-1.58 (m, 6H), 2.41 (s, 4H), 3.10 (s, 3H), 3.72 (s, 2H), 6.44-6.5 (m, 1H), 7.12 (s, 1H), 7.23-7.3 (m, 2H), 7.44-7.58 (m, 2H), 7.80-7.82 (d, 1H, J=8.0 Hz), 7.96 (s, 1H); MS m/z 368 (M+1).

Example-229

N-(2,3-difluorophenyl)-5-methyl-4-(piperidin-1-ylmethyl)isoquinolin-1-amine

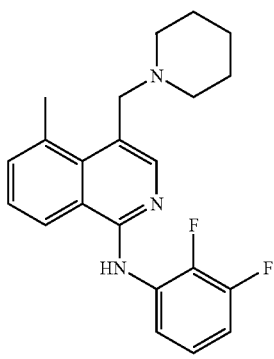 [SMILES: Cc1cccc2c(Nc3cccc(F)c3F)ncc(CN3CCCCC3)c12]

This compound was prepared by using Intermediate-46b and 2,3-difluoroaniline by following the general procedure B; ¹H NMR (400 MHz, CDCl₃) δ 1.44-1.57 (m, 6H), 2.4 (s, 4H), 3.1 (s, 3H), 3.72 (s, 2H), 6.81-6.85 (m, 1H), 7.08-7.11 (m, 1H), 7.29-7.3 (m, 1H), 7.47-7.55 (m, 2H), 7.88-7.89 (d, 1H, J=7.6 Hz), 7.94 (s, 1H), 8.21-8.25 (m, 1H); MS m/z 368 (M+1).

Example-230

N-(5-chloro-2-fluorophenyl)-5-methyl-4-(piperidin-1-ylmethyl)isoquinolin-1-amine

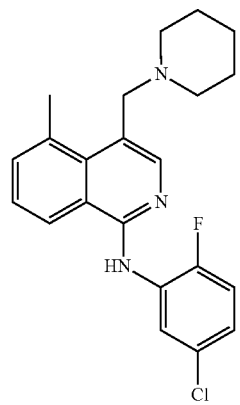 [SMILES: Cc1cccc2c(Nc3cc(Cl)ccc3F)ncc(CN3CCCCC3)c12]

This compound was prepared by using Intermediate-46b and 5-chloro-2-fluoroaniline by following the general procedure B; ¹H NMR (400 MHz, CDCl₃) δ 1.44-1.57 (m, 6H), 2.41 (s, 4H), 3.1 (s, 3H), 3.73 (s, 2H), 6.90-6.94 (m, 1H), 7.05-7.09 (m, 1H), 7.38-7.39 (m, 1H), 7.46-7.54 (m, 2H), 7.84-7.86 (d, 1H, J=8.0 Hz), 7.98 (s, 1H), 8.71-8.73 (m, 1H); MS m/z 384 (M+1).

Example-231

N-(3-chloro-2-fluorophenyl)-5-methyl-4-(piperidin-1-ylmethyl)isoquinolin-1-amine

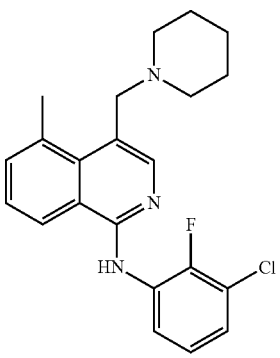 [SMILES: Cc1cccc2c(Nc3cccc(Cl)c3F)ncc(CN3CCCCC3)c12]

This compound was prepared by using Intermediate-46b and 3-chloro-2-fluoroaniline by following the general procedure B; ¹H NMR (400 MHz, CDCl₃) δ 1.44-1.57 (m, 6H), 2.4 (s, 4H), 3.1 (s, 3H), 3.72 (s, 2H), 7.01-7.05 (m, 1H), 7.09-7.11 (m, 1H), 7.32-7.33 (m, 1H), 7.47-7.54 (m, 2H), 7.86-7.88 (d, 1H, J=8.0 Hz), 7.94 (s, 1H), 8.39-8.43 (m, 1H); MS m/z 384 (M+1).

Example-232

N-(3-chlorophenyl)-5-methyl-4-(piperidin-1-ylmethyl)isoquinolin-1-amine

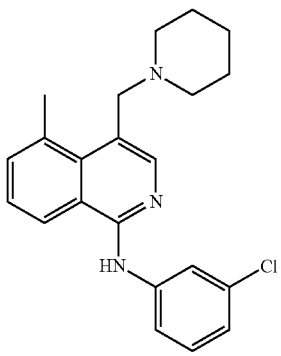 [SMILES: Cc1cccc2c(Nc3cccc(Cl)c3)ncc(CN3CCCCC3)c12]

This compound was prepared by using Intermediate-46b and 3-chloroaniline by following the general procedure B; $^1$H NMR (400 MHz, CDCl$_3$) δ 1.44-1.57 (m, 6H), 2.4 (s, 4H), 3.09 (s, 3H), 3.71 (s, 2H), 7.0-7.05 (m, 2H), 7.25-7.29 (m, 1H), 7.42-7.52 (m, 3H), 7.79-7.84 (m, 2H), 7.93 (s, 1H); MS m/z 366 (M+1).

Example-233

5-Methyl-4-(piperidin-1-ylmethyl)-N-(3-(trifluoromethyl)phenyl)isoquinolin-1-amine

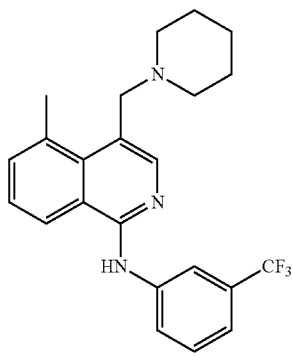 [SMILES: Cc1cccc2c(Nc3cccc(C(F)(F)F)c3)ncc(CN3CCCCC3)c12]

This compound was prepared by using Intermediate-46b and 3-(trifluoromethyl)aniline by following the general procedure B; $^1$H NMR (400 MHz, CDCl$_3$) δ 1.45-1.59 (m, 6H), 2.40 (s, 4H), 3.10 (s, 3H), 3.71 (s, 2H), 7.15 (s, 1H), 7.27-7.30 (m, 1H), 7.45-7.54 (m, 3H), 7.82-7.86 (m, 2H), 7.93-7.95 (m, 2H); MS m/z 400 (M+1).

Example-234

(1-((3-Fluoro-2-methylphenyl)amino)-5-ethylisoquinolin-4-yl)(morpholino)methanone

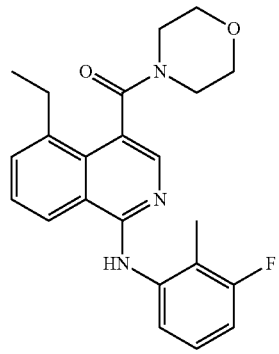 [SMILES: CCc1cccc2c(Nc3cccc(F)c3C)ncc(C(=O)N3CCOCC3)c12]

The desired compound was prepared by using Intermediate-21c and 3-fluoro-2-methylaniline by following the general procedure B; $^1$H NMR (400 MHz, CDCl$_3$) δ 1.27-1.37 (t, 3H), 2.23 (s, 3H), 2.84-2.90 (m, 1H), 3.11-3.16 (m, 1H), 3.31-3.34 (m, 1H), 3.44-3.48 (m, 1H), 3.58-3.69 (m, 3H), 3.74-3.80 (m, 1H), 3.85-3.90 (m, 1H), 4.08-4.12 (m, 1H), 6.89-6.93 (t, 1H), 7.03 (brs, 1H), 7.19-7.24 (m, 1H), 7.48-7.50 (d, 1H), 7.58-7.66 (m, 2H), 7.89-7.91 (m, 1H), 7.92 (s, 1H); MS m/z 394 (M+1).

Example-235

(5-Ethyl-1-((2-fluoro-3-(trifluoromethyl)phenyl)amino)isoquinolin-4-yl)(morpholino)methanone

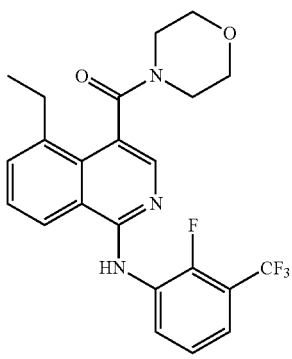 [SMILES: CCc1cccc2c(Nc3cccc(C(F)(F)F)c3F)ncc(C(=O)N3CCOCC3)c12]

This compound was prepared by using Intermediate-21c and 2-fluoro-3-(trifluoromethyl)aniline by following the general procedure B; $^1$H NMR (400 MHz, CDCl$_3$) δ 1.27-1.37 (t, 3H), 2.23 (s, 3H), 2.84-2.90 (m, 1H), 3.11-3.16 (m, 1H), 3.31-3.34 (m, 1H), 3.44-3.48 (m, 1H), 3.58-3.69 (m, 3H), 3.74-3.80 (m, 1H), 3.85-3.90 (m, 1H), 4.08-4.12 (m, 1H), 6.89-6.93 (t, 1H), 7.03 (brs, 1H), 7.19-7.24 (m, 1H), 7.48-7.50 (d, 1H), 7.58-7.66 (m, 2H), 7.89-7.91 (m, 1H), 7.92 (s, 1H); MS m/z 448 (M+1).

Example-236

(1-((3-Chloro-2-fluorophenyl)amino)-5-ethylisoquinolin-4-yl)(morpholino)methanone

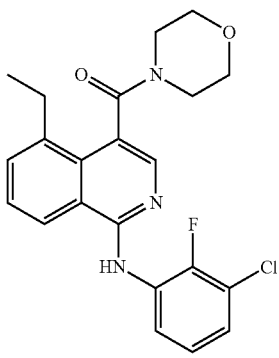 [SMILES: CCc1cccc2c(Nc3cccc(Cl)c3F)ncc(C(=O)N3CCOCC3)c12]

The desired compound was prepared by using Intermediate-21c and 3-chloro-2-fluoroaniline by following the general procedure B; ¹H NMR (400 MHz, CDCl₃) δ 1.26-1.37 (t, 3H), 2.84-2.90 (m, 1H), 3.12-3.16 (m, 1H), 3.30-3.33 (m, 1H), 3.40-3.42 (m, 1H), 3.59-3.67 (m, 3H), 3.79-3.82 (m, 1H), 3.87-3.89 (m, 1H), 4.10-4.12 (m, 1H), 7.09-7.14 (m, 2H), 7.50-7.51 (d, 1H), 7.64-7.67 (m, 2H), 7.91-7.93 (m, 1H), 8.0 (s, 1H), 8.43-8.45 (t, 1H); MS m/z 414 (M+1).

Example-237

(1-((3-Chloro-2-methylphenyl)amino)-5-ethylisoquinolin-4-yl)(morpholino)methanone

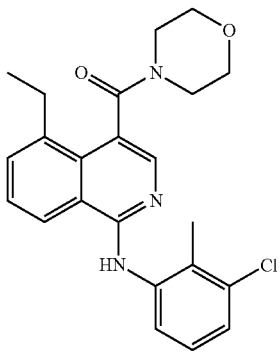 [SMILES: CCc1cccc2c(Nc3cccc(Cl)c3C)ncc(C(=O)N3CCOCC3)c12]

The desired compound was prepared by using Intermediate-21c and 3-chloro-2-methylaniline by following the general procedure B; ¹H NMR (400 MHz, CDCl₃) δ 1.26-1.37 (t, 3H), 2.36 (s, 3H), 2.83-2.89 (m, 1H), 3.10-3.16 (m, 1H), 3.28-3.34 (m, 1H), 3.44-3.48 (m, 1H), 3.58-3.69 (m, 3H), 3.74-3.79 (m, 1H), 3.85-3.89 (m, 1H), 4.07-4.12 (m, 1H), 7.17-7.21 (t, 1H), 7.24-7.25 (d, 1H), 7.52-7.54 (m, 1H), 7.58-7.66 (m, 2H), 7.89-7.9 (m, 2H); MS m/z 410 (M+1).

Example-238

(1-((3-Chloro-2-fluorophenyl)amino)-5-methylisoquinolin-4-yl)(1,1-dioxidothiomorpholino)methanone

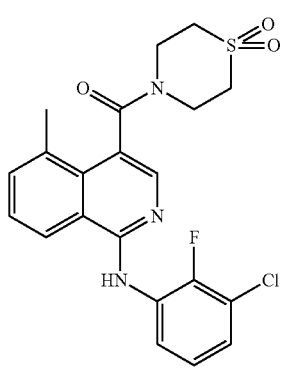 [SMILES: Cc1cccc2c(Nc3cccc(Cl)c3F)ncc(C(=O)N3CCS(=O)(=O)CC3)c12]

The desired compound was prepared by using Intermediate-11g and 3-chloro-2-fluoroaniline by following the general procedure B; ¹H NMR (400 MHz, CDCl₃) δ 2.58 (s, 3H), 2.91-3.29 (m, 4H), 3.77-3.99 (m, 3H), 4.83-4.86 (m, 1H), 7.10-7.18 (m, 2H), 7.53-7.64 (m, 3H), 7.92-7.95 (m, 1H), 8.01 (s, 1H), 8.42-8.48 (m, 1H); MS m/z 448 (M+1).

Example-239

(1-((3-Chlorophenyl)amino)-5-methylisoquinolin-4-yl)(1,1-dioxidothiomorpholino)methanone

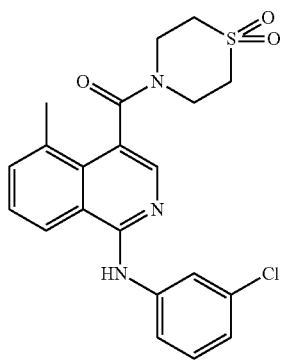 [SMILES: Cc1cccc2c(Nc3cccc(Cl)c3)ncc(C(=O)N3CCS(=O)(=O)CC3)c12]

This compound was prepared by using Intermediate-11q and 3-chloroaniline by following the general procedure B; ¹H NMR (400 MHz, CDCl₃) δ 2.56 (s, 3H), 2.92-3.29 (m, 4H), 3.78-4.14 (m, 3H), 4.82-4.86 (m, 1H), 7.09-7.12 (m, 1H), 7.30-7.34 (m, 2H), 7.48-7.6 (m, 3H), 7.85-7.9 (m, 2H), 8.0 (s, 1H); MS m/z 430 (M+1).

Example-240

(1-((3,5-Difluorophenyl)amino)-5-methylisoquinolin-4-yl)(1,1-dioxidothiomorpholino)methanone

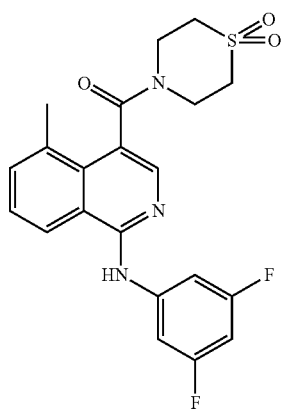 [SMILES: Cc1cccc2c(Nc3cc(F)cc(F)c3)ncc(C(=O)N3CCS(=O)(=O)CC3)c12]

The desired compound was prepared by using Intermediate-11q and 3,5-difluoroaniline by following the general procedure B; ¹H NMR (400 MHz, CDCl₃) δ 2.56 (s, 3H), 2.91-3.31 (m, 4H), 3.78-4.0 (m, 3H), 4.83-4.86 (m, 1H), 6.53-6.59 (m, 1H), 7.34-7.41 (m, 3H), 7.58-7.6 (m, 2H), 7.86-7.89 (m, 1H), 8.01 (s, 1H); MS m/z 432 (M+1).

Example-241

(1-((3-Chlorophenyl)amino)-5-methylisoquinolin-4-yl)(4,4-difluoropiperidin-1-yl)methanone

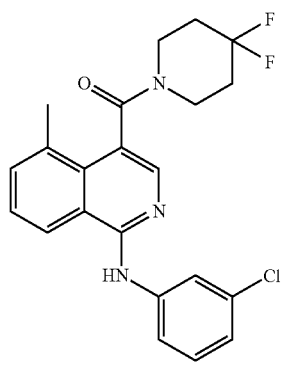 [SMILES: Cc1cccc2c(Nc3cccc(Cl)c3)ncc(C(=O)N3CCC(F)(F)CC3)c12]

This compound was prepared by using Intermediate-11r and 3-chloroaniline by following the general procedure B; ¹H NMR (400 MHz, CDCl₃) δ 1.91-2.2 (m, 4H), 2.58 (s, 3H), 3.35-3.41 (m, 1H), 3.59-3.67 (m, 2H), 4.37-4.42 (m, 1H), 7.06-7.09 (m, 1H), 7.27-7.32 (m, 2H), 7.48-7.55 (m, 3H), 7.85-7.88 (m, 2H), 8.0 (s, 1H); MS m/z 416 (M+1).

Example-242

6-Oxa-3-azabicyclo[3.1.1]heptan-3-yl(1-((2,4-difluorophenyl)amino)-5-methylisoquinolin-4-yl)methanone

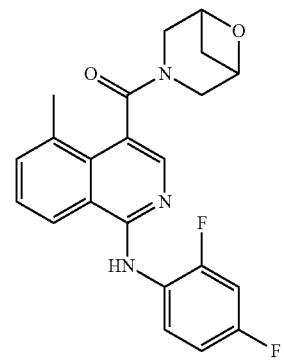 [SMILES: Cc1cccc2c(Nc3ccc(F)cc3F)ncc(C(=O)N3CC4CC(C3)O4)c12]

The desired compound was prepared by using Intermediate-11e and 2,4-difluoroaniline by following the similar procedure as described in Example-1; ¹H NMR (400 MHz, CDCl₃) δ (as mixture of isomers) 1.86-2.06 (m, 2H), 2.65 (s, 3H), 3.26-4.79 (m, 6H), 6.93-6.98 (m, 2H), 7.32 (s, 1H), 7.54-7.59 (m, 2H), 7.90-7.91 (m, 1H), 8.02-8.03 (m, 1H), 8.39-8.45 (m, 1H); MS m/z 396 (M+1).

Example-243

6-Oxa-3-azabicyclo[3.1.1]heptan-3-yl(1-((2-chloro-3-fluorophenyl)amino)-5-methylisoquinolin-4-yl)methanone

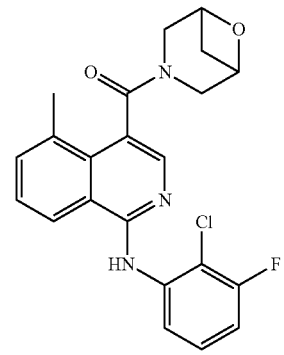 [SMILES: Cc1cccc2c(Nc3cccc(F)c3Cl)ncc(C(=O)N3CC4CC(C3)O4)c12]

This compound was prepared by using Intermediate-11e and 2-chloro-3-fluoroaniline by following the similar procedure as described in Example-1; ¹H NMR (400 MHz, CDCl₃) δ (as mixture of isomers) 1.86-2.06 (m, 2H), 2.66 (s, 3H), 3.26-4.8 (m, 6H), 6.86-6.91 (m, 1H), 7.29-7.34 (m, 1H), 7.58-7.61 (m, 2H), 7.96-7.99 (m, 2H), 8.08-8.1 (m, 1H), 8.48-8.53 (m, 1H); MS m/z 412 (M+1).

Example-244

6-Oxa-3-azabicyclo[3.1.1]heptan-3-yl(1-((2-fluoro-3-(trifluoromethyl)phenyl)amino)-5-methylisoquinolin-4-yl)methanone

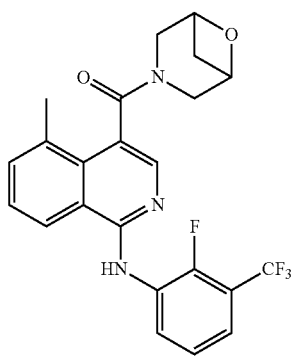 [SMILES: Cc1cccc2c(Nc3cccc(C(F)(F)F)c3F)ncc(C(=O)N3CC4CC(C3)O4)c12]

The desired compound was prepared by using Intermediate-11e and 2-fluoro-3-(trifluoromethyl)aniline by following the similar procedure as described in Example-1; $^1$H NMR (400 MHz, CDCl$_3$) δ (as mixture of isomers) 1.86-1.97 (m, 2H), 2.66 (s, 3H), 3.26-4.8 (m, 6H), 7.27-7.3 (m, 2H), 7.59-7.61 (m, 3H), 7.92-7.94 (m, 1H), 8.07-8.08 (m, 1H), 8.80-8.84 (m, 1H); MS m/z 446 (M+1).

The below examples given in Table-1a were prepared by following the similar procedure as described in Example-1 by taking appropriate intermediates.

The below acid or amide examples were prepared by following the procedure as described in Scheme-8 by taking corresponding ester.

The below amide examples were prepared by following the procedure as described in Scheme-8 by taking corresponding acid.

TABLE-1a

| E. No | Chemical name | Structure | $^1$H NMR/Mass |
|---|---|---|---|
| 245 | 1-((2,5-Bis(trifluoromethyl)phenyl)amino)-N,N,5-trimethyl isoquinolin-4-carboxamide | 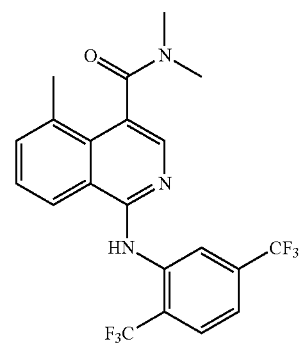 [SMILES: Cc1cccc2c(Nc3cc(C(F)(F)F)ccc3C(F)(F)F)ncc(C(=O)N(C)C)c12] | MS m/z 442 (M + 1) |
| 246 | Methyl 3-((5-chloro-4-(diethyl carbamoyl)isoquinolin-1-yl)amino) benzoate | 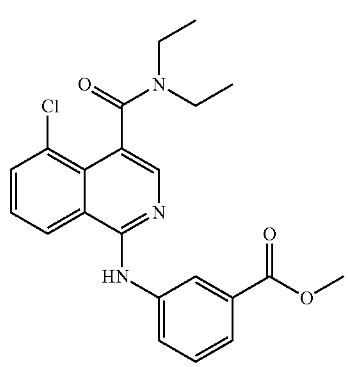 [SMILES: CCN(CC)C(=O)c1cnc(Nc2cccc(C(=O)OC)c2)c2cccc(Cl)c12] | MS m/z 412 (M + 1) |

TABLE-1a-continued

| E. No | Chemical name | Structure | ¹H NMR/Mass |
|---|---|---|---|
| 247 | Methyl 3-((5-chloro-4-(diethyl carbamoyl)isoquinolin-1-yl)amino)-2-methylbenzoate | 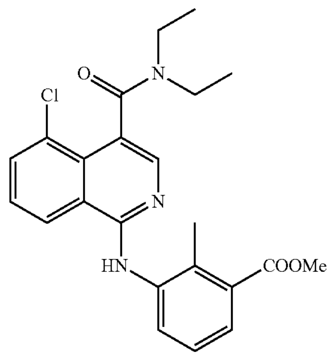 [SMILES: CCN(CC)C(=O)c1cnc(Nc2cccc(C(=O)OC)c2C)c2cccc(Cl)c12] | MS m/z 426 (M + 1) |
| 248 | Methyl 3-((5-chloro-4-(diethyl carbamoyl)isoquinolin-1-yl)amino) benzoate | 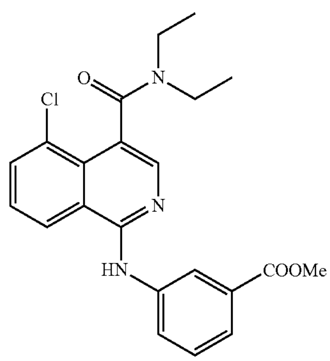 [SMILES: CCN(CC)C(=O)c1cnc(Nc2cccc(C(=O)OC)c2)c2cccc(Cl)c12] | ¹H NMR (400 MHz, CDCl₃) δ: 1.10-1.13 (t, 3H), 1.35-1.38 (t, 3H), 3.20-3.35 (m, 2H), 3.46-3.52 (m, 1H), 3.85-3.92 (m, 1H), 3.93 (s, 3H), 7.35-7.44 (m, 2H), 7.56-7.58 (d, 1H), 7.72-7.74 (d, J = 7.6 Hz, 1H), 7.82 (s, 1H), 7.93-8.01 (m, 2H), 8.26-8.29 (m, 2H); MS m/z 412 (M + 1). |
| 249 | Methyl 2-methyl-3-((5-chloro-4-(diethylcarbamoyl)isoquinolin-1-yl)amino)benzoate | 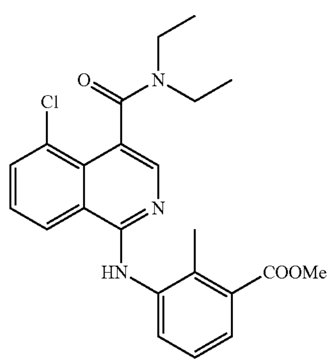 [SMILES: CCN(CC)C(=O)c1cnc(Nc2cccc(C(=O)OC)c2C)c2cccc(Cl)c12] | ¹H NMR (400 MHz, CDCl₃) δ: 1.08-1.11 (t, 3H), 1.26-1.34 (m, 3H), 2.53 (s, 3H), 3.19-3.31 (m, 2H), 3.39-3.48 (m, 1H), 3.78-3.84 (m, 1H), 3.94 (s, 3H), 7.27-7.32 (m, 1H), 7.49-7.53 (m, 1H), 7.70-7.87 (m, 4H), 8.05 (s, 1H); MS m/z 426 (M + 1). |
| 250 | Methyl 2-chloro-3-((5-methyl-4-(piperidin-1-carbonyl)isoquinolin-1-yl)amino)benzoate | 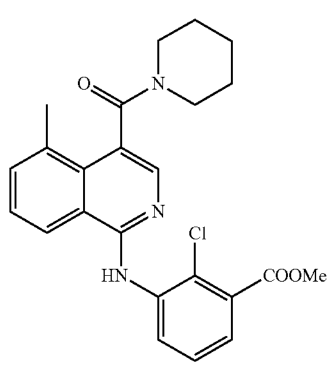 [SMILES: COC(=O)c1cccc(Nc2ncc(C(=O)N3CCCCC3)c3c(C)cccc23)c1Cl] | MS m/z 438 (M + 1). |

TABLE-1a-continued

| E. No | Chemical name | Structure | ¹H NMR/Mass |
|---|---|---|---|
| 251 | N-Ethyl-1-((4-fluoro-3-(trifluoro methyl)phenyl)amino)-N,5-dimethyl isoquinolin-4-carboxamide | 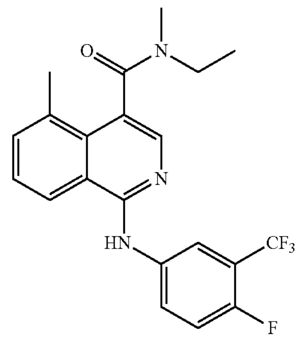 [SMILES: CCN(C)C(=O)c1cnc(Nc2ccc(F)c(C(F)(F)F)c2)c2cccc(C)c12] | MS m/z 406 (M + 1) |
| 252 | 1-((2,3-Dimethylphenyl)amino)-N-ethyl-N,5-dimethylisoquinolin-4-carboxamide | 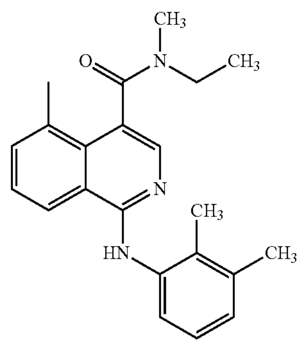 [SMILES: CCN(C)C(=O)c1cnc(Nc2cccc(C)c2C)c2cccc(C)c12] | ¹H NMR (400 MHz, CDCl₃) δ (as mixture of rotamers): 1.11-1.14 (t, J = 7.2 Hz, 3H), 1.27-1.31 (t, J = 7.2 Hz, 3H), 2.24 (s, 3H), 2.37 (s, 3H), 2.59 (s, 3H), 2.91 (s, 3H), 3.12 (s, 3H), 3.13-3.18 (q, J = 7.2 Hz, 1H), 3.34-3.30 (q, J = 7.2 Hz, 1H), 3.57-3.62 (q, J = 7.2 Hz, 1H), 3.76-3.81 (q, J = 7.2 Hz, 1H), 7.01-7.22 (m, 4H), 7.40-7.48 (m, 1H), 7.50-7.60 (m, 1H), 7.61-7.63 (m, 1H), 7.87-7.88 (m, 1H); MS m/z 348 (M + 1) |
| 253 | N-Ethyl-1-((3-fluoro-2-(trifluoro methyl)phenyl)amino)-N,5-dimethyl isoquinolin-4-carboxamide | 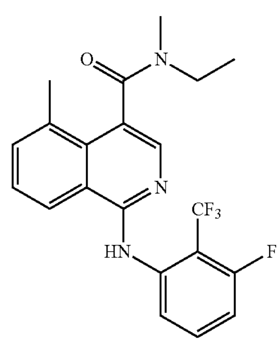 [SMILES: CCN(C)C(=O)c1cnc(Nc2cccc(F)c2C(F)(F)F)c2cccc(C)c12] | ¹H NMR (400 MHz, CDCl₃) δ (as (mixture of rotamers): 1.11-1.14 (t, J = 7.2 Hz, 3H), 1.28-1.32 (t, J = 7.2 Hz, 3H), 2.62 (s, 3H), 2.91 (s, 3H), 3.14 (s, 3H), 3.16-3.21 (q, J = 7.2 Hz, 1H), 3.34-3.39 (q, J = 7.2 Hz, 1H), 3.56-3.61 (q, J = 7.2 Hz, 1H), 3.74-3.79 (q, J = 7.2 Hz, 1H), 7.01-7.10 (m, 1H), 7.52-7.69 (m, 4H), 7.77-7.94 (m, 2H), 8.09-8.11 (m, 1H); MS m/z 406 (M + 1) |
| 254 | 1-((3-Fluoro-2-methylphenyl) amino)-N,N,5-trimethylisoquinolin-4-carboxamide | 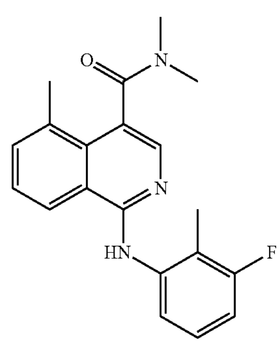 [SMILES: Cc1c(F)cccc1Nc1ncc(C(=O)N(C)C)c2c(C)cccc12] | ¹H NMR (400 MHz, CDCl₃) δ: 2.28 (s, 3H), 2.56 (s, 3H), 2.95 (s, 3H), 3.20 (s, 3H), 7.10-7.20 (m, 3H), 7.43-7.47 (m, 1H), 7.64-7.90 (m, 3H), 8.14-8.28 (m, 1H); MS m/z 338 (M + 1) |

TABLE-1a-continued

| E. No | Chemical name | Structure | ¹H NMR/Mass |
|---|---|---|---|
| 255 | 1-((3-Chloro-2-methylphenyl) amino)-N,N,5-trimethylisoquinolin-4-carboxamide | 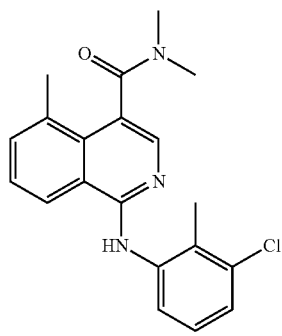 [SMILES: Cc1c(Cl)cccc1Nc1ncc(C(=O)N(C)C)c2c(C)cccc12] | ¹H NMR (400 MHz, CDCl$_3$) δ: 2.43 (s, 3H), 2.56 (s, 3H), 2.97 (s, 3H), 3.19 (s, 3H), 7.10-7.20 (m, 3H), 7.43-7.47 (m, 1H), 7.64-7.90 (m, 3H), 8.10-8.25 (m, 1H); MS m/z 352 (M + 1) |
| 256 | 1-((5-Fluoro-2-methylphenyl) amino)-N,N,5-trimethylisoquinolin-4-carboxamide | 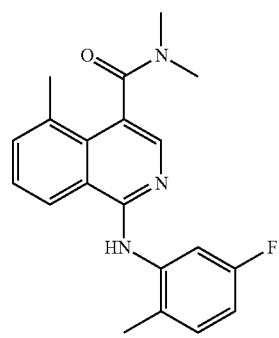 [SMILES: Cc1ccc(F)cc1Nc1ncc(C(=O)N(C)C)c2c(C)cccc12] | ¹H NMR (400 MHz, CDCl$_3$) δ: 2.34 (s, 3H), 2.57 (s, 3H), 2.93 (s, 3H), 3.19 (s, 3H), 6.76-6.81 (m, 1H), 7.18-7.22 (m, 1H), 7.49-7.73 (m, 4H), 7.90-7.92 (m, 2H); MS m/z 338 (M + 1). |
| 257 | 1-((2-Fluoro-3-(trifluoromethyl) phenyl)amino)-N,N,5-trimethyl isoquinolin-4-carboxamide | 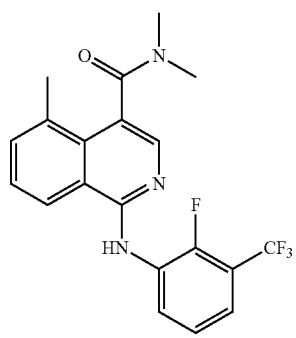 [SMILES: Cc1cccc2c(Nc3cccc(C(F)(F)F)c3F)ncc(C(=O)N(C)C)c12] | ¹H NMR (400 MHz, CDCl$_3$) δ: 2.57 (s, 3H), 2.93 (s, 3H), 3.19 (s, 3H), 7.22-7.26 (m, 1H), 7.31-7.78 (m, 6H), 8.31-8.36 (m, 1H); MS m/z 392 (M + 1). |
| 258 | 1-((3-Fluoro-2-(trifluoromethyl) phenyl)amino)-N,N,5-trimethyl isoquinolin-4-carboxamide | 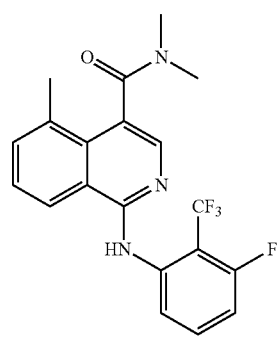 | ¹H NMR (400 MHz, CDCl$_3$) δ: 2.58 (s, 3H), 2.92 (s, 3H), 3.21 (s, 3H), 6.90-6.94 (m, 1H), 7.48-7.64 (m, 3H), 7.83-7.85 (m, 2H), 7.96-8.01 (m, 2H); MS m/z 392 (M + 1). |

TABLE-1a-continued

| E. No | Chemical name | Structure | ¹H NMR/Mass |
|---|---|---|---|
| 259 | N,N,5-Trimethyl-1-((2-methyl-3-(trifluoromethyl)phenyl)amino)isoquinolin-4-carboxamide | 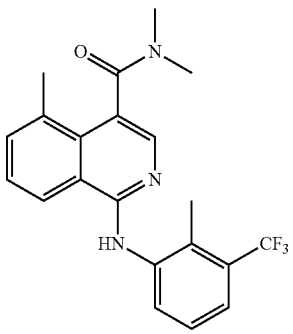 [SMILES: Cc1c(Nc2ncc(C(=O)N(C)C)c3c(C)cccc23)cccc1C(F)(F)F] | ¹H NMR (400 MHz, CDCl$_3$) δ: 2.44 (s, 3H), 2.57 (s, 3H), 2.93 (s, 3H), 3.20 (s, 3H), 7.32-7.36 (m, 2H), 7.50-7.58 (m, 3H), 7.81-7.90 (m, 3H); MS m/z 388 (M + 1). |
| 260 | 1-((2-Chloro-3-fluorophenyl)amino)-N,N,5-trimethylisoquinolin-4-carboxamide | 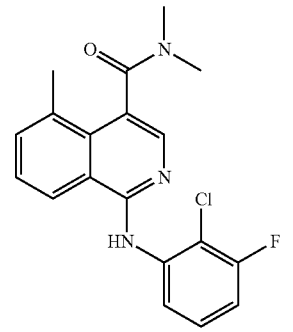 [SMILES: Cc1cccc2c(Nc3cccc(F)c3Cl)ncc(C(=O)N(C)C)c12] | ¹H NMR (400 MHz, CDCl$_3$) δ: 2.59 (s, 3H), 2.92 (s, 3H), 3.22 (s, 3H), 6.85-6.89 (m, 1H), 7.29-7.33 (m, 1H), 7.55-7.60 (m, 2H), 7.92-7.98 (m, 2H), 8.03 (s, 1H), 8.47-8.50 (m, 1H); MS m/z 358 (M + 1). |
| 261 | 1-((3-Chloro-4-fluorophenyl)amino)-N,N,5-trimethylisoquinolin-4-carboxamide | 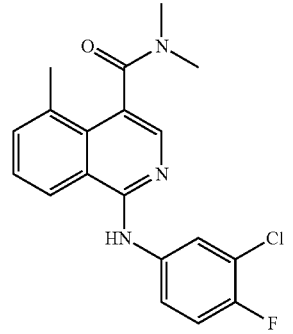 [SMILES: Cc1cccc2c(Nc3ccc(F)c(Cl)c3)ncc(C(=O)N(C)C)c12] | ¹H NMR (400 MHz, CDCl$_3$) δ: 2.55 (s, 3H), 2.92 (s, 3H), 3.21 (s, 3H), 7.12-7.25 (m, 2H), 7.43-7.53 (m, 3H), 7.83-7.87 (m, 2H), 7.93 (s, 1H); MS m/z 358 (M + 1). |
| 262 | 1-((3-Chloro-2-fluorophenyl)amino)-N,N,5-trimethylisoquinolin-4-carboxamide | 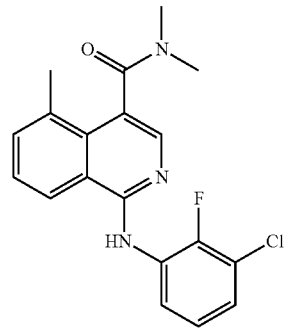 | MS m/z 358 (M + 1) |

TABLE-1a-continued

| E. No | Chemical name | Structure | ¹H NMR/Mass |
|---|---|---|---|
| 263 | 1-((2,3-Difluorophenyl)amino)-N,N,5-trimethylisoquinolin-4-carboxamide | 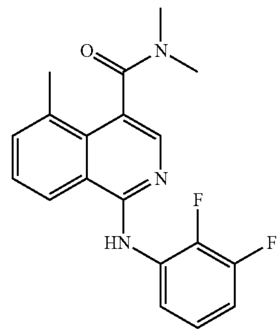 [SMILES: Cc1cccc2c(Nc3cccc(F)c3F)ncc(C(=O)N(C)C)c12] | MS m/z 342 (M + 1) |
| 264 | 1-((5-Chloro-2-fluorophenyl) amino)-N,N,5-trimethylisoquinolin-4-carboxamide | 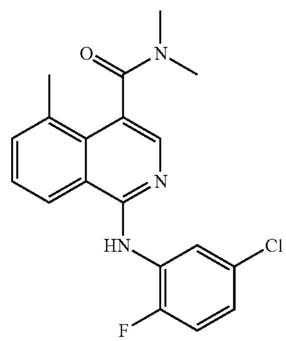 [SMILES: Cc1cccc2c(Nc3cc(Cl)ccc3F)ncc(C(=O)N(C)C)c12] | MS m/z 358 (M + 1) |
| 265 | 1-((2-Chloro-5-fluorophenyl) amino)-N,N,5-trimethylisoquinolin-4-carboxamide | 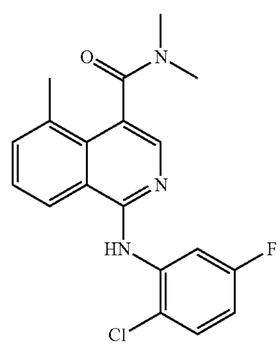 [SMILES: Cc1cccc2c(Nc3cc(F)ccc3Cl)ncc(C(=O)N(C)C)c12] | MS m/z 358 (M + 1) |
| 266 | 1-((2,3-Dimethylphenyl)amino)-N,N,5-trimethylisoquinolin-4-carboxamide | 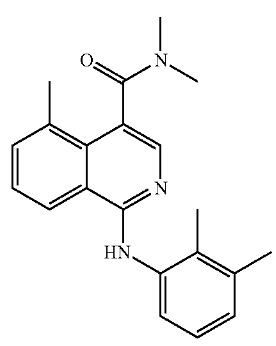 [SMILES: Cc1cccc(Nc2ncc(C(=O)N(C)C)c3c(C)cccc23)c1C] | MS m/z 334 (M + 1) |

TABLE-1a-continued

| E. No | Chemical name | Structure | $^1$H NMR/Mass |
|---|---|---|---|
| 267 | 1-((3,5-Difluorophenyl)amino)-N,N,5-trimethylisoquinolin-4-carboxamide | 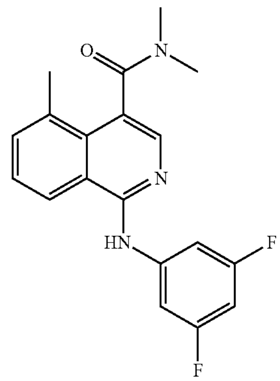 [SMILES: Cc1cccc2c(Nc3cc(F)cc(F)c3)ncc(C(=O)N(C)C)c12] | MS m/z 342 (M + 1) |
| 268 | 1-((3-Chlorophenyl)amino)-N,N,5-trimethylisoquinolin-4-carboxamide | 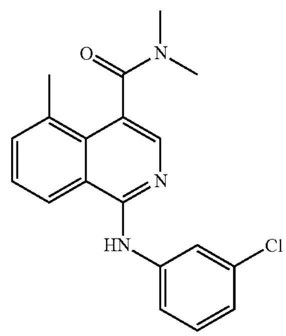 [SMILES: Cc1cccc2c(Nc3cccc(Cl)c3)ncc(C(=O)N(C)C)c12] | MS m/z 340 (M + 1) |
| 269 | N,N,5-Trimethyl-1-((3-(trifluoromethyl)phenyl)amino)isoquinolin-4-carboxamide | 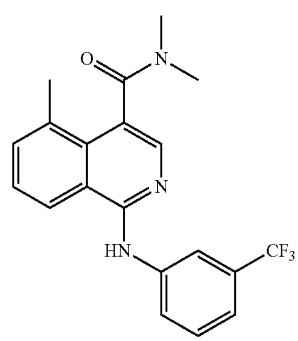 [SMILES: Cc1cccc2c(Nc3cccc(C(F)(F)F)c3)ncc(C(=O)N(C)C)c12] | MS m/z 374 (M + 1) |
| 270 | 1-((2,3-Dichlorophenyl)amino)-N,N,5-trimethylisoquinolin-4-carboxamide | 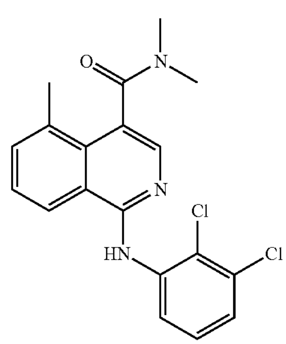 [SMILES: Cc1cccc2c(Nc3cccc(Cl)c3Cl)ncc(C(=O)N(C)C)c12] | MS m/z 374 (M + 1) |

TABLE-1a-continued

| E. No | Chemical name | Structure | ¹H NMR/Mass |
|---|---|---|---|
| 271 | 1-((5-Chloro-2-methylphenyl) amino)-N,N,5-trimethylisoquinolin-4-carboxamide | 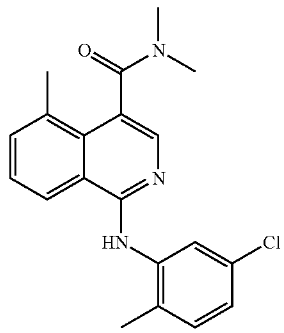 [SMILES: Cc1ccc(Cl)cc1Nc1ncc(C(=O)N(C)C)c2c(C)cccc12] | MS m/z 354 (M + 1) |
| 272 | 1-((4-Chloro-3-methylphenyl) amino)-N,N,5-trimethylisoquinolin-4-carboxamide | 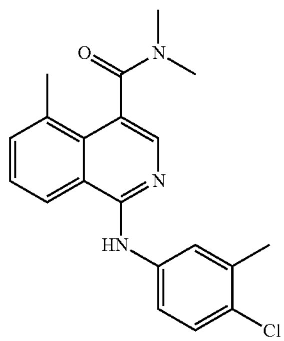 [SMILES: Cc1cc(Nc2ncc(C(=O)N(C)C)c3c(C)cccc23)ccc1Cl] | MS m/z 354 (M + 1) |
| 273 | 1-((2,5-Bis(trifluoromethyl) phenyl)amino)-N,N,5-trimethyl isoquinolin-4-carboxamide | 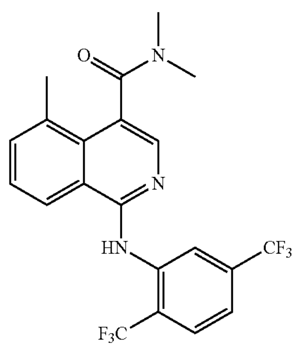 [SMILES: Cc1cccc2c(Nc3cc(C(F)(F)F)ccc3C(F)(F)F)ncc(C(=O)N(C)C)c12] | MS m/z 442 (M + 1) |
| 274 | 1-((2-Methoxy-5-(trifluoromethyl) phenyl)amino)-N,N,5-trimethyl isoquinolin-4-carboxamide | 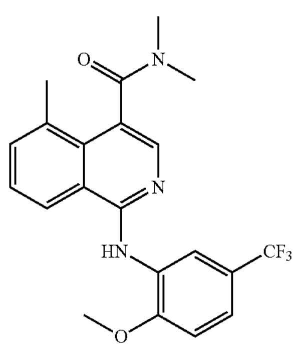 [SMILES: COc1ccc(C(F)(F)F)cc1Nc1ncc(C(=O)N(C)C)c2c(C)cccc12] | MS m/z 404 (M + 1) |

TABLE-1a-continued

| E. No | Chemical name | Structure | ¹H NMR/Mass |
|---|---|---|---|
| 275 | N,N-Diethyl-1-((3-fluoro-2-methyl phenyl)amino)-5-methylisoquinolin-4-carboxamide | 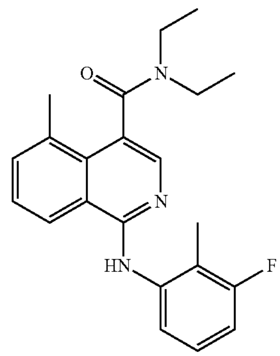 [SMILES: CCN(CC)C(=O)c1cnc(Nc2cccc(F)c2C)c2cccc(C)c12] | ¹H NMR (400 MHz, CDCl$_3$) δ: 1.09-1.12 (t, J = 6.8 Hz, 3H), 1.29-1.33 (t, J = 6.8 Hz, 3H), 2.06 (s, 3H), 2.63 (s, 3H), 3.17-3.22 (q, J = 6.8 Hz, 1H), 3.29-3.35 (q, J = 6.8 Hz, 1H), 3.41-3.46 (q, J = 6.8 Hz, 1H), 3.85-3.90 (q, J = 6.8 Hz, 1H), 6.68-6.98 (m, 2H), 7.20-7.27 (m, 1H), 7.51-7.53 (m, 3H), 7.87-7.95 (m, 2H); MS m/z 366 (M + 1). |
| 276 | 1-((3-Chloro-2-methylphenyl) amino)-N,N-diethyl-5-methyl-isoquinolin-4-carboxamide | 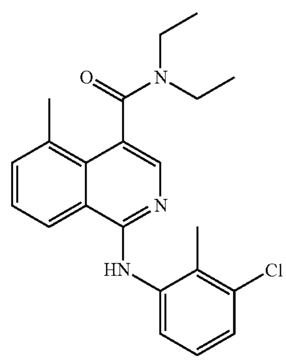 [SMILES: CCN(CC)C(=O)c1cnc(Nc2cccc(Cl)c2C)c2cccc(C)c12] | ¹H NMR (400 MHz, CDCl$_3$) δ: 1.08-1.12 (t, J = 7.2 Hz, 3H), 1.29-1.32 (t, J = 7.2 Hz, 3H), 2.38 (s, 3H), 2.62 (s, 3H), 3.17-3.22 (q, J = 7.2 Hz, 1H), 3.29-3.32 (q, J = 7.2 Hz, 1H), 3.40-3.46 (q, J = 7.2 Hz, 1H), 3.84-3.89 (q, J = 7.2 Hz, 1H), 7.01-7.25 (m, 3H), 7.48-7.55 (m, 3H), 7.87-7.91 (m, 2H); MS m/z 382 (M + 1) |
| 277 | N,N-Diethyl-1-((2-fluoro-3-(trifluoro methyl)phenyl)amino)-5-methyl isoquinolin-4-carboxamide | 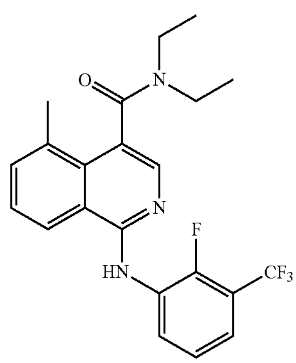 [SMILES: CCN(CC)C(=O)c1cnc(Nc2cccc(C(F)(F)F)c2F)c2cccc(C)c12] | ¹H NMR (400 MHz, CDCl$_3$) δ: 1.10-1.14 (t, J = 7.2 Hz, 3H), 1.31-1.34 (t, J = 7.2 Hz, 3H), 2.64 (s, 3H), 3.17-3.32 (m, 2H), 3.41-3.46 (q, J = 7.2 Hz, 1H), 3.86-3.91 (q, J = 7.2 Hz, 1H), 7.23-7.31 (m, 2H), 7.53-7.59 (m, 3H), 7.92-7.99 (m, 2H), 8.74 (s, 1H); MS m/z 420 (M + 1) |
| 278 | N,N-Diethyl-1-((3-fluoro-2-(trifluoro methyl)phenyl)amino)-5-methyl isoquinolin-4-carboxamide | 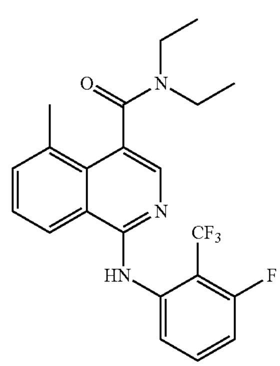 [SMILES: CCN(CC)C(=O)c1cnc(Nc2cccc(F)c2C(F)(F)F)c2cccc(C)c12] | ¹H NMR (400 MHz, CDCl$_3$) δ: 1.10-1.13 (t, J = 7.2 Hz, 3H), 1.30-1.34 (t, J = 7.2 Hz, 3H), 2.63 (s, 3H), 3.17-3.22 (q, J = 7.2 Hz, 1H), 3.28-3.33 (q, J = 7.2 Hz, 1H), 3.41-3.46 (q, J = 7.2 Hz, 1H), 3.87-3.92 (q, J = 7.2 Hz, 1H), 6.08-6.91 (m, 1H), 7.47-7.58 (m, 3H), 7.71-7.84 (m, 2H), 7.98 (s, 1H), 8.03-8.06 (m, 1H); MS m/z 420 (M + 1) |

| E. No | Chemical name | Structure | $^1$H NMR/Mass |
|---|---|---|---|
| 279 | N,N-Diethyl-5-methyl-1-((2-methyl-3-(trifluoromethyl)phenyl)amino) isoquinolin-4-carboxamide | 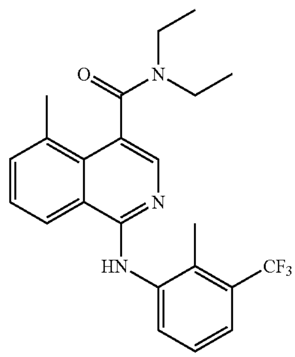 [SMILES: CCN(CC)C(=O)c1cnc(Nc2cccc(C(F)(F)F)c2C)c2cccc(C)c12] | $^1$H NMR (400 MHz, CDCl$_3$) δ: 1.11-1.14 (t, J = 7.2 Hz, 3H), 1.29-1.33 (t, J = 7.2 Hz, 3H), 2.47 (s, 3H), 2.63 (s, 3H), 3.17-3.22 (q, J = 7.2 Hz, 1H), 3.29-3.34 (q, J = 7.2 Hz, 1H), 3.42-3.47 (q, J = 7.2 Hz, 1H), 3.81-3.84 (q, J = 7.2 Hz, 1H), 7.32-7.36 (m, 1H), 7.40-7.73 (m, 4H), 7.83-7.85 (m, 2H), 8.10-8.20 (m, 1H); MS m/z 416 (M + 1) |
| 280 | 1-((2-Chloro-3-fluorophenyl) amino)-N,N-diethyl-5-methyl-isoquinolin-4-carboxamide | 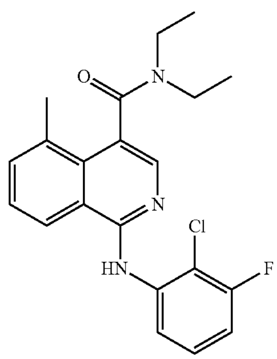 [SMILES: CCN(CC)C(=O)c1cnc(Nc2cccc(F)c2Cl)c2cccc(C)c12] | $^1$H NMR (400 MHz, CDCl$_3$) δ: 1.11-1.14 (t, J = 7.2 Hz, 3H), 1.31-1.34 (t, J = 7.2 Hz, 3H), 2.64 (s, 3H), 3.18-3.32 (m, 2H), 3.43-3.48 (q, J = 7.2 Hz, 1H), 3.84-3.90 (q, J = 7.2 Hz, 1H), 6.93-6.95 (m, 1H), 7.27-7.32 (m, 2H), 7.53-7.61 (m, 3H), 7.96-7.98 (m, 2H); MS m/z 386 (M + 1). |
| 281 | 1-((3-Chloro-4-fluorophenyl) amino)-N,N-diethyl-5-methyl isoquinolin-4-carboxamide | 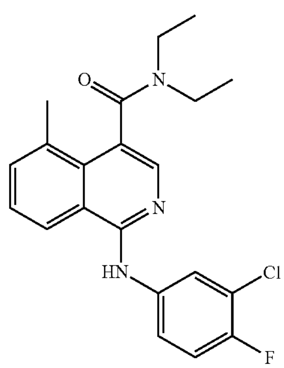 [SMILES: CCN(CC)C(=O)c1cnc(Nc2ccc(F)c(Cl)c2)c2cccc(C)c12] | $^1$H NMR (400 MHz, CDCl$_3$) δ: 1.12-1.15 (t, J = 7.2 Hz, 3H), 1.29-1.33 (t, J = 7.2 Hz, 3H), 2.63 (s, 3H), 3.20-3.31 (m, 2H), 3.42-3.47 (q, J = 7.2 Hz, 1H), 3.80-3.87 (q, J = 7.2 Hz, 1H), 7.01-7.32 (m, 3H), 7.50-7.75 (m, 4H), 8.10 (s, 1H); MS m/z 386 (M + 1). |
| 282 | 1-((3-Chloro-2-fluorophenyl) amino)-N,N-diethyl-5-methyl isoquinolin-4-carboxamide | 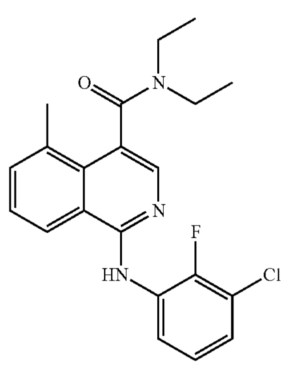 [SMILES: CCN(CC)C(=O)c1cnc(Nc2cccc(Cl)c2F)c2cccc(C)c12] | MS m/z 386 (M + 1) |

| E. No | Chemical name | Structure | ¹H NMR/Mass |
|---|---|---|---|
| 283 | 1-((2,3-Difluorophenyl)amino)-N,N-diethyl-5-methylisoquinolin-4-carboxamide | 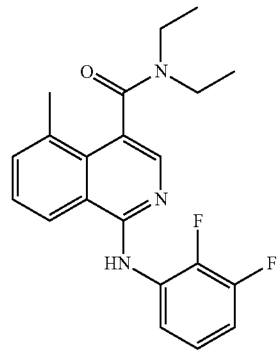 [SMILES: CCN(CC)C(=O)c1cnc(Nc2cccc(F)c2F)c2cccc(C)c12] | MS m/z 370 (M + 1) |
| 284 | 1-((5-Chloro-2-fluorophenyl) amino)-N,N-diethyl-5-methyl isoquinolin-4-carboxamide | 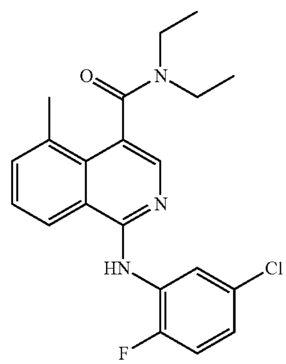 [SMILES: CCN(CC)C(=O)c1cnc(Nc2cc(Cl)ccc2F)c2cccc(C)c12] | MS m/z 386 (M + 1) |
| 285 | 1-((2-Chloro-5-fluorophenyl) amino)-N,N-diethyl-5-methyl isoquinolin-4-carboxamide | 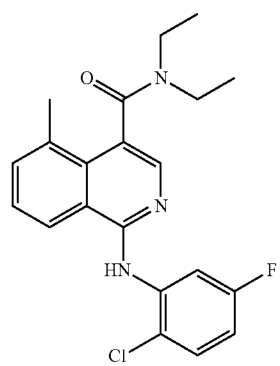 [SMILES: CCN(CC)C(=O)c1cnc(Nc2cc(F)ccc2Cl)c2cccc(C)c12] | MS m/z 386 (M + 1) |
| 286 | 1-((2,3-Dimethylphenyl)amino)-N,N-diethyl-5-methylisoquinolin-4-carboxamide | 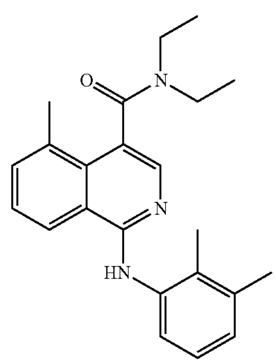 [SMILES: CCN(CC)C(=O)c1cnc(Nc2cccc(C)c2C)c2cccc(C)c12] | MS m/z 362 (M + 1) |

TABLE-1a-continued

| E. No | Chemical name | Structure | ¹H NMR/Mass |
|---|---|---|---|
| 287 | 1-((3,5-Difluorophenyl)amino)-N,N-diethyl-5-methylisoquinolin-4-carboxamide | 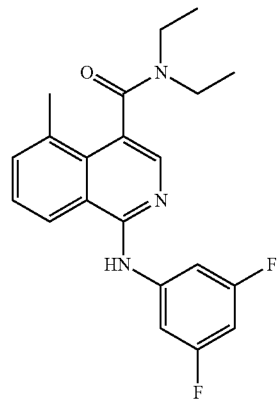 [SMILES: CCN(CC)C(=O)c1cnc(Nc2cc(F)cc(F)c2)c2cccc(C)c12] | MS m/z 370 (M + 1) |
| 288 | 1-((3-Chlorophenyl)amino)-N,N-diethyl-5-methylisoquinolin-4-carboxamide | 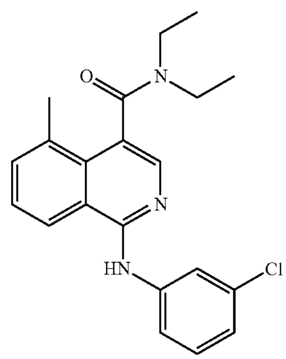 [SMILES: CCN(CC)C(=O)c1cnc(Nc2cccc(Cl)c2)c2cccc(C)c12] | MS m/z 368 (M + 1) |
| 289 | N,N-Diethyl-5-methyl-1-((3-(trifluoromethyl)phenyl)amino) isoquinolin-4-carboxamide | 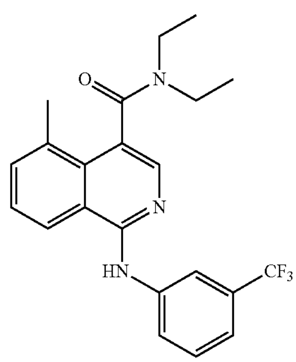 [SMILES: CCN(CC)C(=O)c1cnc(Nc2cccc(C(F)(F)F)c2)c2cccc(C)c12] | MS m/z 402 (M + 1) |
| 290 | N-Ethyl-1-((3-fluoro-2-methyl phenyl)amino)-N,5-dimethyl-isoquinolin-4-carboxamide | 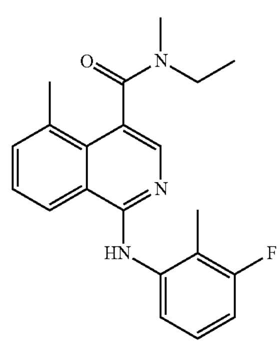 [SMILES: CCN(C)C(=O)c1cnc(Nc2cccc(F)c2C)c2cccc(C)c12] | ¹H NMR (400 MHz, CDCl₃) δ (as mixture of rotamers): 1.11-1.14 (t, J = 7.2 Hz, 3H), 1.28-1.32 (t, J = 7.2 Hz, 3H), 2.22 (s, 3H), 2.60 (s, 3H), 2.89 (s, 3H), 3.14 (s, 3H), 3.16-3.21 (q, J = 7.2 Hz, 1H), 3.34-3.39 (q, J = 7.2 Hz, 1H), 3.56-3.61 (q, J = 7.2 Hz, 1H), 3.74-3.79 (q, J = 7.2 Hz, 1H), 6.80-7.0 (m, 1H), 7.18-7.40 (m, 2H), 7.48-7.80 (m, 3H), 7.90-8.10 (m, 2H); MS m/z 352 (M + 1) |

TABLE-1a-continued

| E. No | Chemical name | Structure | $^1$H NMR/Mass |
|---|---|---|---|
| 291 | 1-((3-Chloro-2-methylphenyl) amino)-N-ethyl-N,5-dimethyl isoquinolin-4-carboxamide | 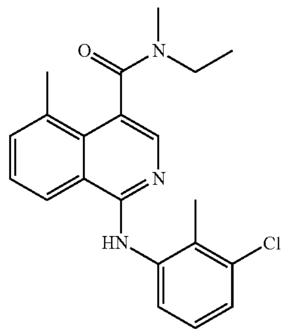 [SMILES: CCN(C)C(=O)c1cnc(Nc2cccc(Cl)c2C)c2cccc(C)c12] | $^1$H NMR (400 MHz, CDCl$_3$) δ (as mixture of rotamers): 1.11-1.14 (t, J = 7.2 Hz, 3H), 1.28-1.32 (t, J = 7.2 Hz, 3H), 2.45 (s, 3H), 2.60 (s, 3H), 2.91 (s, 3H), 3.14 (s, 3H), 3.16-3.21 (q, J = 7.2 Hz, 1H), 3.34-3.39 (q, J = 7.2 Hz, 1H), 3.56-3.61 (q, J = 7.2 Hz, 1H), 3.74-3.79 (q, J = 7.2 Hz, 1H), 7.01-7.10 (m, 1H), 7.52-7.69 (m, 4H), 7.77-7.94 (m, 2H), 8.09-8.11 (m, 1H); MS m/z 368 (M + 1) |
| 292 | N-Ethyl-1-((2-fluoro-3-(trifluoro methyl)phenyl)amino)-N,5-dimethyl isoquinolin-4-carboxamide | 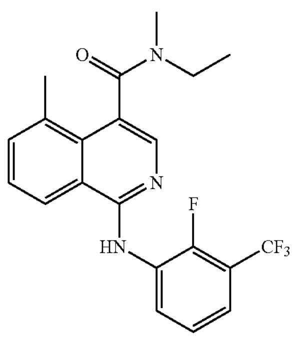 [SMILES: CCN(C)C(=O)c1cnc(Nc2cccc(C(F)(F)F)c2F)c2cccc(C)c12] | $^1$H NMR (400 MHz, CDCl$_3$) δ (as mixture of rotamers): 1.12-1.15 (t, J = 7.2 Hz, 3H), 1.28-1.32 (t, J = 7.2 Hz, 3H), 2.61 (s, 3H), 2.90 (s, 3H), 3.09-3.14 (q, J = 7.2 Hz, 1H), 3.16 (s, 3H), 3.32-3.38 (q, J = 7.2 Hz, 1H), 3.58-3.63 (q, J = 7.2 Hz, 1H), 3.74-3.79 (q, J = 7.2 Hz, 1H), 7.22-7.30 (m, 1H), 7.46-7.70 (m, 3H), 7.90-8.09 (m, 3H), 8.55-8.64 (m, 1H); MS m/z 406 (M + 1) |
| 293 | N-Ethyl-N,5-dimethyl-1-((2-methyl-3-(trifluoromethyl)phenyl) amino) isoquinolin-4-carboxamide | 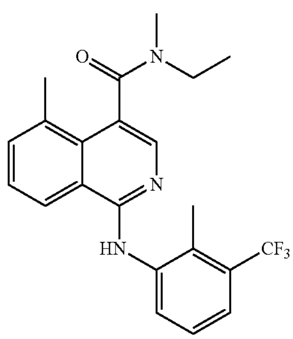 [SMILES: CCN(C)C(=O)c1cnc(Nc2cccc(C(F)(F)F)c2C)c2cccc(C)c12] | $^1$H NMR (400 MHz, CDCl$_3$) δ (as mixture of rotamers): 1.12-1.15 (t, J = 7.2 Hz, 3H), 1.28-1.32 (t, J = 7.2 Hz, 3H), 2.49 (s, 3H), 2.60 (s, 3H), 2.93 (s, 3H), 3.16 (s, 3H), 3.16-3.21 (q, J = 7.2 Hz, 1H), 3.34-3.39 (q, J = 7.2 Hz, 1H), 3.56-3.61 (q, J = 7.2 Hz, 1H), 3.74-3.79 (q, J = 7.2 Hz, 1H), 7.31-7.48 (m, 3H), 7.51-7.75 (m, 4H), 7.85-7.87 (m, 1H); MS m/z 402 (M + 1) |
| 294 | 1-((2-Chloro-3-fluorophenyl) amino)-N-ethyl-N,5-dimethyl isoquinolin-4-carboxamide | 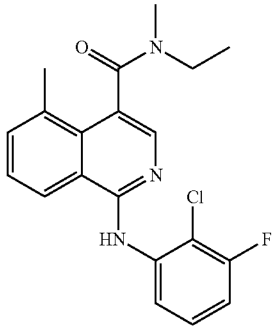 [SMILES: CCN(C)C(=O)c1cnc(Nc2cccc(F)c2Cl)c2cccc(C)c12] | MS m/z 372 (M + 1) |

TABLE-1a-continued

| E. No | Chemical name | Structure | ¹H NMR/Mass |
|---|---|---|---|
| 295 | 1-((3-Chloro-2-fluorophenyl) amino)-N-ethyl-N,5-dimethyl isoquinolin-4-carboxamide | 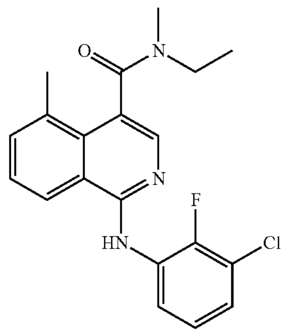 [SMILES: CCN(C)C(=O)c1cnc(Nc2cccc(Cl)c2F)c2cccc(C)c12] | MS m/z 372 (M + 1) |
| 296 | 1-((2,3-Difluorophenyl)amino)-N-ethyl-N,5-dimethylisoquinolin-4-carboxamide | 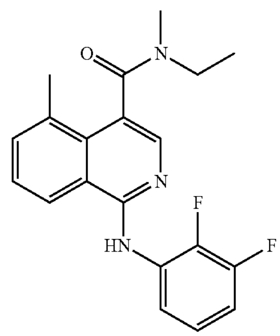 [SMILES: CCN(C)C(=O)c1cnc(Nc2cccc(F)c2F)c2cccc(C)c12] | MS m/z 356 (M + 1) |
| 297 | 1-((3-Chloro-4-fluorophenyl) amino)-N-ethyl-N,5-dimethyl isoquinolin-4-carboxamide | 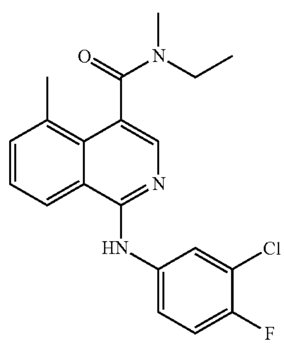 [SMILES: CCN(C)C(=O)c1cnc(Nc2ccc(F)c(Cl)c2)c2cccc(C)c12] | MS m/z 372 (M + 1) |
| 298 | 1-((5-Chloro-2-fluorophenyl) amino)-N-ethyl-N,5-dimethyl isoquinolin-4-carboxamide | 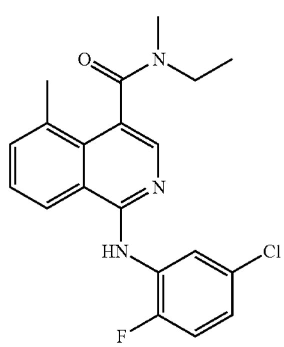 [SMILES: CCN(C)C(=O)c1cnc(Nc2cc(Cl)ccc2F)c2cccc(C)c12] | MS m/z 372 (M + 1) |

| E. No | Chemical name | Structure | $^1$H NMR/Mass |
|---|---|---|---|
| 299 | 1-((2-Chloro-5-fluorophenyl) amino)-N-ethyl-N,5-dimethyl isoquinolin-4-carboxamide | 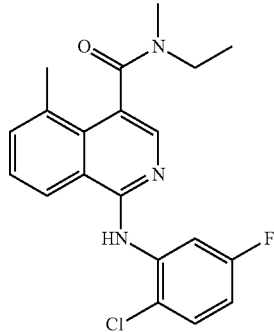 [SMILES: CCN(C)C(=O)c1cnc(Nc2cc(F)ccc2Cl)c2cccc(C)c12] | MS m/z 372 (M + 1) |
| 300 | 1-((3,5-Difluorophenyl)amino)-N-ethyl-N,5-dimethylisoquinolin-4-carboxamide | 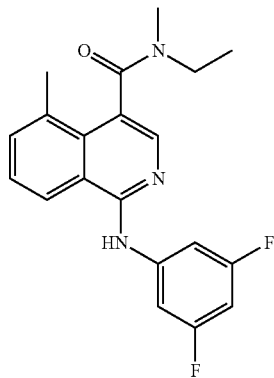 [SMILES: CCN(C)C(=O)c1cnc(Nc2cc(F)cc(F)c2)c2cccc(C)c12] | MS m/z 356 (M + 1) |
| 301 | 1-((3-Chlorophenyl)amino)-N-ethyl-N,5-dimethylisoquinolin-4-carboxamide | 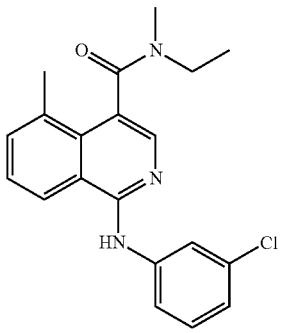 [SMILES: CCN(C)C(=O)c1cnc(Nc2cccc(Cl)c2)c2cccc(C)c12] | MS m/z 354 (M + 1) |
| 302 | N-ethyl-N,5-dimethyl-1-((3-(trifluoromethyl)phenyl)amino) isoquinolin-4-carboxamide | 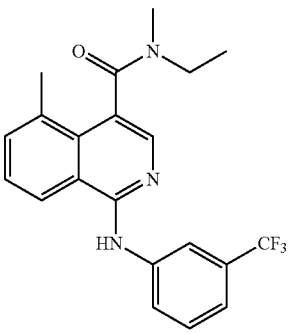 [SMILES: CCN(C)C(=O)c1cnc(Nc2cccc(C(F)(F)F)c2)c2cccc(C)c12] | MS m/z 388 (M + 1) |

TABLE-1a-continued

| E. No | Chemical name | Structure | $^1$H NMR/Mass |
|---|---|---|---|
| 303 | 1-((3-Fluoro-2-methylphenyl) amino)-5-methyl-N,5-dipropyl isoquinolin-4-carboxamide | 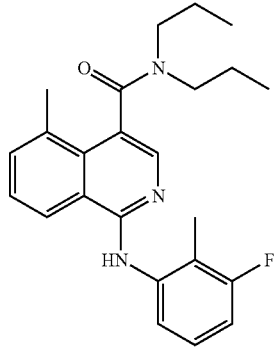 [SMILES: CCCN(CCC)C(=O)c1cnc(Nc2cccc(F)c2C)c2cccc(C)c12] | MS m/z 394 (M + 1) |
| 304 | 1-((3-Chloro-2-methylphenyl) amino)-5-methyl-N,N-dipropyl isoquinolin-4-carboxamide | 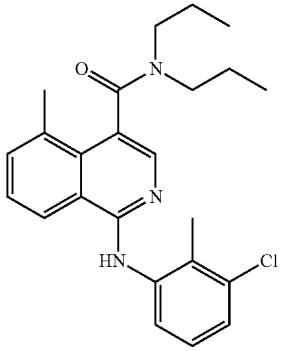 [SMILES: CCCN(CCC)C(=O)c1cnc(Nc2cccc(Cl)c2C)c2cccc(C)c12] | MS m/z 410 (M + 1) |
| 305 | 1-((2-Fluoro-3-(trifluoromethyl)phenyl)amino)-5-methyl-N,N-dipropylisoquinolin-4-carboxamide | 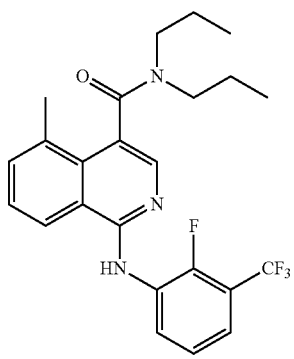 [SMILES: CCCN(CCC)C(=O)c1cnc(Nc2cccc(C(F)(F)F)c2F)c2cccc(C)c12] | MS m/z 448 (M + 1) |
| 306 | 1-((3-Fluoro-2-(trifluoromethyl)phenyl)amino)-5-methyl-N,N-dipropylisoquinolin-4-carboxamide | 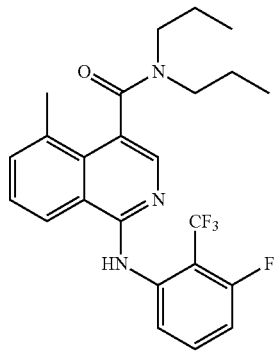 [SMILES: CCCN(CCC)C(=O)c1cnc(Nc2cccc(F)c2C(F)(F)F)c2cccc(C)c12] | MS m/z 448 (M + 1) |

TABLE-1a-continued

| E. No | Chemical name | Structure | ¹H NMR/Mass |
|---|---|---|---|
| 307 | 5-Methyl-1-((2-methyl-3-(trifluoromethyl)phenyl)amino)-N,N-dipropylisoquinolin-4-carboxamide | 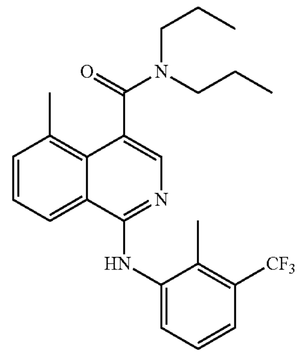 [SMILES: CCCN(CCC)C(=O)c1cnc(Nc2cccc(C(F)(F)F)c2C)c2cccc(C)c12] | MS m/z 444 (M + 1) |
| 308 | 1-((2-Chloro-3-fluorophenyl) amino)-5-methyl-N,N-dipropyl isoquinolin-4-carboxamide | 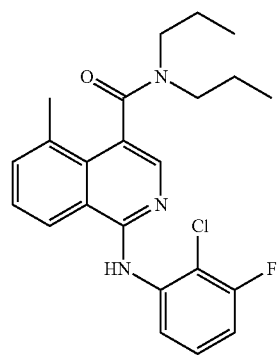 [SMILES: CCCN(CCC)C(=O)c1cnc(Nc2cccc(F)c2Cl)c2cccc(C)c12] | MS m/z 414 (M + 1) |
| 309 | N-Ethyl-1-((3-fluoro-2-methyl phenyl)amino)-5-methyl-N-propyl isoquinolin-4-carboxamide | 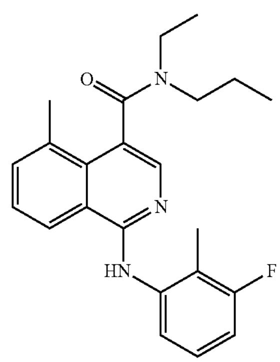 [SMILES: CCCN(CC)C(=O)c1cnc(Nc2cccc(F)c2C)c2cccc(C)c12] | MS m/z 380 (M + 1) |
| 310 | 1-((3-Chloro-2-methylphenyl) amino)-N-ethyl-5-methyl-N-propyl isoquinolin-4-carboxamide | 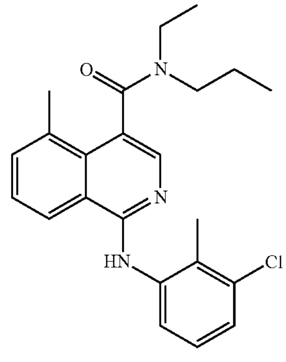 [SMILES: CCCN(CC)C(=O)c1cnc(Nc2cccc(Cl)c2C)c2cccc(C)c12] | MS m/z 396 (M + 1) |

TABLE-1a-continued

| E. No | Chemical name | Structure | ¹H NMR/Mass |
|---|---|---|---|
| 311 | N-Ethyl-1-((5-fluoro-2-methyl phenyl)amino)-5-methyl-N-propyl isoquinolin-4-carboxamide | 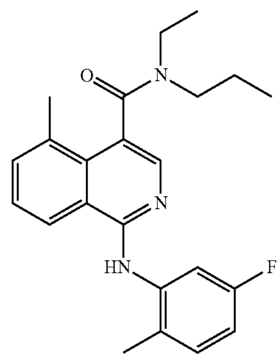 [SMILES: CCCN(CC)C(=O)c1cnc(Nc2cc(F)ccc2C)c2cccc(C)c12] | MS m/z 380 (M + 1) |
| 317 | 5-Chloro-1-((2-chloro-3-(trifluoro methyl)phenyl)amino)-N,N-di methylisoquinolin-4-carboxamide | 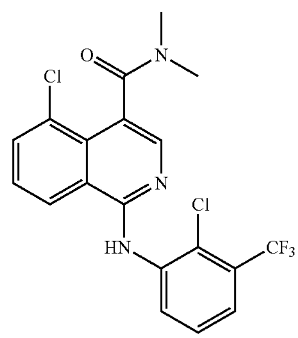 [SMILES: CN(C)C(=O)c1cnc(Nc2cccc(C(F)(F)F)c2Cl)c2cccc(Cl)c12] | ¹H NMR (400 MHz, CDCl₃) δ 2.90 (s, 3H), 3.19 (s, 3H), 7.44-7.46 (d, 2H), 7.60-7.64 (t, 1H), 7.85-7.87 (d, 1H), 8.06-8.08 (m, 2H), 8.23 (s, 1H); MS m/z 429 (M + 1). |
| 318 | 5-Chloro-1-((2-chloro-3-fluoro phenyl)amino)-N,N-dimethyl isoquinolin-4-carboxamide | 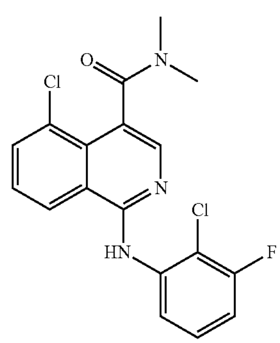 [SMILES: CN(C)C(=O)c1cnc(Nc2cccc(F)c2Cl)c2cccc(Cl)c12] | ¹H NMR (400 MHz, CDCl₃) δ 2.90 (s, 3H), 3.18 (s, 3H), 6.96 (m, 1H), 7.29-7.31 (m, 2H), 7.59-7.63 (t, 1H), 7.87-7.88 (m, 1H), 7.99 (s, 1H), 8.17-8.19 (m, 2H); MS m/z 380 (M + 1). |
| 319 | 5-Chloro-1-((2,3-dimethylphenyl)amino)-N,N-dimethylisoquinolin-4-carboxamide | 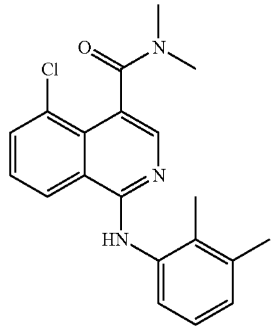 [SMILES: Cc1cccc(Nc2ncc(C(=O)N(C)C)c3c(Cl)cccc23)c1C] | ¹H NMR (400 MHz, CDCl₃) δ 2.20 (s, 3H), 2.36 (s, 3H), 2.90 (s, 3H), 3.20 (s, 3H), 7.12-7.15 (m, 2H), 7.24-7.27 (m, 1H), 7.48-7.52 (t, 1H), 7.79-7.80 (m, 1H), 7.81-7.82 (m, 1H), 7.87 (s, 1H); MS m/z 354 (M + 1). |

TABLE-1a-continued

| E. No | Chemical name | Structure | ¹H NMR/Mass |
|---|---|---|---|
| 320 | 5-Chloro-1-((2,3-dimethylphenyl)amino)-N-ethyl-N-methyl isoquinolin-4-carboxamide | 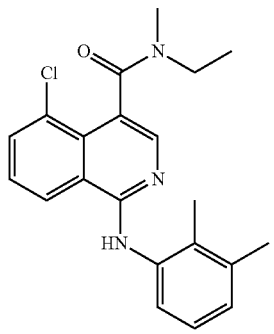 [SMILES: CCN(C)C(=O)c1cnc(Nc2cccc(C)c2C)c2cccc(Cl)c12] | ¹H NMR (400 MHz, CDCl₃) δ (as mixture of rotamers): 1.10-1.17 (m, 3H), 1.26-1.44 (m, 3H), 2.20 (s, 3H), 2.36 (s, 3H), 2.88 (s, 2H), 3.13 (s, 2H), 3.17-3.19 (m, 1H), 3.33-3.38 (m, 1H), 3.54-3.59 (m, 1H), 3.72-3.77 (m, 1H), 7.01-7.17 (m, 3H), 7.22-7.24 (m, 1H), 7.47-7.57 (m, 2H), 7.79-7.86 (m, 3H), 8.04 (s, 2H; MS m/z 368 (M + 1). |
| 321 | 5-Chloro-1-((3-chloro-2-fluoro phenyl)amino)-N,N-diethyl isoquinisoline-4-carboxamide | 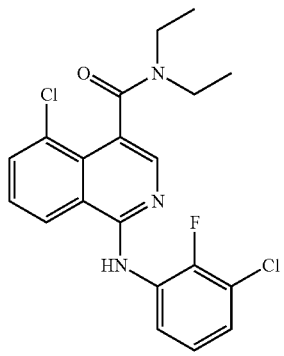 [SMILES: CCN(CC)C(=O)c1cnc(Nc2cccc(Cl)c2F)c2cccc(Cl)c12] | ¹H NMR (400 MHz, CDCl₃) δ (as mixture of rotamers): 1.09-1.12 (t, 3H), 1.30-1.34 (t, 3H), 3.18-3.31 (m, 2H), 3.42-3.51 (m, 1H), 3.81-3.86 (m, 1H), 7.08-7.16 (m, 2H), 7.49 (s, 1H), 7.55-7.59 (t, 1H), 7.80-7.82 (dd, 1H), 7.97-7.99 (dd, 1H), 8.06 (s, 1H), 8.38-8.42 (m, 1H); MS m/z 406 (M + 1). |
| 322 | 5-Chloro-1-((3-chloro-2-methyl phenyl)amino)-N,N-diethyl isoquinolin-4-carboxamide | 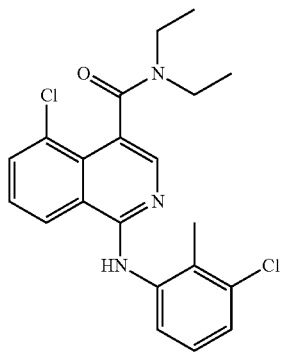 [SMILES: CCN(CC)C(=O)c1cnc(Nc2cccc(Cl)c2C)c2cccc(Cl)c12] | ¹H NMR (400 MHz, CDCl₃) δ (as mixture of rotamers): 1.07-1.09 (t, 3H), 1.36-1.34 (t, 3H), 2.35 (s, 3H), 3.18-3.32 (m, 2H), 3.41-3.46 (m, 1H), 3.81-3.84 (m, 1H), 7.05 (s, 1H), 7.16-7.20 (t, 1H), 7.25-7.26 (d, 1H), 7.48-7.54 (m, 2H), 7.77-7.79 (dd, 1H), 7.95-7.97 (m, 2H); MS m/z 402 (M + 1). |
| 323 | 5-Chloro-N-N-diethyl-1-((3-fluoro-2-methylphenyl)amino) isoquinolin-4-carboxamide | 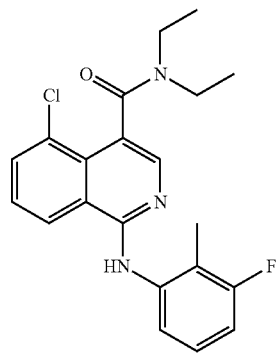 [SMILES: CCN(CC)C(=O)c1cnc(Nc2cccc(F)c2C)c2cccc(Cl)c12] | ¹H NMR (400 MHz, CDCl₃) δ (as mixture of rotamers): 1.08-1.11 (t, 3H), 1.26-1.32 (t, 3H), 2.24 (s, 3H), 3.19-3.32 (m, 2H), 3.42-3.50 (m, 1H), 3.81-3.85 (m, 1H), 6.90-6.94 (t, 1H), 7.19-7.25 (m, 1H), 7.45-7.48 (m, 1H), 7.51-7.55 (t, 1H), 7.79-7.81 (dd, 1H), 7.94-7.96 (d, 1H), 7.99 (s, 1H); MS m/z 386 (M + 1). |

TABLE-1a-continued

| E. No | Chemical name | Structure | ¹H NMR/Mass |
|---|---|---|---|
| 324 | 5-Chloro-N,N-diethyl-1-((3-fluoro-2-(trifluoromethyl)phenyl)amino) isoquinolin-4-carboxamide | 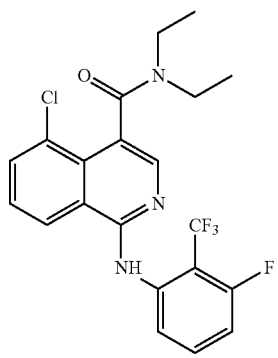 [SMILES: CCN(CC)C(=O)c1cnc(Nc2cccc(F)c2C(F)(F)F)c2cccc(Cl)c12] | ¹H NMR (400 MHz, CDCl₃) δ (as mixture of rotamers): 1.09-1.13 (t, 3H), 1.29-1.33 (t, 3H), 3.19-3.29 (m, 2H), 3.43-3.50 (m, 1H), 3.81-3.86 (m, 1H), 6.96-7.00 (t, 1H), 7.50-7.59 (m, 2H), 7.83-7.85 (d, 1H), 7.89-7.97 (m, 3H); MS m/z 440 (M + 1). |
| 325 | 5-Chloro-N-N-diethyl-1-((2-methyl-3-(trifluoromethyl)phenyl)amino) isoquinolin-4-carboxamide | 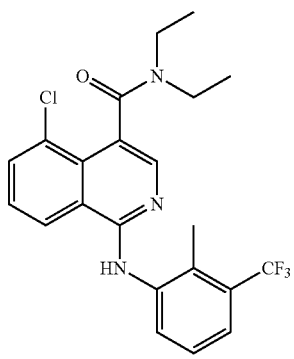 [SMILES: CCN(CC)C(=O)c1cnc(Nc2cccc(C(F)(F)F)c2C)c2cccc(Cl)c12] | ¹H NMR (400 MHz, CDCl₃) δ (as mixture of rotamers): 1.09-1.12 (t, 3H), 1.26-1.34 (t, 3H), 2.44 (s, 3H), 3.19-3.32 (m, 2H), 3.42-3.49 (m, 1H), 3.80-3.85 (m, 1H), 7.33-7.37 (t, 1H), 7.51-7.56 (m, 2H), 7.47 (m, 1H), 7.83-7.83 (d, 1H, J = 7.6 Hz), 7.91 (s, 1H), 7.97-7.99 (d, 1H, J = 8.4 Hz), MS m/z 436 (M + 1). |
| 326 | 5-Chloro-1-((2,3-dichlorophenyl)amino)-N,N-diethylisoquinolin-4-carboxamide | 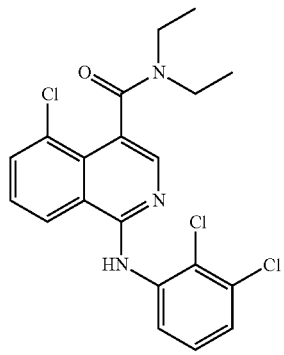 [SMILES: CCN(CC)C(=O)c1cnc(Nc2cccc(Cl)c2Cl)c2cccc(Cl)c12] | ¹H NMR (400 MHz, CDCl₃) δ (as mixture of rotamers): 1.09-1.12 (t, 3H), 1.25-1.34 (t, 3H), 3.19-3.30 (m, 2H), 3.42-3.50 (m, 1H), 3.81-3.88 (m, 1H), 7.19-7.21 (dd, 1H), 7.26-7.30 (m, 1H), 7.58-7.62 (t, 1H, J = 8.4 Hz), 7.82-7.84 (dd, 1H), 8.03-8.06 (m, 3H), 8.51-8.53 (d, 1H); MS m/z 422 (M + 1). |
| 327 | 5-Chloro-N,N-diethyl-1-((2,3,6-trifluorophenyl)amino) isoquinolin-4-carboxamide | 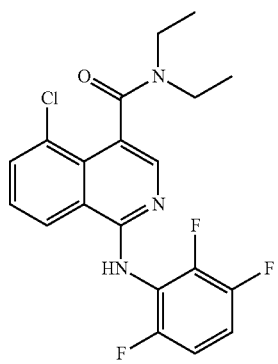 [SMILES: CCN(CC)C(=O)c1cnc(Nc2c(F)ccc(F)c2F)c2cccc(Cl)c12] | ¹H NMR (400 MHz, CDCl₃) δ (as mixture of rotamers): 1.07-1.11 (t, 3H), 1.22-1.34 (t, 3H), 3.18-3.30 (m, 1H), 3.44-3.51 (m, 1H), 3.77-3.84 (m, 1H), 6.88 (s, 1H), 6.94-6.98 (m, 1H), 7.01-7.04 (m, 1H), 7.53-7.57 (t, 1H, J = 8.0 Hz), 7.78-7.80 (dd, 1H), 7.97 (s, 1H), 8.06-8.08 (dd, 1H); MS m/z 408 (M + 1). |

TABLE-1a-continued

| E. No | Chemical name | Structure | ¹H NMR/Mass |
|---|---|---|---|
| 328 | 5-Chloro-N,N-diethyl-1-((2-fluoro-3-(trifluoromethyl)phenyl)amino) isoquinolin-4-carboxamide | 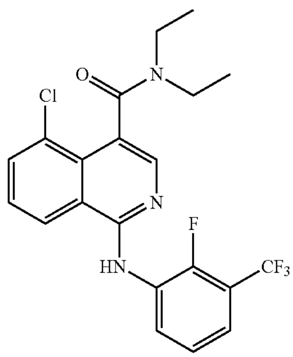 [SMILES: CCN(CC)C(=O)c1cnc(Nc2cccc(C(F)(F)F)c2F)c2cccc(Cl)c12] | ¹H NMR (400 MHz, CDCl$_3$) δ (as mixture of rotamers): 1.09-1.13 (t, 3H), 1.26-1.39 (t, 3H), 3.19-3.30 (m, 2H), 3.42-3.51 (m, 1H), 3.81-3.90 (m, 1H), 7.27-7.32 (m, 2H), 7.53-7.61 (m, 2H), 7.81-7.83 (dd, 1H), 7.98-8.00 (dd, 1H), 8.06 (s, 1H), 8.73-8.78 (m, 1H); MS m/z 440 (M + 1). |
| 329 | 5-Chloro-N,N-dimethyl-1-((2-methyl-3-(trifluoromethyl)phenyl)amino)isoquinolin-4-carboxamide | 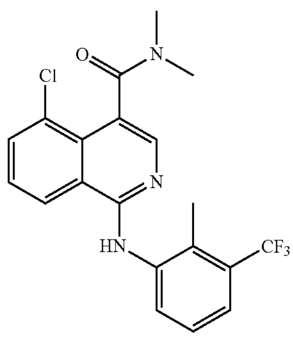 | ¹H NMR (400 MHz, CDCl$_3$) δ: 2.42 (s, 3H), 2.90 (s, 3H), 3.16 (s, 3H), 7.31-7.35 (t, 1H), 7.52-7.56 (m, 2H), 7.69-7.71 (m, 1H), 7.82-7.84 (d, 1H), 7.88 (s, 1H), 8.06-8.08 (m, 1H); MS m/z 408 (M + 1). |
| 330 | 5-Chloro-1-((2-fluoro-3-(trifluoromethyl)phenyl)amino)-N,N-dimethylisoquinolin-4-carboxamide | 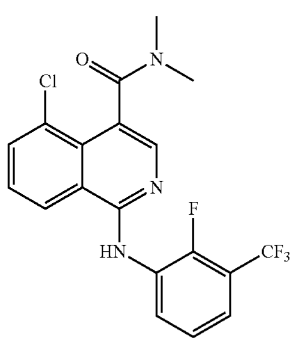 [SMILES: CN(C)C(=O)c1cnc(Nc2cccc(C(F)(F)F)c2F)c2cccc(Cl)c12] | ¹H NMR (400 MHz, CDCl$_3$) δ: 2.89 (s, 3H), 3.20 (s, 3H), 7.27-7.31 (m, 2H), 7.58-7.62 (m, 2H), 7.84-7.85 (dd, 1H), 7.98-8.0 (dd, 1H), 8.08 (s, 1H), 8.75-8.79 (m, 1H); MS m/z 412 (M + 1). |
| 331 | 5-Chloro-N-ethyl-N-methyl-1-((2-methyl-3-(trifluoromethyl)phenyl)amino)isoquinolin-4-carboxamide | 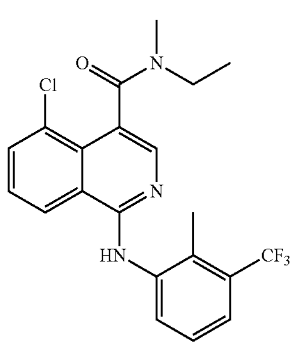 [SMILES: CCN(C)C(=O)c1cnc(Nc2cccc(C(F)(F)F)c2C)c2cccc(Cl)c12] | ¹H NMR (400 MHz, CDCl$_3$) δ (as mixture of rotamers): 1.10-1.13 (t, 3H), 1.22-1.40 (t, 3H), 2.42 (s, 3H), 2.87 (s, 3H), 3.14 (s, 3H), 3.15-3.18 (m, 1H), 3.34-3.37 (s, 3H), 3.55-3.60 (m, 1H), 3.72-3.77 (m, 1H), 7.31-7.39 (m, 3H), 7.51-7.55 (m, 4H), 7.73-7.81 (m, 4H), 7.90-7.93 (d, 2H, J = 10.8 Hz), 8.01-8.03 (d, 2H, J = 7.6 Hz); MS m/z 422 (M + 1). |

TABLE-1a-continued

| E. No | Chemical name | Structure | ¹H NMR/Mass |
|---|---|---|---|
| 332 | 5-Chloro-1-((3-chloro-2-methyl phenyl)amino)-N,N-dimethyl isoquinolin-4-carboxamide | 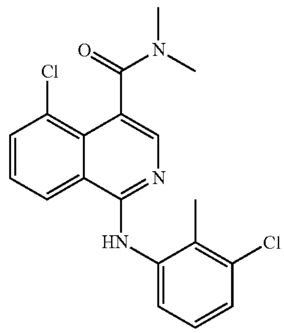 [SMILES: Cc1c(Cl)cccc1Nc1ncc(C(=O)N(C)C)c2c(Cl)cccc12] | ¹H NMR (400 MHz, CDCl$_3$) δ: 2.35 (s, 3H), 2.89 (s, 3H), 3.17 (s, 3H), 7.14-7.18 (t, 2H, J = 8.0 Hz) 7.26-7.30 (m, 1H), 7.45-7.47 (d, 1H, J = 8.0 Hz), 7.51-7.55 (t, 1H, J = 8.0 Hz), 7.79-7.81 (d, 1H, J = 7.2 Hz), 7.96-7.99 (m, 2H); MS m/z 374 (M + 1). |
| 333 | 5-Chloro-1-((3-fluoro-2-(trifluoro methyl)phenyl)amino)-N,N-di methylisoquinolin-4-carboxamide | 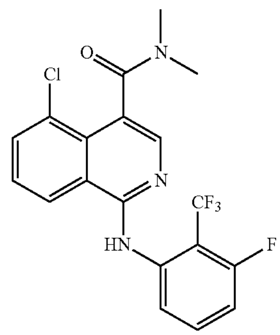 | ¹H NMR (400 MHz, CDCl$_3$) δ: 2.90 (s, 3H), 3.19 (s, 3H), 6.93-6.98 (m, 1H), 7.50-7.61 (m, 2H), 7.78 (s, 1H), 7.85-7.83 (d, 1H, J = 7.2 Hz), 7.92-7.90 (d, 1H, J = 8.4 Hz), 7.99-8.03 (m, 2H); MS m/z 412 (M + 1). |
| 334 | 5-Chloro-N-ethyl-1-((2-fluoro-3-(trifluoromethyl)phenyl)amino)-N-methylisoquinolin-4-carboxamide | 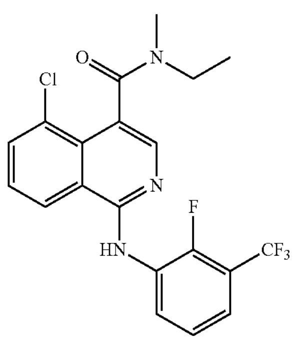 [SMILES: CCN(C)C(=O)c1cnc(Nc2cccc(C(F)(F)F)c2F)c2cccc(Cl)c12] | ¹H NMR (400 MHz, CDCl$_3$) δ (as mixture of rotamers): 1.11-1.15 (t, 3H), 1.29-1.33 (t, 3H), 2.87 (s, 3H), 3.13-3.18 (m, 4H), 3.31-3.36 (m, 1H), 3.60-3.65 (m, 1H), 3.75-3.80 (m, 1H), 7.30-7.31 (m, 4H), 7.57-7.61 (m, 4H), 7.82-7.84 (m, 2H), 7.97-8.01 (m, 2H), 8.06-8.08 (d, 2H, J = 6 Hz), 8.76-8.79 (m, 2H); MS m/z 426 (M + 1). |
| 335 | 5-Chloro-N-ethyl-1-((3-fluoro-2-(trifluoromethyl)phenyl)amino)-N-methylisoquinolin-4-carboxamide | 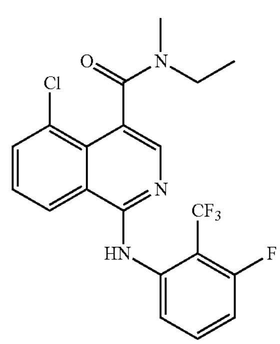 [SMILES: CCN(C)C(=O)c1cnc(Nc2cccc(F)c2C(F)(F)F)c2cccc(Cl)c12] | ¹H NMR (400 MHz, CDCl$_3$) δ (as mixture of rotamers): 1.11-1.15 (t, 3H), 1.27-1.32 (t, 3H), 2.88 (s, 3H), 3.13-3.18 (m, 4H), 3.32-3.37 (m, 1H), 3.58-3.64 (m, 1H), 3.75-3.80 (m, 1H), 6.92-7.01 (m, 2H), 7.50-7.60 (m, 4H), 7.73 (br s, 2H), 7.83-7.85 (d, 2H, J = 7.6 Hz), 7.89-7.91 (d, 2H, J = 8.8 Hz), 8.01-8.04 (m, 4H); MS m/z 426 (M + 1). |

TABLE-1a-continued

| E. No | Chemical name | Structure | ¹H NMR/Mass |
|---|---|---|---|
| 336 | 5-Chloro-1-((2-chloro-3-fluoro phenyl)amino)-N-ethyl-N-methyl isoquinolin-4-carboxamide | 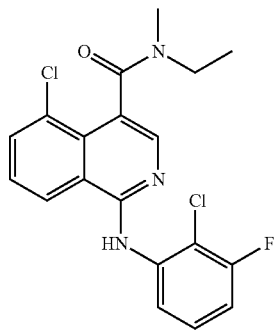 [SMILES: CCN(C)C(=O)c1cnc(Nc2cccc(F)c2Cl)c2cccc(Cl)c12] | ¹H NMR (400 MHz, CDCl$_3$) δ (as mixture of rotamers): 1.11-1.14 (t, 3H), 1.26-1.32 (t, 3H), 2.87 (s, 3H), 3.13-3.20 (m, 4H), 3.30-3.36 (m, 1H), 3.58-3.63 (m, 1H), 3.74-3.79 (m, 1H), 6.90-6.94 (t, 2H, J = 8.4 Hz), 7.28-7.32 (m, 2H), 7.58-7.62 (t, 2H, J = 8.0 Hz), 7.83-7.85 (dd, 2H), 8.03-8.09 (m, 4H), 8.35 (s, 2H); MS m/z 392 (M + 1). |
| 337 | 3-((5-Chloro-4-(diethylcarbamoyl) isoquinolin-1-yl)amino)-2-methyl benzoic acid | 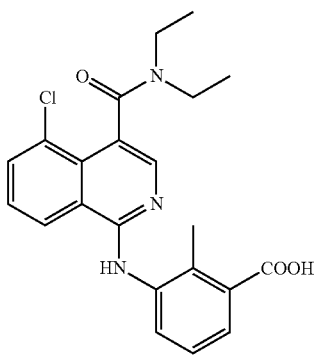 [SMILES: CCN(CC)C(=O)c1cnc(Nc2cccc(C(=O)O)c2C)c2cccc(Cl)c12] | ¹H NMR (400 MHz, CDCl$_3$) δ: 0.96-0.99 (t, 3H), 1.13-1.17 (t, 3H), 2.29 (s, 3H), 3.09-3.15 (m, 2H), 3.24-3.27 (m, 1H), 3.60-3.69 (m, 1H), 7.30-7.33 (t, 1H, J = 7.6 Hz), 7.45-7.47 (d, 1H, J = 7.2 Hz), 7.63-7.67 (m, 3H), 7.90-7.91 (d, 1H, J = 6.8 Hz), 8.56-8.54 (d, 1H, J = 8.0 Hz), 9.36 (s, 1H); MS m/z 412 (M + 1). |
| 338 | 3-((5-Chloro-4-(dimethyl carbamoyl)isoquinolin-1-yl) amino)-2-methylbenzoic acid | 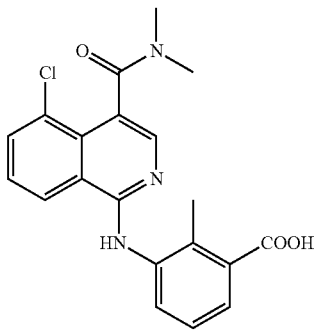 [SMILES: Cc1c(Nc2ncc(C(=O)N(C)C)c3c(Cl)cccc23)cccc1C(=O)O] | ¹H NMR (400 MHz, CDCl$_3$) δ: 2.30 (s, 3H), 2.75 (s, 3H), 2.98 (s, 3H), 7.30-7.34 (t, 1H, J = 7.6 Hz), 7.45-7.47 (d, 1H, J = 7.6 Hz), 7.63-7.67 (m, 3H), 7.92-7.91 (d, 1H, J = 7.2 Hz), 8.56-8.54 (d, 1H, J = 8.4 Hz), 9.36 (s, 1H), 12.92 (s, 1H); MS m/z 384 (M + 1). |
| 339 | 5-Chloro-1-((2-methyl-3-(trifluoro methyl)phenyl)amino)-N,N-di propylisoquinolin-4-carboxamide | 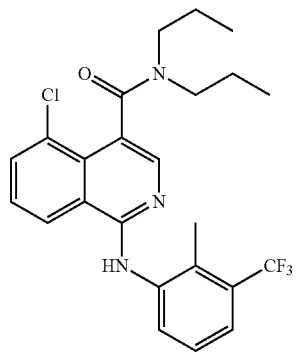 | ¹H NMR (400 MHz, CDCl$_3$) δ: 0.71-0.75 (t, 3H), 0.99-1.02 (t, 3H), 1.50-1.60 (m, 2H), 1.71-1.81 (m, 2H), 2.43 (s, 3H), 3.10-3.15 (m, 2H), 3.34-3.40 (m, 1H), 3.55-3.61 (m, 1H), 7.31-7.35 (t, 1H, J = 8.0 Hz), 7.50-7.59 (m, 2H), 7.73 (s, 1H), 7.80-7.82 (d, 1H, J = 7.2 Hz), 7.87 (s, 1H), 8.02-8.04 (d, 1H, J = 8.0 Hz); MS m/z 464 (M + 1). |

| E. No | Chemical name | Structure | ¹H NMR/Mass |
|---|---|---|---|
| 340 | 2-Chloro-4-((5-chloro-4-(dimethyl carbamoyl)isoquinolin-1-yl)amino) benzoic acid | 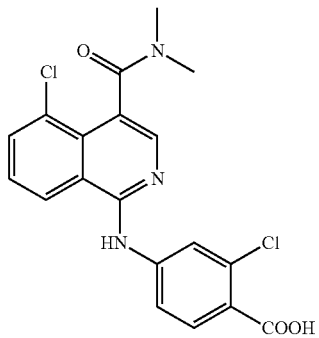 | ¹H NMR (400 MHz, CDCl₃) δ: 2.79 (s, 3H), 3.02 (s, 3H), 7.71-7.75 (t, 1H, J = 8.4 Hz), 7.87-7.99 (m, 4H), 8.14 (s, 1H), 8.60-8.62 (d, 1H, J = 8.0 Hz), 9.82 (s, 1H), 12.97 (s, 1H); MS m/z 464 (M + 1). |
| 341 | 3-((5-Chloro-4-(morpholin-4-carbonyl)isoquinolin-1-yl)amino)-2-methylbenzoic acid | 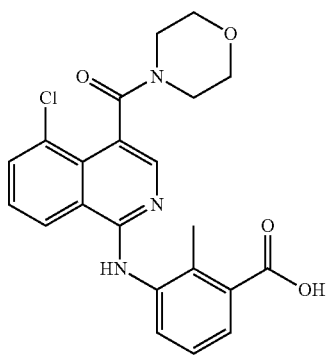 [SMILES: Cc1c(Nc2ncc(C(=O)N3CCOCC3)c3c(Cl)cccc23)cccc1C(=O)O] | ¹H NMR (400 MHz, CDCl₃) δ: 2.35 (s, 3H), 3.12-3.17 (m, 2H), 3.26-3.48 (m, 4H), 3.73-3.83 (m, 2H), 7.36-7.39 (t, 1H, J = 7.2 Hz), 7.51-7.53 (d, 1H), 7.64 (s, 1H), 7.73-7.75 (d, 2H), 8.00-8.02 (d, 1H), 8.76 (s, 1H); MS m/z 426 (M + 1). |
| 342 | 5-Chloro-N,N-diethyl-1-((3-(tri fluoromethyl)phenyl)amino) isoquinolin-4-carboxamide | 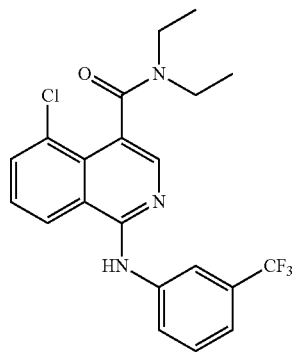 [SMILES: CCN(CC)C(=O)c1cnc(Nc2cccc(C(F)(F)F)c2)c2cccc(Cl)c12] | MS m/z 422 (M + 1) |
| 343 | 5-Chloro-1-((2,4-dichlorophenyl)amino)-N,N-diethylisoquinolin-4-carboxamide | 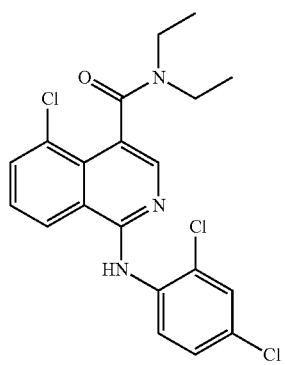 [SMILES: CCN(CC)C(=O)c1cnc(Nc2ccc(Cl)cc2Cl)c2cccc(Cl)c12] | MS m/z 422 (M + 1) |

| E. No | Chemical name | Structure | $^1$H NMR/Mass |
|---|---|---|---|
| 344 | 5-Chloro-N,N-diethyl-1-((2,3,4-trifluorophenyl)amino)isoquinolin-4-carboxamide | 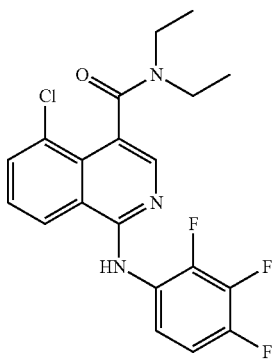 [SMILES: CCN(CC)C(=O)c1cnc(Nc2ccc(F)c(F)c2F)c2cccc(Cl)c12] | MS m/z 408 (M + 1) |
| 345 | 5-Chloro-N,N-diethyl-1-((2,3,5-trifluorophenyl)amino)isoquinolin-4-carboxamide | 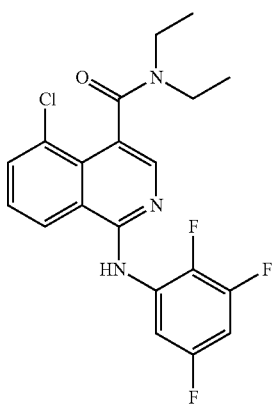 [SMILES: CCN(CC)C(=O)c1cnc(Nc2cc(F)cc(F)c2F)c2cccc(Cl)c12] | MS m/z 408 (M + 1) |
| 346 | 5-Chloro-1-((2,3-difluorophenyl)amino)-N,N-diethylisoquinolin-4-carboxamide | 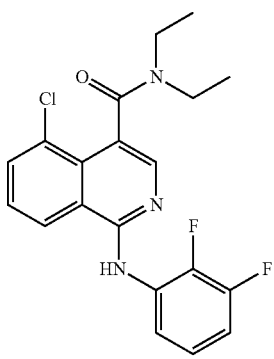 [SMILES: CCN(CC)C(=O)c1cnc(Nc2cccc(F)c2F)c2cccc(Cl)c12] | MS m/z 390 (M + 1) |
| 347 | 5-Chloro-1-((2-chloro-3-fluorophenyl)amino)-N,N-diethyl isoquinolin-4-carboxamide | 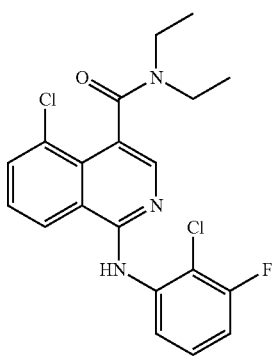 [SMILES: CCN(CC)C(=O)c1cnc(Nc2cccc(F)c2Cl)c2cccc(Cl)c12] | MS m/z 406 (M + 1) |

| E. No | Chemical name | Structure | ¹H NMR/Mass |
|---|---|---|---|
| 348 | 3-((5-Chloro-4-(diethylcarbamoyl)isoquinolin-1-yl)amino)benzoic acid | 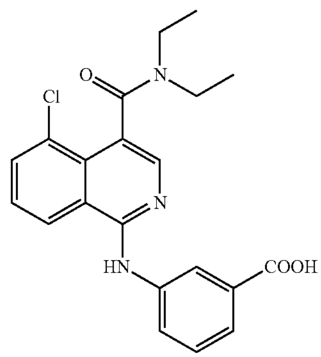 [SMILES: CCN(CC)C(=O)c1cnc(Nc2cccc(C(=O)O)c2)c2cccc(Cl)c12] | MS m/z 398 (M + 1) |
| 349 | 5-Chloro-1-((3-fluoro-2-methyl phenyl)amino)-N,N-dimethyl isoquinolin-4-carboxamide | 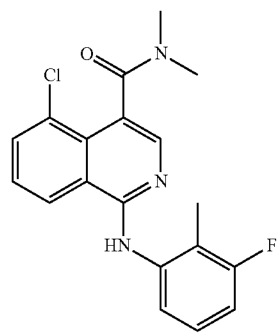 [SMILES: Cc1c(F)cccc1Nc1ncc(C(=O)N(C)C)c2c(Cl)cccc12] | MS m/z 358 (M + 1) |
| 350 | 5-Chloro-1-((2,3-difluorophenyl)amino)-N,N-dimethylisoquinolin-4-carboxamide | 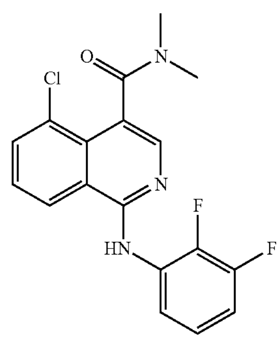 [SMILES: CN(C)C(=O)c1cnc(Nc2cccc(F)c2F)c2cccc(Cl)c12] | MS m/z 362 (M + 1) |
| 351 | 3-((5-Chloro-4-(dipropylcarbamoyl)isoquinolin-1-yl)amino)-2-methyl benzoic acid | 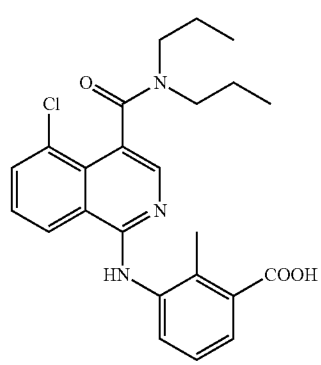 [SMILES: CCCN(CCC)C(=O)c1cnc(Nc2cccc(C(=O)O)c2C)c2cccc(Cl)c12] | MS m/z 440 (M + 1) |

TABLE-1a-continued

| E. No | Chemical name | Structure | ¹H NMR/Mass |
|---|---|---|---|
| 352 | 3-((5-Chloro-4-(dimethyl carbamoyl)isoquinolin-1-yl) amino)-2-fluorobenzoic acid | 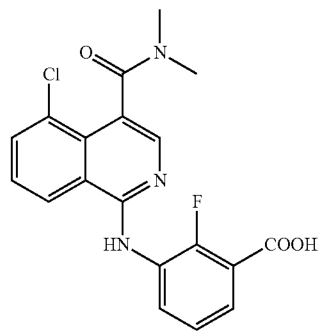 [SMILES: CN(C)C(=O)c1cnc(Nc2cccc(C(=O)O)c2F)c2cccc(Cl)c12] | MS m/z 388 (M + 1) |
| 353 | 3-((5-Chloro-4-(dipropylcarbamoyl) isoquinolin-1-yl)amino)-4-methyl benzoic acid | 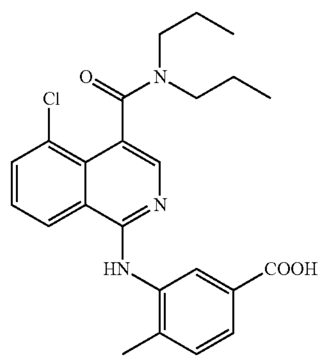 [SMILES: CCCN(CCC)C(=O)c1cnc(Nc2cc(C(=O)O)ccc2C)c2cccc(Cl)c12] | MS m/z 440 (M + 1) |
| 354 | 3-((5-Chloro-4-(ethyl(methyl) carbamoyl)isoquinolin-1-yl) amino)-2-methylbenzoic acid | 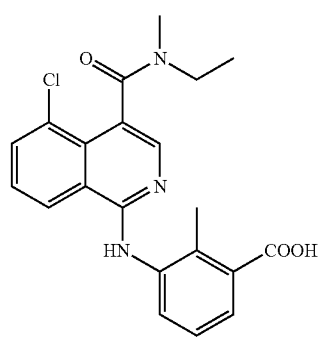 [SMILES: CCN(C)C(=O)c1cnc(Nc2cccc(C(=O)O)c2C)c2cccc(Cl)c12] | MS m/z 398 (M + 1) |
| 355 | 5-Chloro-N-ethyl-N-methyl-1-((2,3,6-trifluorophenyl)amino) isoquinolin-4-carboxamide | 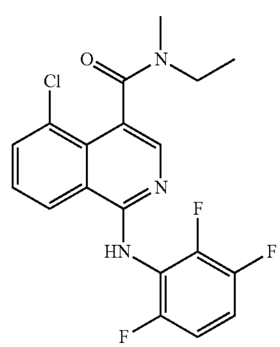 [SMILES: CCN(C)C(=O)c1cnc(Nc2c(F)ccc(F)c2F)c2cccc(Cl)c12] | MS m/z 394 (M + 1) |

TABLE-1a-continued

| E. No | Chemical name | Structure | ¹H NMR/Mass |
|---|---|---|---|
| 356 | 5-Chloro-N-ethyl-1-((3-fluoro-2-methylphenyl)amino)-N-methyl isoquinolin-4-carboxamide | 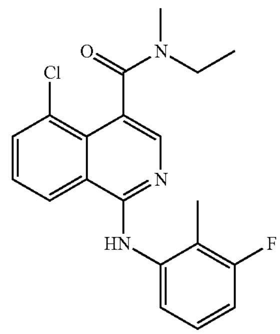 [SMILES: CCN(C)C(=O)c1cnc(Nc2cccc(F)c2C)c2cccc(Cl)c12] | MS m/z 371 (M + 1) |
| 357 | 5-Chloro-1-((3-chloro-2-methyl phenyl)amino)-N-ethyl-N-methyl isoquinolin-4-carboxamide | 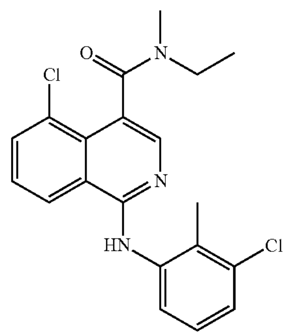 [SMILES: CCN(C)C(=O)c1cnc(Nc2cccc(Cl)c2C)c2cccc(Cl)c12] | MS m/z 388 (M + 1) |
| 358 | 3-((5-Chloro-4-(diethylcarbamoyl)isoquinolin-1-yl)amino)-2-fluoro benzoic acid | 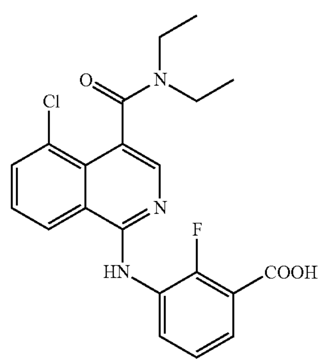 [SMILES: CCN(CC)C(=O)c1cnc(Nc2cccc(C(=O)O)c2F)c2cccc(Cl)c12] | MS m/z 416 (M + 1) |
| 359 | 3-((5-Chloro-4-(dimethyl carbamoyl)isoquinolin-1-yl) amino)-4-methylbenzoic acid | 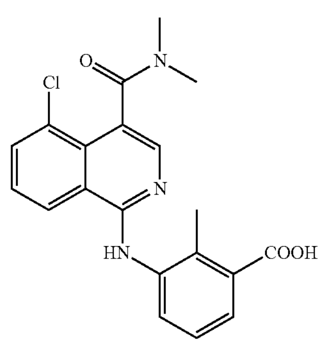 [SMILES: Cc1c(Nc2ncc(C(=O)N(C)C)c3c(Cl)cccc23)cccc1C(=O)O] | MS m/z 384 (M + 1) |

TABLE-1a-continued

| E. No | Chemical name | Structure | ¹H NMR/Mass |
|---|---|---|---|
| 360 | 5-Chloro-N,N-diethyl-1-((2-methyl-3-(methylcarbamoyl)phenyl)amino)isoquinolin-4-carboxamide | 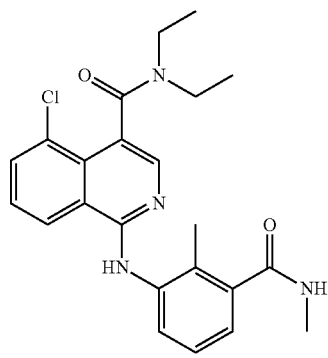 [SMILES: CCN(CC)C(=O)c1cnc(Nc2cccc(C(=O)NC)c2C)c2cccc(Cl)c12] | MS m/z 425 (M + 1) |
| 361 | 5-Chloro-1-((2,3-dimethylphenyl)amino)-N,N-dimethylisoquinolin-4-carboxamide | 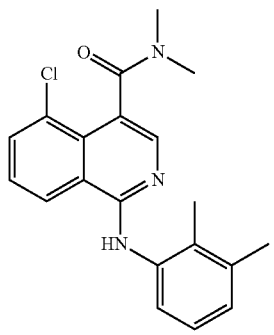 | MS m/z 354 (M + 1) |
| 362 | 3-((5-Chloro-4-(morpholin-4-carbonyl)isoquinolin-1-yl)amino)-4-methylbenzoic acid | 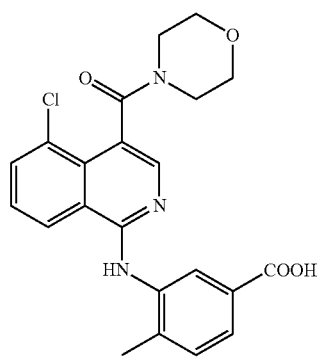 | MS m/z 426 (M + 1) |
| 363 | 5-Chloro-1-((2,3-dichlorophenyl)amino)-N-ethyl-N-methyl isoquinolin-4-carboxamide | 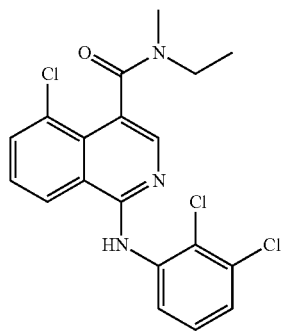 [SMILES: CCN(C)C(=O)c1cnc(Nc2cccc(Cl)c2Cl)c2cccc(Cl)c12] | MS m/z 408 (M + 1) |

TABLE-1a-continued

| E. No | Chemical name | Structure | ¹H NMR/Mass |
|---|---|---|---|
| 364 | 5-Chloro-N,N-diethyl-1-((3-(methyl carbamoyl)phenyl) amino) isoquinolin-4-carboxamide | 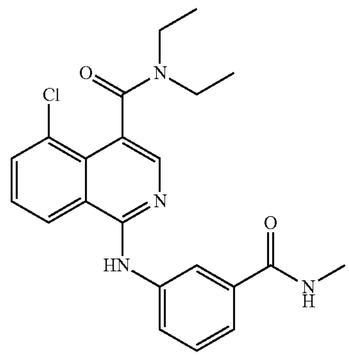 [SMILES: CCN(CC)C(=O)c1cnc(Nc2cccc(C(=O)NC)c2)c2cccc(Cl)c12] | MS m/z 411 (M + 1) |
| 365 | 3-((5-Chloro-4-(diethylcarbamoyl) isoquinolin-1-yl)amino)-4-benzoic acid | 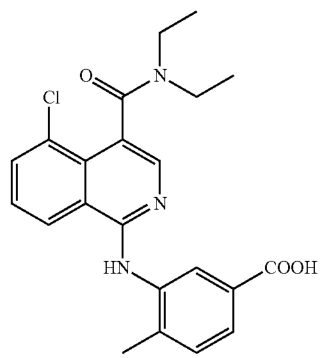 [SMILES: CCN(CC)C(=O)c1cnc(Nc2cc(C(=O)O)ccc2C)c2cccc(Cl)c12] | MS m/z 412 (M + 1) |
| 366 | 3-((5-Chloro-4-(piperidine-1-carbonyl)isoquinolin-1-yl)amino)-4-methylbenzoic acid | 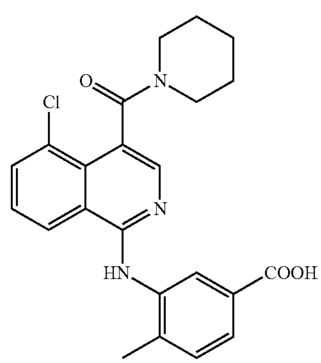 [SMILES: Cc1ccc(C(=O)O)cc1Nc1ncc(C(=O)N2CCCCC2)c2c(Cl)cccc12] | MS m/z 424 (M + 1) |
| 367 | 5-Chloro-1-((2-chloro-3-fluoro phenyl)amino)-N,N-dimethyl isoquinolin-4-carboxamide | 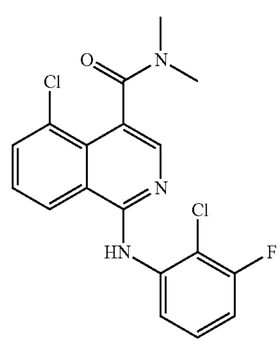 [SMILES: CN(C)C(=O)c1cnc(Nc2cccc(F)c2Cl)c2cccc(Cl)c12] | MS m/z 378 (M + 1) |

TABLE-1a-continued

| E. No | Chemical name | Structure | $^1$H NMR/Mass |
|---|---|---|---|
| 368 | 5-Chloro-1-((2-fluoro-3-(methyl-carbamoyl)phenyl)amino)-N,N-dimethylisoquinolin-4-carboxamide | 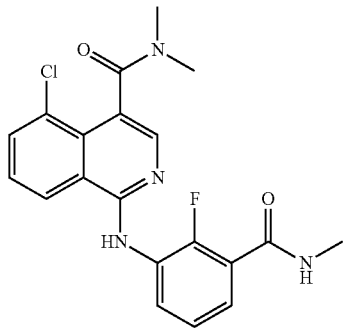 [SMILES: CNC(=O)c1cccc(Nc2ncc(C(=O)N(C)C)c3c(Cl)cccc23)c1F] | MS m/z 401 (M + 1) |
| 369 | 3-((5-Chloro-4-(piperidine-1-carbonyl)isoquinolin-1-yl) amino)-2-methylbenzoic acid | 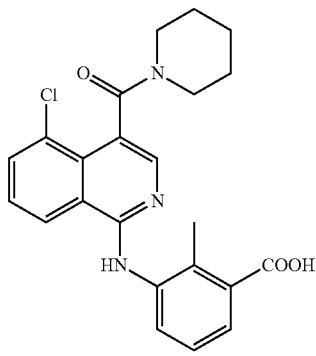 [SMILES: Cc1c(Nc2ncc(C(=O)N3CCCCC3)c3c(Cl)cccc23)cccc1C(=O)O] | MS m/z 424 (M + 1) |
| 370 | 4-((5-Chloro-4-(ethyl(methyl)carbamoyl)isoquinolin-1-yl) amino)-2-methylbenzoic acid | 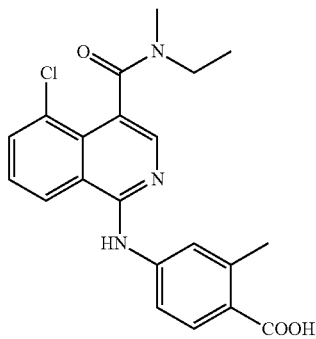 [SMILES: CCN(C)C(=O)c1cnc(Nc2ccc(C(=O)O)c(C)c2)c2cccc(Cl)c12] | MS m/z 398 (M + 1) |
| 371 | 2-Chloro-4-((5-chloro-4-(ethyl(methyl)carbamoyl)isoquinolin-1-yl)amino)benzoic acid | 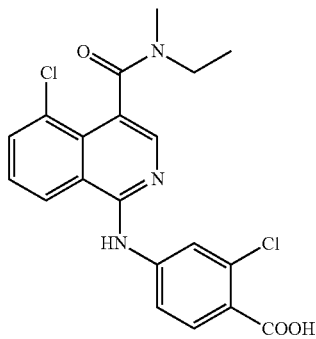 [SMILES: CCN(C)C(=O)c1cnc(Nc2ccc(C(=O)O)c(Cl)c2)c2cccc(Cl)c12] | MS m/z 418 (M + 1) |

TABLE-1a-continued

| E. No | Chemical name | Structure | ¹H NMR/Mass |
|---|---|---|---|
| 372 | 1-((3,5-Bis(trifluoromethyl) phenyl) amino)-5-chloro-N,N-dimethyl isoquinolin-4-carboxamide | 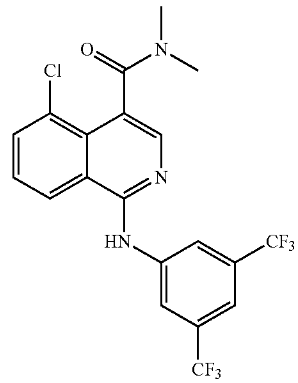 [SMILES: CN(C)C(=O)c1cnc(Nc2cc(C(F)(F)F)cc(C(F)(F)F)c2)c2cccc(Cl)c12] | MS m/z 462 (M + 1) |
| 373 | 5-Chloro-1-((4-fluoro-3-(trifluoro methyl)phenyl)amino)-N,N-dimethylisoquinolin-4-carboxamide | 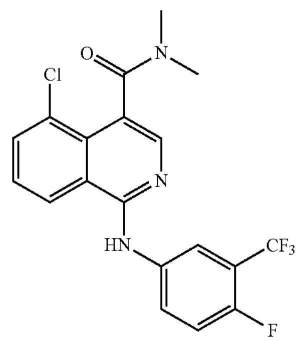 [SMILES: CN(C)C(=O)c1cnc(Nc2ccc(F)c(C(F)(F)F)c2)c2cccc(Cl)c12] | MS m/z 412 (M + 1) |
| 374 | 5-Chloro-1-((5-chloro-2-fluoro phenyl)amino)-N,N-dimethyl isoquinolin-4-carboxamide | 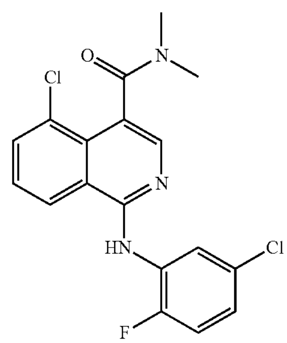 [SMILES: CN(C)C(=O)c1cnc(Nc2cc(Cl)ccc2F)c2cccc(Cl)c12] | MS m/z 378 (M + 1) |
| 375 | 5-Chloro-1-((4-chloro-3-methyl phenyl)amino)-N,N-dimethyl isoquinolin-4-carboxamide | 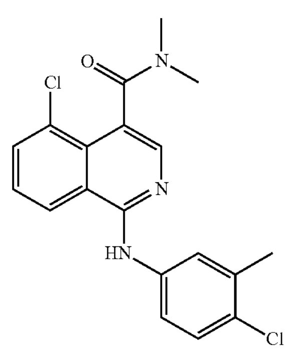 [SMILES: Cc1cc(Nc2ncc(C(=O)N(C)C)c3c(Cl)cccc23)ccc1Cl] | MS m/z 374 (M + 1) |

| E. No | Chemical name | Structure | ¹H NMR/Mass |
|---|---|---|---|
| 376 | 4-((5-Chloro-4-(ethyl(methyl)carbamoyl)isoquinolin-1-yl) amino)-3-methylbenzoic acid | 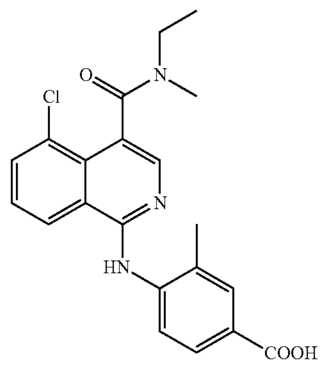 [SMILES: CCN(C)C(=O)c1cnc(Nc2ccc(C(=O)O)cc2C)c2cccc(Cl)c12] | MS m/z 398 (M + 1) |
| 377 | 5-Chloro-1-((2-chloro-3-(trifluoromethyl)phenyl)amino)-N,N-dimethylisoquinolin-4-carboxamide | 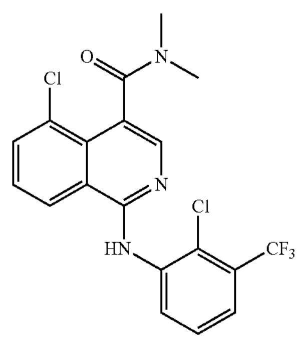 | MS m/z 442 (M + 1) |
| 378 | 4-((5-Chloro-4-(dimethylcarbamoyl)isoquinolin-1-yl) amino)-3-methylbenzoic acid | 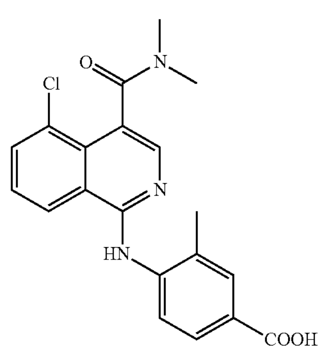 [SMILES: Cc1cc(C(=O)O)ccc1Nc1ncc(C(=O)N(C)C)c2c(Cl)cccc12] | MS m/z 384 (M + 1) |
| 379 | 4-((5-Chloro-4-(dimethylcarbamoyl)isoquinolin-1-yl)amino)-3-fluoro benzoic acid | 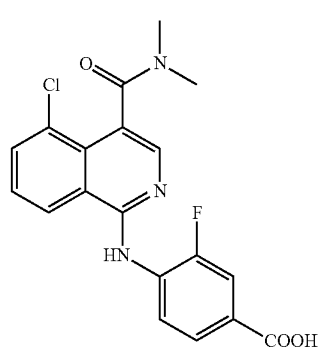 [SMILES: CN(C)C(=O)c1cnc(Nc2ccc(C(=O)O)cc2F)c2cccc(Cl)c12] | MS m/z 388 (M + 1) |

| E. No | Chemical name | Structure | ¹H NMR/Mass |
|---|---|---|---|
| 380 | 5-Chloro-1-((2-fluoro-3-(trifluoro methyl)phenyl)amino)-N-isopropyl-N-methylisoquinolin-4-carboxamide | 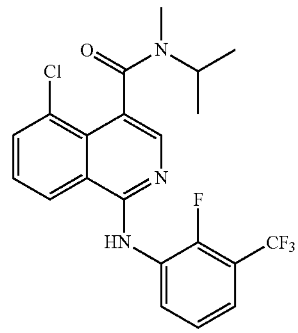 [SMILES: CC(C)N(C)C(=O)c1cnc(Nc2cccc(C(F)(F)F)c2F)c2cccc(Cl)c12] | MS m/z 440 (M + 1) |
| 381 | 5-Chloro-1-((3-fluoro-2-(trifluoro methyl)phenyl)amino)-N-isopropyl-N-methylisoquinolin-4-carboxamide | 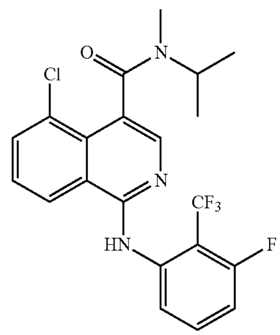 [SMILES: CC(C)N(C)C(=O)c1cnc(Nc2cccc(F)c2C(F)(F)F)c2cccc(Cl)c12] | MS m/z 440 (M + 1) |
| 382 | 5-Chloro-N-isopropyl-N-methyl-1-((2-methyl-3-(trifluoromethyl)phenyl)amino) isoquinolin-4-carboxamide | 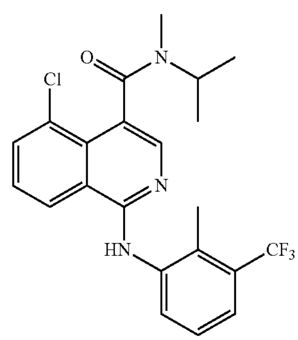 [SMILES: Cc1c(Nc2ncc(C(=O)N(C)C(C)C)c3c(Cl)cccc23)cccc1C(F)(F)F] | MS m/z 436 (M + 1) |
| 383 | 5-Chloro-1-((2-chloro-3-(trifluoro methyl)phenyl)amino)-N-isopropyl-N-methylisoquinolin-4-carboxamide | 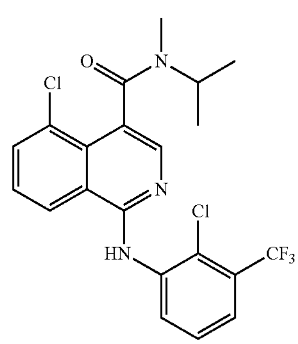 [SMILES: CC(C)N(C)C(=O)c1cnc(Nc2cccc(C(F)(F)F)c2Cl)c2cccc(Cl)c12] | MS m/z 456 (M + 1) |

TABLE-1a-continued

| E. No | Chemical name | Structure | ¹H NMR/Mass |
|---|---|---|---|
| 384 | 5-Chloro-1-((3-chloro-2-methyl phenyl)amino)-N-isopropyl-N-methylisoquinolin-4-carboxamide | 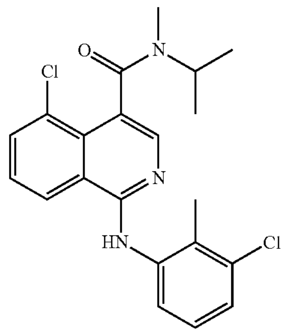 [SMILES: Cc1c(Cl)cccc1Nc1ncc(C(=O)N(C)C(C)C)c2c(Cl)cccc12] | MS m/z 402 (M + 1) |
| 385 | 5-Chloro-1-((3-fluoro-2-methyl phenyl)amino)-N-isopropyl-N-methylisoquinolin-4-carboxamide | 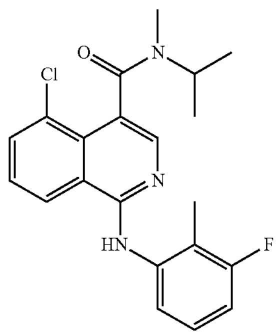 [SMILES: Cc1c(F)cccc1Nc1ncc(C(=O)N(C)C(C)C)c2c(Cl)cccc12] | MS m/z 386 (M + 1) |
| 386 | 2-(5-Chloro-1-((3-chloro-2-methyl phenyl)amino)-N-methyl isoquinolin-4-carboxamido)acetic acid | 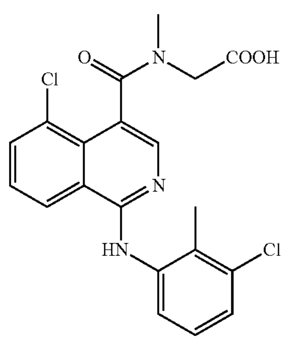 [SMILES: Cc1c(Cl)cccc1Nc1ncc(C(=O)N(C)CC(=O)O)c2c(Cl)cccc12] | MS m/z 418 (M + 1) |
| 387 | 2-(5-Chloro-1-((3-fluoro-2-methyl-phenyl)amino)-N-methyl isoquinolin-4-carboxamido)acetic acid | 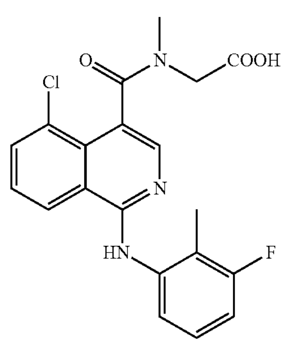 [SMILES: Cc1c(F)cccc1Nc1ncc(C(=O)N(C)CC(=O)O)c2c(Cl)cccc12] | MS m/z 402 (M + 1) |

| E. No | Chemical name | Structure | ¹H NMR/Mass |
|---|---|---|---|
| 388 | 2-(5-Chloro-N-methyl-1-((2-methyl-3-(trifluoromethyl)phenyl)amino) isoquinolin-4-carboxamido)acetic acid | 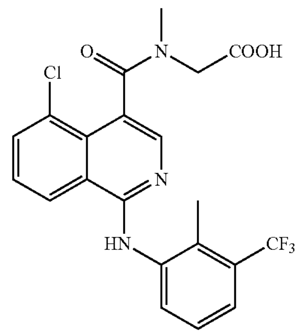 [SMILES: Cc1c(Nc2ncc(C(=O)N(C)CC(=O)O)c3c(Cl)cccc23)cccc1C(F)(F)F] | MS m/z 452 (M + 1) |
| 389 | 2-(5-Chloro-1-((2-fluoro-3-(trifluoromethyl)phenyl)amino)-N-methyl isoquinolin-4-carboxamido)acetic acid | 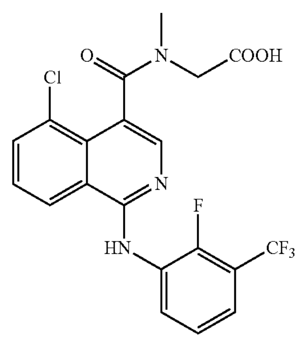 [SMILES: CN(CC(=O)O)C(=O)c1cnc(Nc2cccc(C(F)(F)F)c2F)c2cccc(Cl)c12] | MS m/z 456 (M + 1) |
| 390 | 2-(5-Chloro-1-((3-fluoro-2-(trifluoromethyl)phenyl)amino)-N-methyl isoquinolin-4-carboxamido)acetic acid | 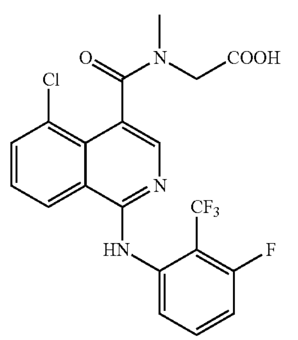 [SMILES: CN(CC(=O)O)C(=O)c1cnc(Nc2cccc(F)c2C(F)(F)F)c2cccc(Cl)c12] | MS m/z 456 (M + 1) |
| 391 | 5-Chloro-1-((3-(dimethyl carbamoyl)-2-methylphenyl)amino)-N,N-diethylisoquinolin-4-carboxamide | 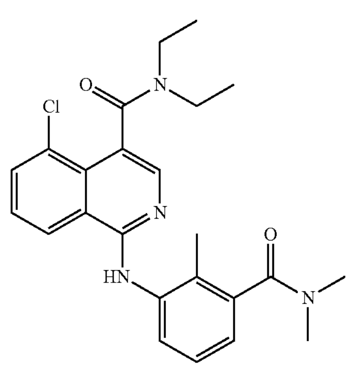 [SMILES: CCN(CC)C(=O)c1cnc(Nc2cccc(C(=O)N(C)C)c2C)c2cccc(Cl)c12] | ¹H NMR (400 MHz, CDCl₃) δ: 1.08-1.12 (t, 3H), 1.26-1.28 (t, 3H), 2.08 (s, 3H), 2.95 (s, 3H), 3.16 (s, 3H), 3.21-3.28 (m, 2H), 3.42-3.47 (m, 1H), 3.79-3.80 (m, 1H), 7.04-7.09 (m, 1H), 7.21-7.29 (m, 1H), 7.53-7.58 (m, 2H), 7.75-7.89 (m, 2H), 8.21-8.25 (m, 1H); MS m/z 439 (M + 1). |

TABLE-1a-continued

| E. No | Chemical name | Structure | ¹H NMR/Mass |
|---|---|---|---|
| 392 | 5-Chloro-N,N-diethyl-1-((3-(methyl carbamoyl)-2-methylphenyl) amino)isoquinolin-4-carboxamide | 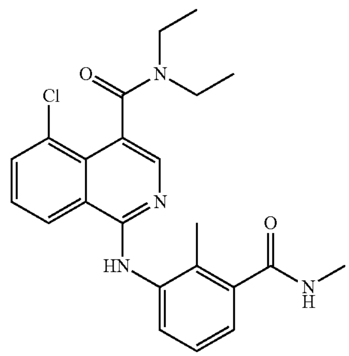 [SMILES: CCN(CC)C(=O)c1cnc(Nc2cccc(C(=O)NC)c2C)c2cccc(Cl)c12] | ¹H NMR (400 MHz, CDCl$_3$) δ: 1.05-1.08 (t, 3H), 1.26-1.31 (t, 3H), 2.21 (s, 3H), 3.01-3.02 (d, 3H), 3.16-3.28 (m, 2H), 3.40-3.45 (m, 1H), 3.62-3.67 (q, 1H), 3.79-3.84 (m, 1H), 7.15-7.23 (m, 2H), 7.47-7.55 (m, 2H), 7.74-7.76 (d, J = 7.6 Hz, 2H), 7.85 (s, 1H), 8.13-8.15 (d, J = 8.4 Hz, 1H); MS m/z 425 (M + 1). |
| 393 | 5-Chloro-N,N-diethyl-1-((3-(methyl carbamoyl)phenyl) amino) isoquinolin-4-carboxamide | 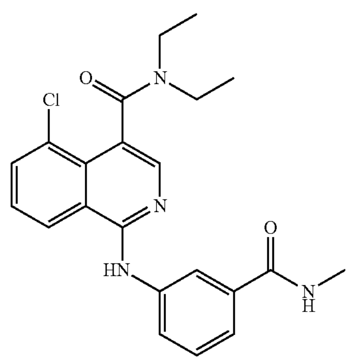 [SMILES: CCN(CC)C(=O)c1cnc(Nc2cccc(C(=O)NC)c2)c2cccc(Cl)c12] | MS m/z 411 (M + 1). |
| 394 | 5-Chloro-N,N-dimethyl-1-((3-(methylcarbamoyl)-2-fluorophenyl) amino)isoquinolin-4-carboxamide | 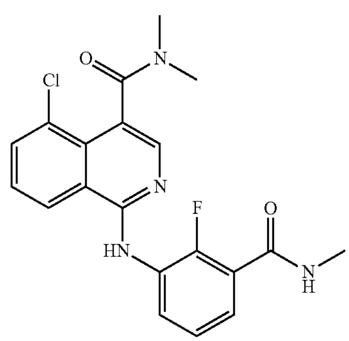 [SMILES: CNC(=O)c1cccc(Nc2ncc(C(=O)N(C)C)c3c(Cl)cccc23)c1F] | ¹H NMR (400 MHz, CDCl$_3$) δ: 2.90 (s, 3H), 3.06 (s, 3H), 3.16-3.19 (d, 3H), 3.71-3.77 (q, 1H), 7.23-7.27 (m, 1H), 7.52-7.59 (m, 1H), 7.62-7.67 (m, 1H), 7.77-7.83 (m, 1H), 8.0 (s, 1H), 8.05-8.06 (d, 1H), 8.35-8.37 (m, 1H); MS m/z 401 (M + 1). |
| 395 | 5-Chloro-1-((3-chloro-4-(methyl carbamoyl)phenyl) amino)-N,N-dimethylisoquinolin-4-carboxamide | 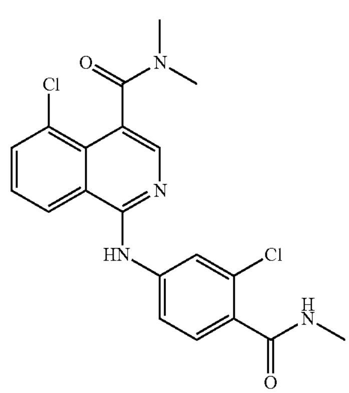 [SMILES: CNC(=O)c1ccc(Nc2ncc(C(=O)N(C)C)c3c(Cl)cccc23)cc1Cl] | ¹H NMR (400 MHz, CDCl$_3$) δ: 2.91 (s, 3H), 3.01-3.08 (m, 3H), 3.23 (s, 3H), 6.70 (br s, 1H), 7.36-7.39 (m, 1H), 7.44-7.48 (t, J = 8.0 Hz, 1H), 7.53-7.55 (d, J = 8.4 Hz, 1H), 7.64-7.66 (d, J = 7.6 Hz, 1H), 7.74-7.77 (d, 2H), 8.20-8.22 (d, 1H), 9.34 (s, 1H); MS m/z 417 (M + 1). |

| E. No | Chemical name | Structure | ¹H NMR/Mass |
|---|---|---|---|
| 396 | 5-Chloro-1-((3-chloro-4-(methyl carbamoyl)phenyl)amino)-N-ethyl-N-methylisoquinolin-4-carboxamide | 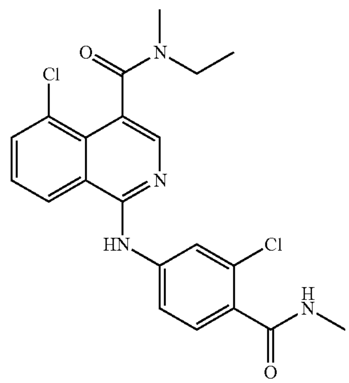 [SMILES: CCN(C)C(=O)c1cnc(Nc2ccc(C(=O)NC)c(Cl)c2)c2cccc(Cl)c12] | ¹H NMR (400 MHz, CDCl₃) δ (as mixture of rotamers): 1.13-1.16 (t, 3H), 1.26-1.32 (t, 3H), 2.90 (s, 3H), 3.01-3.06 (d, 3H), 3.20 (s, 3H), 3.32-3.37 (m, 1H), 3.57-3.62 (m, 1H), 3.80-3.85 (m, 1H), 6.72 (br s, 1H), 7.32-7.48 (m, 2H), 7.53-7.57 (t, J = 8.0 Hz, 1H), 7.63-7.66 (m, 1H), 7.71-7.77 (m, 2H), 8.20-8.22 (m, 1H); MS m/z 431 (M + 1). |
| 397 | 3-((5-Chloro-4-(mopholin-4-carbonyl)isoquinolin-1-yl)amino)-N-ethyl-2-methylbenzamide | 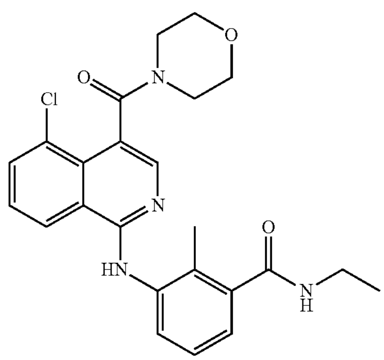 [SMILES: CCNC(=O)c1cccc(Nc2ncc(C(=O)N3CCOCC3)c3c(Cl)cccc23)c1C] | ¹H NMR (400 MHz, CDCl₃) δ: 1.41-1.44 (t, 3H), 1.98 (s, 3H), 3.09-3.12 (m, 1H), 3.28-3.36 (m, 2H), 3.46-3.52 (m, 3H), 3.63-3.75 (m, 4H), 3.86-3.96 (m, 2H), 4.10-4.11 (m, 1H), 7.30-7.35 (m, 1H), 7.81-7.94 (m, 3H), 8.04-8.12 (m, 1H), 8.19-8.26 (m, 1H), 8.69 (s, 1H), 8.90-9.07 (m, 1H); MS m/z 453 (M + 1). |
| 398 | 3-((5-Chloro-4-(piperidin-1-carbonyl)isoquinolin-1-yl)amino)-N-ethyl-2-methylbenzamide | 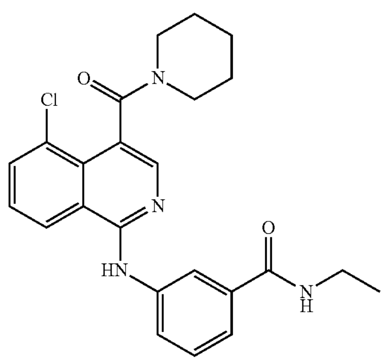 | ¹H NMR (400 MHz, CDCl₃) δ: 1.11-1.13 (t, 3H), 1.23-1.25 (m, 1H), 1.33-1.37 (m, 2H), 1.50-1.62 (m, 3H), 2.12 (s, 3H), 3.04-3.10 (m, 1H), 3.21-3.28 (m, 3H), 3.3.-3.39 (m, 2H), 3.81-3.84 (m, 1H), 7.17-7.19 (dd, 1H), 7.24-7.27 (t, J = 7.6 Hz, 1H), 7.32-7.37 (dd, 1H), 7.62-7.66 (m, 2H), 7.89-7.91 (dd, 1H), 8.32 (s, 1H), 8.33-8.35 (t, 1H), 8.54-8.56 (d, J = 7.6 Hz, 1H); MS m/z 451 (M + 1). |
| 399 | Methyl 3-((5-methyl-4-(piperidin-1-carbonyl)isoquinolin-1-yl)amino) benzoate | 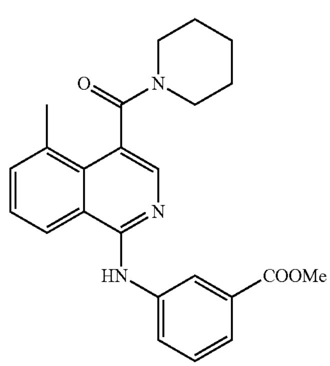 | ¹H NMR (400 MHz, CDCl₃) δ: 1.51-1.71 (m, 6H), 2.61 (s, 3H), 3.16-3.21 (m, 1H), 3.42-3.50 (m, 2H), 3.94 (s, 3H), 4.12-4.20 (m, 1H), 7.36-7.53 (m, 4H), 7.75-7.89 (m, 2H), 7.97 (s, 1H), 8.01-8.21 (m, 2H); MS m/z 404 (M + 1). |

TABLE-1a-continued

| E. No | Chemical name | Structure | ¹H NMR/Mass |
|---|---|---|---|
| 400 | 3-((5-Methyl-4-(piperidine-1-carbonyl)isoquinolin-1-yl)amino) benzoic acid | 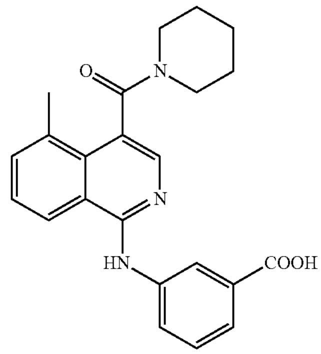 [SMILES: Cc1cccc2c(Nc3cccc(C(=O)O)c3)ncc(C(=O)N3CCCCC3)c12] | ¹H NMR (400 MHz, dMSO-d$_6$) δ: 1.51-1.71 (m, 6H), 2.61 (s, 3H), 3.16-3.21 (m, 1H), 3.42-3.50 (m, 2H), 3.94 (s, 3H), 4.12-4.20 (m, 1H), 7.44-7.66 (m, 4H), 7.81 (s, 1H), 8.12-8.49 (m, 3H), 9.52 (brs, 1H), 12.92 (brs, 1H); MS m/z 390 (M + 1). |
| 401 | Methyl 3-((5-methyl-4-(morpholin-4-carbonyl)isoquinolin-1-yl)amino) benzoate | 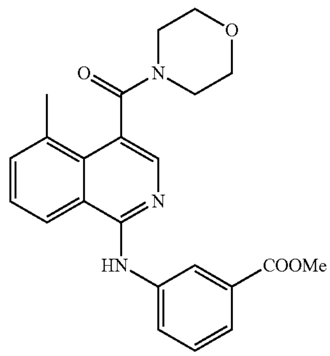 | ¹H NMR (400 MHz, CDCl$_3$) δ: 2.62 (s, 3H), 3.27-4.92 (m, 7H), 3.95 (s, 3H), 4.13-4.16 (m, 1H), 7.35 (s, 1H), 7.46-7.57 (m, 3H), 7.77-7.79 (m, 2H), 8.0 (s, 1H), 8.01-8.23 (m, 2H); MS m/z 406 (M + 1). |
| 402 | 3-((5-Methyl-4-(morpholin-4-carbonyl)isoquinolin-1-yl)amino) benzoic acid | 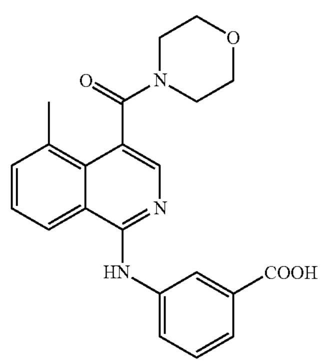 [SMILES: Cc1cccc2c(Nc3cccc(C(=O)O)c3)ncc(C(=O)N3CCOCC3)c12] | ¹H NMR (400 MHz, dMSO-d$_6$) δ: 2.61 (s, 3H), 3.16-4.05 (m, 8H), 7.44-7.64 (m, 4H), 7.87 (s, 1H), 8.12-8.49 (m, 3H), 9.55 (s, 1H), 12.92 (brs, 1H); MS m/z 392 (M + 1). |
| 403 | 4-((5-Chloro-4-(dimethyl carbamoyl)isoquinolin-1-yl) amino)-3-methylbenzoic acid | 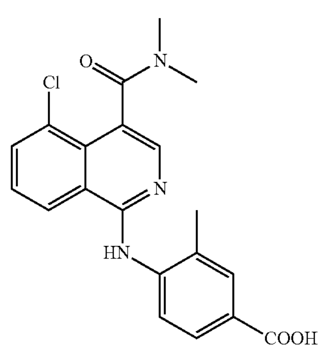 [SMILES: Cc1cc(C(=O)O)ccc1Nc1ncc(C(=O)N(C)C)c2c(Cl)cccc12] | ¹H NMR (400 MHz, dMSO-d$_6$) δ: 2.22 (s, 3H), 2.76 (s, 3H), 2.99 (s, 3H), 7.48-7.51 (d, J = 8.4 Hz, 1H), 7.65-7.69 (t, J = 8.4 Hz, 1H), 7.75 (s, 1H), 7.78-7.80 (dd, 1H), 7.86 (s, 1H), 7.92-7.94 (d, J = 7.6 Hz, 1H), 8.54-8.56 (d, J = 8.0 Hz, 1H), 9.29 (s, 1H), 12.76 (brs, 1H); MS m/z 384 (M + 1). |

| E. No | Chemical name | Structure | ¹H NMR/Mass |
|---|---|---|---|
| 404 | 3-((5-Chloro-4-(diethylcarbamoyl)isoquinolin-1-yl)amino)-2-fluoro benzoic acid | 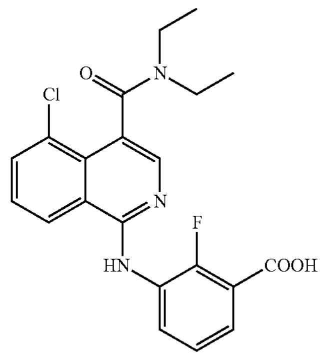 [SMILES: CCN(CC)C(=O)c1cnc(Nc2cccc(C(=O)O)c2F)c2cccc(Cl)c12] | ¹H NMR (400 MHz, dMSO-d₆) δ: 0.97-1.0 (t, 3H), 1.14-1.17 (t, 3H), 3.10-3.15 (m, 2H), 3.25-3.34 (m, 1H), 3.61-3.69 (m, 1H), 7.28-7.32 (t, J = 8.0 Hz, 1H), 7.62-7.75 (m, 4H), 7.92-7.94 (d, J = 7.6 Hz, 1H), 8.52-8.54 (d, J = 8.4 Hz, 1H), 9.45 (s, 1H), 13.28 (brs, 1H); MS m/z 416 (M + 1). |
| 405 | N,N-Dimethyl-3-((5-methyl-4-(morpholin-4-carbonyl)isoquinolin-1-yl)amino)benzamide | 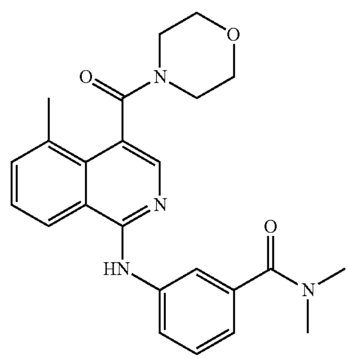 [SMILES: Cc1cccc2c(Nc3cccc(C(=O)N(C)C)c3)ncc(C(=O)N3CCOCC3)c12] | ¹H NMR (400 MHz, CDCl₃) δ: 2.61 (s, 3H), 3.08 (s, 3H), 3.14 (s, 3H), 3.29-4.16 (m, 8H), 7.12-7.14 (m, 1H), 7.39-7.56 (m, 4H), 7.75-7.90 (m, 3H), 7.97 (s, 1H); MS m/z 419 (M + 1). |
| 406 | (5-Methyl-1-((3-(morpholin-4-carbonyl)phenyl)amino)isoquinolin-4-yl)(morpholino)methanone | 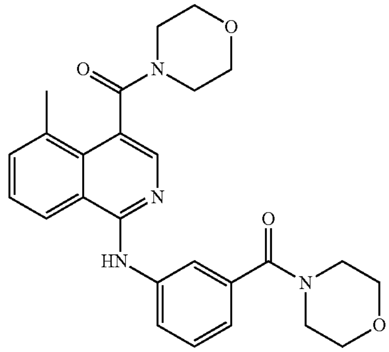 [SMILES: Cc1cccc2c(Nc3cccc(C(=O)N4CCOCC4)c3)ncc(C(=O)N3CCOCC3)c12] | MS m/z 461 (M + 1). |

The below examples given in Table-1b were prepared by following the similar procedure as described in Example-132 by taking appropriate intermediates.

The below acid or amide examples were prepared by following the procedure as described in Scheme-8 by taking corresponding ester compound.

The below amide examples were prepared by following the procedure as described in Scheme-8 by taking corresponding acid compound.

TABLE 1b

| E. No | Chemical name | Structure | Mass/$^1$H NMR |
|---|---|---|---|
| 407 | Methyl 3-((5-methyl-4-(piperidin-1-carbonyl)naphthalen-1-yl)amino) benzoate | 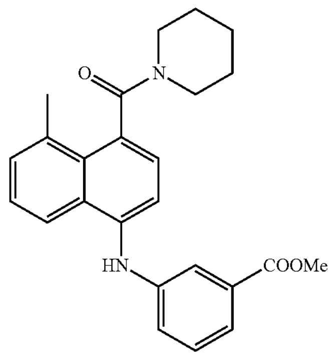 [SMILES: COC(=O)c1cccc(Nc2ccc(C(=O)N3CCCCC3)c3c(C)cccc23)c1] | $^1$H NMR (400 MHz, CDCl$_3$) δ: 1.44-2.03 (m, 6H), 2.69 (s, 3H), 3.07-3.13 (m, 1H), 3.30-3.35 (m, 1H), 3.45-3.51 (m, 1H), 3.91 (s, 3H), 3.93-4.21 (m, 1H), 6.06 (s, 1H), 7.01-7.17 (m, 1H), 7.30-7.44 (m, 5H), 7.54-7.61 (m, 1H), 7.68-7.69 (m, 1H), 7.97-7.99 (m, 1H); MS m/z 403 (M+). |
| 408 | Methyl 3-((5-methyl-4-(morpholin-4-carbonyl)naphthalen-1-yl)amino) benzoate | 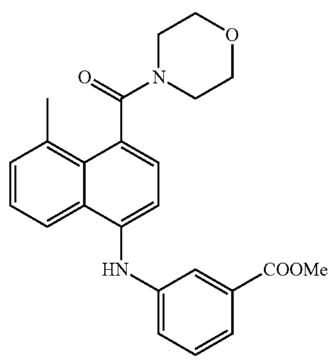 [SMILES: COC(=O)c1cccc(Nc2ccc(C(=O)N3CCOCC3)c3c(C)cccc23)c1] | $^1$H NMR (400 MHz, CDCl$_3$) δ: 2.69 (s, 3H), 3.22-3.26 (m, 1H), 3.29-3.23 (m, 1H), 3.56-3.61 (m, 1H), 3.63-3.69 (m, 2H), 3.76-3.82 (m, 1H), 3.89-3.94 (m, 4H), 4.12-4.16 (m, 1H), 6.10 (s, 1H), 7.18-7.23 (m, 1H), 7.29-7.31 (m, 1H), 7.32-7.37 (m, 2H), 7.40-7.46 (m, 2H), 7.62 (d, J = 8.0 Hz, 1H), 7.72 (s, 1H), 7.98-8.00 (m, 1H); MS m/z 405 (M+). |
| 409 | Methyl 2-methyl-3-((5-methyl-4-(piperidin-1-carbonyl)naphthalen-1-yl)amino)benzoate | 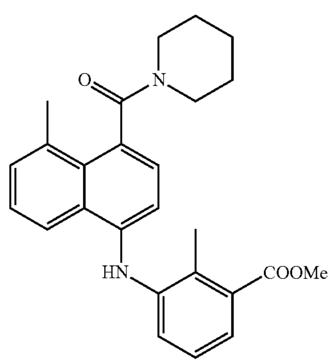 [SMILES: COC(=O)c1cccc(Nc2ccc(C(=O)N3CCCCC3)c3c(C)cccc23)c1C] | $^1$H NMR (400 MHz, CDCl$_3$) δ: 1.44-1.50 (m, 2H), 1.63-1.77 (m, 4H), 2.51 (s, 3H), 2.69 (s, 3H), 3.06-3.13 (m, 1H), 3.29-3.34 (m, 1H), 3.45-3.51 (m, 1H), 3.94 (s, 3H), 4.16-4.19 (m, 1H), 5.90 (s, 1H), 6.91 (d, J = 7.6 Hz, 1H), 7.09-7.11 (m, 1H), 7.16 (t, J = 8.0 Hz, 1H), 7.21 (d, J = 7.6 Hz, 1H), 7.38-7.44 (m, 2H), 7.52 (dd, J = 7.6 Hz, 1.2 Hz, 1H), 7.96 (dd, J = 8.0 Hz, 1.6 Hz, 1H); MS m/z 417 (M + 1). |

TABLE 1b-continued

| E. No | Chemical name | Structure | Mass/¹H NMR |
|---|---|---|---|
| 410 | Methyl 2-methyl-3-((5-methyl-4-(morpholin-4-carbonyl)naphthalen-1-yl)amino)benzoate | 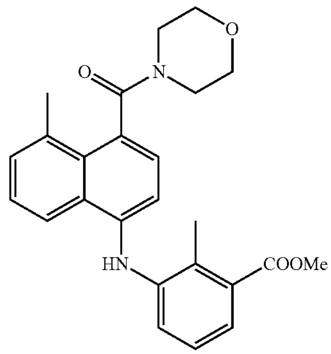 [SMILES: COC(=O)c1cccc(Nc2ccc(C(=O)N3CCOCC3)c3c(C)cccc23)c1C] | ¹H NMR (400 MHz, CDCl$_3$) δ: 2.50 (s, 3H), 2.69 (s, 3H), 3.21-3.32 (m, 2H), 3.47-3.58 (m, 1H), 3.64-3.89 (m, 4H), 3.94 (s, 3H), 4.11-4.14 (m, 1H), 5.94 (s, 1H), 6.86 (d, J = 7.6 Hz, 1H), 7.13-7.22 (m, 3H), 7.42-7.46 (m, 2H), 7.56 (d, J = 7.2 Hz, 1H), 7.98 (d, J = 7.6 Hz, 1H); MS m/z 419 (M + 1). |
| 411 | Methyl 2-methyl-3-((5-methyl-4-(diethylcarbamoyl)naphthalen-1-yl)amino)benzoate | 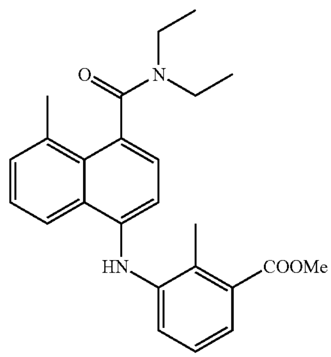 [SMILES: CCN(CC)C(=O)c1ccc(Nc2cccc(C(=O)OC)c2C)c2cccc(C)c12] | ¹H NMR (400 MHz, CDCl$_3$) δ: 1.06 (t, J = 7.2 Hz, 3H), 1.33 (t, J = 7.2 Hz, 3H), 2.51 (s, 3H), 2.69 (s, 3H), 3.11-3.15 (m, 1H), 3.22-3.26 (m, 1H), 3.43-3.48 (m, 1H), 3.84-3.89 (m, 1H), 3.94 (s, 3H), 5.89 (s, 1H), 6.92 (d, J = 7.6 Hz, 1H), 7.97 (d, J = 7.6 Hz, 1H), 7.16 (t, J = 8.0 Hz, 1H), 7.22 (d, J = 7.6 Hz, 1H), 7.38-7.44 (m, 2H), 7.50-7.53 (m, 1H), 7.95-7.98 (m, 1H); MS m/z 405 (M+). |
| 412 | Methyl 3-(3-((5-methyl-4-(piperidin-1-carbonyl)naphthalen-1-yl)amino)propanoate | 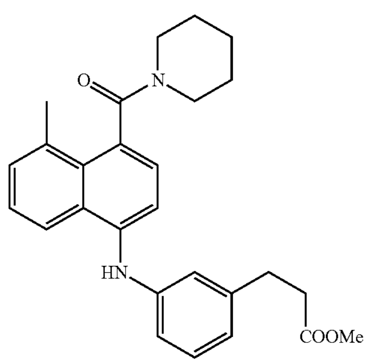 [SMILES: COC(=O)CCc1cccc(Nc2ccc(C(=O)N3CCCCC3)c3c(C)cccc23)c1] | MS m/z 431 (M + 1). |
| 413 | N-Ethyl-4-((2-fluoro-3-(trifluoromethyl)phenyl)amino)-N,8-dimethyl-1-naphthamide | 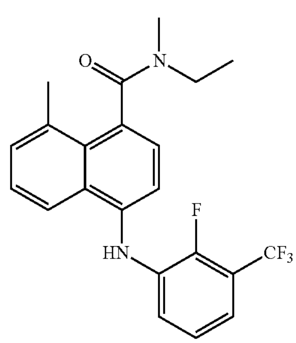 [SMILES: CCN(C)C(=O)c1ccc(Nc2cccc(C(F)(F)F)c2F)c2cccc(C)c12] | ¹H NMR (400 MHz, CDCl$_3$) δ (as mixture of rotamers): 1.10 (t, J = 7.2 Hz, 3H), 1.33 (t, J = 7.2 Hz, 3H), 2.67 (s, 3H), 2.68 (s, 3H), 2.83 (s, 3H), 3.02-3.11 (m, 1H), 3.19 (s, 3H), 3.24-3.33 (m, 1H), 3.65-3.80 (m, 2H), 6.14-6.19 (m, 2H), 6.99-7.07 (m, 6H), 7.30-7.35 (m, 2H), 7.40-7.47 (m, 6H), 7.99 (d, J = 8.0 Hz, 2H); MS m/z 405 (M + 1). |

TABLE 1b-continued

| E. No | Chemical name | Structure | Mass/¹H NMR |
|---|---|---|---|
| 414 | N-Ethyl-4-((5-fluoro-2-methylphenyl)amino)-N,8-dimethyl-1-naphthamide | 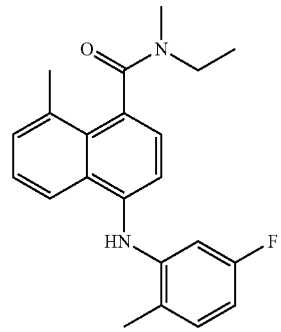 [SMILES: CCN(C)C(=O)c1ccc(Nc2cc(F)ccc2C)c2cccc(C)c12] | MS m/z 351 (M + 1) |
| 415 | N-Ethyl-4-((3-fluoro-2-(trifluoro methyl)phenyl)amino)-N,8-dimethyl-1-naphthamide | 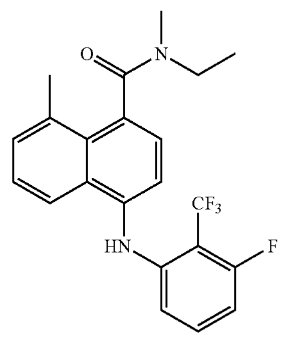 [SMILES: CCN(C)C(=O)c1ccc(Nc2cccc(F)c2C(F)(F)F)c2cccc(C)c12] | ¹H NMR (400 MHz, CDCl₃) δ (as mixture of rotamers): 1.11 (t, J = 7.2 Hz, 3H), 1.32 (t, J = 7.2 Hz, 3H), 2.66 (s, 3H), 2.68 (s, 3H), 2.83 (s, 3H), 3.02-3.11 (m, 1H), 3.19 (s, 3H), 3.24-3.33 (m, 1H), 3.65-3.80 (m, 2H), 5.93-5.98 (m, 2H), 6.46-6.63 (m, 4H), 7.01-7.17 (m, 4H), 7.41-7.46 (m, 6H), 7.86-7.93 (d, J = 8.0 Hz, 2H); MS m/z 405 (M + 1). |
| 416 | N,N-Diethyl-8-methyl-4-((2-methyl-3-(trifluoromethyl)phenyl)amino)-1-naphthamide | 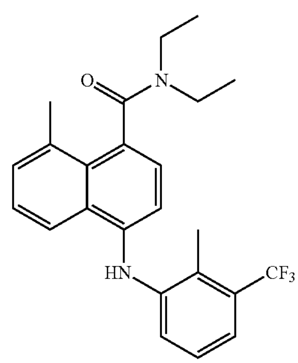 [SMILES: CCN(CC)C(=O)c1ccc(Nc2cccc(C(F)(F)F)c2C)c2cccc(C)c12] | ¹H NMR (400 MHz, CDCl₃) δ (as mixture of rotamers): 1.07 (t, J = 7.2 Hz, 3H), 1.33 (t, J = 7.2 Hz, 3H), 2.43 (s, 3H), 2.70 (s, 3H), 3.09-3.18 (m, 1H), 3.21-3.29 (m, 1H), 3.43-3.51 (m, 1H), 3.82-3.88 (m, 1H), 7.00 (d, J = 7.6 Hz, 1H), 7.06 (d, J = 8.4 Hz, 1H), 7.17 (t, J = 8.0 Hz, 1H), 7.25 (d, J = 7.6 Hz, 1H), 7.30-7.31 (m, 1H), 7.35-7.54 (m, 2H), 7.94-7.97 (m, 1H); MS m/z 415 (M + 1). |
| 417 | N,N-Diethyl-4-((3-fluoro-2-methyl phenyl)amino)-8-methyl-1-naphthamide | 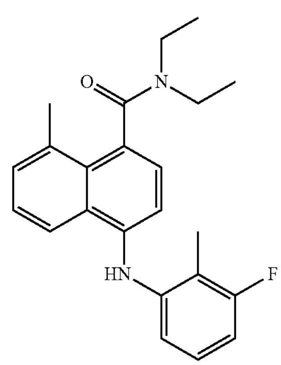 [SMILES: CCN(CC)C(=O)c1ccc(Nc2cccc(F)c2C)c2cccc(C)c12] | ¹H NMR (400 MHz, CDCl₃) δ (as mixture of rotamers): 1.06 (t, J = 7.2 Hz, 3H), 1.31 (t, J = 7.2 Hz, 3H), 2.23 (s, 3H), 2.69 (s, 3H), 3.10-3.15 (m, 1H), 3.22-3.27 (m, 1H), 3.44-3.51 (m, 1H), 3.84-3.89 (m, 1H), 5.82 (s, 1H), 6.71-6.75 (m, 2H), 7.01-7.07 (m, 2H), 7.23-7.25 (m, 1H), 7.38-7.54 (m, 2H), 7.96-7.98 (m, 1H); MS m/z 365 (M + 1). |

TABLE 1b-continued

| E. No | Chemical name | Structure | Mass/¹H NMR |
|---|---|---|---|
| 418 | 4-((3-Chloro-2-methylphenyl)amino)-N,N-diethyl-8-methyl-1-naphthamide | 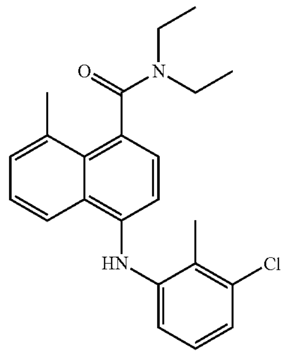 [SMILES: CCN(CC)C(=O)c1ccc(Nc2cccc(Cl)c2C)c2cccc(C)c12] | ¹H NMR (400 MHz, CDCl₃) δ (as mixture of rotamers): 1.06 (t, J = 7.2 Hz, 3H), 1.33 (t, J = 7.2 Hz, 3H), 2.37 (s, 3H), 2.69 (s, 3H), 3.10-3.15 (m, 1H), 3.22-3.27 (m, 1H), 3.44-3.49 (m, 1H), 3.84-3.89 (m, 1H), 5.84 (s, 1H), 6.83 (d, J = 7.6 Hz, 1H), 6.96 (d, J = 8.0 Hz, 1H), 7.03 (t, J = 8.0 Hz, 1H), 7.07-7.09 (m, 1H), 7.23 (d, J = 7.6 Hz, 1H), 7.38-7.54 (m, 2H), 7.95-7.97 (m, 1H); MS m/z 381 (M + 1). |
| 419 | N,N-Diethyl-4-((2-fluoro-3-(trifluoromethyl)phenyl)amino)-8-methyl-1-naphthamide | 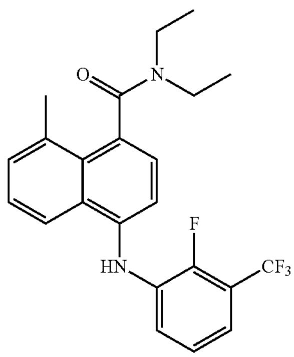 [SMILES: CCN(CC)C(=O)c1ccc(Nc2cccc(C(F)(F)F)c2F)c2cccc(C)c12] | ¹H NMR (400 MHz, CDCl₃) δ (as mixture of rotamers): 1.08 (t, J = 7.2 Hz, 3H), 1.34 (t, J = 7.2 Hz, 3H), 2.70 (s, 3H), 3.11-3.18 (m, 1H), 3.20-3.26 (m, 1H), 3.46-3.51 (m, 1H), 3.85-3.90 (m, 1H), 6.17-6.18 (m, 1H), 7.01-7.07 (m, 3H), 7.33 (d, J = 7.6 Hz, 1H), 7.40-7.47 (m, 3H), 7.99-8.01 (m, 1H); MS m/z 419 (M + 1). |
| 420 | 4-((2-Chloro-3-fluorophenyl)amino)-N,N-diethyl-8-methyl-1-naphthamide | 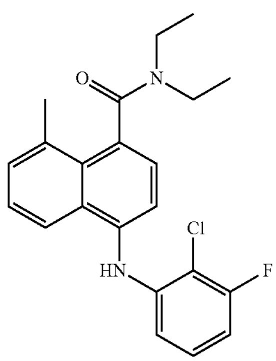 [SMILES: CCN(CC)C(=O)c1ccc(Nc2cccc(F)c2Cl)c2cccc(C)c12] | ¹H NMR (400 MHz, CDCl₃) δ (as mixture of rotamers): 1.08 (t, J = 7.2 Hz, 3H), 1.34 (t, J = 7.2 Hz, 3H), 2.70 (s, 3H), 3.11-3.16 (m, 1H), 3.20-3.24 (m, 1H), 3.46-3.52 (m, 1H), 3.85-3.90 (m, 1H), 6.42 (s, 1H), 6.57-6.59 (m, 1H), 6.62-6.67 (m, 1H), 6.97-7.02 (m, 1H), 7.34 (d, J = 7.6 Hz, 1H), 7.39-7.46 (m, 3H), 7.97-7.99 (m, 1H); MS m/z 385 (M + 1). |
| 421 | 4-((3-Chloro-2-fluorophenyl)amino)-N,N-diethyl-8-methyl-1-naphthamide | 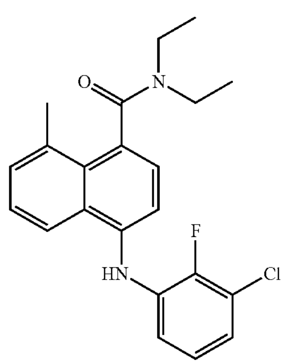 [SMILES: CCN(CC)C(=O)c1ccc(Nc2cccc(Cl)c2F)c2cccc(C)c12] | ¹H NMR (400 MHz, CDCl₃) δ (as mixture of rotamers): 1.07 (t, J = 7.2 Hz, 3H), 1.34 (t, J = 7.2 Hz, 3H), 2.70 (s, 3H), 3.12-3.15 (m, 1H), 3.20-3.24 (m, 1H), 3.45-3.50 (m, 1H), 3.85-3.88 (m, 1H), 6.11 (s, 1H), 6.79-6.82 (m, 1H), 6.87-6.89 (m, 2H), 7.30-7.32 (m, 1H), 7.39-7.46 (m, 3H), 7.99-8.01 (m, 1H); MS m/z 385 (M + 1). |

TABLE 1b-continued

| E. No | Chemical name | Structure | Mass/¹H NMR |
|---|---|---|---|
| 422 | 4-((2,3-Dimethylphenyl)amino)-N,N-diethyl-8-methyl-1-naphthamide | 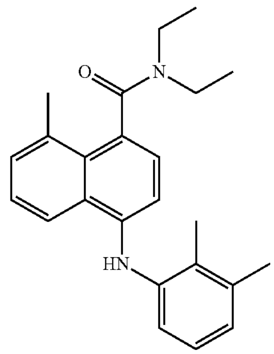 [SMILES: CCN(CC)C(=O)c1ccc(Nc2cccc(C)c2C)c2cccc(C)c12] | ¹H NMR (400 MHz, CDCl$_3$) δ (as mixture of rotamers): 1.04 (t, J = 7.2 Hz, 3H), 1.32 (t, J = 7.2 Hz, 3H), 2.19 (s, 3H), 2.37 (s, 3H), 2.68 (s, 3H), 3.09-3.14 (m, 1H), 3.23-3.29 (m, 1H), 3.42-3.47 (m, 1H), 3.83-3.88 (m, 1H), 5.89 (s, 1H), 6.78 (d, J = 8.0 Hz, 1H), 6.92 (d, J = 8.0 Hz, 1H), 6.96 (d, J = 7.6 Hz, 1H), 7.07 (t, J = 7.6 Hz, 1H), 7.17 (d, J = 7.6 Hz, 1H), 7.37-7.44 (m, 2H), 7.99-8.00 (m, 1H); MS m/z 361 (M + 1). |
| 423 | N,N-Diethyl-4-((3-fluoro-2-(trifluoromethyl)phenyl)amino)-8-methyl-1-naphthamide | 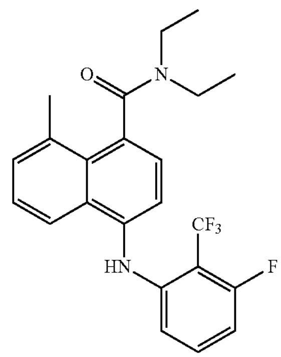 [SMILES: CCN(CC)C(=O)c1ccc(Nc2cccc(F)c2C(F)(F)F)c2cccc(C)c12] | ¹H NMR (400 MHz, CDCl$_3$) δ (as mixture of rotamers): 1.08 (t, J = 7.2 Hz, 3H), 1.35 (t, J = 7.2 Hz, 3H), 2.70 (s, 3H), 3.11-3.18 (m, 1H), 3.19-3.23 (m, 1H), 3.47-3.52 (m, 1H), 3.85-3.90 (m, 1H), 6.45-6.61 (m, 3H), 7.11-7.17 (m, 1H), 7.34 (d, J = 7.6 Hz, 1H), 7.39-7.45 (m, 3H), 7.91-7.93 (m, 1H); MS m/z 419 (M + 1). |
| 424 | 4-((2-Chloro-3-fluorophenyl)amino)-N,N,8-trimethyl-1-naphthamide | 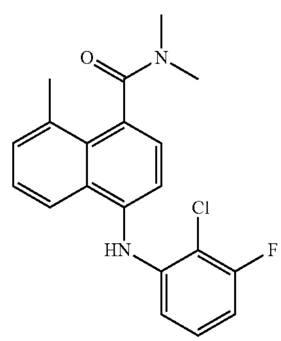 [SMILES: Cc1cccc2c(Nc3cccc(F)c3Cl)ccc(C(=O)N(C)C)c12] | ¹H NMR (400 MHz, CDCl$_3$) δ: 2.64 (s, 3H), 2.85 (s, 3H), 3.23 (s, 3H), 6.43 (brs, 1H), 6.57-6.63 (m, 1H), 6.64-6.67 (m, 1H), 6.96-7.02 (m, 1H), 7.35 (d, J = 7.6 Hz, 1H), 7.41-7.53 (m, 3H), 7.97-8.0 (m, 1H); MS m/z 357 (M + 1). |
| 425 | 4-((2-Fluoro-3-(trifluoromethyl)phenyl)amino)-N,N,8-trimethyl-1-naphthamide | 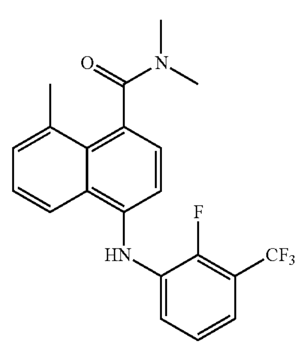 [SMILES: Cc1cccc2c(Nc3cccc(C(F)(F)F)c3F)ccc(C(=O)N(C)C)c12] | ¹H NMR (400 MHz, CDCl$_3$) δ: 2.64 (s, 3H), 2.85 (s, 3H), 3.23 (s, 3H), 6.18 (brs, 1H), 7.01-7.07 (m, 3H), 7.30-7.33 (m, 1H), 7.41-7.54 (m, 3H), 8.0 (d, J = 7.6 Hz, 1H); MS m/z 391 (M + 1). |

TABLE 1b-continued

| E. No | Chemical name | Structure | Mass/$^1$H NMR |
|---|---|---|---|
| 426 | 4-((2,3-Dimethylphenyl)amino)-N,N,8-trimethyl-1-naphthamide | 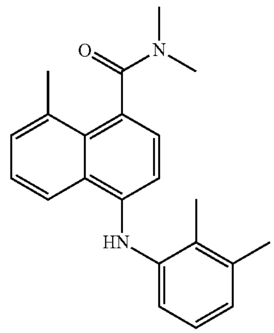 [SMILES: Cc1cccc(Nc2ccc(C(=O)N(C)C)c3c(C)cccc23)c1C] | $^1$H NMR (400 MHz, CDCl$_3$) δ: 2.19 (s, 3H), 2.37 (s, 3H), 2.62 (s, 3H), 2.84 (s, 3H), 3.19 (s, 3H), 6.77 (d, J = 8.0 Hz, 1H), 6.92 (d, J = 7.6 Hz, 1H), 6.97 (d, J = 7.6 Hz, 1H), 7.06 (d, J = 7.6 Hz, 1H), 7.18 (d, J = 7.6 Hz, 1H), 7.38-7.44 (m, 3H), 8.00 (d, J = 8.0 Hz, 1H); MS m/z 333 (M + 1). |
| 427 | N,N,8-Trimethyl-4-((2-methyl-3-(trifluoromethyl)phenyl)amino)-1-naphthamide | 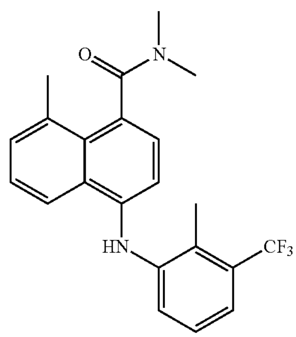 [SMILES: Cc1c(Nc2ccc(C(=O)N(C)C)c3c(C)cccc23)cccc1C(F)(F)F] | $^1$H NMR (400 MHz, CDCl$_3$) δ: 2.43 (s, 3H), 2.63 (s, 3H), 2.85 (s, 3H), 3.21 (s, 3H), 6.99 (d, J = 7.6 Hz, 1H), 7.06 (d, J = 8.0 Hz, 1H), 7.17 (t, J = 7.6 Hz, 1H), 7.25-7.27 (m, 2H), 7.33 (d, J = 7.6 Hz, 1H), 7.41-7.43 (m, 2H), 7.95-7.97 (m, 1H); MS m/z 387 (M + 1). |
| 428 | 4-((3-Fluoro-2-(trifluoromethyl)phenyl)amino)-N,N,8-trimethyl-1-naphthamide | 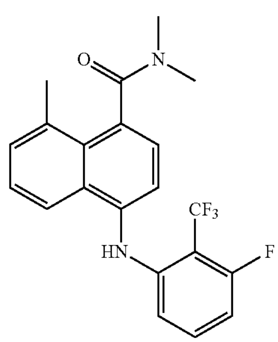 [SMILES: Cc1cccc2c(Nc3cccc(F)c3C(F)(F)F)ccc(C(=O)N(C)C)c12] | $^1$H NMR (400 MHz, CDCl$_3$) δ: 2.64 (s, 3H), 2.85 (s, 3H), 3.23 (s, 3H), 5.95-5.98 (m, 1H), 6.46-6.62 (m, 2H), 7.01-7.17 (m, 1H), 7.33-7.35 (m, 1H), 7.41-7.54 (m, 3H), 7.93-7.95 (m, 1H); MS m/z 391 (M + 1). |
| 429 | 4-((3-Fluoro-2-methylphenyl)amino)-N,N,8-trimethyl-1-naphthamide | 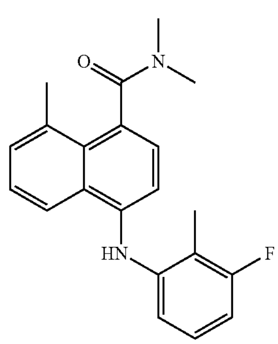 [SMILES: Cc1c(F)cccc1Nc1ccc(C(=O)N(C)C)c2c(C)cccc12] | $^1$H NMR (400 MHz, CDCl$_3$) δ: 2.22 (s, 3H), 2.63 (s, 3H), 2.84 (s, 3H), 3.21 (s, 3H), 5.83 (s, 1H), 6.70-6.75 (m, 2H), 7.02-7.07 (m, 2H), 7.25 (d, J = 7.6 Hz, 1H), 7.39-7.44 (m, 2H), 7.96-7.99 (m, 1H); MS m/z 337 (M + 1). |

TABLE 1b-continued

| E. No | Chemical name | Structure | Mass/¹H NMR |
|---|---|---|---|
| 430 | 4-((3-Chloro-2-methylphenyl)amino)-N,N,8-trimethyl-1-naphthamide | 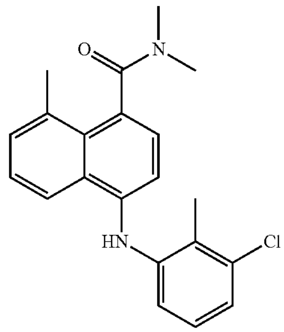 [SMILES: Cc1c(Cl)cccc1Nc1ccc(C(=O)N(C)C)c2c(C)cccc12] | ¹H NMR (400 MHz, CDCl$_3$) δ: 2.37 (s, 3H), 2.62 (s, 3H), 2.84 (s, 3H), 3.22 (s, 3H), 6.84 (dd, J = 8.0 Hz, J = 0.8 Hz, 1H), 6.95 (d, J = 8.0 Hz, 1H), 7.03 (t, J = 7.6 Hz, 1H), 7.09 (dd, J = 8.0 Hz, J = 1.2 Hz, 1H), 7.23 (d, J = 7.6 Hz, 1H), 7.39-7.44 (m, 2H), 7.95-7.97 (m, 1H); MS m/z 353 (M + 1). |
| 431 | 4-((3-Chloro-2-fluorophenyl)amino)-N,N,8-trimethyl-1-naphthamide | 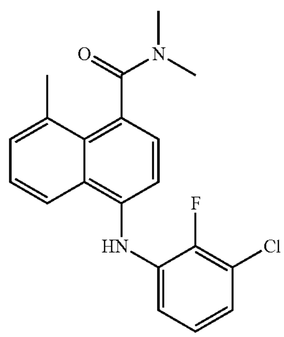 [SMILES: Cc1cccc2c(Nc3cccc(Cl)c3F)ccc(C(=O)N(C)C)c12] | ¹H NMR (400 MHz, CDCl$_3$) δ: 2.64 (s, 3H), 2.84 (s, 3H), 3.22 (s, 3H), 6.06 (s, 1H), 6.78-6.89 (m, 3H), 7.32 (d, J = 7.6 Hz, 1H), 7.39-7.53 (m, 3H), 8.00 (d, J = 8.0 Hz, 1H); MS m/z 357 (M + 1). |
| 432 | N,N-Diethyl-4-((5-fluoro-2-methylphenyl)amino)-8-methyl-1-naphthamide | 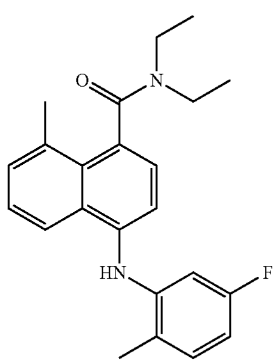 [SMILES: CCN(CC)C(=O)c1ccc(Nc2cc(F)ccc2C)c2cccc(C)c12] | MS m/z 365 (M + 1) |
| 433 | 3-((4-(Diethylcarbamoyl)-5-methylnaphthalen-1-yl)amino)-2-methyl benzoic acid | 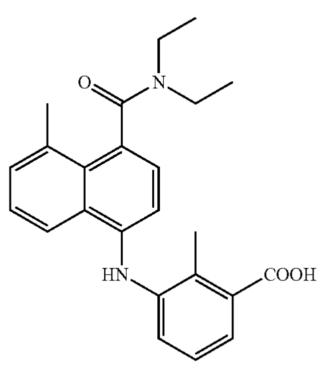 [SMILES: CCN(CC)C(=O)c1ccc(Nc2cccc(C(=O)O)c2C)c2cccc(C)c12] | MS m/z 391 (M + 1), 413 (M+ Na) |

TABLE 1b-continued

| E. No | Chemical name | Structure | Mass/$^1$H NMR |
|---|---|---|---|
| 434 | 4-((2,3-Difluorophenyl)amino)-N,N-diethyl-8-methyl-1-naphthamide | 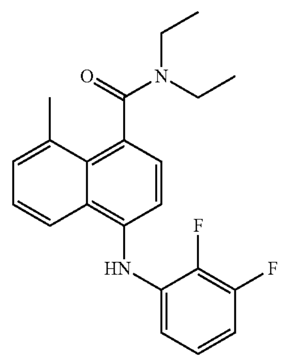 [SMILES: CCN(CC)C(=O)c1ccc(Nc2cccc(F)c2F)c2cccc(C)c12] | MS m/z 369 (M + 1) |
| 435 | 2-Chloro-3-((4-(diethylcarbamoyl)-5-methylnaphthalen-1-yl)amino) benzoic acid | 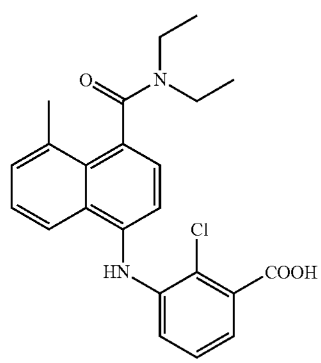 [SMILES: CCN(CC)C(=O)c1ccc(Nc2cccc(C(=O)O)c2Cl)c2cccc(C)c12] | MS m/z 411 (M + 1), 433 (M + Na) |
| 436 | 4-((2,5-Bis(trifluoromethyl)phenyl)amino)-N,N-diethyl-8-methyl-1-naphthamide | 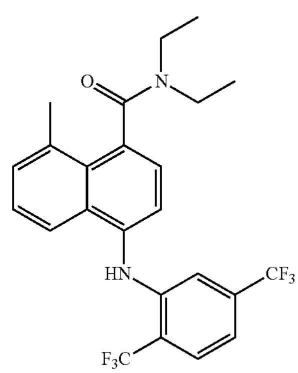 [SMILES: CCN(CC)C(=O)c1ccc(Nc2cc(C(F)(F)F)ccc2C(F)(F)F)c2cccc(C)c12] | MS m/z 469 (M + 1) |
| 437 | N,N-Diethyl-4-((2-methoxy-5-(trifluoromethyl)phenyl)amino)-8-methyl-1-naphthamide | 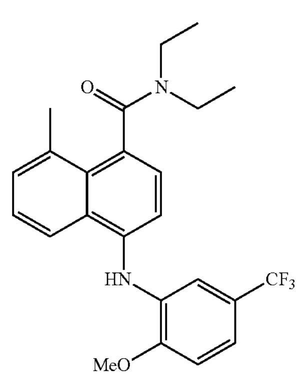 [SMILES: CCN(CC)C(=O)c1ccc(Nc2cc(C(F)(F)F)ccc2OC)c2cccc(C)c12] | MS m/z 431 (M + 1) |

TABLE 1b-continued

| E. No | Chemical name | Structure | Mass/$^1$H NMR |
|---|---|---|---|
| 438 | 3-((4-(Dimethylcarbamoyl)-5-methylnaphthalen-1-yl)amino)-2-methylbenzoic acid | 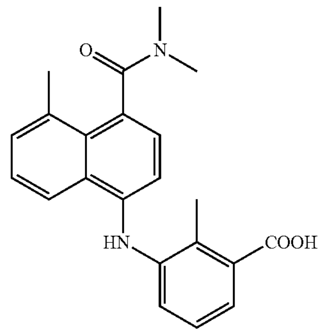 [SMILES: Cc1c(Nc2ccc(C(=O)N(C)C)c3c(C)cccc23)cccc1C(=O)O] | MS m/z 363 (M + 1), 385 (M + Na) |
| 439 | 3-((4-(Dimethylcarbamoyl)-5-methylnaphthalen-1-yl)amino)-2-fluorobenzoic acid | 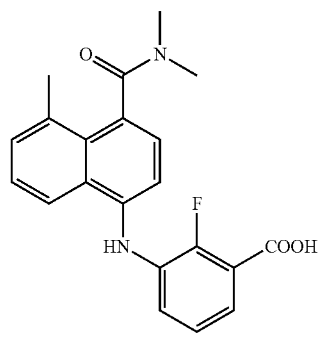 [SMILES: Cc1cccc2c(Nc3cccc(C(=O)O)c3F)ccc(C(=O)N(C)C)c12] | MS m/z 367 (M + 1), 389 (M + Na) |
| 440 | 4-((5-Chloro-2-methylphenyl)amino)-N,N,8-trimethyl-1-naphthamide | 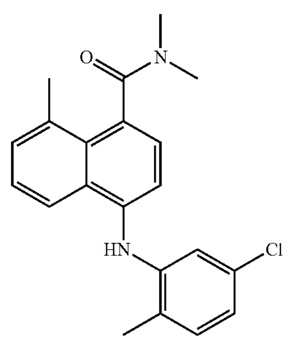 [SMILES: Cc1ccc(Cl)cc1Nc1ccc(C(=O)N(C)C)c2c(C)cccc12] | MS m/z 353 (M + 1) |
| 441 | 4-((5-Chloro-2-fluorophenyl)amino)-N,N,8-trimethyl-1-naphthamide | 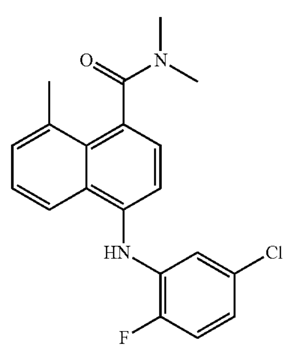 [SMILES: Cc1cccc2c(Nc3cc(Cl)ccc3F)ccc(C(=O)N(C)C)c12] | MS m/z 357 (M + 1) |

TABLE 1b-continued

| E. No | Chemical name | Structure | Mass/$^1$H NMR |
|---|---|---|---|
| 442 | 4-((2-Chloro-5-methylphenyl)amino)-N,N,8-trimethyl-1-naphthamide | 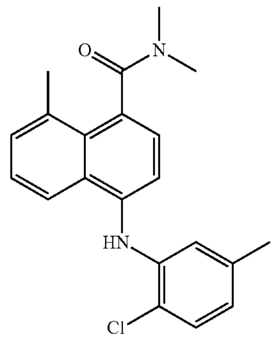 [SMILES: Cc1ccc(Cl)c(Nc2ccc(C(=O)N(C)C)c3c(C)cccc23)c1] | MS m/z 353 (M + 1) |
| 443 | 4-((4-Chloro-3-methylphenyl)amino)-N,N,8-trimethyl-1-naphthamide | 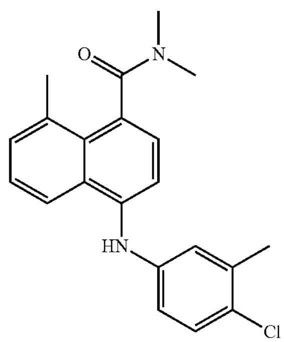 [SMILES: Cc1cc(Nc2ccc(C(=O)N(C)C)c3c(C)cccc23)ccc1Cl] | MS m/z 353 (M + 1) |
| 444 | 4-((2,3-Difluorophenyl)amino)-N,N,8-trimethyl-1-naphthamide | 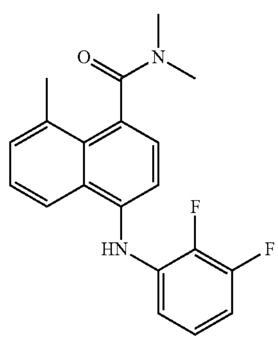 [SMILES: Cc1cccc2c(Nc3cccc(F)c3F)ccc(C(=O)N(C)C)c12] | MS m/z 341 (M + 1) |
| 445 | 4-((5-Fluoro-2-methylphenyl)amino)-N,N,8-trimethyl-1-naphthamide | 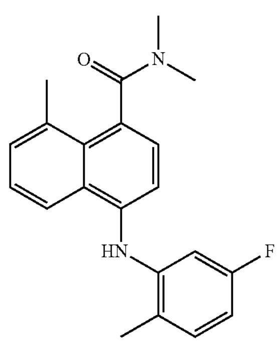 [SMILES: Cc1ccc(F)cc1Nc1ccc(C(=O)N(C)C)c2c(C)cccc12] | MS m/z 337 (M + 1) |

TABLE 1b-continued

| E. No | Chemical name | Structure | Mass/¹H NMR |
|---|---|---|---|
| 446 | 4-((4-Fluoro-3-(trifluoromethyl)phenyl)amino)-N,N,8-trimethyl-1-naphthamide | 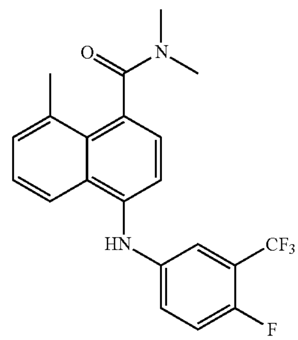 [SMILES: Cc1cccc2c(Nc3ccc(F)c(C(F)(F)F)c3)ccc(C(=O)N(C)C)c12] | MS m/z 391 (M + 1) |
| 447 | 4-((2-Chloro-5-fluorophenyl)amino)-N,N,8-trimethyl-1-naphthamide | 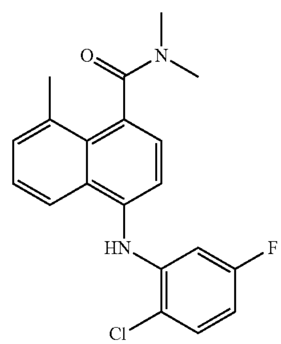 [SMILES: Cc1cccc2c(Nc3cc(F)ccc3Cl)ccc(C(=O)N(C)C)c12] | MS m/z 357 (M + 1) |
| 448 | 4-((3-Chloro-4-fluorophenyl)amino)-N,N,8-trimethyl-1-naphthamide | 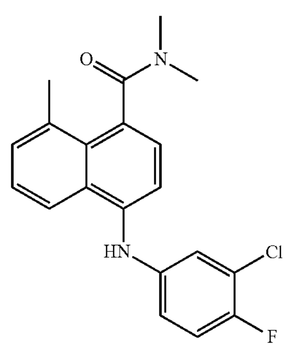 [SMILES: Cc1cccc2c(Nc3ccc(F)c(Cl)c3)ccc(C(=O)N(C)C)c12] | MS m/z 357 (M + 1) |
| 449 | N-Ethyl-4-((2-fluoro-3-(trifluoromethyl)phenyl)amino)-N,8-dimethyl-1-naphthamide | 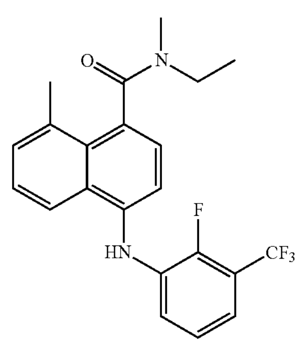 [SMILES: CCN(C)C(=O)c1ccc(Nc2cccc(C(F)(F)F)c2F)c2cccc(C)c12] | ¹H NMR (400 MHz, CDCl₃) δ (as mixture of rotamers): 1.10 (t, J = 7.2 Hz, 3H), 1.33 (t, J = 7.2 Hz, 3H), 2.67 (s, 3H), 2.68 (s, 3H), 2.83 (s, 3H), 3.02-3.11 (m, 1H), 3.19 (s, 3H), 3.24-3.33 (m, 1H), 3.65-3.80 (m, 2H), 6.14-6.19 (m, 2H), 6.99-7.07 (m, 6H), 7.30-7.35 (m, 2H), 7.40-7.47 (m, 6H), 7.99 (d, J = 8.0 Hz, 2H); MS m/z 405 (M + 1). |

TABLE 1b-continued

| E. No | Chemical name | Structure | Mass/¹H NMR |
|---|---|---|---|
| 450 | N-Ethyl-4-((3-fluoro-2-methylphenyl)amino)-N,8-dimethyl-1-naphthamide | 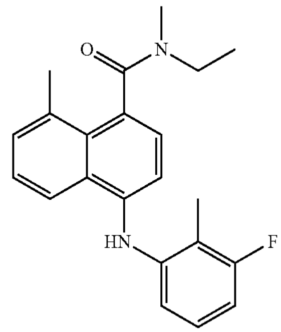 [SMILES: CCN(C)C(=O)c1ccc(Nc2cccc(F)c2C)c2cccc(C)c12] | ¹H NMR (400 MHz, CDCl$_3$) δ (as mixture of rotamers): 1.11 (t, J = 7.2 Hz, 3H), 1.32 (t, J = 7.2 Hz, 3H), 2.23 (s, 3H), 2.40 (s, 3H), 2.67 (s, 3H), 2.68 (s, 3H), 2.83 (s, 3H), 3.02-3.08 (m, 1H), 3.17 (s, 3H), 3.27-3.32 (m, 1H), 3.64-3.77 (m, 2H), 6.70-6.73 (m, 3H), 7.01-7.06 (m, 3H), 7.22-7.26 (m, 3H), 7.30-7.44 (m, 5H), 7.99-8.02 (m, 2H); MS m/z 351 (M + 1). |
| 451 | 4-((2-Chloro-3-fluorophenyl)amino)-N-ethyl-N,8-dimethyl-1-naphthamide | 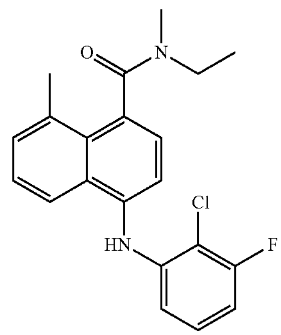 [SMILES: CCN(C)C(=O)c1ccc(Nc2cccc(F)c2Cl)c2cccc(C)c12] | ¹H NMR (400 MHz, CDCl$_3$) δ (as mixture of rotamers): 1.11 (t, J = 7.2 Hz, 3H), 1.33 (t, J = 7.2 Hz, 3H), 2.67 (s, 6H), 2.84 (s, 3H), 3.05-3.19 (m, 1H), 3.19 (s, 3H), 3.26-3.27 (m, 1H), 3.68-3.80 (m, 2H), 6.33 (s, 2H), 6.57-6.67 (m, 4H), 6.99-7.01 (m, 2H), 7.32-7.54 (m, 8H), 7.98-8.00 (m, 2H); MS m/z 370 (M + 1). |
| 452 | N-Ethyl-N,8-dimethyl-4-((2-methyl-3-(trifluoromethyl)phenyl)amino)-1-naphthamide | 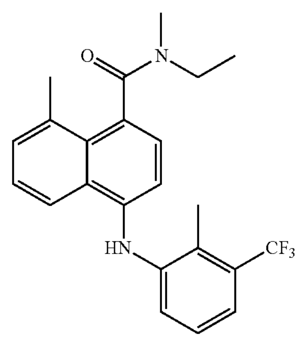 [SMILES: CCN(C)C(=O)c1ccc(Nc2cccc(C(F)(F)F)c2C)c2cccc(C)c12] | ¹H NMR (400 MHz, CDCl$_3$) δ (as mixture of rotamers): 1.11 (t, J = 7.2 Hz, 3H), 1.32 (t, J = 7.2 Hz, 3H), 2.43 (s, 6H), 2.67 (s, 3H), 2.68 (, 3H), 2.86 (s, 3H), 3.05-3.08 (m, 1H), 3.19 (s, 3H), 3.26-3.32 (m, 1H), 3.63-3.74 (m, 2H), 6.99-7.00 (m, 4H), 7.01-7.08 (m, 4H), 7.15-7.23 (m, 4H), 7.41-7.59 (m, 4H), 7.93-7.94 (m, 2H); MS m/z 401 (M + 1). |
| 453 | 4-((2,3-Dimethylphenyl)amino)-N-ethyl-N,8-dimethyl-1-naphthamide | 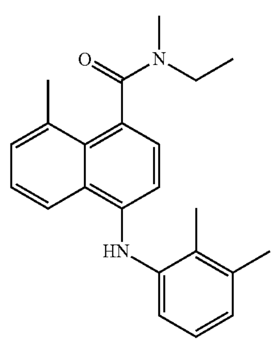 [SMILES: CCN(C)C(=O)c1ccc(Nc2cccc(C)c2C)c2cccc(C)c12] | ¹H NMR (400 MHz, CDCl$_3$) δ (as mixture of rotamers): 1.09 (t, J = 7.2 Hz, 3H), 1.33 (t, J = 7.2 Hz, 3H), 2.19 (s, 3H), 2.37 (s, 6H), 2.43 (s, 6H), 2.64 (s, 3H), 2.65 (, 3H), 2.82 (s, 3H), 3.02-3.05 (m, 1H), 3.16 (s, 3H), 3.28-3.31 (m, 1H), 3.50-3.78 (m, 2H), 6.76-6.79 (m, 2H), 6.92-6.96 (m, 3H), 7.01-7.19 (m, 5H), 7.32-7.54 (m, 4H), 7.98-7.99 (m, 2H); MS m/z 347 (M + 1). |

TABLE 1b-continued

| E. No | Chemical name | Structure | Mass/¹H NMR |
|---|---|---|---|
| 454 | N-Ethyl-4-((5-fluoro-2-methylphenyl)amino)-N,8-dimethyl-1-naphthamide | 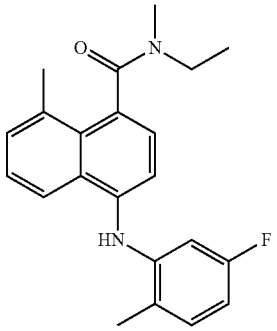 [SMILES: CCN(C)C(=O)c1ccc(Nc2cc(F)ccc2C)c2cccc(C)c12] | MS m/z 351 (M + 1) |
| 455 | N-Ethyl-4-((4-fluoro-3-(trifluoromethyl)phenyl)amino)-N,8-dimethyl-1-naphthamide | 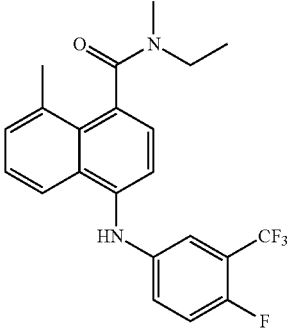 [SMILES: CCN(C)C(=O)c1ccc(Nc2ccc(F)c(C(F)(F)F)c2)c2cccc(C)c12] | ¹H NMR (400 MHz, CDCl₃) δ (as mixture of rotamers): 1.12 (t, J = 7.2 Hz, 3H), 1.34 (t, J = 7.2 Hz, 3H), 2.67 (s, 3H), 2.68 (, 3H), 2.83 (s, 3H), 3.07-3.12 (m, 1H), 3.19 (s, 3H), 3.28-3.32 (m, 1H), 3.63-3.79 (m, 2H), 6.61-6.62 (m, 2H), 6.91-6.97 (m, 2H), 7.07-7.10 (m, 2H), 7.20-7.30 (m, 4H), 7.38-7.54 (m, 6H), 7.82-7.84 (m, 1H), 7.91-7.83 (m, 1H); MS m/z 405 (M + 1). |
| 456 | 4-((3-Chloro-2-methylphenyl)amino)-N-ethyl-N,8-dimethyl-1-naphthamide | 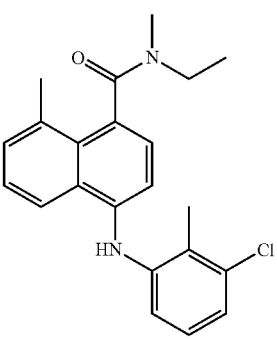 [SMILES: CCN(C)C(=O)c1ccc(Nc2cccc(Cl)c2C)c2cccc(C)c12] | MS m/z 367 (M + 1) |
| 457 | 4-((5-Chloro-2-methylphenyl)amino)-N-ethyl-N,8-dimethyl-1-naphthamide | 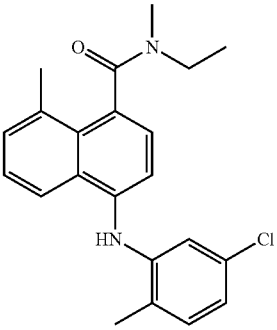 [SMILES: CCN(C)C(=O)c1ccc(Nc2cc(Cl)ccc2C)c2cccc(C)c12] | MS m/z 367 (M + 1) |

TABLE 1b-continued

| E. No | Chemical name | Structure | Mass/$^1$H NMR |
|---|---|---|---|
| 458 | 4-((2,3-Difluorophenyl)amino)-N-ethyl-N,8-dimethyl-1-naphthamide | 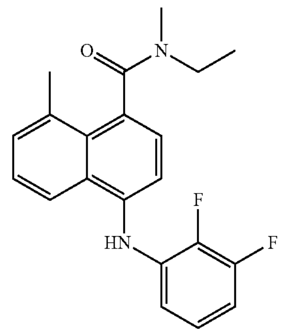 [SMILES: CCN(C)C(=O)c1ccc(Nc2cccc(F)c2F)c2cccc(C)c12] | MS m/z 355 (M + 1) |
| 459 | 4-((2-Chloro-5-fluorophenyl)amino)-N-ethyl-N,8-dimethyl-1-naphthamide | 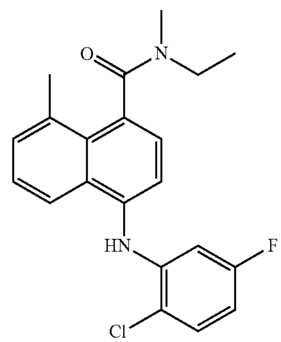 [SMILES: CCN(C)C(=O)c1ccc(Nc2cc(F)ccc2Cl)c2cccc(C)c12] | MS m/z 370 (M + 1) |
| 460 | 3-((4-(Dipropylcarbamoyl)-5-methylnaphthalen-1-yl)amino)-2-methylbenzoic acid | 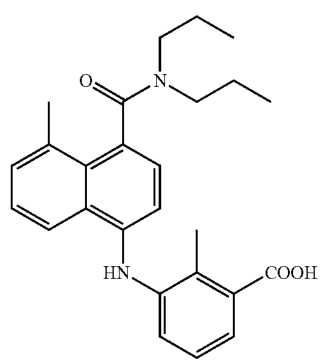 [SMILES: CCCN(CCC)C(=O)c1ccc(Nc2cccc(C(=O)O)c2C)c2cccc(C)c12] | MS m/z 419 (M + 1) |
| 461 | 2-Methyl-3-((5-methyl-4-(piperidin-1-carbonyl)naphthalen-1-yl)amino) benzoic acid | 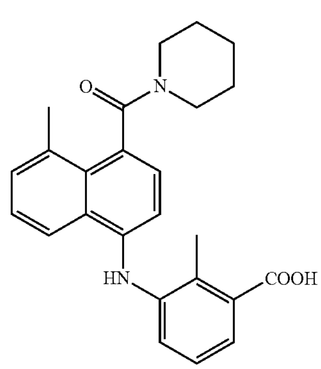 [SMILES: Cc1c(Nc2ccc(C(=O)N3CCCCC3)c3c(C)cccc23)cccc1C(=O)O] | $^1$H NMR (400 MHz, dMSO-d$_6$) δ: 1.39-1.41 (m, 2H), 1.55-1.99 (m, 4H), 2.33 (s, 3H), 2.54 (s, 3H), 3.02-3.09 (m, 1H), 3.19-3.20 (m, 1H), 3.22-3.29 (m, 1H), 4.02-4.04 (m, 1H), 6.48 (d, J = 7.6 Hz, 1H), 7.10-7.12 (m, 2H), 7.22 (t, J = 8.0 H, 1H), 7.38-7.48 (m, 2H), 7.49-7.50 (m, 1H), 7.94 (s, 1H), 8.16-8.18 (m, 1H), 12.90 (s, 1H); MS m/z 403 (M + 1). |

TABLE 1b-continued

| E. No | Chemical name | Structure | Mass/¹H NMR |
|---|---|---|---|
| 462 | 2-Methyl-3-((5-methyl-4-(morpholin-4-carbonyl)naphthalen-1-yl)amino)benzoic acid | 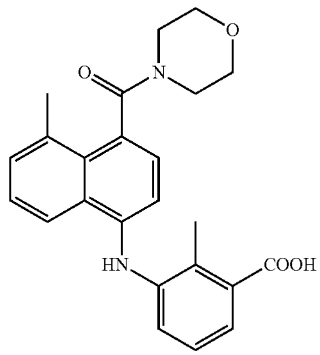 [SMILES: Cc1c(Nc2ccc(C(=O)N3CCOCC3)c3c(C)cccc23)cccc1C(=O)O] | ¹H NMR (400 MHz, dMSO-d$_6$) δ: 2.32 (s, 3H), 2.55 (s, 3H), 3.12-3.34 (m, 3H), 3.39-3.52 (m, 3H), 3.62-3.72 (m, 1H), 3.84-3.87 (m, 1H), 6.39-6.51 (m, 1H), 7.12-7.26 (m, 3H), 7.39-7.51 (m, 3H), 7.99 (s, 1H), 8.18-8.20 (m, 1H), 12.92 (s, 1H); MS m/z 405 (M + 1). |
| 463 | 4-Methyl-3-((5-methyl-4-(piperidin-1-carbonyl)naphthalen-1-ylamino) benzoic acid | 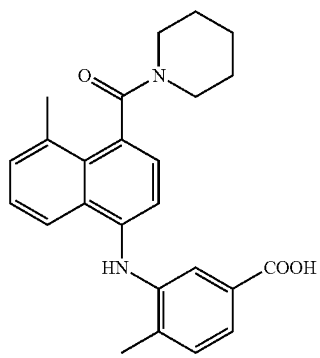 [SMILES: Cc1ccc(C(=O)O)cc1Nc1ccc(C(=O)N2CCCCC2)c2c(C)cccc12] | ¹H NMR (400 MHz, dMSO-d$_6$) δ: 1.39-1.41 (m, 2H), 1.56-1.99 (m, 4H), 2.26 (s, 3H), 2.55 (s, 3H), 3.04-3.09 (m, 1H), 3.19-3.21 (m, 1H), 3.22-3.29 (m, 1H), 3.98-4.04 (m, 1H), 6.69 (d, J = 8.0 Hz, 1H), 7.17 (d, J = 7.6 Hz, 1H), 7.35-7.43 (m, 4H), 7.51-7.54 (m, 1H), 7.86 (s, 1H), 8.11-8.13 (m, 1H), 12.71 (s, 1H); MS m/z 403 (M + 1). |
| 464 | 4-((5-Methyl-4-(piperidin-1-carbonyl)naphthalen-1-yl)amino)-3-(trifluoromethyl)benzoic acid | 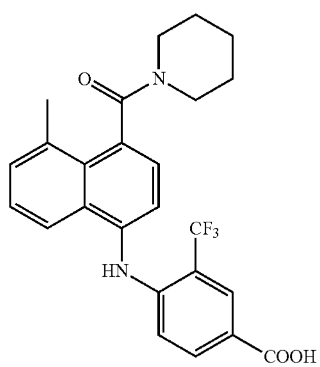 [SMILES: Cc1cccc2c(Nc3ccc(C(=O)O)cc3C(F)(F)F)ccc(C(=O)N3CCCCC3)c12] | ¹H NMR (400 MHz, dMSO-d$_6$) δ: 1.39-1.41 (m, 2H), 1.56-1.99 (m, 4H), 2.60 (s, 3H), 3.07-3.11 (m, 1H), 3.16-3.38 (m, 2H), 4.00-4.06 (m, 1H), 6.31 (d, J = 8.4 Hz, 1H), 7.40-7.48 (m, 4H), 7.74-7.78 (m, 2H), 8.01-8.09 (m, 1H), 8.41 (s, 1H), 12.67 (s, 1H); MS m/z 457 (M + 1). |
| 465 | 3-(3-((5-Methyl-4-(piperidin-1-carbonyl)naphthalen-1-yl)amino) propanoic acid | 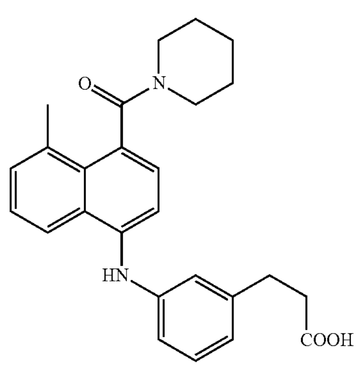 [SMILES: Cc1cccc2c(Nc3cccc(CCC(=O)O)c3)ccc(C(=O)N3CCCCC3)c12] | MS m/z 417 (M + 1). |

TABLE 1b-continued

| E. No | Chemical name | Structure | Mass/$^1$H NMR |
|---|---|---|---|
| 466 | 3-((5-Methyl-4-(piperidin-1-carbonyl)naphthalen-1-yl)amino) benzoic acid | 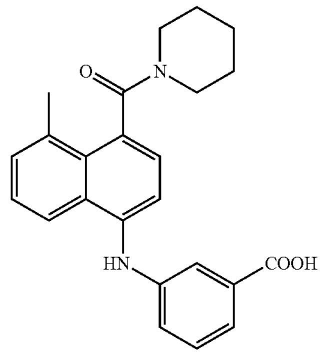 [SMILES: Cc1cccc2c(Nc3cccc(C(=O)O)c3)ccc(C(=O)N3CCCCC3)c12] | $^1$H NMR (400 MHz, CDCl$_3$) δ: 1.43-1.67 (m, 6H), 2.56 (s, 3H), 2.51 (s, 3H), 3.04-3.09 (m, 1H), 3.21-3.29 (m, 2H), 3.96-3.99 (m, 1H), 7.21-7.25 (m, 2H), 7.30-7.34 (m, 2H), 7.38-7.45 (m, 3H), 7.60 (s, 1H), 8.09-8.11 (m, 1H), 8.48 (s, 1H); MS m/z 389 (M + 1). |
| 467 | 3-((5-Methyl-4-(morpholin-4-carbonyl)naphthalen-1-yl)amino) benzoic acid | 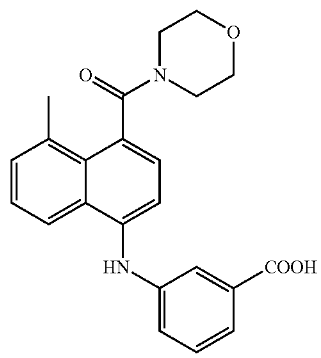 [SMILES: Cc1cccc2c(Nc3cccc(C(=O)O)c3)ccc(C(=O)N3CCOCC3)c12] | MS m/z 391 (M + 1). |

E. No is Example Number

Example-468

8-Chloro-N,N-dimethyl-4-((2-methyl-3-(trifluoromethyl)phenyl)amino)-1-naphthamide

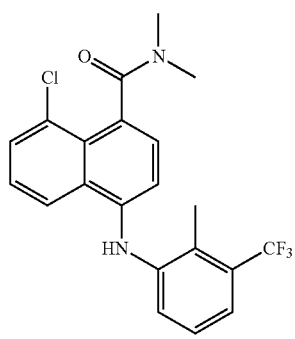 [SMILES: Cc1c(Nc2ccc(C(=O)N(C)C)c3c(Cl)cccc23)cccc1C(F)(F)F]

Step-1: 5-Methoxynaphthalen-1-amine

To a stirred suspension of NaH (7.5 g, 188.0 mmol) in DMF (500 mL) was added a solution of 5-amino-1-naphthol (25.0 g, 157 mmol) dropwise at 0° C. After the addition, mixture was stirred for 30 min at 0° C. and for 1 h at RT. Then a solution of iodomethane (9.82 mL, 157 mmol) in DMF (25 mL) was added dropwise to the mixture at 0° C. and the reaction mixture was allowed to RT and stirred overnight. It was slowly quenched with ice and extracted with EtOAc. The combined organic layers were washed with water, brine, and dried. The solvent was removed under reduced pressure and the residue was purified by column chromatography to afford the title compound (23.0 g, 85%).

Step-2: 1-Chloro-5-methoxynaphthalene

To a stirred solution of $^t$BuNO$_2$ (28.7 mL, 239.0 mmol) in CH$_3$CN (300 mL) was added, CuCl$_2$ (21.4 g, 159 mmol) at 0° C. After the addition, the mixture was stirred for 30 min at 0° C. and then a solution of 5-methoxynaphthalen-1-amine (23.0 g, 133 mmol) (step-1 intermediate) in CH$_3$CN (300 mL) was added dropwise to the mixture at 0° C. The reaction mixture was stirred at 0° C. for 30 min and then warmed to room temperature, and stirred for 1 h. It was quenched with 2N HCl (200 mL), and the aq. layer was extracted with EtOAc. The combined organic layer was washed with water, brine, and dried over Na$_2$SO$_4$. The solvent was removed under reduced pressure and the residue was purified by column chromatography to afford chloro derivative (9.2 g, 36%).

Step-3: 8-Chloro-4-methoxy-1-naphthaldehyde

To a stirred solution of 1-chloro-5-methoxynaphthalene (step-2 intermediate) (9.2 g, 47.8 mmol) in toluene (20 mL) and DMF (5.55 mL) at 0° C. was added, POCl$_3$ (5.4 mL, 57.3 mmol) slowly. The reaction mixture was stirred at 0° C. for 45 min and then heated to reflux for 6-8 h. The dark red solution was cooled to RT and poured into a mixture of ice (50 mL) and 10% aq. NaOH (100 mL) with stirring. Aq. layer was extracted with EtOAc and the combined organic layer was washed with 2 N HCl, water, brine, dried and filtered. The solvent was evaporated and the crude product was washed with hexane, to provide the desired aldehyde intermediate as a reddish brown solid (2.1 g, 20%).

Step-4: 8-Chloro-4-methoxy-1-naphthoic acid

To a mixture of 8-chloro-4-methoxy-1-naphthaldehyde (step-3 intermediate) (2.0 g, 9.06 mmol) in tBuOH (20 mL) and 2-methyl-2-butene (14.4 mL, 136.0 mmol) at 0° C. was added a solution of $NaClO_2$ (4.1 g, 45.3 mmol) and $NaH_2PO_4.H_2O$ (6.3 g, 45.3 mmol) in $H_2O$ (16 mL) dropwise. The resulting solution was stirred at RT for 24 h. The solvent was evaporated and the crude mixture was basified with 10% NaOH solution and then washed with EtOAc. The aqueous layer was acidified with 1 N HCl and again extracted with EtOAc. The combined organic layer was washed with water, brine, dried ($Na_2SO_4$) and filtered. The solvent was evaporated to provide the desired acid as pale yellow solid (1.7 g, 80%).

Step-5: 8-Chloro-4-methoxy-N,N-dimethyl-1-naphthamide

To a mixture of 8-chloro-4-methoxy-1-naphthoic acid (step-4 intermediate) (0.5 g, 2.11 mmol) in $CH_2Cl_2$ (5 mL) was added, $SOCl_2$ (0.31 mL, 4.22 mmol, 2.0 eq.) and the mixture was stirred at RT for 3 h. The solvent was evaporated under reduced pressure and the crude product was dissolved in DCM (10 mL). To this, DIPEA (0.74 mL, 4.23 mmol) was added followed by dimethylamine (1.5 eq.) and the reaction mixture was stirred at RT for 3 h and then quenched with ice. The aqueous layer was extracted with dichloromethane and the combined organic layer was washed with sat. $NaHCO_3$ solution, water, brine, dried over $Na_2SO_4$ and filtered. The solvent was evaporated to provide the desired amide derivative (528 mg, 95%) this was used in the next step without any further purification.

Step-6: 8-Chloro-4-hydroxy-N,N-dimethyl-1-naphthamide 8-chloro-4-methoxy-N,N-dimethyl-1-naphthamide (step-5 intermediate) (0.5 g, 1.90 mmol) in DCM (15 mL) was cooled to −78° C. Then, $BBr_3$ (0.72 mL, 7.58 mmol) in DCM (7.5 mL) was added dropwise to the mixture at −78° C. The reaction mixture was warmed to RT and stirred for 2 h, and quenched with brine solution. The aqueous layer was extracted with DCM, and the combined organic layer was washed with, water, brine, dried over $Na_2SO_4$ and filtered. The solvent was evaporated to provide the desired phenol as pale brown solid (445 mg, 94%) that was used in next step without any further purification.

Step-7: 5-Chloro-4-(dimethylcarbamoyl)naphthalen-1-yl trifluoromethanesulfonate To a mixture of 8-chloro-4-methoxy-1-naphthoic acid (step-6 intermediate) (0.14 g, 0.561 mmol) in DCM (5 mL) was added, DIPEA (0.20 mL, 1.12 mmol) at 0° C. After 5 min stirring, $Tf_2O$ (0.11 mL, 0.67 mmol) was added to it. The resulting mixture was stirred for 2 h before quenching with ice water. The aqueous layer was extracted with DCM, and the combined organic layer was washed with, water, brine, dried over $Na_2SO_4$ and filtered. The solvent was removed under reduced pressure and the residue was purified by column chromatography to furnish the desired trifliate intermediate as a pale yellow oil (100 mg, 47%).

Step-8: 8-Chloro-N,N-dimethyl-4-((2-methyl-3-(trifluoromethyl)phenyl)amino)-1-naphthamide In a 15 mL sealed tube, $Pd(OAc)_2$ (3.0 mg, 0.013 mmol) and BINAP (16 mg, 0.026 mmol) were dissolved in dry and degassed toluene (5 mL). After stirring for 5 minutes, the above triflate derivative (step-7 intermediate) (100 mg, 0.262 mmol) was added and the mixture was stirred for another 10 minutes. Then, $Cs_2CO_3$ (300 mg, 0.917 mmol) and 2-methyl-3-trifluoromethyl aniline (50 mg, 0.288 mmol) were added to the mixture. The reaction mixture was stirred for 15 min at RT and then heated to 110° C. overnight. It was cooled to RT and then filtered through celite and washed with EtOAc. The solvent was evaporated under reduced pressure and the crude product was purified by column chromatography to yield the desired compound as an offwhite solid (40 mg, 37.5%).

$^1$H NMR (400 MHz, $CDCl_3$) δ: 2.23 (s, 3H), 2.73 (s, 3H), 3.0 (s, 3H), 6.66 (d, J=8.0 Hz, 1H), 7.20 (d, J=7.6 Hz, 1H), 7.25 (d, J=7.6 Hz, 1H), 7.34 (t, J=8.0 Hz, 1H), 7.44 (d, J=7.6 Hz, 1H), 7.51-7.55 (m, 1H), 7.73-7.75 (m, 1H), 8.17 (s, 1H), 8.27-8.30 (m, 1H); MS m/z 407 (M+1).

Example-469

8-Chloro-4-((3-fluoro-2-(trifluoromethyl)phenyl)amino)-N,N-dimethyl-1-naphthamide

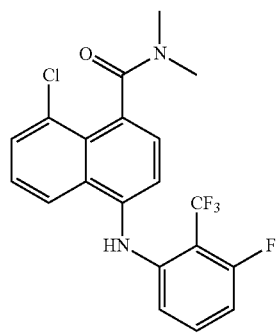

The title compound was prepared by following the similar procedure as described in Step-8 of Example-468 by taking Step-7 intermediate of Example-468 and 3-fluoro-2-(trifluoromethyl)aniline. $^1$H NMR (400 MHz, $CDCl_3$) δ 2.73 (s, 3H), 3.02 (s, 3H), 6.52-6.78 (m, 1H), 6.97-7.09 (m, 1H), 7.18 (d, J=7.6 Hz, 1H), 7.36 (d, J=7.6 Hz, 1H), 7.39-7.43 (m, 1H), 7.53 (t, J=7.6 Hz, 1H), 7.71-7.76 (m, 1H), 7.95-8.11 (m, 1H); MS m/z 411 (M+1).

Example-470

8-Chloro-4-((2-fluoro-3-(trifluoromethyl)phenyl)amino)-N,N-dimethyl-1-naphthamide

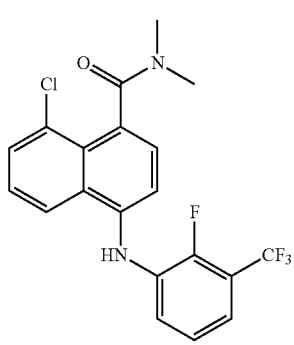

The title compound was prepared by following the similar procedure as described in Step-8 of Example-468 by taking Step-7 intermediate of Example-468 and 2-fluoro-3-(trifluoromethyl)aniline. $^1$H NMR (400 MHz, CDCl$_3$) δ 2.74 (s, 3H), 3.02 (s, 3H), 7.17-7.27 (m, 4H), 7.35 (d, J=7.6 Hz, 1H), 7.53-7.57 (m, 1H), 7.75-7.77 (m, 1H), 8.20-8.23 (m, 1H), 8.57 (s, 1H); MS m/z 411 (M+1).

Example-471

3-((5-Chloro-4-(piperidin-1-carbonyl)naphthalen-1-yl)amino)-2-methylbenzoic acid

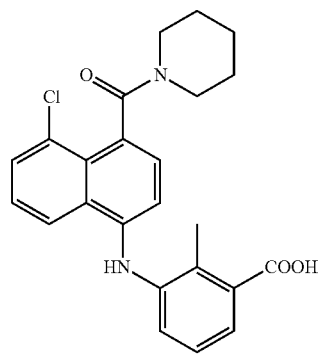 [SMILES: Cc1c(Nc2ccc(C(=O)N3CCCCC3)c3c(Cl)cccc23)cccc1C(=O)O]

The title compound was prepared by following the similar procedure as described in Step-8 of Example-468 by taking Step-7 intermediate of Example-468 and 3-amino-2-methylbenzoic acid. $^1$H NMR (400 MHz, dMSO-d$_6$) □□ 1.30-1.34 (m, 1H), 1.47-1.63 (m, 5H), 2.32 (s, 3H), 3.02-3.04 (m, 1H), 3.15-3.33 (m, 2H), 3.84-3.89 (m, 1H), 6.45 (d, J=7.6 Hz, 1H), 7.19 (t, J=7.6 Hz, 2H), 7.27 (d, J=8.0 Hz, 1H), 7.49-7.56 (m, 2H), 7.70-7.75 (m, 1H), 8.15 (s, 1H), 8.32-8.35 (m, 1H), 12.91 (brs, 1H); MS m/z 423 (M+1).

The below examples given in Table-1c are prepared by following the similar procedure as described in Example-132 by taking appropriate intermediates TABLE 1c

| E. No | Chemical name | Structure |
|---|---|---|
| 472 | 2-Methyl-3-((5-methyl-4-(piperidine-1-carbonyl)naphthalen-1-yl)amino)benzonitrile | 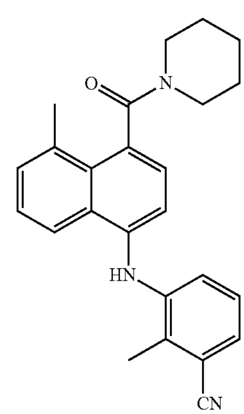 [SMILES: Cc1c(C#N)cccc1Nc1ccc(C(=O)N2CCCCC2)c2c(C)cccc12] |

TABLE 1c-continued

| E. No | Chemical name | Structure |
|---|---|---|
| 473 | (8-Methyl-4-((2-methyl-3-(1-methyl-1H-tetrazol-5-yl)phenyl)amino)naphthalen-1-yl)(piperidin-1-yl)methanone | 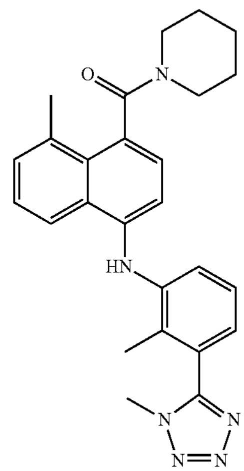 [SMILES: Cc1c(Nc2ccc(C(=O)N3CCCCC3)c3c(C)cccc23)cccc1-c1nnnn1C] |
| 474 | N,N,8-Trimethyl-4-((3-(1-methyl-1H-tetrazol-5-yl)phenyl)amino)-1-naphthamide | 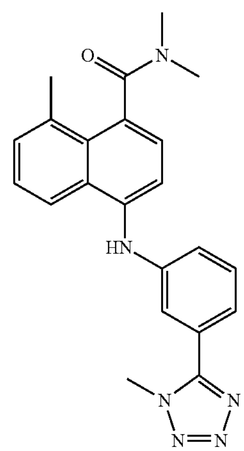 [SMILES: Cc1cccc2c(Nc3cccc(-c4nnnn4C)c3)ccc(C(=O)N(C)C)c12] |
| 475 | N,N-diethyl-8-methyl-4-((2-methyl-3-(1-methyl-1H-tetrazol-5-yl)phenyl)amino)-1-naphthamide | 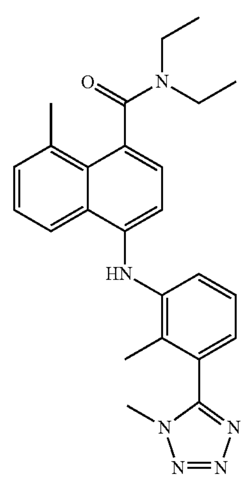 [SMILES: CCN(CC)C(=O)c1ccc(Nc2cccc(-c3nnnn3C)c2C)c2cccc(C)c12] |

TABLE 1c-continued

| E. No | Chemical name | Structure |
|---|---|---|
| 476 | 2-Methyl-3-((5-methyl-4-(morpholine-4-carbonyl)naphthalen-1-yl)amino)benzonitrile | 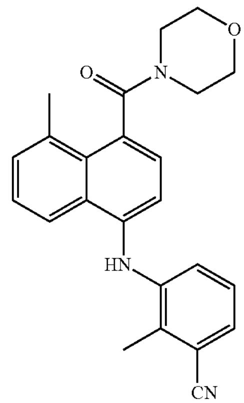 [SMILES: Cc1c(C#N)cccc1Nc1ccc(C(=O)N2CCOCC2)c2c(C)cccc12] |
| 477 | 3-((5-Chloro-4-(piperidine-1-carbonyl)naphthalen-1-yl)amino)-2-methylbenzonitrile | 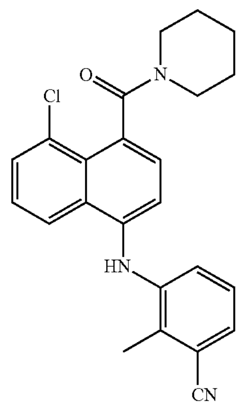 [SMILES: Cc1c(C#N)cccc1Nc1ccc(C(=O)N2CCCCC2)c2c(Cl)cccc12] |
| 478 | 8-Chloro-N,N-dimethyl-4-((3-(1-methyl-1H-tetrazol-5-yl)phenyl)amino)-1-naphthamide | 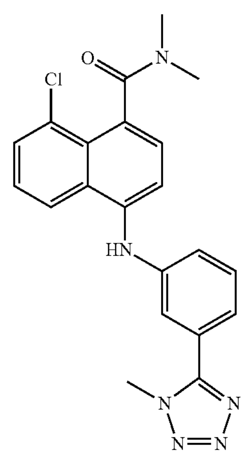 [SMILES: CN(C)C(=O)c1ccc(Nc2cccc(-c3nnnn3C)c2)c2cccc(Cl)c12] |

TABLE 1c-continued
| E. No | Chemical name | Structure |
|---|---|---|
| 479 | 8-Chloro-N,N-diethyl-4-((3-(1-methyl-1H-tetrazol-5-yl)phenyl)amino)-1-naphthamide | 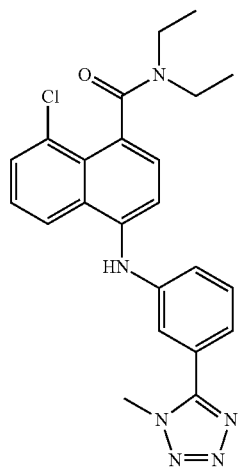 [SMILES: CCN(CC)C(=O)c1ccc(Nc2cccc(-c3nnnn3C)c2)c2cccc(Cl)c12] |
| 480 | (8-Chloro-4-((2-methyl-3-(1-methyl-1H-tetrazol-5-yl)phenyl)amino)naphthalen-1-yl)(piperidin-1-yl)methanone | 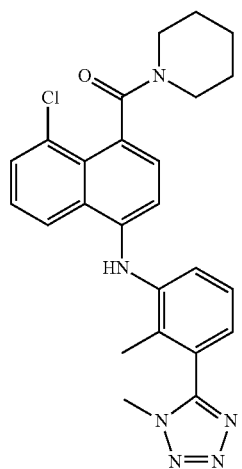 [SMILES: Cc1c(Nc2ccc(C(=O)N3CCCCC3)c3c(Cl)cccc23)cccc1-c1nnnn1C] |

TABLE 1c-continued
| E. No | Chemical name | Structure |
|---|---|---|
| 481 | (8-Chloro-4-((3-(1-methyl-1H-tetrazol-5-yl)phenyl)amino)naphthalen-1-yl)(piperidin-1-yl)methanone | 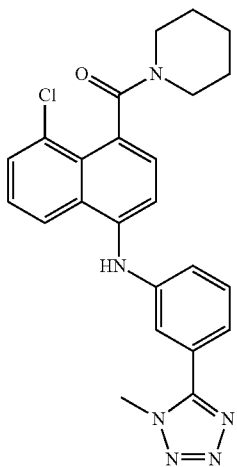 |
| 482 | 3-((5-Fluoro-4-(morpholine-4-carbonyl)naphthalen-1-yl)amino)-2-methylbenzonitrile | 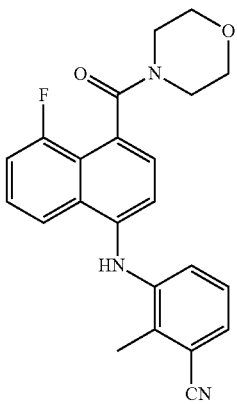 [SMILES: Cc1c(C#N)cccc1Nc1ccc(C(=O)N2CCOCC2)c2c(F)cccc12] |
| 483 | N,N-Diethyl-8-fluoro-4-((2-methyl-3-(1-methyl-1H-tetrazol-5-yl)phenyl)amino)-1-naphthamide | 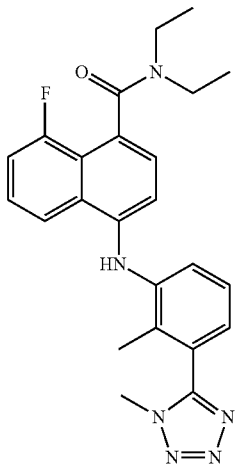 |

TABLE 1c-continued

| E. No | Chemical name | Structure |
|---|---|---|
| 484 | 8-fluoro-N,N-dimethyl-4-((3-(1-methyl-1H-tetrazol-5-yl)phenyl)amino)-1-naphthamide: | 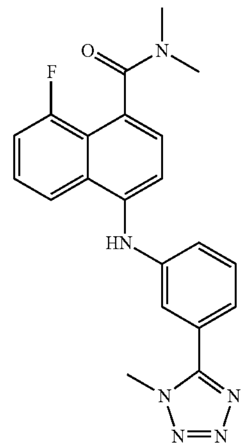 [SMILES: CN(C)C(=O)c1ccc(Nc2cccc(-c3nnnn3C)c2)c2cccc(F)c12] |
| 485 | (8-Fluoro-4-((2-methyl-3-(1-methyl-1H-tetrazol-5-yl)phenyl)amino)naphthalen-1-yl)(piperidin-1-yl)methanone | 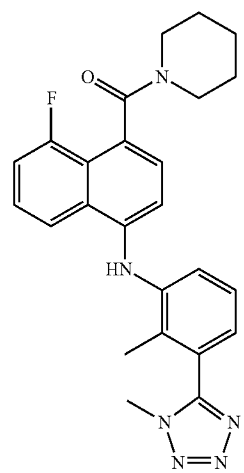 |
| 486 | (8-Fluoro-4-((3-(1-methyl-1H-tetrazol-5-yl)phenyl)amino)naphthalen-1-yl)(piperidin-1-yl)methanone | 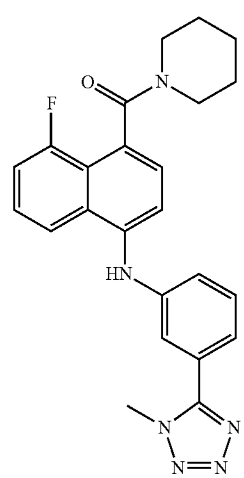 [SMILES: Cn1nnnc1-c1cccc(Nc2ccc(C(=O)N3CCCCC3)c3c(F)cccc23)c1] |

TABLE 1c-continued
| E. No | Chemical name | Structure |
|---|---|---|
| 487 | 3-((5-Fluoro-4-(piperidine-1-carbonyl)naphthalen-1-yl)amino)-2-methylbenzoic acid | 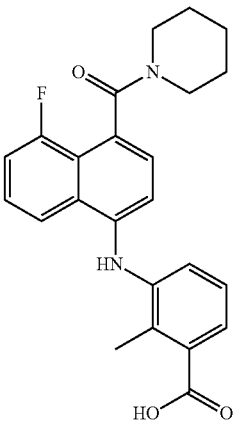 [SMILES: Cc1c(Nc2ccc(C(=O)N3CCCCC3)c3c(F)cccc23)cccc1C(=O)O] |
| 488 | Methyl 3-((5-chloro-4-(diethylcarbamoyl)naphthalen-1-yl)amino)benzoate | 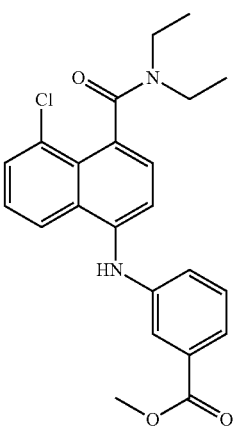 [SMILES: CCN(CC)C(=O)c1ccc(Nc2cccc(C(=O)OC)c2)c2cccc(Cl)c12] |
| 489 | Methyl 3-((4-(dimethylcarbamoyl)-5-fluoronaphthalen-1-yl)amino)-2-methylbenzoate | 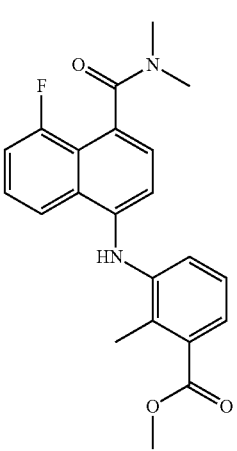 [SMILES: COC(=O)c1cccc(Nc2ccc(C(=O)N(C)C)c3c(F)cccc23)c1C] |

TABLE 1c-continued
| E. No | Chemical name | Structure |
|---|---|---|
| 490 | 5-((5-Chloro-4-(piperidine-1-carbonyl)naphthalen-1-yl)amino)-2-methylbenzoic acid | 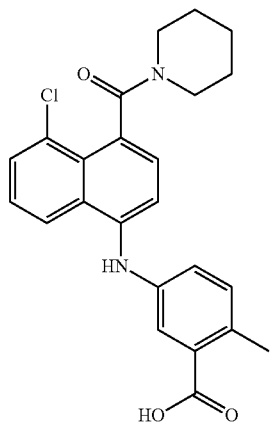 [SMILES: Cc1ccc(Nc2ccc(C(=O)N3CCCCC3)c3c(Cl)cccc23)cc1C(=O)O] |
| 491 | Methyl 3-((5-fluoro-4-(morpholine-4-carbonyl)naphthalen-1-yl)amino)-4-methylbenzoate | 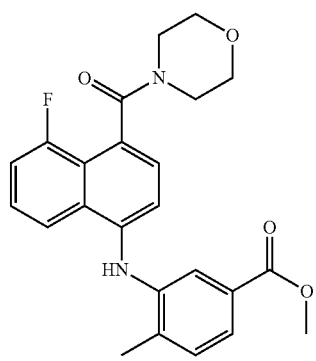 [SMILES: COC(=O)c1ccc(C)c(Nc2ccc(C(=O)N3CCOCC3)c3c(F)cccc23)c1] |
| 492 | 2-Methyl-3-((5-methyl-4-(piperidine-1-carbonyl)naphthalen-1-yl)amino)benzamide: | 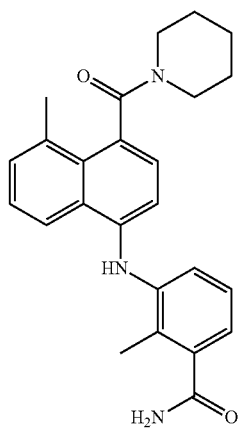 |

TABLE 1c-continued
| E. No | Chemical name | Structure |
|---|---|---|
| 493 | N,N,2-Trimethyl-3-((5-methyl-4-(morpholine-4-carbonyl)naphthalen-1-yl)amino)benzamide: | 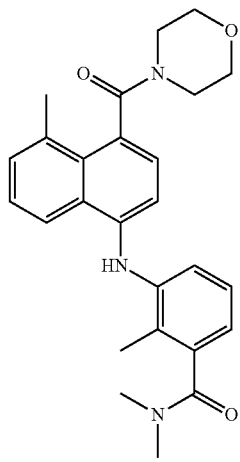 [SMILES: Cc1c(Nc2ccc(C(=O)N3CCOCC3)c3c(C)cccc23)cccc1C(=O)N(C)C] |
| 494 | 4-((3-Carbamoylphenyl)amino)-N,N,8-trimethyl-1-naphthamide: | 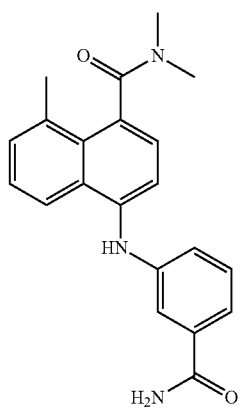 [SMILES: Cc1cccc2c(Nc3cccc(C(N)=O)c3)ccc(C(=O)N(C)C)c12] |
| 495 | 4-((3-Carbamoyl-2-methylphenyl)amino)-N,N-diethyl-8-methyl-1-naphthamide | 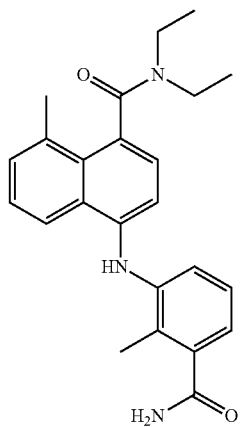 [SMILES: CCN(CC)C(=O)c1ccc(Nc2cccc(C(N)=O)c2C)c2cccc(C)c12] |

TABLE 1c-continued

| E. No | Chemical name | Structure |
|---|---|---|
| 496 | N,N,2-Trimethyl-5-((5-methyl-4-(piperidine-1-carbonyl)naphthalen-1-yl)amino)benzamide | 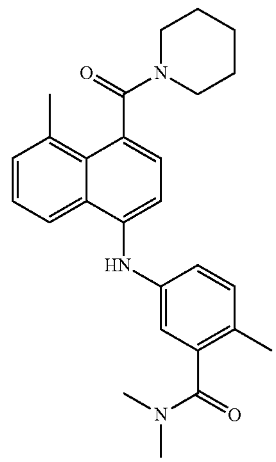 [SMILES: Cc1ccc(Nc2ccc(C(=O)N3CCCCC3)c3c(C)cccc23)cc1C(=O)N(C)C] |
| 497 | 5-((5-Fluoro-4-(piperidine-1-carbonyl)naphthalen-1-yl)amino)-N,N,2-trimethylbenzamide | 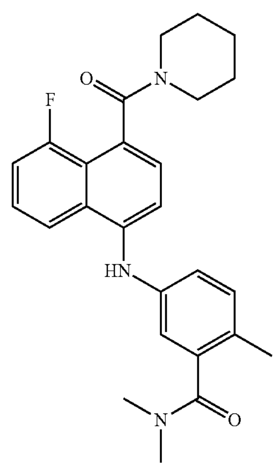 |
| 498 | 3-((5-Fluoro-4-(morpholine-4-carbonyl)naphthalen-1-yl)amino)-N,N,2-trimethylbenzamide | 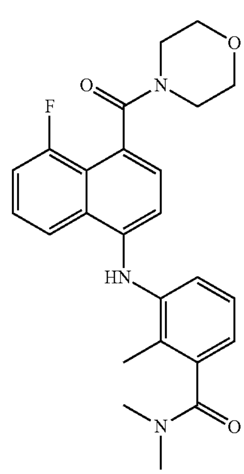 [SMILES: Cc1c(Nc2ccc(C(=O)N3CCOCC3)c3c(F)cccc23)cccc1C(=O)N(C)C] |

TABLE 1c-continued

| E. No | Chemical name | Structure |
|---|---|---|
| 499 | 4-((3-Carbamoyl-2-methylphenyl)amino)-8-chloro-N,N-dimethyl-1-naphthamide: | 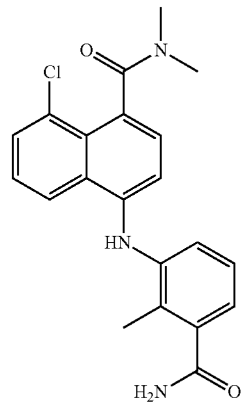 [SMILES: Cc1c(Nc2ccc(C(=O)N(C)C)c3c(Cl)cccc23)cccc1C(N)=O] |
| 500 | 8-Chloro-4-((3-(dimethylcarbamoyl)phenyl)amino)-N,N-diethyl-1-naphthamide: | 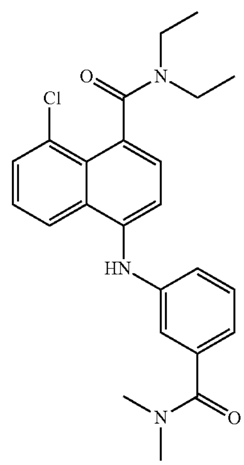 [SMILES: CCN(CC)C(=O)c1ccc(Nc2cccc(C(=O)N(C)C)c2)c2cccc(Cl)c12] |
| 501 | 3-((5-Fluoro-4-(piperidine-1-carbonyl)naphthalen-1-yl)amino)-2-methylbenzamide | 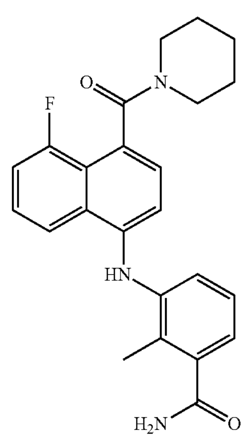 [SMILES: Cc1c(Nc2ccc(C(=O)N3CCCCC3)c3c(F)cccc23)cccc1C(N)=O] |

PHARMACOLOGICAL ACTIVITY

Certain illustrative compounds within the scope of the invention are screened for $CB_2$ activity according to the procedure given below. The screening of the compounds may also be carried out by other methods and procedures known to skilled in the art.

In-Vitro Assay Method for Determination of cAMP in Functional $hCB_2$—CHO Stable Cells:

Recombinant CHO-$hCB_2$ cells (procured from Perkin Elmer Inc. USA) were propagated and maintained in Ham's F-12 complete medium containing 10% heat inactivated FBS (Sigma.UK) and 1× penstrep. For assay, $0.1 \times 10^6$ to $1.0 \times 10^6$ CHO-$hCB_2$ cells were seeded in T-25 flask and grown to mid-log phase in culture media without antibiotics for 2-3 days. On the day of assay cell monolayer was washed twice with PBS (pH.7.4) and then cells were detached with PBS-EDTA, centrifuged and resuspended in assay buffer (KRBG containing: 115 mM NaCl, 5 mM KCl, 24 mM $NaHCO_3$, 10 mM Glucose, 1 mM $MgCl_2$, 2.5 mM $CaCl_2$, 10 mM HEPES, 1 mM IBMX and 0.1-0.5 g/l BSA). The test is performed in $96^{1/2}$ area black well plates. For agonist testing, 20 µl cells/ well were mixed with 20 μl of sample and 10 μl of forskolin (with final concentration of 10 μM) and incubated for 20 to 40 min at room temperature in incubator. The plate was then processed for the cAMP determination using cAMP Femto-2 HTRF kit (Cisbio, Germany) as per the manual. 25 μl each of D2 and cryptate (prepared in lysis buffer) was added to the plate and incubated for additional 1 h followed by reading in FeraStar FS (BMG Labtech, Germany) with HTRF settings (Excitation/Emission filter: 665/620 nm). cAMP calibrator/standards were added in the plate with range of 70 nM to 0.01 nM and 4-parameter curve fit (based on DF values) was used for calculation of cAMP concentration of sample wells. For calculation of cAMP % activity, vehicle control (0.4% v/v DMSO) was set to 0% and forskolin control wells as 100%.

Through the use of the above described assays, compounds were found to exhibit agonistic or antagonistic activity, to be particularly well suited for the treatment of the diseases or disorders as described herein above.

The concentration of compound required to stimulate a half-maximal response ($EC_{50}$) was determined using the GraphPad Prism software (version 5).

The compounds prepared were tested using the above assay procedure and the results obtained are given below. The $EC_{50}$ (nM) values of the compounds are set forth in Table-2 wherein "A" refers to an $EC_{50}$ value of less than 10 nM and "B" refers to an $EC_{50}$ value in range of 10.01 to 1000 nM.

Activity data has been given in Table-2 for representative compounds.

TABLE 2

| Compound (Example number) | $EC_{50}$ Range (nM) |
| --- | --- |
| 1, 2, 3, 4, 6, 13, 21, 22, 23, 24, 27, 28, 29, 33, 34, 37, 39, 40, 61, 65, 75, 77, 85, 87, 88, 90, 92, 94, 96, 114, 116, 118, 119, 124, 128, 129, 131, 134, 143, 150, 152, 155, 161, 166, 170, 172, 179, 201, 249, 257, 277, 279, 292, 317, 322, 325, 328-336, 357, 363, 407-411, 413, 427, 449, 452, 453, 456 | A |
| 5, 7, 12, 60, 102, 183, 187, 180, 190, 197, 282, 355, 381, 384, 469 | B |

Thus, certain compounds of the present invention are shown to have activity against $CB_2$ receptors.

In-Vitro Assay Method for Determination of cAMP in Functional $hCB_1$—HEK Stable Cells:

Recombinant $hCB_1$-HEK cells (clone 8) overexpressing human $CB_1$ was developed in-house by electroporation of hCB1-pCI neo plasmid in HEK cells as per kits manual (Amaxa. Inc. U.S.A.). $hCB_1$ was cloned in pCI neo vector Promega Inc. USA) and sequenced for DNA sequence authenticity with NCBI reference sequence: NM_016083. hCB1-HEK cells (clone 8) were propagated and maintained in DMEM complete medium supplemented with 10% heat inactivated FBS (Sigma. U.S.A), 400 μg/ml of G418 and 1x penstrep. For assay, 0.6-1.0×10⁶ hCB1-HEK cells were seeded in T-25 flask and grown to mid-log phase in complete culture medium as mentioned above for 2-3 days. One day prior to assay, cell monolayer was washed once with PBS (pH.7.4) and then serum starved for overnight in DMEM medium containing 0.2% bovine serum albumin (devoid of antibiotics, FBS and penstrep). On the day of assay, cells were trypsinized using 0.025% trypsin-EDTA, centrifuged and resuspended in assay buffer (KRBG containing: 115 mM NaCl, 5 mM KCl, 24 mM $NaHCO_3$, 10 mM Glucose, 1 mM $MgCl_2$, 2.5 mM $CaCl_2$, 10 mM HEPES, 1 mM IBMX and 0.1-0.5 g/l BSA) at a concentration of 2.5×10⁵ cells/ml. The test is performed in 96$^{1/2}$ area black well plates. For agonist testing, 20 μl cells/well were mixed with 20 μl of compound and 10 μl of forskolin (with final concentration of 10 μM) and incubated for 40 min at 25° C. incubator. The plates were then processed for cAMP determination using cAMP Femto-2 HTRF kit (Cisbio, Germany) as per the kit manual. 25 μl each of D2 and cryptate (prepared in lysis buffer) was added to the plate and incubated for additional 1 h followed by reading in FeraStar FS (BMG Labtech, Germany) with HTRF settings (Excitation/Emission filter: 665/620 nm). cAMP calibrator/standards were added in the plate with range of 70 nM to 0.01 nM and 4-parameter curve fit (based on DF values) was used for calculation of cAMP concentration of sample wells. For calculation of compound mediated inhibition of forskolin stimulated % cAMP activity, vehicle control (0.4% v/v DMSO) was set to 0% and forskolin control wells were set as 100%. Assay was validated using CP55940, WIN-55212-2 and SR144528 as reference compounds.

The compounds prepared were tested using the above assay procedure and the results obtained are given below. The $EC_{50}$ (nM) values of the compounds are set forth in Table-3 wherein "A" refers to an $EC_{50}$ value of less than 100 nM and "B" refers to an $EC_{50}$ value greater than 100 nM.

Activity data has been given in Table-3 for representative compounds.

TABLE 3

| Example No. | CB1 $EC_{50}$ (nM) |
| --- | --- |
| Example-1 | B |
| Example-2 | B |
| Example-13 | A |
| Example-56 | B |
| Example-155 | A |
| Example-179 | B |
| Example-183 | B |
| Example-218 | A |
| Example-225 | A |
| Example-241 | A |

Thus, certain compounds of the present invention are shown to have activity against $CB_1$ receptors.

FCA (Freund's Complete Adjuvant)—Induced Inflammatory Hyperalgesia:

Freund's Complete Adjuvant (FCA), containing heat killed *Mycobacterium tuberculosis* (2 mg/ml) in incomplete Freund's adjuvant, injected (50 μl) into the plantar region of the paw of rats induces an inflammatory pain. Mechanical hyperalgesia (3 days post-FCA) was assessed by measuring hind paw withdrawal thresholds with Dynamic planter aesthesiometer.

TABLE 4

Induced Inflammatory Hyperalgesia:

| Example No. | Dose (mg/kg) | % Improvement (MEAN ± S.E.M.) in Paw withdrawal Threshold | | |
| --- | --- | --- | --- | --- |
| | | 1 h | 2 h | 4 h |
| Example-2 | 10 | 33.6 ± 13.6 | 46.9 ± 15 | 54.6 ± 12.3* |
| Example-4 | 10 | 60.9 ± 12* | 42.9 ± 8.7* | 43.9 ± 17.4* |
| Example-134 | 10 | 6.8 ± 8.8 | 25.8 ± 5.2 | −1.6 ± 8.0 |
| Example-143 | 10 | 16.7 ± 15.0 | 25.1 ± 17.8 | 18.3 ± 18.5 |
| Example-257 | 30 | 44.4 ± 23.3 | 52.8 ± 19.1 | — |

*$p < 0.05$,
**$p < 0.01$,
***$p > 0.001$, compared to FDA/vehicle group by Dunnett's test FCA (Freund's Complete Adjuvant)—Induced Inflammatory Allodynia:

An emulsion of Freund's Complete Adjuvant (FCA), containing heat killed *Mycobacterium tuberculosis* (4 mg/ml) in incomplete Freund's adjuvant and saline (1:1) at a final concentration of 2 mg/ml, when injected (150 μl) into the plantar region of the paw of rats induces an inflammatory pain. Mechanical allodynia (7 days after injection) was assessed by measuring hind paw withdrawal thresholds with von Frey filaments. The 50% paw withdrawal threshold was determined using up and down method of Dixon and as per the Chaplan method.

TABLE 5

Induced Inflammatory Allodynia:

| Example No. | Dose (mg/kg) | % Improvement (MEAN ± S.E.M.) in Paw withdrawal Threshold | |
|---|---|---|---|
| | | 1 h | 2 h |
| Example-22 | 10 | 17.7 ± 7.1 | 30.7 ± 8.8** |
| Example-39 | 10 | 2.10 ± 1.87 | 10.22 ± 4.68 |
| Example-40 | 10 | 12.8 ± 4.6 | 13.8 ± 4.5 |

*$p < 0.05$,
**$p < 0.001$,
***$p > 0.0001$, compared to FCA/vehicle group by Dunnett's test Chronic Constriction Injury (CCI)—Induced Neuropathic Pain (Bennett's Model):

Chronic constriction injury (CCI) of sciatic nerve in rats induces mechanical allodynia in this Bennet's neuropathic pain model. Rats were anesthetized using ketamine/xylazine (50/5 mg/kg, i.p.) and the left sciatic nerve was exposed at mid thigh level through a small incision. Four loose ligatures of 4-0 chromic cat gut (Ethicon—Johnson & Johnson) at 1 mm space were placed around the sciatic nerve after the bifurcation of common sciatic nerve. After 10-15 days, mechanical allodynia was assessed by measuring hind paw withdrawal thresholds with von Frey filaments. The 50% paw withdrawal threshold was determined using up and down method of Dixon and as per the Chaplan method.

TABLE 6

Induced Neuropathic Pain

| Example No. | Dose (mg/kg) | % Improvement (MEAN ± S.E.M.) in Paw withdrawal Threshold | |
|---|---|---|---|
| | | 1 h | 2 h |
| Example-22 | 10 | 61.8 ± 10.1*** | 70.2 ± 9.5*** |
| Example-39 | 10 | 11.6 ± 12.8 | 0.7 ± 1.1 |
| Example-40 | 10 | 21.6 ± 10.6 | 11.2 ± 2.9 |

*$p < 0.05$,
**$p < 0.01$,
***$p > 0.0001$, compared to CCI/vehicle group by Dunnett's test Thus, the compounds of the present invention have been shown to decrease pain in vivo, indicating potential for use of the compounds of the present invention in the treating, preventing, managing or lessening the severity of the diseases disorders or conditions associated with modulation of cannabinoid receptors.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

The invention claimed is:
1. A compound of Formula (I):

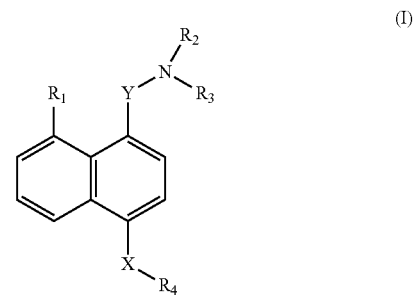

wherein,
W is —N— or —CH—;
when W is N, X is selected from $NR_a$ and O; when W is —CH—, X is $NR_a$;
Y is —C(O)—;
$R_1$ is selected from hydrogen, alkyl, halogen, cycloalkyl, and haloalkyl;
with the proviso that when W is —N— then $R_1$ is not hydrogen;
$R_2$ is selected from hydrogen, alkyl, cycloalkyl, cycloalkylalkyl, aryl, arylalkyl, heteroaryl, heteroarylalkyl, heterocyclyl, and heterocyclylalkyl;
$R_3$ is selected from alkyl, cycloalkyl, cycloalkylalkyl, aryl, arylalkyl, heteroaryl, heteroarylalkyl, heterocyclyl, and heterocyclylalkyl; or
$R_2$ and $R_3$, together with the nitrogen atom to which they are attached, may form a substituted or an unsubstituted 4 to 10 membered heterocyclic ring;
$R_4$ is selected from aryl, cycloalkyl, heteroaryl and heterocyclyl;
$R_a$ is selected from hydrogen, alkyl or cycloalkyl;
$R_b$ is selected from hydrogen, alkyl or cycloalkyl; and
wherein alkyl, cycloalkyl, aryl, heteroaryl, heterocyclyl, heterocyclic ring, cycloalkylalkyl, arylalkyl, heteroarylalkyl, heterocyclylalkyl, haloalkyl, wherever they occur may optionally be substituted with one or more, same or different substituents, and wherein the substitutents are independently selected from hydroxy, halo, cyano, nitro, oxo (=O), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, alkyl-C(O)OR$^x$, —C(O)OR$^x$, —C(O)R$^x$, —C(S) R$^x$, —C(O)NR$_a$R$_b$, —NR$^x$C(O)NR$_a$R$_b$, —N(R$^x$)S(O) R$^y$, —N(R$^x$)S(O)$_2$R$^y$, —NR$_a$R$_b$, —NR$^x$C(O)R$^y$, —NR$^x$C(S)R$^y$, —NR$^x$C(S)NR$_a$R$_b$, —S(O)$_2$NR$_a$R$_b$, —OR$^x$, —OC(O)R$^x$, —OC(O)NR$_a$R$_b$, —R$^x$C(O)OR$^y$, —R$^x$C(O)NR$_a$R$_b$, —R$^x$C(O)R$^y$, —SR$^y$, and —S(O)$_2$R$^x$;
wherein at each occurrence, R$^x$, R$^y$ and R$^z$ are independently selected from hydrogen, alkyl, haloalkyl, alkenyl, alkynyl, aryl, arylalkyl, cycloalkyl, cycloalkenyl, heteroaryl, heterocyclyl, heterocyclylalkyl and heteroarylalkyl;
or its pharmaceutically acceptable salt thereof.

2. The compound of claim 1, having the Formula (II):

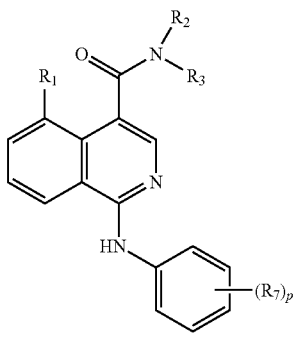

(II)

wherein,
R₁ is halogen, alkyl or cycloalkyl;
R₇, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR_c, —NR_aR_b and —C(O)NR_aR_b;
R₂ is selected from hydrogen, alkyl, cycloalkyl, cycloalkylalkyl, aryl, arylalkyl, heteroaryl, heteroarylalkyl, heterocyclyl, and heterocyclylalkyl;
R₃ is selected from alkyl, cycloalkyl, cycloalkylalkyl, aryl, arylalkyl, heteroaryl, heteroarylalkyl, heterocyclyl, and heterocyclylalkyl;
R_a and R_b are independently selected from hydrogen, alkyl and cycloalkyl;
R_c is alkyl and
'p' is an integer ranging from 0 to 3, both inclusive;
or its pharmaceutically acceptable salt thereof.

3. The compound of claim 1, having the Formula (III):

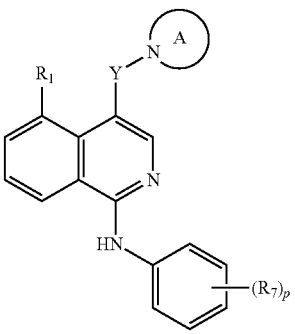

(III)

wherein,
ring A is a substituted or an unsubstituted 4 to 10 membered heterocyclic ring wherein substituents on ring A may be on same or different ring atom;
Y is —C(O)—;
R₁ is halogen, alkyl or cycloalkyl;
R₇, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR_c, —NR_aR_b and —C(O)NR_aR_b;
R_a and R_b are independently selected from hydrogen, alkyl and cycloalkyl;
R_c is alkyl; and
'p' is an integer ranging from 0 to 3, both inclusive;
or its pharmaceutically acceptable salt thereof.

4. The compound of claim 1, having the Formula (IV):

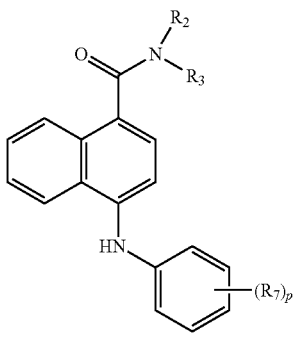

(IV)

wherein,
R₇, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR_c, —NR_aR_b and —C(O)NR_aR_b;
R₂ is selected from hydrogen, alkyl, cycloalkyl, cycloalkylalkyl, aryl, arylalkyl, heteroaryl, heteroarylalkyl, heterocyclyl, and heterocyclylalkyl;
R₃ is selected from alkyl, cycloalkyl, cycloalkylalkyl, aryl, arylalkyl, heteroaryl, heteroarylalkyl, heterocyclyl, and heterocyclylalkyl; or
R₂ and R₃, together with the nitrogen atom to which they are attached, may form a substituted or unsubstituted 4 to 10 membered heterocyclic ring;
R_a and R_b are independently selected from hydrogen, alkyl and cycloalkyl;
R_c is alkyl; and
'p' is an integer ranging from 0 to 3, both inclusive;
or its pharmaceutically acceptable salt thereof.

5. The compound of claim 1, having the formula (V):

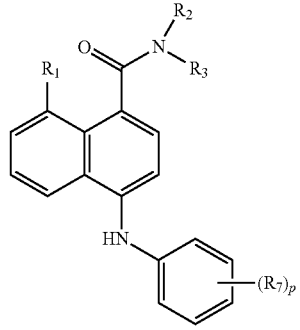

(V)

wherein,
R₁ is halogen, alkyl or cycloalkyl;
R₇, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR_c, —NR_aR_b and —C(O)NR_aR_b;
R₂ is selected from hydrogen, alkyl, cycloalkyl, cycloalkylalkyl, aryl, arylalkyl, heteroaryl, heteroarylalkyl, heterocyclyl, and heterocyclylalkyl;
R₃ is selected from alkyl, cycloalkyl, cycloalkylalkyl, aryl, arylalkyl, heteroaryl, heteroarylalkyl, heterocyclyl, and heterocyclylalkyl; or
R₂ and R₃, together with the nitrogen atom to which they are attached, may form a substituted or unsubstituted 4 to 10 membered heterocyclic ring;

$R_a$ and $R_b$ are independently selected from hydrogen, alkyl and cycloalkyl;
$R_c$ is alkyl; and
'p' is an integer ranging from 0 to 3, both inclusive;
or its pharmaceutically acceptable salt thereof.

6. The compound of claim 1, having the Formula (VI):

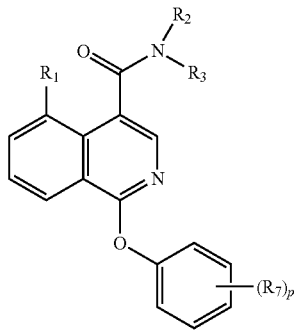

(VI)

wherein,
$R_1$ is halogen, alkyl or cycloalkyl;
$R_7$, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;
$R_2$ is selected from hydrogen, alkyl, cycloalkyl, cycloalkylalkyl, aryl, arylalkyl, heteroaryl, heteroarylalkyl, heterocyclyl, and heterocyclylalkyl;
$R_3$ is selected from alkyl, cycloalkyl, cycloalkylalkyl, aryl, arylalkyl, heteroaryl, heteroarylalkyl, heterocyclyl, and heterocyclylalkyl; or
$R_2$ and $R_3$, together with the nitrogen atom to which they are attached, may form a substituted or unsubstituted 4 to 10 membered heterocyclic ring;
$R_a$ and $R_b$ are independently selected from hydrogen, alkyl and cycloalkyl;
$R_c$ is alkyl; and
'p' is an integer ranging from 0 to 3, both inclusive;
or its pharmaceutically acceptable salt thereof.

7. The compound of claim 1, having the Formula (VII):

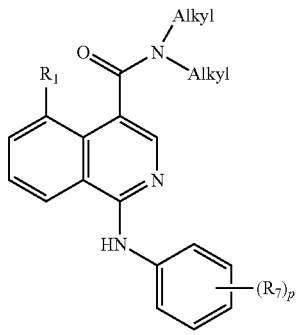

(VII)

wherein,
$R_1$ is halogen or alkyl;
$R_7$, which may be same or different at each occurrence, is independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;
$R_a$ and $R_b$ are independently selected from hydrogen, alkyl and cycloalkyl;

$R_c$ is alkyl; and
'p' is an integer ranging from 0 to 3, both inclusive;
or its pharmaceutically acceptable salt thereof.

8. The compound of claim 1, wherein W is N.
9. The compound of claim 1, wherein W is CH.
10. The compound of claim 1, wherein $R_1$ is halogen, alkyl or cycloalkyl.
11. The compound of claim 1, wherein $R_2$ is hydrogen or alkyl.
12. The compound of claim 1, wherein $R_3$ is selected from alkyl, cycloalkyl, heteroaryl, heteroarylalkyl, heterocyclyl and heterocyclylalkyl.
13. The compound of claim 1, wherein $R_2$ and $R_3$, together with the nitrogen atom to which they are attached, may form a substituted or an unsubstituted 4 to 10 membered heterocyclic ring.
14. The compound of claim 13, wherein the 4 to 10 membered heterocyclic ring is substituted or an unsubstituted monocyclic, fused or bridged bicyclic, or spirocyclic ring.
15. The compound of claim 13, wherein the 4 to 10 membered heterocyclic ring is selected from azetidine, pyrrolidine, piperidine, piperazine, morpholine, dioxidothiomorpholine, 6-oxa-3-azabicyclo[3.1.1]heptane, 2-oxa-5-azabicyclo[2.2.1]heptane, 3-azabicyclo[3.1.0]hexane, 3-oxa-9-azabicyclo[3.3.1]nonane, 2-oxa-6-azaspiro[3.3]heptane, 2-oxa-6-azaspiro[3.5]nonane and 2-oxa-7-azaspiro[3.5]nonane.
16. The compound of claim 14, wherein the substituents may be same or different and are independently selected from halo, alkyl and aryl.
17. The compound of claim 1, wherein $R_4$ is aryl wherein the aryl is substituted or unsubstitiuted.
18. The compound of claim 17, wherein the substituent(s) on the aryl may be one or more, same or different, and are independently selected from halogen, cyano, nitro, hydroxy, alkyl, haloalkyl, hydroxyalkyl, cycloalkyl, alkoxy, haloalkoxy, cycloalkoxy, —C(O)OH, —C(O)OR$_c$, —NR$_a$R$_b$ and —C(O)NR$_a$R$_b$;
$R_a$ and $R_b$ are independently selected from hydrogen, alkyl and cycloalkyl;
$R_c$ is alkyl.
19. The compound of claim 1, wherein when W is N, X is selected from NH and O; when W is CH, X is NH; Y is —C(O)—; $R_1$ is a halogen, substituted or unsubstituted alkyl or cycloalkyl; $R_2$ is hydrogen or alkyl; $R_3$ is selected from alkyl, cycloalkyl, cycloalkylalkyl, aryl, arylalkyl, heteroaryl, heteroarylalkyl, heterocyclyl, and heterocyclylalkyl, or $R_2$ and $R_3$, together with the nitrogen atom to which they are attached, may form a substituted or an unsubstituted 4 to 10 membered heterocyclic ring, wherein the heterocyclic ring is a substituted or an unsubstituted azetidine, pyrrolidine, piperidine, piperazine, morpholine, dioxidothiomorpholine, 6-oxa-3-azabicyclo[3.1.1]heptane, 2-oxa-5-azabicyclo[2.2.1]heptane, 3-azabicyclo[3.1.0]hexane, 3-oxa-9-azabicyclo[3.3.1]nonane, 2-oxa-6-azaspiro[3.3]heptane, 2-oxa-6-azaspiro[3.5]nonane or 2-oxa-7-azaspiro[3.5]nonane; $R_4$ is a substituted or an unsubstituted aryl where the substituents on aryl are same or different and are independently halogen, hydroxy, alkyl or alkoxy.
20. The compound of claim 1, wherein W is N or CH; X is NH; Y is —C(O)—; $R_1$ is a halogen, substituted or an unsubstituted alkyl or cycloalkyl; $R_2$ is hydrogen or alkyl; $R_3$ is selected from alkyl, cycloalkyl, cycloalkylalkyl, aryl, arylalkyl, heteroaryl, heteroarylalkyl, heterocyclyl, and heterocyclylalkyl, or $R_2$ and $R_3$ together with the nitrogen atom to which they are attached, may form a substituted or an unsubstituted 4 to 10 membered heterocyclic ring, wherein the heterocyclic ring is a substituted or an unsubstituted azetidine, pyrrolidine, piperidine, piperazine, morpholine, dioxidothiomorpholine, 6-oxa-3-azabicyclo[3.1.1]heptane, 2-oxa-5-azabicyclo[2.2.1]heptane, 3-azabicyclo[3.1.0]hexane, 3-oxa-9-azabicyclo[3.3.1]nonane, 2-oxa-6-azaspiro[3.3]heptane, 2-oxa-6-azaspiro[3.5]nonane or 2-oxa-7-azaspiro[3.5]nonane; and $R_4$ is a substituted or an unsubstituted aryl where the substituents on aryl are same or different and are independently halogen, hydroxy, alkyl or alkoxy.

21. A compound which is selected from:
- (1-((3-Chlorophenyl)amino)-5-methylisoquinolin-4-yl)(morpholino)methanone;
- (1-((3-Fluorophenyl)amino)-5-methylisoquinolin-4-yl)(morpholino)methanone;
- (1-((3,5-Difluorophenyl)amino)-5-methylisoquinolin-4-yl)(morpholino)methanone;
- (5-Methyl-1-((3-(trifluoromethyl)phenyl)amino)isoquinolin-4-yl)(morpholino)methanone;
- (1-((4-Fluorophenyl)amino)-5-methylisoquinolin-4-yl)(morpholino)methanone;
- (1-((4-Fluoro-3-(trifluoromethyl)phenyl)amino)-5-methylisoquinolin-4-yl)(morpholino) methanone;
- (1-((2,4-Difluorophenyl)amino)-5-methylisoquinolin-4-yl)(morpholino)methanone;
- (1-((3,4-Difluorophenyl)amino)-5-methylisoquinolin-4-yl)(morpholino)methanone;
- (1-((2,3-Difluorophenyl)amino)-5-methylisoquinolin-4-yl)(morpholino)methanone;
- (1-((3-Chloro-2-fluorophenyl)amino)-5-methylisoquinolin-4-yl)(morpholino)methanone;
- (1-((3-Chloro-4-fluorophenyl)amino)-5-methylisoquinolin-4-yl)(morpholino)methanone;
- (1-(((3-Fluoromethyl)phenyl)amino)-5-methylisoquinolin-4-yl)(morpholino)methanone;
- (1-(((3-Difluoromethyl)phenyl)amino)-5-methylisoquinolin-4-yl)(morpholino)methanone;
- 1-((3-Chlorophenyl)amino)-5-methyl-N-((tetrahydro-2H-pyran-4-yl)methyl)isoquinolin-4-carboxamide;
- 1-((3,5-Difluorophenyl)amino)-5-methyl-N-((tetrahydro-2H-pyran-4-yl)methyl)isoquinolin-4-carboxamide;
- 1-((3-Fluorophenyl)amino)-5-methyl-N-((tetrahydro-2H-pyran-4-yl)methyl)isoquinolin-4-carboxamide;
- 1-((4-Fluorophenyl)amino)-5-methyl-N-((tetrahydro-2H-pyran-4-yl)methyl)isoquinolin-4-carboxamide;
- N-(tert-Butyl)-1-((3-chlorophenyl)amino)-5-methylisoquinolin-4-carboxamide;
- N-(tert-Butyl)-1-((3-fluorophenyl)amino)-5-methylisoquinolin-4-carboxamide;
- N-(tert-Butyl)-1-((3,5-difluorophenyl)amino)-5-methylisoquinolin-4-carboxamide;
- (1-((3-Fluorophenyl)amino)-5-methylisoquinolin-4-yl)(piperidino)methanone;
- (1-((3-Chlorophenyl)amino)-5-methylisoquinolin-4-yl)(piperidin-1-yl)methanone;
- (5-Methyl-1-(((3-trifluoromethyl)phenyl)amino)isoquinolin-4-yl)(piperidin-1-yl)methanone;
- (1-((3,5-Difluorophenyl)amino)-5-methylisoquinolin-4-yl)(piperidin-1-yl)methanone;
- (1-((2,4-Dichlorophenyl)amino)-5-methylisoquinolin-4-yl)(piperidin-1-yl)methanone;
- (1-((4-Fluorophenyl)amino)-5-methylisoquinolin-4-yl)(piperidin-1-yl)methanone;
- (1-((4-Fluoro-3-(trifluoromethyl)phenyl)amino)-5-methylisoquinolin-4-yl)(piperidin-1-yl)methanone;
- (1-((2,4,5-Trifluorophenyl)amino)-5-methylisoquinolin-4-yl)(piperidin-1-yl)methanone;
- (1-((2,4-Difluorophenyl)amino)-5-methylisoquinolin-4-yl)(piperidin-1-yl)methanone;
- (1-((3,4-Difluorophenyl)amino)-5-methylisoquinolin-4-yl)(piperidin-1-yl)methanone;
- (5-Methyl-1-(((4-trifluoromethyl)phenyl)amino)isoquinolin-4-yl)(piperidin-1-yl)methanone;
- (1-((2-Chloro-4-(trifluoromethyl)phenyl)amino)-5-methylisoquinolin-4-yl)(piperidin-1-yl)methanone;
- (1-((2,3-Difluorophenyl)amino)-5-methylisoquinolin-4-yl)(piperidin-1-yl)methanone;
- (1-((2,5-Difluorophenyl)amino)-5-methylisoquinolin-4-yl)(piperidin-1-yl)methanone;
- (1-((4-Chlorophenyl)amino)-5-methylisoquinolin-4-yl)(piperidin-1-yl)methanone;
- (1-((3-Chloro-4-fluorophenyl)amino)-5-methylisoquinolin-4-yl)(piperidin-1-yl)methanone;
- (1-((3-(Fluoromethyl)phenyl)amino)-5-methylisoquinolin-4-yl)(piperidin-1-yl)methanone;
- (1-((3-(Difluoromethyl)phenyl)amino)-5-methylisoquinolin-4-yl)(piperidin-1-yl)methanone;
- 6-Oxa-3-azabicyclo[3.1.1]heptan-3-yl(1-((3-chlorophenyl)amino)-5-methylisoquinolin-4-yl)methanone;
- 6-Oxa-3-azabicyclo[3.1.1]heptan-3-yl(5-methyl-1-((3-(trifluoromethyl)phenyl)amino) isoquinolin-4-yl)methanone;
- (5-Methyl-1-((3-(trifluoromethyl)phenyl)amino)isoquinolin-4-yl)(2-oxa-6-azaspiro[3.3]heptan-6-yl)methanone;
- (5-Methyl-1-((3-chlorophenyl)amino)isoquinolin-4-yl)(2-oxa-6-azaspiro[3.3]heptan-6-yl)methanone;
- (5-Methyl-1-((2,4,5-trifluorophenyl)amino)isoquinolin-4-yl)(2-oxa-6-azaspiro[3.3]heptan-6-yl)methanone;
- (1-((4-Fluoro-3-(trifluoromethyl)phenyl)amino)-5-methylisoquinolin-4-yl)(2-oxa-6-azaspiro[3.3]heptan-6-yl)methanone;
- (5-Methyl-1-((3-fluorophenyl)amino)isoquinolin-4-yl)(2-oxa-6-azaspiro[3.3]heptan-6-yl)methanone;
- (5-Methyl-1-((2,3-difluorophenyl)amino)isoquinolin-4-yl)(2-oxa-6-azaspiro[3.3]heptan-6-yl)methanone;
- (5-Methyl-1-((4-fluorophenyl)amino)isoquinolin-4-yl)(2-oxa-6-azaspiro[3.3]heptan-6-yl)methanone;
- (5-Methyl-1-((2,4-difluorophenyl)amino)isoquinolin-4-yl)(2-oxa-6-azaspiro[3.3]heptan-6-yl)methanone;
- (5-Methyl-1-((3,5-difluorophenyl)amino)isoquinolin-4-yl)(2-oxa-6-azaspiro[3.3]heptan-6-yl)methanone;
- (1-((3-Chlorophenyl)amino)-5-methylisoquinolin-4-yl)(2-oxa-6-azaspiro[3.5]nonan-6-yl)methanone;
- (5-Methyl-1-((3-(trifluoromethyl)phenyl)amino)isoquinolin-4-yl)(2-oxa-6-azaspiro[3.5]nonan-6-yl)methanone;
- (3,5-Dimethylpiperazin-1-yl)(5-methyl-1-((3-(trifluoromethyl)phenyl)amino)isoquinolin-4-yl)methanone;
- (3,5-Dimethylpiperazin-1-yl)(5-methyl-1-((3-chlorophenyl)amino)isoquinolin-4-yl)methanone;
- (1-(4-Fluorophenoxy)-5-methylisoquinolin-4-yl)(morpholino)methanone;
- (1-(3,4-Difluorophenoxy)-5-methylisoquinolin-4-yl)(morpholino)methanone;
- (1-(2-Chloro-4-fluorophenoxy)-5-methylisoquinolin-4-yl)(morpholino)methanone;
- (1-(4-Fluorophenoxy)-5-methylisoquinolin-4-yl)(piperidin-1-yl)methanone;
- (1-(3,4-Difluorophenoxy)-5-methylisoquinolin-4-yl)(piperidin-1-yl)methanone;
- (1-(2-Chloro-4-fluorophenoxy)-5-methylisoquinolin-4-yl)(piperidin-1-yl)methanone;

6-Oxa-3-azabicyclo[3.1.1]heptan-3-yl(1-((3-chloro-4-fluorophenyl)amino)-5-methylisoquinolin-4-yl)methanone;
6-Oxa-3-azabicyclo[3.1.1]heptan-3-yl(1-((3-chloro-2-fluorophenyl)amino)-5-methylisoquinolin-4-yl)methanone;
6-Oxa-3-azabicyclo[3.1.1]heptan-3-yl(1-((3-fluorophenyl)amino)-5-methylisoquinolin-4-yl)methanone;
6-Oxa-3-azabicyclo[3.1.1]heptan-3-yl(1-((3-methylphenyl)amino)-5-methylisoquinolin-4-yl)methanone;
6-Oxa-3-azabicyclo[3.1.1]heptan-3-yl(1-((3-fluoro-2-methylphenyl)amino)-5-methylisoquinolin-4-yl)methanone;
6-Oxa-3-azabicyclo[3.1.1]heptan-3-yl(1-((3-chloro-2-methylphenyl)amino)-5-methyl isoquinolin-4-yl)methanone;
6-Oxa-3-azabicyclo[3.1.1]heptan-3-yl(1-((5-chloro-2-methylphenyl)amino)-5-methyl isoquinolin-4-yl)methanone;
6-Oxa-3-azabicyclo[3.1.1]heptan-3-yl(1-((2-fluoro-3-methylphenyl)amino)-5-methylisoquinolin-4-yl)methanone;
6-Oxa-3-azabicyclo[3.1.1]heptan-3-yl(1-((2,3-difluorophenyl)amino)-5-methylisoquinolin-4-yl)methanone;
6-Oxa-3-azabicyclo[3.1.1]heptan-3-yl(1-((3,5-difluorophenyl)amino)-5-methylisoquinolin-4-yl)methanone;
2-Oxa-5-azabicyclo[2.2.1]heptan-5-yl(1-((3-chlorophenyl)amino)-5-methylisoquinolin-4-yl)methanone;
2-Oxa-5-azabicyclo[2.2.1]heptan-5-yl(1-((3-(trifluoromethyl)phenyl)amino)-5-methyl isoquinolin-4-yl)methanone;
2-Oxa-5-azabicyclo[2.2.1]heptan-5-yl(1-((3-chloro-2-fluorophenyl)amino)-5-methylisoquinolin-4-yl)methanone;
2-Oxa-5-azabicyclo[2.2.1]heptan-5-yl(1-((3-chloro-4-fluorophenyl)amino)-5-methylisoquinolin-4-yl)methanone;
2-Oxa-5-azabicyclo[2.2.1]heptan-5-yl(1-((3-methylphenyl)amino)-5-methylisoquinolin-4-yl)methanone;
3-Azabicyclo[3.1.0]hexan-3-yl(1-((3-chlorophenyl)amino)-5-methylisoquinolin-4-yl)methanone;
3-Azabicyclo[3.1.0]hexan-3-yl(1-((3-(trifluoromethyl)phenyl)amino)-5-methylisoquinolin-4-yl)methanone;
3-Azabicyclo[3.1.0]hexan-3-yl(1-((3-fluoro-2-methylphenyl)amino)-5-methylisoquinolin-4-yl)methanone;
3-Oxa-9-azabicyclo[3.3.1]nonan-9-yl(1-((3-chlorophenyl)amino)-5-methylisoquinolin-4-yl)methanone;
3-Oxa-9-azabicyclo[3.3.1]nonan-9-yl(1-((3-(trifluoromethyl)phenyl)amino)-5-methyl isoquinolin-4-yl)methanone;
3-Oxa-9-azabicyclo[3.3.1]nonan-9-yl(1-((3-fluoro-2-methylphenyl)amino)-5-methyl isoquinolin-4-yl)methanone;
(5-Methyl-1-(m-tolylamino)isoquinolin-4-yl)(morpholino)methanone;
(1-((3-Fluoro-4-methylphenyl)amino)-5-methylisoquinolin-4-yl)(morpholino) methanone;
(1-((3-Fluoro-2-methylphenyl)amino)-5-methylisoquinolin-4-yl)(morpholino) methanone;
(1-((2-Fluoro-3-methylphenyl)amino)-5-methylisoquinolin-4-yl)(morpholino) methanone;
(1-((4-Fluoro-3-methylphenyl)amino)-5-methylisoquinolin-4-yl)(morpholino) methanone;
(1-((2-Chloro-5-methylphenyl)amino)-5-methylisoquinolin-4-yl)(morpholino) methanone;
(1-((3-Chloro-2-methylphenyl)amino)-5-methylisoquinolin-4-yl)(morpholino) methanone;
(1-((5-Chloro-2-methylphenyl)amino)-5-methylisoquinolin-4-yl)(morpholino) methanone;
(1-((3-Chloro-4-methylphenyl)amino)-5-methylisoquinolin-4-yl)(morpholino) methanone;
(1-((2,4-Dichlorophenyl)amino)-5-methylisoquinolin-4-yl)(morpholino)methanone;
(5-Methyl-1-(m-tolylamino)isoquinolin-4-yl)(piperidin-1-yl)methanone;
(1-((3-Chloro-4-methylphenyl)amino)-5-methylisoquinolin-4-yl)(piperidin-1-yl)methanone;
(1-((2-Chloro-5-methylphenyl)amino)-5-methylisoquinolin-4-yl)(piperidin-1-yl)methanone;
(1-((4-Fluoro-3-methylphenyl)amino)-5-methylisoquinolin-4-yl)(piperidin-1-yl)methanone;
(1-((3-Fluoro-4-methylphenyl)amino)-5-methylisoquinolin-4-yl)(piperidin-1-yl)methanone;
(1-((3-Fluoro-2-methylphenyl)amino)-5-methylisoquinolin-4-yl)(piperidin-1-yl)methanone;
(1-((2-Fluoro-3-methylphenyl)amino)-5-methylisoquinolin-4-yl)(piperidin-1-yl)methanone;
(5-Methyl-1-((3-(trifluoromethyl)phenyl)amino)isoquinolin-4-yl)(2-phenylmorpholino) methanone;
N-cyclohexyl-1-((3-fluorophenyl)amino)-5-methylisoquinolin-4-carboxamide;
N-cyclohexyl-1-((3,5-difluorophenyl)amino)-5-methylisoquinolin-4-carboxamide;
(1-((3-Chlorophenyl)amino)-5-methylisoquinolin-4-yl)(pyrrolidin-1-yl)methanone;
(1-((3-Fluorophenyl)amino)-5-methylisoquinolin-4-yl)(pyrrolidin-1-yl)methanone;
(1-((3,5-Difluorophenyl)amino)-5-methylisoquinolin-4-yl)(pyrrolidin-1-yl)methanone;
(1-((2,4-Difluorophenyl)amino)-5-methylisoquinolin-4-yl)(pyrrolidin-1-yl)methanone;
Azetidin-1-yl(1-((3,5-difluorophenyl)amino)-5-methyl-isoquinolin-4-yl)methanone;
Azetidin-1-yl(1-((4-fluorophenyl)amino)-5-methylisoquinolin-4-yl)methanone;
(1-((3-Chloro-2-methylphenyl)amino)-5-methylisoquinolin-4-yl)(piperidin-1-yl)methanone;
(1-((5-Chloro-2-methylphenyl)amino)-5-methylisoquinolin-4-yl)(piperidin-1-yl)methanone;
(5-Methyl-1-((3-(trifluoromethyl)phenyl)amino)isoquinolin-4-yl) (2-oxa-7-azaspiro[3.5]nonan-7-yl)methanone;
(1-((3-Fluorophenyl)amino)-5-methylisoquinolin-4-yl)(2-oxa-7-azaspiro[3.5]nonan-7-yl)methanone;
(1-((3-Chlorophenyl)amino)-5-methylisoquinolin-4-yl)(2-oxa-7-azaspiro[3.5]nonan-7-yl)methanone;
(5-Cyclopropyl-1-(m-tolylamino)isoquinolin-4-yl)(morpholino)methanone;
(1-((3-Chlorophenyl)amino)-5-cyclopropylisoquinolin-4-yl)(morpholino)methanone;
(5-Cyclopropyl-1-(2-fluoro-3-methylphenyl)amino)isoquinolin-4-yl)(morpholino)methanone;
(5-Cyclopropyl-1-(2,3-difluorophenyl)amino)isoquinolin-4-yl)(morpholino)methanone;
(5-Cyclopropyl-1-(2,3,6-trifluorophenyl)amino)isoquinolin-4-yl)(morpholino) methanone;
(5-Cyclopropyl-1-((3-(trifluoromethyl)phenyl)amino)isoquinolin-4-yl)(morpholino)methanone
(5-Cyclopropyl-1-((2-fluoro-3-(trifluoromethyl)phenyl)amino)isoquinolin-4-yl)(morpholino)methanone;

(1-((3-Chlorophenyl)amino)-5-cyclopropylisoquinolin-4-yl)(piperidin-1-yl)methanone;
(1-((3-Chloro-2-fluorophenyl)amino)-5-cyclopropylisoquinolin-4-yl)(piperidin-1-yl)methanone;
(1-((2,3-Difluorophenyl)amino)-5-cyclopropylisoquinolin-4-yl)(piperidin-1-yl)methanone
(1-((2,3-Difluorophenyl)amino)-5-ethylisoquinolin-4-yl)(morpholino)methanone;
(1-((2,3-Difluorophenyl)amino)-5-ethylisoquinolin-4-yl)(piperidin-1-yl)methanone;
(1-((2,4-Difluorophenyl)amino)-5-ethylisoquinolin-4-yl)(piperidin-1-yl)methanone;
(1-((3,5-Difluorophenyl)amino)-5-ethylisoquinolin-4-yl)(piperidin-1-yl)methanone;
(1-((3-Chlorophenyl)amino)-5-ethylisoquinolin-4-yl)(piperidin-1-yl)methanone;
(1-((3-Chloro-2-fluorophenyl)amino)-5-ethylisoquinolin-4-yl)(piperidin-1-yl)methanone;
(5-Ethyl-1-((2-Fluoro-3-(trifluoromethyl)phenyl)amino)isoquinolin-4-yl)(piperidin-1-yl)methanone;
(1-((3-Fluoro-2-methylphenyl)amino)-5-ethylisoquinolin-4-yl)(piperidin-1-yl)methanone;
(1-((3-Chloro-2-methylphenyl)amino)-5-ethylisoquinolin-4-yl)(piperidin-1-yl)methanone;
(4-((3-Chlorophenyl)amino)-8-methylnaphthalen-1-yl)(morpholino)methanone;
(4-((3-Fluorophenyl)amino)-8-methylnaphthalen-1-yl)(morpholino)methanone;
(8-Methyl-4-((3-trifluoromethyl)phenyl)amino)naphthalen-1-yl)(morpholino) methanone;
(4-((2,3-Difluorophenyl)amino)-8-methylnaphthalen-1-yl)(morpholino)methanone;
(4-((3,4-Difluorophenyl)amino)-8-methylnaphthalen-1-yl)(morpholino)methanone;
(4-((2,4-Difluorophenyl)amino)-8-methylnaphthalen-1-yl)(morpholino)methanone;
(4-((3,5-Difluorophenyl)amino)-8-methylnaphthalen-1-yl)(morpholino)methanone;
(4-((3-Chloro-4-fluorophenyl)amino)-8-methylnaphthalen-1-yl)(morpholino)methanone;
(4-((4-Fluoro-3-(trifluoromethyl)phenyl)amino)-8-methylnaphthalen-1-yl) (morpholino)methanone;
(4-((3-Chlorophenyl)amino)-8-methylnaphthalen-1-yl)(piperidin-1-yl)methanone;
(4-((3-Fluorophenyl)amino)-8-methylnaphthalen-1-yl)(piperidin-1-yl)methanone;
(8-Methyl-4-((3-trifluoromethyl)phenyl)amino)naphthalen-1-yl)(piperidin-1-yl)methanone;
(4-((2,3-Difluorophenyl)amino)-8-methylnaphthalen-1-yl)(piperidin-1-yl)methanone;
(4-((3,4-Difluorophenyl)amino)-8-methylnaphthalen-1-yl)(piperidin-1-yl)methanone;
(4-((2,4-Difluorophenyl)amino)-8-methylnaphthalen-1-yl)(piperidin-1-yl)methanone;
(4-((3,5-Difluorophenyl)amino)-8-methylnaphthalen-1-yl)(piperidin-1-yl)methanone;
(4-((3-Chloro-4-fluorophenyl)amino)-8-methylnaphthalen-1-yl)(piperidin-1-yl)methanone;
(4-((4-Fluoro-3-(trifluoromethyl)phenyl)amino)-8-methylnaphthalen-1-yl)(piperidin-1-yl)methanone;
(8-Methyl-4-(m-tolylamino)naphthalen-1-yl)(morpholino)methanone;
(4-((4-Fluoro-3-methylphenyl)amino)-8-methylnaphthalen-1-yl)(morpholino) methanone;
(4-((3-Fluoro-4-methylphenyl)amino)-8-methylnaphthalen-1-yl)(morpholino)methanone;
(4-((3-Fluoro-2-methylphenyl)amino)-8-methylnaphthalen-1-yl)(morpholino) methanone;
(4-((3-Chloro-4-methylphenyl)amino)-8-methylnaphthalen-1-yl)(morpholino) methanone;
(4-((3-Chloro-2-methylphenyl)amino)-8-methylnaphthalen-1-yl)(morpholino) methanone;
(4-((3-(Fluoromethyl)phenyl)amino)-8-methylnaphthalen-1-yl)(morpholino)methanone;
(4-((3-(Difluoromethyl)phenyl)amino)-8-methylnaphthalen-1-yl)(morpholino) methanone;
(4-((4-Chlorophenyl)amino)-8-methylnaphthalen-1-yl)(piperidin-1-yl)methanone;
(4-((4-Fluorophenyl)amino)-8-methylnaphthalen-1-yl)(piperidin-1-yl)methanone;
(4-((3-(Difluoromethyl)phenyl)amino)-8-methylnaphthalen-1-yl)(piperidin-1-yl)methanone;
(4-((3-Methoxyphenyl)amino)-8-methylnaphthalen-1-yl)(piperidin-1-yl)methanone;
(4-((3-(Trifluoromethyl)phenyl)amino)-8-methylnaphthalen-1-yl)(pyrrolidin-1-yl)methanone;
2-Oxa-5-azabicyclo[2.2.1]heptan-5-yl(4-((2,3-difluorophenyl)amino)-8-methyl naphthalen-1-yl)methanone;
2-Oxa-5-azabicyclo[2.2.1]heptan-5-yl(4-((3-(difluoromethyl)phenyl)amino)-8-methyl naphthalen-1-yl)methanone;
3-Azabicyclo[3.1.0]hexan-3-yl(4-((3-fluorophenyl)amino)-8-methylnaphthalen-1-yl)methanone;
3-Azabicyclo[3.1.0]hexan-3-yl(4-((2,3-difluorophenyl)amino)-8-methylnaphthalen-1-yl)methanone;
3-Azabicyclo[3.1.0]hexan-3-yl(4-((3-(difluoromethyl)phenyl)amino)-8-methylnaphthalen-1-yl)methanone;
3-Azabicyclo[3.1.0]hexan-3-yl(8-methyl-4-(m-tolylamino)naphthalen-1-yl)methanone;
3-Azabicyclo[3.1.0]hexan-3-yl(4-((3-chlorophenyl)amino)-8-methylnaphthalen-1-yl)methanone;
3-Azabicyclo[3.1.0]hexan-3-yl(4-((3-fluoro-2-methylphenyl)amino)-8-methylnaphthalen-1-yl)methanone;
3-Azabicyclo[3.1.0]hexan-3-yl(4-((3-fluoro-4-methylphenyl)amino)-8-methyl naphthalen-1-yl)methanone;
6-Oxa-3-azabicyclo[3.1.1]heptan-3-yl(4-((2,3-difluorophenyl)amino)-8-methyl naphthalen-1-yl)methanone;
6-Oxa-3-azabicyclo[3.1.1]heptan-3-yl(4-((3-fluoro-2-methylphenyl)amino)-8-methyl naphthalen-1-yl) methanone;
6-Oxa-3-azabicyclo[3.1.1]heptan-3-yl(4-((3-chlorophenyl)amino)-8-methyl naphthalene-1-yl)methanone;
6-Oxa-3-azabicyclo[3.1.1]heptan-3-yl(4-((3-(trifluoromethyl)phenyl)amino)-8-methyl naphthalene-1-yl) methanone;
6-Oxa-3-azabicyclo[3.1.1]heptan-3-yl(4-((3-chloro-2-fluorophenyl)amino)-8-methylnaphthalen-1-yl)methanone;
6-Oxa-3-azabicyclo[3.1.1]heptan-3-yl(4-((3-chloro-4-fluorophenyl)amino)-8-methylnaphthalen-1-yl)methanone;
(4-((2,3-Difluorophenyl)amino)-8-methylnaphthalen-1-yl)(2-oxa-6-azaspiro[3.3]heptan-6-yl methanone;
(4-((3-Chlorophenyl)amino)naphthalen-1-yl)(morpholino)methanone;
4-((3-Chlorophenyl)amino)-N-((tetrahydro-2H-pyran-4-yl)methyl)-1-naphthamide;
4-((3-Chlorophenyl)amino)-N-(pyridin-4-ylmethyl)-1-naphthamide;
N-Butyl-4-((3-chlorophenyl)amino)-1-naphthamide;

(4-((3-Fluorophenyl)amino)naphthalen-1-yl)(morpholino)methanone;
4-((3-Fluorophenyl)amino)-N-((tetrahydro-2H-pyran-4-yl)methyl)-1-naphthamide;
4-((3-Fluorophenyl)amino)-N-(pyridin-4-ylmethyl)-1-naphthamide;
N-Butyl-4-((3-fluorophenyl)amino)-1-naphthamide;
(4-((3,5-Difluorophenyl)amino)naphthalen-1-yl)(morpholino)methanone;
4-((3,5-Difluorophenyl)amino)-N-((tetrahydro-2H-pyran-4-yl)methyl)-1-naphthamide;
4-((3,5-Difluorophenyl)amino)-N-(pyridin-4-ylmethyl)-1-naphthamide;
(4-((3,5-Difluorophenyl)amino)naphthalen-1-yl)(3,5-dimethylmorpholino)methanone;
(4-((3,5-Difluorophenyl)amino)naphthalen-1-yl)(piperidin-1-yl)methanone;
(4-((2,4-Difluorophenyl)amino)naphthalen-1-yl)(morpholino)methanone;
4-((2,4-Difluorophenyl)amino)-N-((tetrahydro-2H-pyran-4-yl)methyl)-1-naphthamide;
4-((2,4-Difluorophenyl)amino)-N-(pyridin-4-ylmethyl)-1-naphthamide;
N-Butyl-4-((2,4-difluorophenyl)amino)-1-naphthamide;
(4-((2,4-Difluorophenyl)amino)naphthalen-1-yl)(piperidin-1-yl)methanone;
(4-((2,4-Dichlorophenyl)amino)naphthalen-1-yl)(morpholino)methanone;
4-((2,4-Dichlorophenyl)amino)-N-((tetrahydro-2H-pyran-4-yl)methyl)-1-naphthamide;
4-((2,4-Dichlorophenyl)amino)-N-(pyridin-4-ylmethyl)-1-naphthamide;
N-Butyl-4-((2,4-dichlorophenyl)amino)-1-naphthamide;
Morpholino(4-((3-(trifluoromethyl)phenyl)amino)naphthalen-1-yl)methanone;
Piperidin-1-yl(4-((3-(trifluoromethyl)phenyl)amino)naphthalen-1-yl)methanone;
(4-((4-Fluoro-3-(trifluoromethyl)phenyl)amino)naphthalen-1-yl)(morpholino) methanone;
(4-((4-Fluoro-3-(trifluoromethyl)phenyl)amino)naphthalen-1-yl)(piperidin-1-yl)methanone;
Morpholino(4-((3-(fluoromethyl)phenyl)amino)naphthalen-1-yl)methanone;
(4-((3-(Fluoromethyl)phenyl)amino)naphthalen-1-yl)(piperidin-1-yl)methanone;
(4-((3-(Difluoromethyl)phenyl)amino)naphthalen-1-yl)(morpholino)methanone;
(4-((3-(Difluoromethyl)phenyl)amino)naphthalen-1-yl)(piperidin-1-yl)methanone;
(5-Chloro-1-((3-chlorophenyl)amino)isoquinolin-4-yl)(piperidin-1-yl)methanon;
(5-Chloro-1-((3-fluoro-2-methylphenyl)amino)isoquinolin-4-yl)(piperidin-1-yl)methanone;
(5-Chloro-1-((2,3-difluorophenyl)amino)isoquinolin-4-yl) (piperidin-1-yl)methanone;
(5-Chloro-1-((3-chlorophenyl)amino)isoquinolin-4-yl) (morpholino)methanone;
(5-Chloro-1-((3-fluoro-2-methylphenyl)amino)isoquinolin-4-yl)(morpholino)methanone;
(5-Chloro-1-((2,3-difluorophenyl)amino)isoquinolin-4-yl)(morpholino)methanone;
(1-((3-Fluoro-2-methylphenyl)amino)-5-ethylisoquinolin-4-yl)(morpholino)methanone;
(5-Ethyl-1-((2-fluoro-3-(trifluoromethyl)phenyl)amino)isoquinolin-4-yl)(morpholino)methanone;
(1-((3-Chloro-2-fluorophenyl)amino)-5-ethylisoquinolin-4-yl)(morpholino)methanone;
(1-((3-Chloro-2-methylphenyl)amino)-5-ethylisoquinolin-4-yl)(morpholino)methanone;
(1-((3-Chloro-2-fluorophenyl)amino)-5-methylisoquinolin-4-yl)(1,1-dioxidothiomorpholino) methanone;
(1-((3-Chlorophenyl)amino)-5-methylisoquinolin-4-yl) (1,1-dioxidothiomorpholino) methanone;
(1-((3,5-Difluorophenyl)amino)-5-methylisoquinolin-4-yl)(1,1-dioxidothiomorpholino) methanone;
(1-((3-Chlorophenyl)amino)-5-methylisoquinolin-4-yl) (4,4-difluoropiperidin-1-yl)methanone;
6-Oxa-3-azabicyclo[3.1.1]heptan-3-yl(1-((2,4-difluorophenyl)amino)-5-methylisoquinolin-4-yl)methanone;
6-Oxa-3-azabicyclo[3.1.1]heptan-3-yl(1-((2-chloro-3-fluorophenyl)amino)-5-methyl isoquinolin-4-yl)methanone;
6-Oxa-3-azabicyclo[3.1.1]heptan-3-yl(1-((2-fluoro-3-(trifluoromethyl)phenyl)amino)-5-methylisoquinolin-4-yl)methanone;
1-((2,5-Bis(trifluoromethyl)phenyl)amino)-N,N,5-trimethyl isoquinolin-4-carboxamide;
Methyl 3-((5-chloro-4-(diethyl carbamoyl)isoquinolin-1-yl)amino)benzoate;
Methyl 3-((5-chloro-4-(diethyl carbamoyl)isoquinolin-1-yl)amino)-2-methylbenzoate;
Methyl 3-((5-chloro-4-(diethyl carbamoyl)isoquinolin-1-yl)amino)benzoate;
Methyl 2-methyl-3-((5-chloro-4-(diethylcarbamoyl)isoquinolin-1-yl)amino)benzoate;
Methyl 2-chloro-3-((5-methyl-4-(piperidin-1-carbonyl)isoquinolin-1-yl)amino)benzoate;
N-Ethyl-1-((4-fluoro-3-(trifluoro methyl)phenyl)amino)-N,5-dimethyl isoquinolin-4-carboxamide;
1-((2,3-Dimethylphenyl)amino)-N-ethyl-N,5-dimethyl-isoquinolin-4-carboxamide;
N-Ethyl-1-((3-fluoro-2-(trifluoro methyl)phenyl)amino)-N,5-dimethyl isoquinolin-4-carboxamide;
1-((3-Fluoro-2-methylphenyl)amino)-N,N,5-trimethyl-isoquinolin-4-carboxamide;
1-((3-Chloro-2-methylphenyl)amino)-N,N,5-trimethyl-isoquinolin-4-carboxamide;
1-((5-Fluoro-2-methylphenyl)amino)-N,N,5-trimethyl-isoquinolin-4-carboxamide;
1-((2-Fluoro-3-(trifluoromethyl)phenyl)amino)-N,N,5-trimethyl isoquinolin-4-carboxamide;
1-((3-Fluoro-2-(trifluoromethyl)phenyl)amino)-N,N,5-trimethyl isoquinolin-4-carboxamide;
N,N,5-Trimethyl-1-((2-methyl-3-(trifluoromethyl)phenyl)amino)isoquinolin-4-carboxamide;
1-((2-Chloro-3-fluorophenyl)amino)-N,N,5-trimethylisoquinolin-4-carboxamide;
1-((3-Chloro-4-fluorophenyl)amino)-N,N,5-trimethylisoquinolin-4-carboxamide;
1-((3-Chloro-2-fluorophenyl)amino)-N,N,5-trimethylisoquinolin-4-carboxamide;
1-((2,3-Difluorophenyl)amino)-N,N,5-trimethylisoquinolin-4-carboxamide;
1-((5-Chloro-2-fluorophenyl)amino)-N,N,5-trimethylisoquinolin-4-carboxamide;
1-((2-Chloro-5-fluorophenyl)amino)-N,N,5-trimethylisoquinolin-4-carboxamide;
1-((2,3-Dimethylphenyl)amino)-N,N,5-trimethylisoquinolin-4-carboxamide;
1-((3,5-Difluorophenyl)amino)-N,N,5-trimethylisoquinolin-4-carboxamide;
1-((3-Chlorophenyl)amino)-N,N,5-trimethylisoquinolin-4-carboxamide;

N,N,5-Trimethyl-1-((3-(trifluoro methyl)phenyl)amino) isoquinolin-4-carboxamide;
1-((2,3-Dichlorophenyl)amino)-N,N,5-trimethylisoquinolin-4-carboxamide;
1-((5-Chloro-2-methylphenyl)amino)-N,N,5-trimethylisoquinolin-4-carboxamide;
1-((4-Chloro-3-methylphenyl)amino)-N,N,5-trimethylisoquinolin-4-carboxamide;
1-((2,5-Bis(trifluoromethyl)phenyl)amino)-N,N,5-trimethyl isoquinolin-4-carboxamide;
1-((2-Methoxy-5-(trifluoromethyl)phenyl)amino)-N,N,5-trimethyl isoquinolin-4-carboxamide;
N,N-Diethyl-1-((3-fluoro-2-methyl phenyl)amino)-5-methylisoquinolin-4-carboxamide;
1-((3-Chloro-2-methylphenyl)amino)-N,N-diethyl-5-methyl isoquinolin-4-carboxamide;
N,N-Diethyl-1-((2-fluoro-3-(trifluoro methyl)phenyl)amino)-5-methyl isoquinolin-4-carboxamide;
N,N-Diethyl-1-((3-fluoro-2-(trifluoro methyl)phenyl)amino)-5-methyl isoquinolin-4-carboxamide;
N,N-Diethyl-5-methyl-1-((2-methyl-3-(trifluoromethyl)phenyl)amino) isoquinolin-4-carboxamide;
1-((2-Chloro-3-fluorophenyl)amino)-N,N-diethyl-5-methyl isoquinolin-4-carboxamide;
1-((3-Chloro-4-fluorophenyl)amino)-N,N-diethyl-5-methyl isoquinolin-4-carboxamide;
1-((3-Chloro-2-fluorophenyl)amino)-N,N-diethyl-5-methyl isoquinolin-4-carboxamide;
1-((2,3-Difluorophenyl)amino)-N,N-diethyl-5-methylisoquinolin-4-carboxamide;
1-((5-Chloro-2-fluorophenyl)amino)-N,N-diethyl-5-methyl isoquinolin-4-carboxamide;
1-((2-Chloro-5-fluorophenyl)amino)-N,N-diethyl-5-methyl isoquinolin-4-carboxamide;
1-((2,3-Dimethylphenyl)amino)-N,N-diethyl-5-methyl-isoquinolin-4-carboxamide;
1-((3,5-Difluorophenyl)amino)-N,N-diethyl-5-methylisoquinolin-4-carboxamide;
1-((3-Chlorophenyl)amino)-N,N-diethyl-5-methylisoquinolin-4-carboxamide;
N,N-Diethyl-5-methyl-1-((3-(trifluoromethyl)phenyl)amino)isoquinolin-4-carboxamide;
N-Ethyl-1-((3-fluoro-2-methyl phenyl)amino)-N,5-dimethyl isoquinolin-4-carboxamide;
1-((3-Chloro-2-methylphenyl)amino)-N-ethyl-N,5-dimethyl isoquinolin-4-carboxamide;
N-Ethyl-1-((2-fluoro-3-(trifluoro methyl)phenyl)amino)-N,5-dimethyl isoquinolin-4-carboxamide;
N-Ethyl-N,5-dimethyl-1-((2-methyl-3-(trifluoromethyl)phenyl)amino)isoquinolin-4-carboxamide;
1-((2-Chloro-3-fluorophenyl)amino)-N-ethyl-N,5-dimethyl isoquinolin-4-carboxamide;
1-((3-Chloro-2-fluorophenyl)amino)-N-ethyl-N,5-dimethyl isoquinolin-4-carboxamide;
1-((2,3-Difluorophenyl)amino)-N-ethyl-N,5-dimethylisoquinolin-4-carboxamide;
1-((3-Chloro-4-fluorophenyl)amino)-N-ethyl-N,5-dimethyl isoquinolin-4-carboxamide;
1-((5-Chloro-2-fluorophenyl)amino)-N-ethyl-N,5-dimethyl isoquinolin-4-carboxamide;
1-((2-Chloro-5-fluorophenyl)amino)-N-ethyl-N,5-dimethyl isoquinolin-4-carboxamide;
1-((3,5-Difluorophenyl)amino)-N-ethyl-N,5-dimethylisoquinolin-4-carboxamide;
1-((3-Chlorophenyl)amino)-N-ethyl-N,5-dimethylisoquinolin-4-carboxamide;
N-ethyl-N,5-dimethyl-1-((3-(trifluoromethyl)phenyl)amino) isoquinolin-4-carboxamide;
1-((3-Fluoro-2-methylphenyl)amino)-5-methyl-N,N-dipropyl isoquinolin-4-carboxamide;
1-((3-Chloro-2-methylphenyl)amino)-5-methyl-N,N-dipropyl isoquinolin-4-carboxamide;
1-((2-Fluoro-3-(trifluoromethyl)phenyl)amino)-5-methyl-N,N-dipropylisoquinolin-4-carboxamide;
1-((3-Fluoro-2-(trifluoromethyl)phenyl)amino)-5-methyl-N,N-dipropylisoquinolin-4-carboxamide;
5-Methyl-1-((2-methyl-3-(trifluoro methyl)phenyl)amino)-N,N-dipropylisoquinolin-4-carboxamide;
1-((2-Chloro-3-fluorophenyl)amino)-5-methyl-N,N-dipropyl isoquinolin-4-carboxamide;
N-Ethyl-1-((3-fluoro-2-methyl phenyl)amino)-5-methyl-N-propyl isoquinolin-4-carboxamide;
1-((3-Chloro-2-methylphenyl)amino)-N-ethyl-5-methyl-N-propyl isoquinolin-4-carboxamide;
N-Ethyl-1-((5-fluoro-2-methyl phenyl)amino)-5-methyl-N-propyl isoquinolin-4-carboxamide;
N-Ethyl-1-((3-fluoro-2-(trifluoro methyl)phenyl)amino)-5-methyl-N-propylisoquinolin-4-carboxamide;
2-Methyl-3-((5-methyl-4-(piperidin-1-carbonyl)isoquinolin-1-yl)amino)benzoic acid;
2-Methyl-3-((5-methyl-4-(morpholin-4-carbonyl)isoquinolin-1-yl)amino)benzoic acid;
3-((4-(Dimethylcarbamoyl)-5-methylisoquinolin-1-yl) amino)-2-methylbenzoic acid;
3-((4-(Diethylcarbamoyl)-5-methylisoquinolin-1-yl) amino)-2-methylbenzoic acid;
5-Chloro-1-((2-chloro-3-(trifluoro methyl)phenyl)amino)-N,N-dimethylisoquinolin-4-carboxamide;
5-Chloro-1-((2-chloro-3-fluoro phenyl)amino)-N,N-dimethyl isoquinolin-4-carboxamide;
5-Chloro-1-((2,3-dimethylphenyl)amino)-N,N-dimethylisoquinolin-4-carboxamide;
5-Chloro-1-((2,3-dimethylphenyl)amino)-N-ethyl-N-methyl isoquinolin-4-carboxamide;
5-Chloro-1-((3-chloro-2-fluoro phenyl)amino)-N,N-diethyl isoquinoline-4-carboxamide;
5-Chloro-1-((3-chloro-2-methyl phenyl)amino)-N,N-diethyl isoquinolin-4-carboxamide;
5-Chloro-N,N-diethyl-1-((3-fluoro-2-methylphenyl) amino)isoquinolin-4-carboxamide;
5-Chloro-N,N-diethyl-1-((3-fluoro-2-(trifluoromethyl) phenyl)amino)isoquinolin-4-carboxamide;
5-Chloro-N,N-diethyl-1-((2-methyl-3-(trifluoromethyl) phenyl)amino)isoquinolin-4-carboxamide;
5-Chloro-1-((2,3-dichlorophenyl)amino)-N,N-diethylisoquinolin-4-carboxamide;
5-Chloro-N,N-diethyl-1-((2,3,6-trifluorophenyl)amino) isoquinolin-4-carboxamide;
5-Chloro-N,N-diethyl-1-((2-fluoro-3-(trifluoromethyl) phenyl)amino)isoquinolin-4-carboxamide;
5-Chloro-N,N-dimethyl-1-((2-methyl-3-(trifluoromethyl) phenyl)amino)isoquinolin-4-carboxamide;
5-Chloro-1-((2-fluoro-3-(trifluoromethyl)phenyl)amino)-N,N-dimethylisoquinolin-4-carboxamide;
5-Chloro-N-ethyl-N-methyl-1-((2-methyl-3-(trifluoromethyl)phenyl)amino)isoquinolin-4-carboxamide;
5-Chloro-1-((3-chloro-2-methylphenyl)amino)-N,N-dimethylisoquinolin-4-carboxamide;
5-Chloro-1-((3-fluoro-2-(trifluoromethyl)phenyl)amino)-N,N-dimethylisoquinolin-4-carboxamide;
5-Chloro-N-ethyl-1-((2-fluoro-3-(trifluoromethyl)phenyl)amino)-N-methylisoquinolin-4-carboxamide;

5-Chloro-N-ethyl-1-((3-fluoro-2-(trifluoromethyl)phenyl)amino)-N-methylisoquinolin-4-carboxamide;
5-Chloro-1-((2-chloro-3-fluoro phenyl)amino)-N-ethyl-N-methyl isoquinolin-4-carboxamide;
3-((5-Chloro-4-(diethylcarbamoyl)isoquinolin-1-yl)amino)-2-methyl benzoic acid;
3-((5-Chloro-4-(dimethyl carbamoyl)isoquinolin-1-yl)amino)-2-methylbenzoic acid;
5-Chloro-1((2-methyl-3-(trifluoro methyl)phenyl)amino)-N,N-dipropylisoquinolin-4-carboxamide;
2-Chloro-4-((5-chloro-4-(dimethyl carbamoyl)isoquinolin-1-yl)amino)benzoic acid;
3-((5-Chloro-4-(morpholin-4-carbonyl)isoquinolin-1-yl)amino)-2-methylbenzoic acid;
5-Chloro-N,N-diethyl-1-((3-(trifluoromethyl)phenyl)amino) isoquinolin-4-carboxamide;
5-Chloro-1-((2,4-dichlorophenyl)amino)-N,N-diethylisoquinolin-4-carboxamide;
5-Chloro-N,N-diethyl-1-((2,3,4-trifluorophenyl)amino) isoquinolin-4-carboxamide;
5-Chloro-N,N-diethyl-1-((2,3,5-trifluorophenyl)amino) isoquinolin-4-carboxamide;
5-Chloro-1-((2,3-difluorophenyl)amino)-N,N-diethylisoquinolin-4-carboxamide;
5-Chloro-1-((2-chloro-3-fluoro phenyl)amino)-N,N-diethyl isoquinolin-4-carboxamide;
3-((5-Chloro-4-(diethylcarbamoyl)isoquinolin-1-yl)amino)benzoic acid;
5-Chloro-1-((3-fluoro-2-methyl phenyl)amino)-N,N-dimethyl isoquinolin-4-carboxamide;
5-Chloro-1-((2,3-difluorophenyl)amino)-N,N-dimethyl-isoquinolin-4-carboxamide;
3-((5-Chloro-4-(dipropylcarbamoyl) isoquinolin-1-yl)amino)-2-methyl benzoic acid;
3-((5-Chloro-4-(dimethyl carbamoyl)isoquinolin-1-yl)amino)-2-fluorobenzoic acid;
3-((5-Chloro-4-(dipropylcarbamoyl)isoquinolin-1-yl)amino)-4-methyl benzoic acid;
3-((5-Chloro-4-(ethyl(methyl)carbamoyl)isoquinolin-1-yl)amino)-2-methylbenzoic acid;
5-Chloro-N-ethyl-N-methyl-1-((2,3,6-trifluorophenyl)amino)isoquinolin-4-carboxamide;
5-Chloro-N-ethyl-1-((3-fluoro-2-methylphenyl)amino)-N-methylisoquinolin-4-carboxamide;
5-Chloro-1-((3-chloro-2-methylphenyl)amino)-N-ethyl-N-methylisoquinolin-4-carboxamide;
3-((5-Chloro-4-(diethylcarbamoyl)isoquinolin-1-yl)amino)-2-fluoro benzoic acid;
3-((5-Chloro-4-(dimethyl carbamoyl)isoquinolin-1-yl)amino)-4-methylbenzoic acid;
5-Chloro-N,N-diethyl-1-((2-methyl-3-(methylcarbamoyl)phenyl)amino)isoquinolin-4-carboxamide;
5-Chloro-1-((2,3-dimethylphenyl)amino)-N,N-dimethyl-isoquinolin-4-carboxamide;
3-((5-Chloro-4-(morpholin-4-carbonyl)isoquinolin-1-yl)amino)-4-methylbenzoic acid;
5-Chloro-1-((2,3-dichlorophenyl)amino)-N-ethyl-N-methyl isoquinolin-4-carboxamide;
5-Chloro-N,N-diethyl-1-((3-(methyl carbamoyl)phenyl)amino)isoquinolin-4-carboxamide;
3-((5-Chloro-4-(diethylcarbamoyl)isoquinolin-1-yl)amino)-4-methyl benzoic acid;
3-((5-Chloro-4-(piperidine-1-carbonyl)isoquinolin-1-yl)amino)-4-methylbenzoic acid;
5-Chloro-1-((2-chloro-3-fluoro phenyl)amino)-N,N-dimethyl isoquinolin-4-carboxamide;
5-Chloro-1-((2-fluoro-3-(methyl carbamoyl)phenyl)amino)-N,N-dimethylisoquinolin-4-carboxamide;
3-((5-Chloro-4-(piperidine-1-carbonyl)isoquinolin-1-yl)amino)-2-methylbenzoic acid;
4-((5-Chloro-4-(ethyl(methyl)carbamoyl)isoquinolin-1-yl)amino)-2-methylbenzoic acid;
2-Chloro-4-((5-chloro-4-(ethyl(methyl)carbamoyl)isoquinolin-1-yl)amino)benzoic acid;
1-((3,5-Bis(trifluoromethyl)phenyl)amino)-5-chloro-N,N-dimethylisoquinolin-4-carboxamide;
5-Chloro-1-((4-fluoro-3-(trifluoromethyl)phenyl)amino)-N,N-dimethylisoquinolin-4-carboxamide;
5-Chloro-1-((5-chloro-2-fluoro phenyl)amino)-N,N-dimethyl isoquinolin-4-carboxamide;
5-Chloro-1-((4-chloro-3-methyl phenyl)amino)-N,N-dimethyl isoquinolin-4-carboxamide;
4-((5-Chloro-4-(ethyl(methyl)carbamoyl)isoquinolin-1-yl)amino)-3-methylbenzoic acid;
5-Chloro-1-((2-chloro-3-(trifluoromethyl)phenyl)amino)-N,N-dimethylisoquinolin-4-carboxamide;
4-((5-Chloro-4-(dimethyl carbamoyl)isoquinolin-1-yl)amino)-3-methylbenzoic acid;
4-((5-chloro-4-(dimethylcarbamoyl)isoquinolin-1-yl)amino)-3-fluoro benzoic acid;
5-Chloro-1-((2-fluoro-3-(trifluoromethyl)phenyl)amino)-N-isopropyl-N-methyl isoquinolin-4-carboxamide;
5-Chloro-1-((3-fluoro-2-(trifluoro methyl)phenyl)amino)-N-isopropyl-N-methylisoquinolin-4-carboxamide;
5-Chloro-N-isopropyl-N-methyl-1-((2-methyl-3-(trifluoromethyl)phenyl)amino)isoquinolin-4-carboxamide;
5-Chloro-1-((2-chloro-3-(trifluoromethyl)phenyl)amino)-N-isopropyl-N-methyl isoquinolin-4-carboxamide;
5-Chloro-1-((3-chloro-2-methylphenyl)amino)-N-isopropyl-N-methylisoquinolin-4-carboxamide;
5-Chloro-1-((3-fluoro-2-methylphenyl)amino)-N-isopropyl-N-methylisoquinolin-4-carboxamide;
2-(5-Chloro-1-((3-chloro-2-methylphenyl)amino)-N-methylisoquinolin-4-carboxamido) acetic acid;
2-(5-Chloro-1-((3-fluoro-2-methylphenyl)amino)-N-methylisoquinolin-4-carboxamido) acetic acid;
2-(5-Chloro-N-methyl-1-((2-methyl-3-(trifluoromethyl)phenyl)amino)isoquinolin-4-carboxamido)acetic acid;
2-(5-Chloro-1-((2-fluoro-3-(trifluoromethyl)phenyl)amino)-N-methylisoquinolin-4-carboxamido)acetic acid
2-(5-Chloro-1-((3-fluoro-2-(trifluoromethyl)phenyl)amino)-N-methylisoquinolin-4-carboxamido)acetic acid;
5-Chloro-1-((3-(dimethylcarbamoyl)-2-methylphenyl)amino)-N,N-diethylisoquinolin-4-carboxamide;
5-Chloro-N,N-diethyl-1-((3-(methyl carbamoyl)-2-methylphenyl)amino)isoquinolin-4-carboxamide;
5-Chloro-N,N-diethyl-1-((3-(methylcarbamoyl)phenyl)amino)isoquinolin-4-carboxamide;
5-Chloro-N,N-dimethyl-1-((3-(methylcarbamoyl)-2-fluorophenyl)amino)isoquinolin-4-carboxamide;
5-Chloro-1-((3-chloro-4-(methylcarbamoyl)phenyl)amino)-N,N-dimethylisoquinolin-4-carboxamide;
5-Chloro-1-((3-chloro-4-(methylcarbamoyl)phenyl)amino)-N-ethyl-N-methylisoquinolin-4-carboxamide;
3-((5-Chloro-4-(morpholin-4-carbonyl)isoquinolin-1-yl)amino)-N-ethyl-2-methyl benzamide;
3-((5-Chloro-4-(piperidin-1-carbonyl)isoquinolin-1-yl)amino)-N-ethyl-2-methyl benzamide;
Methyl 3-((5-methyl-4-(piperidin-1-carbonyl)isoquinolin-1-yl)amino)benzoate;

3-((5-Methyl-4-(piperidine-1-carbonyl)isoquinolin-1-yl)amino)benzoic acid;
Methyl 3-((5-methyl-4-(morpholin-4-carbonyl)isoquinolin-1-yl)amino)benzoate;
3((5-Methyl-4-(morpholin-4-carbonyl)isoquinolin-1-yl)amino)benzoic acid;
4-((5-Chloro-4-(dimethyl carbamoyl)isoquinolin-1-yl)amino)-3-methylbenzoic acid;
3-((5-Chloro-4-(diethylcarbamoyl)isoquinolin-1-yl)amino)-2-fluoro benzoic acid;
N,N-Dimethyl-3-((5-methyl-4-(morpholin-4-carbonyl)isoquinolin-1-yl)amino)benzamide;
(5-Methyl-1-((3-(morpholin-4-carbonyl)phenyl)amino)isoquinolin-4-yl)(morpholino)methanone;
Methyl 3-((5-methyl-4-(piperidin-1-carbonyl)naphthalen-1-yl)amino)benzoate;
Methyl 3-((5-methyl-4-(morpholin-4-carbonyl)naphthalen-1-yl)amino)benzoate;
Methyl 2-methyl-3-((5-methyl-4-(piperidin-1-carbonyl)naphthalen-1-yl)amino)benzoate;
Methyl 2-methyl-3-((5-methyl-4-(morpholin-4-carbonyl)naphthalen-1-yl)amino)benzoate;
Methyl 2-methyl-3-((5-methyl-4-(diethylcarbamoyl)naphthalen-1-yl)amino)benzoate;
Methyl 3-(3-((5-methyl-4-(piperidin-1-carbonyl)naphthalen-1-yl)amino)propanoate;
N-Ethyl-4-((2-fluoro-3-(trifluoro methyl)phenyl)amino)-N,8-dimethyl-1-naphthamide;
N-Ethyl-4-((5-fluoro-2-methyl phenyl)amino)-N,8-dimethyl-1-naphthamide;
N-Ethyl-4-((3-fluoro-2-(trifluoro methyl)phenyl)amino)-N,8-dimethyl-1-naphthamide;
N,N-Diethyl-8-methyl-4-((2-methyl-3-(trifluoromethyl)phenyl)amino)-1-naphthamide;
N,N-Diethyl-4-((3-fluoro-2-methyl phenyl)amino)-8-methyl-1-naphthamide;
4-((3-Chloro-2-methylphenyl)amino)-N,N-diethyl-8-methyl-1-naphthamide;
N,N-Diethyl-4-((2-fluoro-3-(trifluoro methyl)phenyl)amino)-8-methyl-1-naphthamide;
4-((2-Chloro-3-fluorophenyl)amino)-N,N-diethyl-8-methyl-1-naphthamide;
4-((3-Chloro-2-fluorophenyl)amino)-N,N-diethyl-8-methyl-1-naphthamide;
4-((2,3-Dimethylphenyl)amino)-N,N-diethyl-8-methyl-1-naphthamide;
N,N-Diethyl-4-((3-fluoro-2-(trifluoro methyl)phenyl)amino)-8-methyl-1-naphthamide;
4-((2-Chloro-3-fluorophenyl)amino)-N,N,8-trimethyl-1-naphthamide;
4-((2-Fluoro-3-(trifluoromethyl)phenyl)amino)-N,N,8-trimethyl-1-naphthamide;
4-((2,3-Dimethylphenyl)amino)-N,N,8-trimethyl-1-naphthamide;
N,N,8-Trimethyl-4-((2-methyl-3-(trifluoromethyl)phenyl)amino)-1-naphthamide;
4-((3-Fluoro-2-(trifluoromethyl)phenyl)amino)-N,N,8-trimethyl-1-naphthamide;
4-((3-Fluoro-2-methylphenyl)amino)-N,N,8-trimethyl-1-naphthamide;
4-((3-Chloro-2-methylphenyl)amino)-N,N,8-trimethyl-1-naphthamide;
4-((3-Chloro-2-fluorophenyl)amino)-N,N,8-trimethyl-1-naphthamide;
N,N-Diethyl-4-((5-fluoro-2-methyl phenyl)amino)-8-methyl-1-naphthamide;
3-((4-(Diethylcarbamoyl)-5-methyl naphthalen-1-yl)amino)-2-methyl benzoic acid;
4-((2,3-Difluorophenyl)amino)-N,N-diethyl-8-methyl-1-naphthamide;
2-Chloro-3-((4-(diethylcarbamoyl)-5-methylnaphthalen-1-yl)amino)benzoic acid;
4-((2,5-Bis(trifluoromethyl)phenyl)amino)-N,N-diethyl-8-methyl-1-naphthamide;
N,N-Diethyl-4-((2-methoxy-5-(trifluoromethyl)phenyl)amino)-8-methyl-1-naphthamide;
3-((4-(Dimethylcarbamoyl)-5-methylnaphthalen-1-yl)amino)-2-methylbenzoic acid;
3-((4-(Dimethylcarbamoyl)-5-methylnaphthalen-1-yl)amino)-2-fluorobenzoic acid;
4-((5-Chloro-2-methylphenyl)amino)-N,N,8-trimethyl-1-naphthamide;
4-((5-Chloro-2-fluorophenyl)amino)-N,N,8-trimethyl-1-naphthamide;
4-((2-Chloro-5-methylphenyl)amino)-N,N,8-trimethyl-1-naphthamide;
4-((4-Chloro-3-methylphenyl)amino)-N,N,8-trimethyl-1-naphthamide;
4-((2,3-Difluorophenyl)amino)-N,N,8-trimethyl-1-naphthamide;
4-((5-Fluoro-2-methylphenyl)amino)-N,N,8-trimethyl-1-naphthamide;
4-((4-Fluoro-3-(trifluoromethyl)phenyl)amino)-N,N,8-trimethyl-1-naphthamide;
4-((2-Chloro-5-fluorophenyl)amino)-N,N,8-trimethyl-1-naphthamide;
4-((3-Chloro-4-fluorophenyl)amino)-N,N,8-trimethyl-1-naphthamide;
N-Ethyl-4-((2-fluoro-3-(trifluoro methyl)phenyl)amino)-N,8-dimethyl-1-naphthamide;
N-Ethyl-4-((3-fluoro-2-methyl phenyl)amino)-N,8-dimethyl-1-naphthamide;
4-((2-Chloro-3-fluorophenyl)amino)-N-ethyl-N,8-dimethyl-1-naphthamide;
N-Ethyl-N,8-dimethyl-4-((2-methyl-3-(trifluoromethyl)phenyl)amino)-1-naphthamide;
4-((2,3-Dimethylphenyl)amino)-N-ethyl-N,8-dimethyl-1-naphthamide;
N-Ethyl-4-((5-fluoro-2-methyl phenyl)amino)-N,8-dimethyl-1-naphthamide;
N-Ethyl-4-((4-fluoro-3-(trifluoro methyl)phenyl)amino)-N,8-dimethyl-1-naphthamide;
4-((3-Chloro-2-methylphenyl)amino)-N-ethyl-N,8-dimethyl-1-naphthamide;
4-((5-Chloro-2-methylphenyl)amino)-N-ethyl-N,8-dimethyl-1-naphthamide;
4-((2,3-Difluorophenyl)amino)-N-ethyl-N,8-dimethyl-1-naphthamide;
4-((2-Chloro-5-fluorophenyl)amino)-N-ethyl-N,8-dimethyl-1-naphthamide;
3-((4-(Dipropylcarbamoyl)-5-methylnaphthalen-1-yl)amino)-2-methylbenzoic acid;
2-Methyl-3-((5-methyl-4-(piperidin-1-carbonyl)naphthalen-1-yl)amino)benzoic acid;
2-Methyl-3-((5-methyl-4-(morpholin-4-carbonyl)naphthalen-1-yl)amino)benzoic acid;
4-Methyl-3-((5-methyl-4-(piperidin-1-carbonyl)naphthalen-1-yl)amino)benzoic acid;
4-((5-Methyl-4-(piperidin-1-carbonyl)naphthalen-1-yl)amino)-3-(trifluoromethyl)benzoic acid;
3-(3-((5-Methyl-4-(piperidin-1-carbonyl)naphthalen-1-yl)amino) propanoic acid;

3-((5-Methyl-4-(piperidin-1-carbonyl)naphthalen-1-yl) amino)benzoic acid;
3-((5-Methyl-4-(morpholin-4-carbonyl)naphthalen-1-yl) amino)benzoic acid;
8-Chloro-N,N-dimethyl-4-((2-methyl-3-(trifluoromethyl) phenyl)amino)-1-naphthamide;
8-Chloro-4-((3-fluoro-2-(trifluoromethyl)phenyl)amino)-N,N-dimethyl-1-naphthamide;
8-Chloro-4-((2-fluoro-3-(trifluoromethyl)phenyl)amino)-N,N-dimethyl-1-naphthamide;
2-Methyl-3-((5-methyl-4-(piperidine-1-carbonyl)naphthalen-1-yl)amino)benzonitrile;
(8-Methyl-4-((2-methyl-3-(1-methyl-1H-tetrazol-5-yl) phenyl)amino)naphthalen-1-yl)(piperidin-1-yl)methanone;
N,N,8-Trimethyl-4-((3-(1-methyl-1H-tetrazol-5-yl)phenyl)amino)-1-naphthamide;
N,N-diethyl-8-methyl-4-((2-methyl-3-(1-methyl-1H-tetrazol-5-yl)phenyl)amino)-1-naphthamide;
2-Methyl-3-((5-methyl-4-(morpholine-4-carbonyl)naphthalen-1-yl)amino)benzonitrile;
3-((5-Chloro-4-(piperidine-1-carbonyl)naphthalen-1-yl) amino)-2-methylbenzonitrile;
8-Chloro-N,N-dimethyl-4-((3-(1-methyl-1H-tetrazol-5-yl)phenyl)amino)-1-naphthamide;
8-Chloro-N,N-diethyl-4-((3-(1-methyl-1H-tetrazol-5-yl) phenyl)amino)-1-naphthamide;
(8-Chloro-4-((2-methyl-3-(1-methyl-1H-tetrazol-5-yl) phenyl)amino)naphthalen-1-yl)(piperidin-1-yl)methanone;
(8-Chloro-4-((3-(1-methyl-1H-tetrazol-5-yl)phenyl) amino)naphthalen-1-yl)(piperidin-1-yl)methanone;
3-((5-Fluoro-4-(morpholine-4-carbonyl)naphthalen-1-yl) amino)-2-methylbenzonitrile;
N,N-Diethyl-8-fluoro-4-((2-methyl-3-(1-methyl-1H-tetrazol-5-yl)phenyl)amino)-1-naphthamide;
8-fluoro-N,N-dimethyl-4((3-(1-methyl-1H-tetrazol-5-yl) phenyl)amino)-1-naphthamide;
(8-Fluoro-4-((2-methyl-3-(1-methyl-1H-tetrazol-5-yl) phenyl)amino)naphthalen-1-yl)(piperidin-1-yl)methanone;
(8-Fluoro-4-((3-(1-methyl-1H-tetrazol-5-yl)phenyl) amino)naphthalen-1-yl)(piperidin-1-yl)methanone;
3-((5-Fluoro-4-(piperidine-1-carbonyl)naphthalen-1-yl) amino)-2-methylbenzoic acid;
Methyl 3-((5-chloro-4-(diethylcarbamoyl)naphthalen-1-yl)amino)benzoate;
Methyl 3-((4-(dimethylcarbamoyl)-5-fluoronaphthalen-1-yl)amino)-2-methyl benzoate;
5-((5-Chloro-4-(piperidine-1-carbonyl)naphthalen-1-yl) amino)-2-methylbenzoic acid;
Methyl 3-((5-fluoro-4-(morpholine-4-carbonyl)naphthalen-1-yl)amino)-4-methyl benzoate;
2-Methyl-3-((5-methyl-4-(piperidine-1-carbonyl)naphthalen-1-yl)amino)benzamide;
N,N,2-Trimethyl-3-((5-methyl-4-(morpholine-4-carbonyl)naphthalen-1-yl)amino)benzamide;
4-((3-Carbamoylphenyl)amino)-N,N,8-trimethyl-1-naphthamide;
4-((3-Carbamoyl-2-methylphenyl)amino)-N,N-diethyl-8-methyl-1-naphthamide;
N,N,2-Trimethyl-5-((5-methyl-4-(piperidine-1-carbonyl) naphthalen-1-yl)amino)benzamide;
5-((5-Fluoro-4-(piperidine-1-carbonyl)naphthalen-1-yl) amino)-N,N,2-trimethylbenzamide;
3-((5-Tluoro-4-(morpholine-4-carbonyl)naphthalen-1-yl) amino)-N,N,2-trimethylbenzamide;
4-((3-Carbamoyl-2-methylphenyl)amino)-8-chloro-N,N-dimethyl-1-naphthamide;
8-Chloro-4-((3-(dimethylcarbamoyl)phenyl)amino)-N,N-diethyl-1-naphthamide; and
3-((5-Fluoro-4-(piperidine-1-carbonyl)naphthalen-1-yl) amino)-2-methylbenzamide or pharmaceutically acceptable salt thereof.

22. A pharmaceutical composition comprising one or more compounds of Formula (I) according to claim 1, and one or more pharmaceutically acceptable excipients.

* * * * *